United States Patent
Bonyhadi et al.

(10) Patent No.: US 11,821,027 B2
(45) Date of Patent: Nov. 21, 2023

(54) EPIGENETIC ANALYSIS OF CELL THERAPY AND RELATED METHODS

(71) Applicant: Juno Therapeutics, Inc., Seattle, WA (US)

(72) Inventors: Mark L. Bonyhadi, Sammamish, WA (US); David G. Kugler, Seattle, WA (US); Timothy G. Johnstone, Seattle, WA (US); Ronald James Hause, Jr., Seattle, WA (US); Lucas J. Thompson, Seattle, WA (US); Ryan P. Larson, Seattle, WA (US)

(73) Assignee: Juno Therapeutics, Inc., Seattle, WA (US)

( * ) Notice: Subject to any disclaimer, the term of this patent is extended or adjusted under 35 U.S.C. 154(b) by 772 days.

(21) Appl. No.: 16/476,856

(22) PCT Filed: Jan. 10, 2018

(86) PCT No.: PCT/US2018/013227
§ 371 (c)(1),
(2) Date: Jul. 9, 2019

(87) PCT Pub. No.: WO2018/132518
PCT Pub. Date: Jul. 19, 2018

(65) Prior Publication Data
US 2019/0345543 A1 Nov. 14, 2019

Related U.S. Application Data

(60) Provisional application No. 62/596,662, filed on Dec. 8, 2017, provisional application No. 62/551,752, filed on Aug. 29, 2017, provisional application No. 62/444,802, filed on Jan. 10, 2017.

(51) Int. Cl.
| | |
|---|---|
| *C12Q 1/6827* | (2018.01) |
| *G16B 30/10* | (2019.01) |
| *C12Q 1/6806* | (2018.01) |
| *C12Q 1/6869* | (2018.01) |
| *C12Q 1/6886* | (2018.01) |
| *G16B 20/20* | (2019.01) |
| *G16B 40/10* | (2019.01) |
| *G16B 20/10* | (2019.01) |

(52) U.S. Cl.
CPC ......... *C12Q 1/6827* (2013.01); *C12Q 1/6806* (2013.01); *C12Q 1/6869* (2013.01); *C12Q 1/6886* (2013.01); *G16B 20/10* (2019.02); *G16B 20/20* (2019.02); *G16B 30/10* (2019.02); *G16B 40/10* (2019.02); *C12Q 2600/142* (2013.01); *C12Q 2600/154* (2013.01); *C12Q 2600/156* (2013.01)

(58) Field of Classification Search
CPC ............... C12Q 1/6806; C12Q 1/6869; C12Q 2600/154; C12Q 2600/156; C12Q 1/6827; C12Q 2600/142; G16B 20/20; A61K 2039/5156; C07K 14/7051
See application file for complete search history.

(56) References Cited

U.S. PATENT DOCUMENTS

| | | |
|---|---|---|
| 4,452,773 A | 6/1984 | Molday |
| 4,690,915 A | 9/1987 | Rosenberg |
| 5,087,616 A | 2/1992 | Myers et al. |
| 5,200,084 A | 4/1993 | Liberti |
| 6,040,177 A | 3/2000 | Riddell |
| 6,410,319 B1 | 6/2002 | Raubitschek et al. |
| 6,451,995 B1 | 9/2002 | Cheung et al. |
| 7,070,995 B2 | 7/2006 | Jensen |
| 7,265,209 B2 | 9/2007 | Jensen |
| 7,354,762 B2 | 4/2008 | Jensen |
| 7,446,179 B2 | 11/2008 | Jensen et al. |
| 7,446,190 B2 | 11/2008 | Sadelain et al. |
| 7,446,191 B2 | 11/2008 | Jensen |

(Continued)

FOREIGN PATENT DOCUMENTS

| | | |
|---|---|---|
| EP | 452342 | 11/1994 |
| WO | WO 1996/013593 | 5/1996 |

(Continued)

OTHER PUBLICATIONS

US 8,252,592 B2, 08/2012, Jensen (withdrawn)

(Continued)

*Primary Examiner* — Joseph G. Dauner
(74) *Attorney, Agent, or Firm* — MORRISON & FOERSTER LLP

(57) ABSTRACT

Provided herein are methods of identifying genomic region(s) predictive of an outcome of treatment with a cell therapy and/or of a phenotype of function of the cells. In some embodiments, the methods include epigenetic and/or epigenomic analyses of the cells in connection with methods for preparing engineered cells for cell therapy and/or predicting response to a cell therapy, e.g., engineered cells for cell therapy. In some embodiments, the methods include steps to assess, characterize and analyze changes or modifications in an epigenetic property of gene region or regions, such as chromatin accessibility, nucleosome occupancy, histone modification, spatial chromosomal conformation, transcription factor occupancy and/or DNA methylation. In some embodiments, the epigenetic and/or epigenomic analysis includes determining the epigenetic properties of a cell, e.g., an engineered cell for cell therapy.

29 Claims, 45 Drawing Sheets
Specification includes a Sequence Listing.

(56) References Cited

U.S. PATENT DOCUMENTS

| | | | |
|---|---|---|---|
| 8,324,353 | B2 | 12/2012 | Jensen |
| 8,339,645 | B2 | 12/2012 | Nakawaki |
| 8,389,282 | B2 | 3/2013 | Sadelain et al. |
| 8,479,118 | B2 | 7/2013 | Lyndersay et al. |
| 8,802,374 | B2 | 8/2014 | Jensen |
| 8,822,647 | B2 | 9/2014 | Jensen |
| 8,911,993 | B2 | 12/2014 | June et al. |
| 9,092,401 | B2 | 7/2015 | Richards et al. |
| 2002/0131960 | A1 | 9/2002 | Sadelain et al. |
| 2002/0150914 | A1 | 10/2002 | Anderson et al. |
| 2003/0170238 | A1 | 9/2003 | Gruenberg et al. |
| 2003/0223994 | A1 | 12/2003 | Hoogenboom et al. |
| 2004/0191260 | A1 | 9/2004 | Reiter et al. |
| 2006/0034850 | A1 | 2/2006 | Weldanz et al. |
| 2007/0099253 | A1 | 5/2007 | Erkhov et al. |
| 2009/0226474 | A1 | 9/2009 | Weidanz et al. |
| 2009/0304679 | A1 | 12/2009 | Weidanz et al. |
| 2010/0120098 | A1 | 5/2010 | Grunenwald et al. |
| 2011/0003380 | A1 | 1/2011 | Miltenyi |
| 2013/0149337 | A1 | 6/2013 | Cooper et al. |
| 2013/0225417 | A1 | 8/2013 | Srinivasan et al. |
| 2013/0287748 | A1 | 10/2013 | June et al. |
| 2014/0121116 | A1 | 5/2014 | Richards et al. |
| 2014/0271635 | A1 | 9/2014 | Brogdon et al. |
| 2014/0294841 | A1 | 10/2014 | Scheinberg et al. |
| 2015/0134267 | A1 | 5/2015 | Patterson et al. |
| 2016/0060691 | A1 | 3/2016 | Gireso et al. |
| 2016/0140289 | A1 | 5/2016 | Gibiansky et al. |
| 2016/0371431 | A1 | 12/2016 | Haque et al. |
| 2016/0377631 | A1 | 12/2016 | Kuchroo et al. |
| 2017/0051035 | A1 | 2/2017 | Payne et al. |
| 2017/0211143 | A1 | 7/2017 | Shendure et al. |
| 2017/0357562 | A1 | 12/2017 | Rickard et al. |
| 2018/0258149 | A1* | 9/2018 | Motz ............. A61K 39/001119 |

FOREIGN PATENT DOCUMENTS

| | | | |
|---|---|---|---|
| WO | WO 1996/018105 | 6/1996 | |
| WO | WO 1999/018129 | 4/1999 | |
| WO | WO 1999/060120 | 11/1999 | |
| WO | WO 2000/014257 | 3/2000 | |
| WO | WO 2003/020763 | 3/2003 | |
| WO | WO 2003/068201 | 8/2003 | |
| WO | WO 2004/033685 | 4/2004 | |
| WO | WO 2006/000830 | 1/2006 | |
| WO | WO 2009/072003 | 6/2009 | |
| WO | WO 2010/033140 | 3/2010 | |
| WO | WO 2011/044186 | 4/2011 | |
| WO | WO 2012/129514 | 9/2012 | |
| WO | WO 2013/071154 | 5/2013 | |
| WO | WO 2013/123061 | 8/2013 | |
| WO | WO 2013/126726 | 8/2013 | |
| WO | WO 2013/135454 | 9/2013 | |
| WO | WO 2013/166321 | 11/2013 | |
| WO | WO 2014/031687 | 2/2014 | |
| WO | WO 2014/055668 | 4/2014 | |
| WO | WO 2014/189957 | 11/2014 | |
| WO | WO 2015/077717 | 5/2015 | |
| WO | WO 2015/102536 | 7/2015 | |
| WO | WO 2015/130968 | 9/2015 | |
| WO | WO 2015/159295 | 10/2015 | |
| WO | WO 2016/057705 | 4/2016 | |
| WO | WO 2016/061396 | 4/2016 | |
| WO | WO 2016/092070 | 6/2016 | |
| WO | WO-2017049166 A1 * | 3/2017 | ............. A61K 35/17 |
| WO | WO 2017/218908 | 12/2017 | |
| WO | WO 2018/204427 | 11/2018 | |

OTHER PUBLICATIONS

Crompton et al. Cellular and Molecular Immunology. 2016. 13:502-513. (Year: 2016).*

Ackermann et al., "Integration of ATAC-seq and RNA-seq identifies human alpha cell and beta cell signature genes." Mol Metab. Mar. 2016; 5(3): 233-244.

Aleksic, et al., "Beyond library size: a field guide to NGS normalization," BioRxiv (2014) doi: https://doi.org/10.1101/006403.

Anonymous, "ATAC-seq Data Standards and Prototype Processing Pipeline," available at https://www.encodeproject.org/atac-seq, Dec. 2017.

Appleby et al., "New Technologies for Ultra-High Throughput Genotyping in Plants," Methods Mol. Biol. 2009; 513:19-39.

Aran et al., "xCell: Digitally Portraying the Tissue Cellular Heterogeneity Landscape," Genome Biology (2017) 18:220.

Baum et al., "Retrovirus Vectors: Toward the Plentivirus?" Molecular Therapy, (2006) 13:1050-1063.

Best et al., "Transcriptional insights into the CD8+ T cell response to infection and memory T cell formation," Nature Immunology (2013) 14:404-412 and Supplemental data.

Bhat et al., "Stochastics of Cellular Differentiation Explained by Epigenetics: The Case of T-Cell Differentiation and Functional Plasticity." Scand J Immunol. Oct. 2017;86(4):184-195.

Bonyhadi, M. "Adoptive T cell Therapy: Delivering CAR, TCR and TIL from Research to Reality" Presentation at Cambridge Healthtech Institute's 5th Annual Immuno-Oncology Summit, Aug. 28-Sep. 1, 2017, Boston, MA; 35 pgs.

Brentjens et al., "CD19-targeted T cells rapidly induce molecular remissions in adults with chemotherapy-refractory acute lymphoblastic leukemia," Sci Transl Med. (2013) 5(177):177ra38.

Buenrostro et al., "ATAC-seq: A Method for Assaying Chromatin Accessibility Genome-Wide" Curr Protoc Mol Biol. 2015; 109: 21.29.1-21.29.9.

Buenrostro et al., "Single-cell chromatin accessibility reveals principles of regulatory variation." Nature. Jul. 2, 20153; 523(7561): 486-490.

Buenrostro et al., "Transposition of native chromatin for fast and sensitive epigenomic profiling of open chromatin, DNA-binding proteins and nucleosome position." Nat Methods. Dec. 2013;10(12):1213-8.

Bustos et al., "Genome-wide chromatin accessibility, DNA methylation and gene expression analysis of histone deacetylase inhibition in triple-negative breast cancer." Genom Data. Feb. 14, 2017;12:14-16.

Caruccuio, "Preparation of Next-Generation Sequencing Libraries Using Nextera™ Technology: Simultaneous DNA Fragmentation and Adaptor Tagging by In Vitro Transposition," Methods Mol. Biol. (2011) 733: 241-55.

Castiello et al., "Differential gene expression profile of first-generation and second-generation rapamycin-resistant allogeneic T cells," Cytotherapy 2013 15:598-609.

Cavaletti et al., "Chemotherapy-induced peripheral neurotoxicity," Nature Reviews Neurology (2010) 6, 657-666.

Chaussabel et al., "A Modular Analysis Framework for Blood Genomics Studies: Application to Systemic Lupus Erythematosus," (2008), Immunity 29(1): 150-164.

Chen et al., "ATAC-see reveals the accessible genome by transposase-mediated imaging and sequencing." Nat Methods. Dec. 2016; 13(12): 1013-1020.

Chervin et al., "Engineering higher affinity T cell receptors using a T cell display system," J Immunol Methods, (2008) 339(2):175-84.

Cheson et al., "Recommendations for initial evaluation, staging, and response assessment of Hodgkin and non-Hodgkin lymphoma: the Lugano classification," J Clin Oncol (2014) 20(27):3059-3068.

Cheson, "Staging and response assessment in lymphomas: the new Lugano classification," Chin Clin Oncol (2015) 4(1):5.

Cho et al. "Human mammalian cell sorting using a highly integrated microfabricated fluorescence-activated cell sorter (µFACS)," Lab Chip (2010) 10:1567-1573.

Chothia et al., "The outline structure of the T-cell alpha beta receptor," EMBO J. (1988) 7(12):3745-3755.

Chu et al., "Large-scale profiling of microRNAs for The Cancer Genome Atlas," Nucleic Acids Research, 2016, (44:1) e3 (9pgs).

Clackson, T. et al. "Making Antibody Fragments Using Phage Display Libraries," Nature (1991) 352:624-628.

(56) References Cited

OTHER PUBLICATIONS

Cohen et al., "Recognition of fresh human tumor by human peripheral blood lymphocytes transduced with a bicistronic retroviral vector encoding a murine anti-p53 TCR," J Immunol. (2005) 175:5799-5808.

Cohen et al., "Recombinant antibodies with MHC-restricted, peptide-specific, T-cell receptor-like specificity: new tools to study antigen presentation and TCR-peptide-MHC interactions," J Mol Recognit. (2003) 16(5):324-332.

Conesa et al., "A survey of best practices for RNA-seq data analysis," Genome Biology (2016) 17:13.

Corces et al., "An improved ATAC-seq protocol reduces background and enables interrogation of frozen tissues." Nat Methods. Oct. 2017; 14(10): 959-962.

Cusanovich et al., "Multiplex single-cell profiling of chromatin accessibility by combinatorial cellular indexing." Science. May 22, 2015;348(6237):910-4.

Davie et al., "Discovery of transcription factors and regulatory regions driving in vivo tumor development by ATAC-seq and FAIRE-seq open chromatin profiling." PLOS Genet. Feb. 13, 2015;11(2):e1004994.

Davila et al., "CD19 CAR-targeted T cells induce long-term remission and B Cell Aplasia in an immunocompetent mouse model of B cell acute lymphoblastic leukemia," PLoS One (2013) 8(4):e61338.

Davila et al., "Efficacy and toxicity management of 19-28z CAR T cell therapy in B cell acute lymphoblastic leukemia," Sci Transl Med (2014) 6:224ra25.

Denk et al., "Persistent Alterations in Microglial Enhancers in a Model of Chronic Pain," Cell Reports 2016 15:1771-1781.

Denny et al., "Nfib Promotes Metastasis through a Widespread Increase in Chromatin Accessibility." Cell. Jul. 14, 2016;166(2):328-342.

Dirks et al., "Genome-wide epigenomic profiling for biomarker discovery." Clin Epigenetics. Nov. 21, 2016;8:122.

Eisenhauer, E.A. et al. (2009) "New response evaluation criteria in solid tumors: Revised RECIST guideline (version 1.1)." Eur. J. Cancer 45: 228-247.

Fedorov et al., "PD-1- and CTLA-4-based inhibitory chimeric antigen receptors (iCARs) divert off-target immunotherapy responses," Sci Transl Med. (2013) 5(215):215ra172.

Feng et al., "Position effects are influenced by the orientation of a transgene with respect to flanking chromatin." Mol Cell Biol. Jan. 2001;21(1):298-309.

Fox et al., Applications of Ultra-high-Throughput Sequencing, Methods Mol Biol. (2009);553:79-108.

Frecha et al., "Advances in the field of lentivector-based transduction of T and B lymphocytes for gene therapy," Molecular Therapy: The Journal of the American Society of Gene Therapy (2010) 18:1748-1757.

Gensterblum et al., "CD4+CD28+KIR+CD11ahi T cells correlate with disease activity and are characterized by a pro-inflammatory epigenetic and transcriptional profile in lupus patients." J Autoimmun. Jan. 2018;86:19-28.

Godin et al., "Microfluidics and photonics for Bio-System-on-a-Chip: a review of advancements in technology towards a microfluidic flow cytometry chip," J Biophotonics (2008) 1(5):355-376.

Grupp et al., "Chimeric antigen receptor-modified T cells for acute lymphoid leukemia," N. Engl. J. Med. (2013) 368:1509-1518.

Hackett et al., "A transposon and transposase system for human application," Molecular Therapy: The Journal of the American Society of Gene Therapy (2010) 18:674-683.

Hallek, M. et al. "Guidelines for the Diagnosis and Treatment of Chronic Lymphocytic Leukemia: A Report From the International Workshop on Chronic Lymphocytic Leukemia Updating the National Cancer Institute-Working Group 1996 Guidelines," Blood (2008) 111:(12):5446-5456 and Errata, Blood, (Dec. 15, 2008). 112(13) 5259.

Henning et al., "Epigenetic control of CD8+ T cell differentiation." Nat Rev Immunol. May 2018;18(5):340-356.

Hermans et al., "The VITAL assay: a versatile fluorometric technique for assessing CTL- and NKT-mediated cytotoxicity against multiple targets in vitro and in vivo," J. Immunological Methods (2004) 285(1): 25-40.

Holler et al., "In vitro evolution of a T cell receptor with high affinity for peptide/MHC," Proc Natl Acad Sci USA, (2000) 97(10):5387-92.

Holler et al., "TCRs with high affinity for foreign pMHC show self-reactivity," Nat Immunol (2003) 4(1):55-62.

Hudecek et al., "Receptor affinity and extracellular domain modifications affect tumor recognition by ROR1-specific chimeric antigen receptor T cells," Clin Cancer Res. Jun. 15, 2013;19(12):3153-3164.

Hudecek et al., "The nonsignaling extracellular spacer domain of chimeric antigen receptors is decisive for in vivo antitumor activity," Cancer Immunol Res (2015) 3(2):125-135.

Imelfort et al., "De novo sequencing of plant genomes using second-generation technologies," Brief Bioinform. 2009 10:609-18.

Janeway et al., Immunobiology: The Immune System in Health and Disease, 3rd ED., Current Biology Publications (1997), p. 4:33.

Johnson et al., "Imaging for Staging and Response Assessment in Lymphoma," Radiology (2015) 276(2):323-338.

Jores et al., "Resolution of hypervariable regions in T-cell receptor beta chains by a modified Wu-Kabat index of amino acid diversity.," PNAS (1990) 87(23):9138-9142.

Juno Corporate Presentation. Retrieved on http://ir.junotherapeutics.com. Retrieved on Jan. 2018.

Juno Corporate Presentation. Retrieved on http://ir.junotherapeutics.com. Retrieved on Sep. 2017.

Kaper et al., "Whole-genome haplotyping by dilution, amplification, and sequencing," Proc. Natl. Acad. Sci. (2013) 110:5552-7.

Kent W. J., "BLAT—The BLAST-Like Alignment Tool," Genome Research 4: 656-664 (2002).

Klebanoff et al., "Sorting through subsets: Which T cell populations mediate highly effective adoptive immunotherapy?," J Immunother. (2012) 35(9): 651-660.

Kochenderfer et al., "B cell depletion and remissions of malignancy along with cytokine associated toxicity in a clinical trial of anti-CD 19 chimeric-antigen receptor-transduced T cells," Blood (2012) 119(12):2709-2720.

Kochenderfer et al., "Construction and preclinical evaluation of an anti-CD19 chimeric antigen receptor," J. Immunotherapy (2009) 32(7): 689-702.

Kochenderfer et al., "Treating B-cell cancer with T cells expressing anti-CD19 chimeric antigen receptors," Nature Reviews Clinical Oncology (2013) 10, 267-276.

Koh et al., "Rapid chromatin repression by Aire provides precise control of immune tolerance." Nat Immunol. Feb. 2018;19(2):162-172.

Kotb, "Bacterial pyrogenic exotoxins as superantigens," Clinical Microbiology Reviews, (1995) 8:411-426.

Kumasaka et al., "Fine-mapping cellular QTLs with RASQUAL and ATAC-seq," Nat Genet. Feb. 2016 ; 48(2): 206-213.

Kurucz et al., "A bacterially expressed single-chain Fv construct from the 2B4 T-cell receptor," PNAS (1993) 90(9):3830-3834.

Langmead et al., "Ultrafast and memory-efficient alignment of short DNA sequences to the human genome," Genome Biology (2009) 10(3):R25.1-R25.10.

Larkin et al., "Clustal W and Clustal X version 2.0," Bioinformatics, (2007) 23:2947-2948.

Lee et al., "Current concepts in the diagnosis and management of cytokine release syndrome," Blood. (2014) 124(2):188-95.

Lefranc et al., "IMGT unique numbering for immunoglobulin and T cell receptor variable domains and Ig superfamily V-like domains," Dev Comp Immunol (2003) 27(1):55-77.

Ll et al., "Directed evolution of human T-cell receptors with picomolar affinities by phage display," Nat Biotechnol. (2005) 23:349-354.

Li et al., "The Sequence Alignment/Map format and SAMtools," Bioinformatics, 2009, 25(16):2078-9.

Ling et al., "B-cell and plasma cell antigens: new and previously defined clusters," Leucocyte typing 111. (1987) 302-355.

(56) References Cited

OTHER PUBLICATIONS

Lipman et al., "Rapid and sensitive protein similarity searches," Science (1985) 227(4693):1435-41.
Margulies, M. et al. (Sep. 15, 2005, e-pub. Jul. 31, 2005). "Genome Sequencing in Open Microfabricated High Density Picoliter Reactors," Nature 437(7057):376-380.
Marine et al, Evaluation of a Transposase Protocol for Rapid Generation of Shotgun High-Throughput Sequencing Libraries from Nanogram Quantities of DNA, Appl. Environ. Microbiol. (2011) 77:8071-9.
Martinez et al., "The Transcription Factor NFAT Promotes Exhaustion of Activated CD8+ T Cells," Immunity (2015) 42(2):265-278.
Milani et al., "Cell freezing protocol suitable for ATAC-Seq on motor neurons derived from human induced pluripotent stem cells." Sci Rep. May 5, 2016;6:25474.
Miskimen et al., "Assay for Transposase-Accessible Chromatin Using Sequencing (ATAC-seq) Data Analysis." Curr Protoc Hum Genet. Jan. 11, 2017;92:20.4.1-20.4.13.
Mognol et al., "Exhaustion-associated regulatory regions in CD8+ tumor-infiltrating T cells." Proc Natl Acad Sci U S A. Mar. 28, 2017;114(13):E2776-E2785.
Morozova et al., "Applications of next-generation sequencing technologies in functional genomics," Genomics. 2008 92:255-64.
Moskowitz et al., "Epigenomics of human CD8 T cell differentiation and aging." Sci Immunol. Feb. 2017;2(8). pii: eaag0192.
Ning et al. "SSAHA: A Fast Search Method for Large DNA Databases," Genome Research (2001) 11:1725-1729.
Novosiadly et al., "High-content molecular profiling of T-cell therapy in oncology," Oncolytics (2016) 3, 16009.
Parkhurst et al., "Characterization of genetically modified T-cell receptors that recognize the CEA:691-699 peptide in the context of HLA-A2.1 on human colorectal cancer cells," Clin Cancer Res. (2009) 15:169-180.
Pauken et al., "Epigenetic stability of exhausted T cells limits durability of reinvigoration by PD-1 blockade." Science. Dec. 2, 2016;354(6316):1160-1165.
Pearson et al. "Improved Tools For Biological Sequence Comparison," Proc. Natl. Acad. Sci. USA (1988) 85(8):2444-2448.
Philiip et al., "Chromatin states define tumour-specific T cell dysfunction and reprogramming." Nature. May 25, 2017;545(7655):452-456.
Portolano et al., "Lack of Promiscuity in Autoantigen-Specific H and L Chain Combinations as Revealed by Human H And L Chain 'Roulette'," The Journal of Immunology (1993) 150(3):880-887.
Qu et al., "Chromatin Accessibility Landscape of Cutaneous T Cell Lymphoma and Dynamic Response to HDAC Inhibitors." Cancer Cell. Jul. 10, 2017;32(1):27-41.e4.
Qu et al., "Individuality and Variation of Personal Regulomes in Primary Human T Cells," Cell Syst. Jul. 29, 2015; 1(1): 51-61.
Raj et al., "msCentipede: Modeling Heterogeneity across Genomic Sites and Replicates Improves Accuracy in the Inference of Transcription Factor Binding" PLoS One Sep. 2015;10(9): e0138030.
Ren et al., "Intra-subject variability in human bone marrow stromal cell (BMSC) replicative senescence: molecular changes associated with BMSC senescence," Stem Cell Res. Nov. 2013;11(3):1060-73.
Rendeiro et al., "Chromatin accessibility maps of chronic lymphocytic leukaemia identify subtype-specific epigenome signatures and transcription regulatory networks." Nat Commun. Jun. 27, 2016;7:11938.
Robinson et al., "A scaling normalization method for differential expression analysis of RNA-seq data," Genome Biology (2010) 11:R25.
Ronaghi et al., "Real-Time DNA Sequencing Using Detection of Pyrophosphate Release," Analytical Biochemistry 1996 242: 84-9.
Rosenberg, et al., "Cell transfer immunotherapy for metastatic solid cancer—what clinicians need to know," Nat Rev Clin Oncol. (2011) 8(10):577-85.
Sadelain et al., "The basic principles of chimeric antigen receptor design," Cancer Discov. (2013) 3(4): 388-398.
Savic et al., "Mapping genome-wide transcription factor binding sites in frozen tissues," Epigenetics & Chromatin, 2013 6:30.
Scharer et al., "ATAC-seq on biobanked specimens defines a unique chromatin accessibility structure in naïve SLE B cells." Scientific Reports 2016; 6:27030.
Schep et al., "Structured nucleosome fingerprints enable high-resolution mapping of chromatin architecture within regulatory regions." Genome Res. Nov. 2015;25(11):1757-70.
Schlueter et al., "Specificity and Binding Properties of a Single-chain T Cell Receptor," J. Mol. Biol. (1996) 256: 859.
Schuler et al. "SYFPEITHI, Database for Searching and T-Cell Epitope Prediction. in Immunoinformatics," Methods in Molecular Biology, (2007) vol. 409(1): 75-93, 2007.
Schumann et al., "Generation of knock-in primary human T cells using Cas9 ribonucleoproteins." Proc Natl Acad Sci U S A. Aug. 18, 2015;112(33):10437-42.
Scott-Browne et al., "Dynamic changes in chromatin accessibility in CD8+ T cells responding to viral infection." Immunity. Dec. 20, 2016; 45(6): 1327-1340.
Sen et al., "The epigenetic landscape of T cell exhaustion." Science. Dec. 2, 2016;354(6316):1165-1169.
Shendure et al., "Accurate Multiplex Polony Sequencing of an Evolved Bacterial Genome," Science 2005 309: 1728-32.
Sievers et al., Fast, scalable generation of high-quality protein multiple sequence alignments using Clustal Omega, Mol Syst Biol 7, article 539 (2011).
Singh et al., "ProPred: prediction of HLA-DR binding," Bioinformatics (2001) 17(12):1236-1237.
Slater et al., Automated generation of heuristics for biological sequence comparison, BMC Bioinformatics (2005) 6:31.
Soo Hoo et al. Characterization of a single-chain T-cell receptor expressed in *Escherichia coli*, PNAS (USA) 89, 4759-4763 (1992).
Steinhauser et al., "A comprehensive comparison of tools for differential ChIP-seq analysis," Briefings in Bioinformatics, 17(6), 2016, 953-966.
Sung et al., "Genome-wide footprinting: ready for prime time?" Nat Methods. (2016) 13(3): 222-228.
Terakura et al., "Generation of CD19-chimeric antigen receptor modified CD8+ T cells derived from virus-specific central memory T cells," Blood. (2012) 119(1):72-82.
Themeli et al., "Generation of tumor-targeted human T lymphocytes from induced pluripotent stem cells for cancer therapy," Nat Biotechnol. (2013) 31(10): 928-933.
Tsukahara et al., "CD19 target-engineered T-cells accumulate at tumor lesions in human B-cell lymphoma xenograft mouse models," Biochem Biophys Res Commun (2013) 438(1): 84-89.
Turtle et al., "Engineered T cells for anti-cancer therapy," Curr. Opin. Immunol. (2012) 24(5): 633-639.
Ucar et al., "The chromatin accessibility signature of human immune aging stems from CD8+ T cells." J Exp Med. Oct. 2, 2017;214(10):3123-3144.
Van Rensburg et al., "Chromatin structure of two genomic sites for targeted transgene integration in induced pluripotent stem cells and hematopoietic stem cells." Gene Ther. Feb. 2013;20(2):201-14.
Varela-Rohena et al., "Control of HIV-1 immune escape by CD8 T cells expressing enhanced T-cell receptor," Nat Med. (2008) 14:1390-1395.
Wadhwa et al., "Receptor mediated glycotargeting," J. Drug Targeting (1995) 3(2):111-127.
Wang et al., "Phenotypic and Functional Attributes of Lentivirus Modified CD19-specific Human CD8+ Central Memory T Cells Manufactured at Clinical Scale," J Immunother. (2012) 35(9):689-701.
Weng et al., "The molecular basis of the memory T cell response: differential gene expression and its epigenetic regulation," Nat Rev Immunol. (2012) 12(4):306-15.
Wu et al., "Adoptive T-cell therapy using autologous tumor-infiltrating lymphocytes for metastatic melanoma: current status and future outlook," Cancer (2012) 18(2): 160-175.
Wulfing et al., :Correctly Folded T-cell Receptor Fragments in the Periplasm of *Escherichia coli*, J. Mol. Biol. 242, 655 (1994).
Xu et al., "Cytokine release syndrome in cancer immunotherapy with chimeric antigen receptor engineered T cells," Cancer Letters (2014) 343:172-78.

(56) References Cited

OTHER PUBLICATIONS

Yadon et al., "Chromatin Remodeling around Nucleosome-Free Regions Leads to Repression of Noncoding RNA Transcription," Mol. Cell. Biol. (2010) 30(21):5110-5122.

Yu et al., "Epigenetic landscapes reveal transcription factors that regulate CD8+ T cell differentiation." Nat Immunol. May 2017;18(5):573-582.

Zhang et al., "Epigenetic manipulation restores functions of defective $CD8^+$ T cells from chronic viral infection." Mol Ther. Sep. 2014;22(9):1698-706.

* cited by examiner

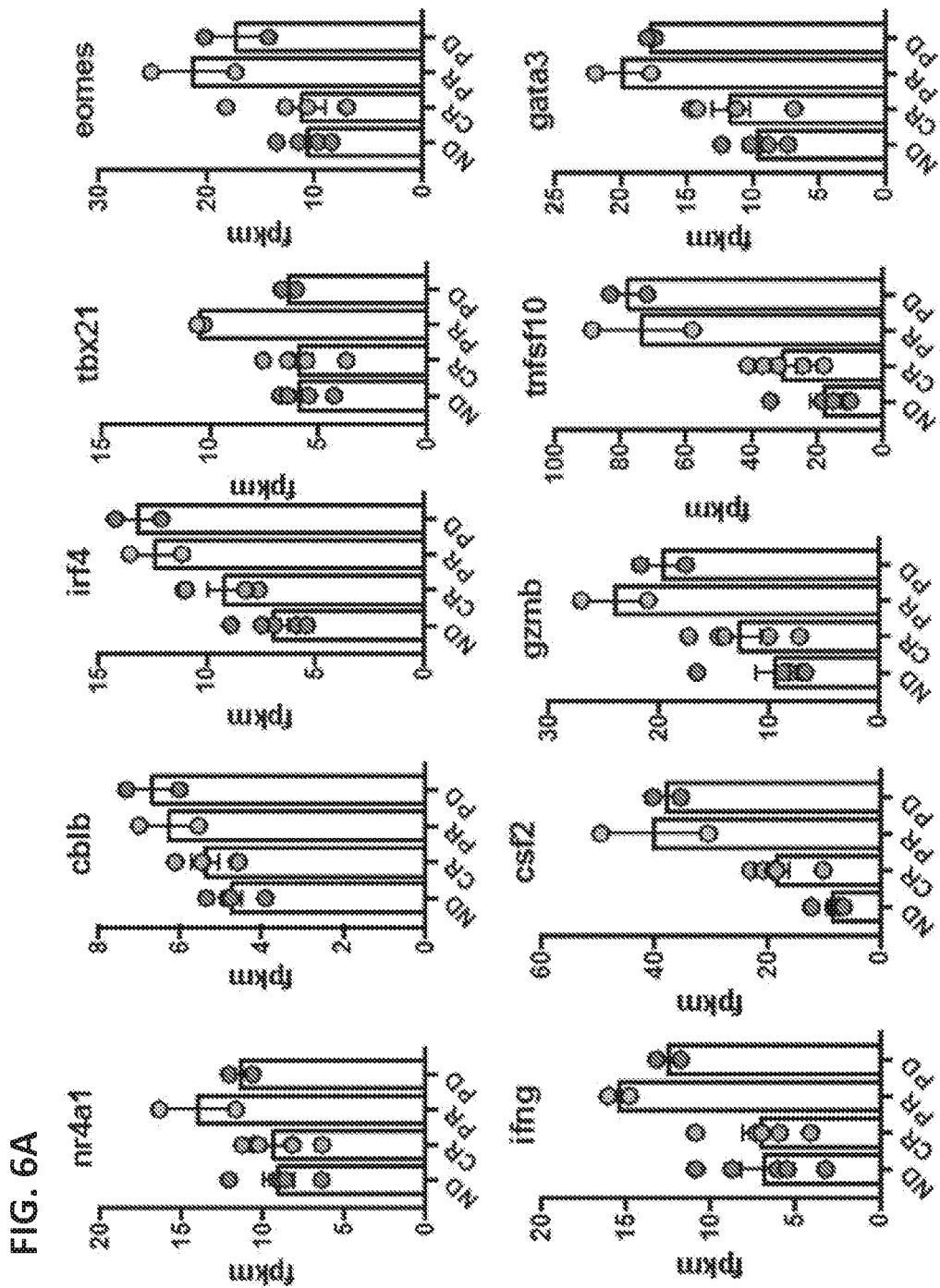

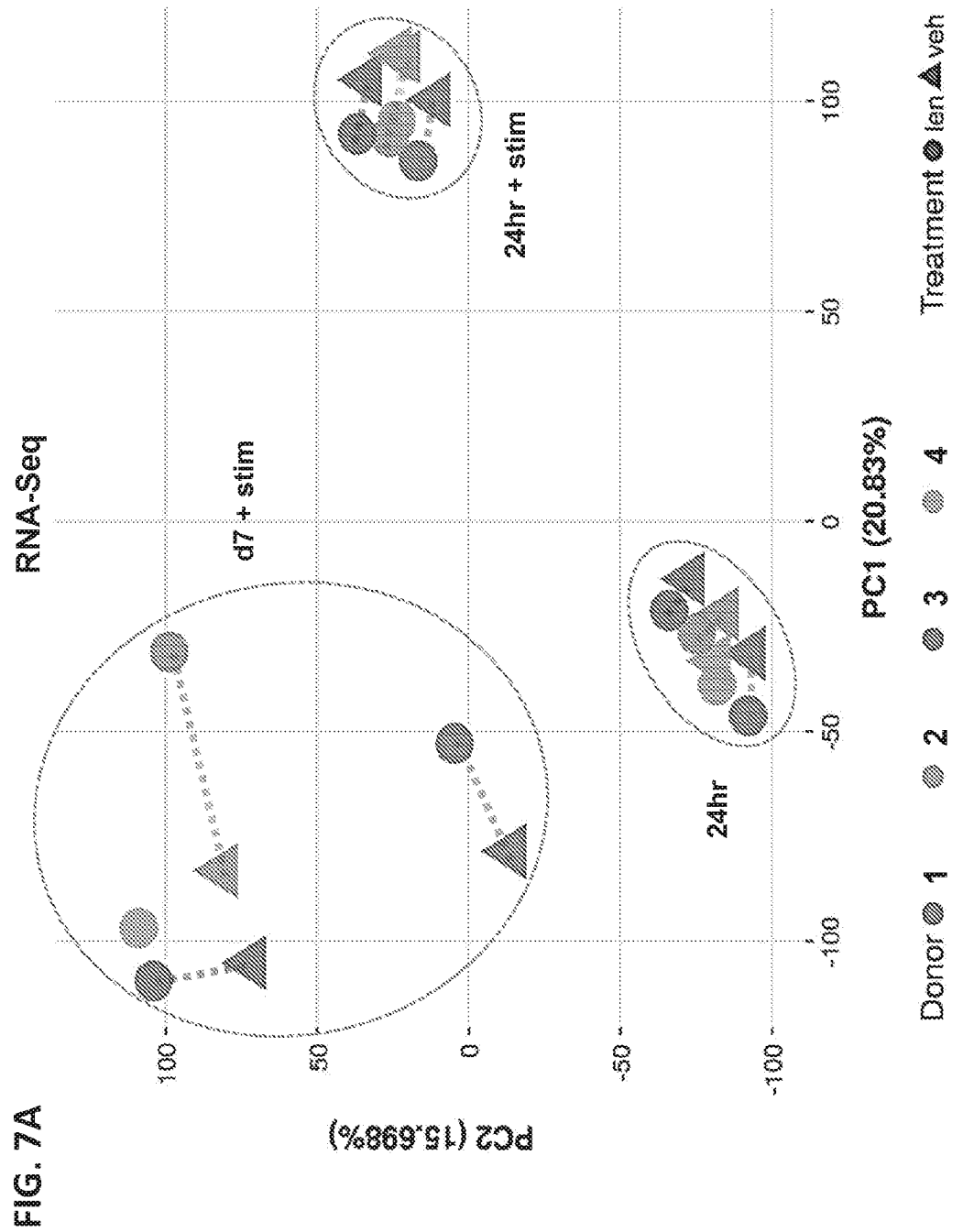

FIG. 11

| Motif Name | Motif | Log P-value | % of Target Sequences with Motif |
|---|---|---|---|
| Atf3(bZIP)/GBM-ATF3 | ATGASTCA | -7.66E+01 | 61.90% |
| BATF(bZIP)/Th17-BATF | ATGASTCA | -7.54E+01 | 61.56% |
| Fra1(bZIP)/BT549-Fra1 | ATGASTCA | -7.39E+01 | 58.50% |
| AP-1(bZIP)/ThioMac-PU.1 | ATGASTCA | -7.33E+01 | 62.24% |
| JunB(bZIP)/DendriticCells-Junb | ATGASTCA | -7.17E+01 | 58.16% |
| Fosl2(bZIP)/3T3L1-Fosl2 | ATGASTCA | -6.18E+01 | 46.94% |
| Jun-AP1(bZIP)/K562-cJun | ATGASTCA | -5.14E+01 | 39.12% |
| Smad3(MAD)/NPC-Smad3 | TGTCT | -4.50E+01 | 56.46% |
| NFkB-p65(RHD)/GM12787-p65 | GGGATTTCC | -4.41E+01 | 29.59% |
| RUNX1(Runt)/Jurkat-RUNX1 | AACCACA | -4.04E+01 | 50.00% |
| RUNX(Runt)/HPC7-Runx1 | AACCACA | -3.77E+01 | 41.16% |
| Bach2(bZIP)/OCILy7-Bach2 | TGCTGASTCA | -3.62E+01 | 26.53% |

FIG. 12A CDP

FIG. 12B CMAT

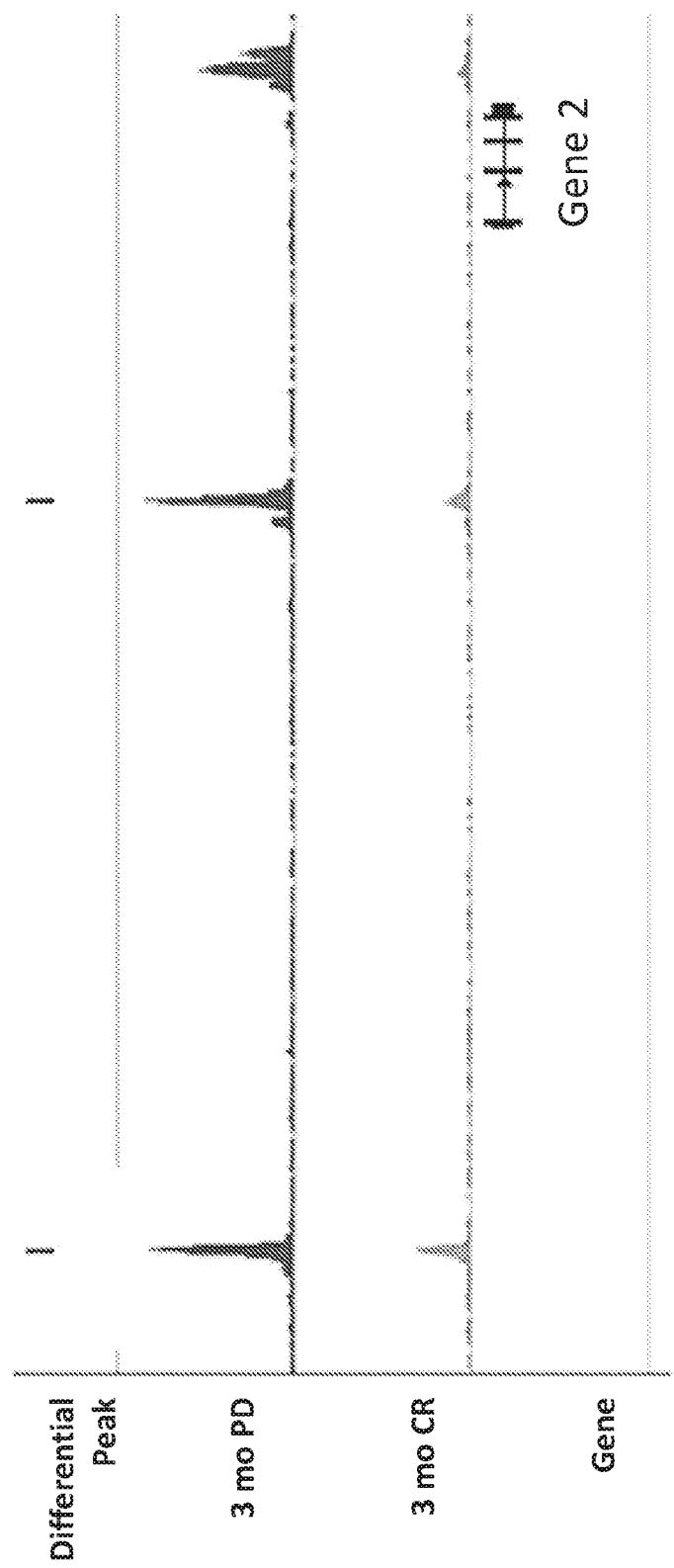

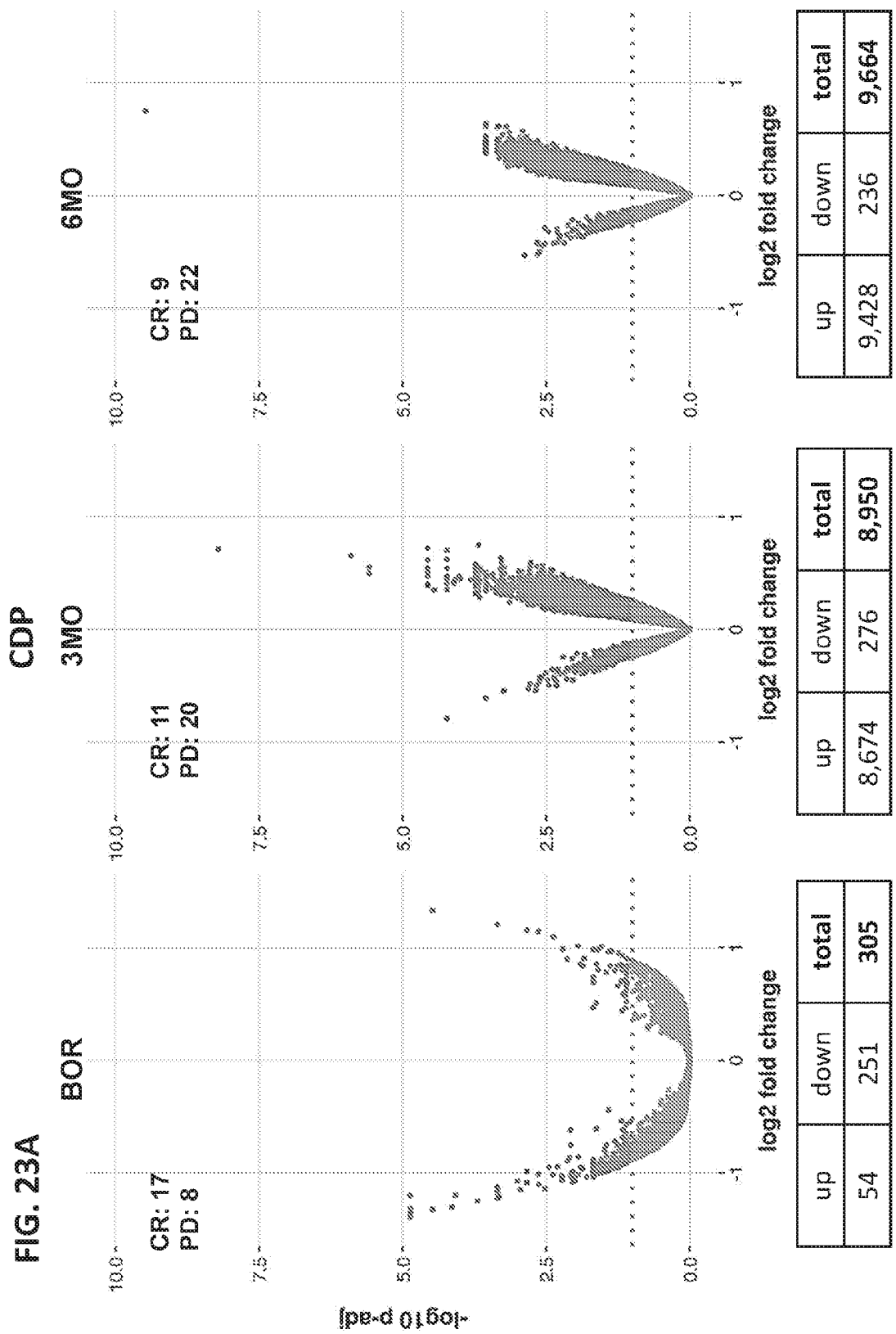

SEQUENCE LISTING

<160> NUMBER OF SEQ ID NOS: 59

<210> SEQ ID NO 1
<211> LENGTH: 12
<212> TYPE: PRT
<213> ORGANISM: Homo sapiens
<220> FEATURE:
<223> OTHER INFORMATION: Spacer (IgG4hinge)

<400> SEQUENCE: 1

Glu Ser Lys Tyr Gly Pro Pro Cys Pro Pro Cys Pro
1               5                   10

<210> SEQ ID NO 2
<211> LENGTH: 36
<212> TYPE: DNA
<213> ORGANISM: Homo sapiens
<220> FEATURE:
<223> OTHER INFORMATION: Spacer (IgG4hinge)

<400> SEQUENCE: 2
gaatctaagt acggaccgcc ctgcccccct tgccct                         36

<210> SEQ ID NO 3
<211> LENGTH: 119
<212> TYPE: PRT
<213> ORGANISM: Homo sapiens
<220> FEATURE:
<223> OTHER INFORMATION: Hinge-CH3 spacer

<400> SEQUENCE: 3

Glu Ser Lys Tyr Gly Pro Pro Cys Pro Pro Cys Pro Gly Gln Pro Arg
1               5                   10                  15

Glu Pro Gln Val Tyr Thr Leu Pro Pro Ser Gln Glu Glu Met Thr Lys
            20                  25                  30

Asn Gln Val Ser Leu Thr Cys Leu Val Lys Gly Phe Tyr Pro Ser Asp
        35                  40                  45

Ile Ala Val Glu Trp Glu Ser Asn Gly Gln Pro Glu Asn Asn Tyr Lys
    50                  55                  60

Thr Thr Pro Pro Val Leu Asp Ser Asp Gly Ser Phe Phe Leu Tyr Ser
65                  70                  75                  80

```
Arg Leu Thr Val Asp Lys Ser Arg Trp Gln Glu Gly Asn Val Phe Ser
                85                  90                  95

Cys Ser Val Met His Glu Ala Leu His Asn His Tyr Thr Gln Lys Ser
            100                 105                 110

Leu Ser Leu Ser Leu Gly Lys
        115
```

<210> SEQ ID NO 4
<211> LENGTH: 229
<212> TYPE: PRT
<213> ORGANISM: Homo sapiens
<220> FEATURE:
<223> OTHER INFORMATION: Hinge-CH2-CH3 spacer

<400> SEQUENCE: 4

```
Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225
```

<210> SEQ ID NO 5
<211> LENGTH: 282
<212> TYPE: PRT
<213> ORGANISM: Homo sapiens
<220> FEATURE:
<223> OTHER INFORMATION: IgD-hinge-Fc

<400> SEQUENCE: 5

```
Arg Trp Pro Glu Ser Pro Lys Ala Gln Ala Ser Ser Val Pro Thr Ala
1               5                   10                  15

Gln Pro Gln Ala Glu Gly Ser Leu Ala Lys Ala Thr Thr Ala Pro Ala
            20                  25                  30
```

-continued

```
Thr Thr Arg Asn Thr Gly Arg Gly Gly Glu Lys Lys Lys Glu Lys
         35                  40                  45
Glu Lys Glu Glu Gln Glu Gly Arg Glu Thr Lys Thr Pro Glu Cys Pro
     50                  55                  60
Ser His Thr Gln Pro Leu Gly Val Tyr Leu Leu Thr Pro Ala Val Gln
 65                  70                  75                  80
Asp Leu Trp Leu Arg Asp Lys Ala Thr Phe Thr Cys Phe Val Val Gly
                 85                  90                  95
Ser Asp Leu Lys Asp Ala His Leu Thr Trp Glu Val Ala Gly Lys Val
            100                 105                 110
Pro Thr Gly Gly Val Glu Glu Gly Leu Leu Glu Arg His Ser Asn Gly
        115                 120                 125
Ser Gln Ser Gln His Ser Arg Leu Thr Leu Pro Arg Ser Leu Trp Asn
    130                 135                 140
Ala Gly Thr Ser Val Thr Cys Thr Leu Asn His Pro Ser Leu Pro Pro
145                 150                 155                 160
Gln Arg Leu Met Ala Leu Arg Glu Pro Ala Ala Gln Ala Pro Val Lys
                165                 170                 175
Leu Ser Leu Asn Leu Leu Ala Ser Ser Asp Pro Pro Glu Ala Ala Ser
            180                 185                 190
Trp Leu Leu Cys Glu Val Ser Gly Phe Ser Pro Pro Asn Ile Leu Leu
        195                 200                 205
Met Trp Leu Glu Asp Gln Arg Glu Val Asn Thr Ser Gly Phe Ala Pro
    210                 215                 220
Ala Arg Pro Pro Pro Gln Pro Gly Ser Thr Thr Phe Trp Ala Trp Ser
225                 230                 235                 240
Val Leu Arg Val Pro Ala Pro Pro Ser Pro Gln Pro Ala Thr Tyr Thr
                245                 250                 255
Cys Val Val Ser His Glu Asp Ser Arg Thr Leu Leu Asn Ala Ser Arg
            260                 265                 270
Ser Leu Glu Val Ser Tyr Val Thr Asp His
        275                 280

<210> SEQ ID NO 6
<211> LENGTH: 24
<212> TYPE: PRT
<213> ORGANISM: Artificial Sequence
<220> FEATURE:
<223> OTHER INFORMATION: T2A

<400> SEQUENCE: 6

Leu Glu Gly Gly Gly Glu Gly Arg Gly Ser Leu Leu Thr Cys Gly Asp
 1               5                  10                  15
Val Glu Glu Asn Pro Gly Pro Arg
             20

<210> SEQ ID NO 7
<211> LENGTH: 357
<212> TYPE: PRT
<213> ORGANISM: Artificial Sequence
<220> FEATURE:
<223> OTHER INFORMATION: tEGFR

<400> SEQUENCE: 7

Met Leu Leu Leu Val Thr Ser Leu Leu Leu Cys Glu Leu Pro His Pro
 1               5                  10                  15
Ala Phe Leu Leu Ile Pro Arg Lys Val Cys Asn Gly Ile Gly Ile Gly
```

```
            20                  25                  30
Glu Phe Lys Asp Ser Leu Ser Ile Asn Ala Thr Asn Ile Lys His Phe
         35                  40                  45

Lys Asn Cys Thr Ser Ile Ser Gly Asp Leu His Ile Leu Pro Val Ala
 50                  55                  60

Phe Arg Gly Asp Ser Phe Thr His Thr Pro Pro Leu Asp Pro Gln Glu
 65                  70                  75                  80

Leu Asp Ile Leu Lys Thr Val Lys Glu Ile Thr Gly Phe Leu Leu Ile
                 85                  90                  95

Gln Ala Trp Pro Glu Asn Arg Thr Asp Leu His Ala Phe Glu Asn Leu
            100                 105                 110

Glu Ile Ile Arg Gly Arg Thr Lys Gln His Gly Gln Phe Ser Leu Ala
            115                 120                 125

Val Val Ser Leu Asn Ile Thr Ser Leu Gly Leu Arg Ser Leu Lys Glu
            130                 135                 140

Ile Ser Asp Gly Asp Val Ile Ile Ser Gly Asn Lys Asn Leu Cys Tyr
145                 150                 155                 160

Ala Asn Thr Ile Asn Trp Lys Lys Leu Phe Gly Thr Ser Gly Gln Lys
                165                 170                 175

Thr Lys Ile Ile Ser Asn Arg Gly Glu Asn Ser Cys Lys Ala Thr Gly
            180                 185                 190

Gln Val Cys His Ala Leu Cys Ser Pro Glu Gly Cys Trp Gly Pro Glu
            195                 200                 205

Pro Arg Asp Cys Val Ser Cys Arg Asn Val Ser Arg Gly Arg Glu Cys
            210                 215                 220

Val Asp Lys Cys Asn Leu Leu Glu Gly Glu Pro Arg Glu Phe Val Glu
225                 230                 235                 240

Asn Ser Glu Cys Ile Gln Cys His Pro Glu Cys Leu Pro Gln Ala Met
                245                 250                 255

Asn Ile Thr Cys Thr Gly Arg Gly Pro Asp Asn Cys Ile Gln Cys Ala
            260                 265                 270

His Tyr Ile Asp Gly Pro His Cys Val Lys Thr Cys Pro Ala Gly Val
            275                 280                 285

Met Gly Glu Asn Asn Thr Leu Val Trp Lys Tyr Ala Asp Ala Gly His
            290                 295                 300

Val Cys His Leu Cys His Pro Asn Cys Thr Tyr Gly Cys Thr Gly Pro
305                 310                 315                 320

Gly Leu Glu Gly Cys Pro Thr Asn Gly Pro Lys Ile Pro Ser Ile Ala
            325                 330                 335

Thr Gly Met Val Gly Ala Leu Leu Leu Leu Val Val Ala Leu Gly
            340                 345                 350

Ile Gly Leu Phe Met
            355
```

<210> SEQ ID NO 8
<211> LENGTH: 27
<212> TYPE: PRT
<213> ORGANISM: Homo sapiens
<220> FEATURE:
<223> OTHER INFORMATION: CD28
<300> PUBLICATION INFORMATION:
<308> DATABASE ACCESSION NUMBER: UniProt P10747
<309> DATABASE ENTRY DATE: 1989-07-01

<400> SEQUENCE: 8

Phe Trp Val Leu Val Val Val Gly Gly Val Leu Ala Cys Tyr Ser Leu

```
                1               5                  10                 15
Leu Val Thr Val Ala Phe Ile Ile Phe Trp Val
                20                  25
```

<210> SEQ ID NO 9
<211> LENGTH: 66
<212> TYPE: PRT
<213> ORGANISM: Homo sapiens
<220> FEATURE:
<223> OTHER INFORMATION: CD28
<300> PUBLICATION INFORMATION:
<308> DATABASE ACCESSION NUMBER: UniProt P10747
<309> DATABASE ENTRY DATE: 1989-07-01

<400> SEQUENCE: 9

```
Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
                20                  25                  30

Phe Pro Gly Pro Ser Lys Pro Phe Trp Val Leu Val Val Val Gly Gly
            35                  40                  45

Val Leu Ala Cys Tyr Ser Leu Leu Val Thr Val Ala Phe Ile Ile Phe
        50                  55                  60

Trp Val
65
```

<210> SEQ ID NO 10
<211> LENGTH: 41
<212> TYPE: PRT
<213> ORGANISM: Homo sapiens
<220> FEATURE:
<223> OTHER INFORMATION: CD28
<300> PUBLICATION INFORMATION:
<308> DATABASE ACCESSION NUMBER: UniProt P10747
<309> DATABASE ENTRY DATE: 1989-07-01

<400> SEQUENCE: 10

```
Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
                20                  25                  30

Pro Arg Asp Phe Ala Ala Tyr Arg Ser
            35                  40
```

<210> SEQ ID NO 11
<211> LENGTH: 41
<212> TYPE: PRT
<213> ORGANISM: Homo sapiens
<220> FEATURE:
<223> OTHER INFORMATION: CD28

<400> SEQUENCE: 11

```
Arg Ser Lys Arg Ser Arg Gly Gly His Ser Asp Tyr Met Asn Met Thr
1               5                   10                  15

Pro Arg Arg Pro Gly Pro Thr Arg Lys His Tyr Gln Pro Tyr Ala Pro
                20                  25                  30

Pro Arg Asp Phe Ala Ala Tyr Arg Ser
            35                  40
```

<210> SEQ ID NO 12
<211> LENGTH: 42
<212> TYPE: PRT
<213> ORGANISM: Homo sapiens

```
<220> FEATURE:
<223> OTHER INFORMATION: 4-1BB
<300> PUBLICATION INFORMATION:
<308> DATABASE ACCESSION NUMBER: UniProt Q07011.1
<309> DATABASE ENTRY DATE: 1995-02-01

<400> SEQUENCE: 12

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 13
<211> LENGTH: 112
<212> TYPE: PRT
<213> ORGANISM: Homo sapiens
<220> FEATURE:
<223> OTHER INFORMATION: CD3 zeta

<400> SEQUENCE: 13

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 14
<211> LENGTH: 112
<212> TYPE: PRT
<213> ORGANISM: Homo sapiens
<220> FEATURE:
<223> OTHER INFORMATION: CD3 zeta

<400> SEQUENCE: 14

Arg Val Lys Phe Ser Arg Ser Ala Glu Pro Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

```
<210> SEQ ID NO 15
<211> LENGTH: 112
<212> TYPE: PRT
<213> ORGANISM: Homo sapiens
<220> FEATURE:
<223> OTHER INFORMATION: CD3 zeta

<400> SEQUENCE: 15

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 16
<211> LENGTH: 335
<212> TYPE: PRT
<213> ORGANISM: Artificial Sequence
<220> FEATURE:
<223> OTHER INFORMATION: tEGFR

<400> SEQUENCE: 16

Arg Lys Val Cys Asn Gly Ile Gly Ile Gly Glu Phe Lys Asp Ser Leu
1               5                   10                  15

Ser Ile Asn Ala Thr Asn Ile Lys His Phe Lys Asn Cys Thr Ser Ile
            20                  25                  30

Ser Gly Asp Leu His Ile Leu Pro Val Ala Phe Arg Gly Asp Ser Phe
        35                  40                  45

Thr His Thr Pro Pro Leu Asp Pro Gln Glu Leu Asp Ile Leu Lys Thr
    50                  55                  60

Val Lys Glu Ile Thr Gly Phe Leu Leu Ile Gln Ala Trp Pro Glu Asn
65                  70                  75                  80

Arg Thr Asp Leu His Ala Phe Glu Asn Leu Glu Ile Ile Arg Gly Arg
                85                  90                  95

Thr Lys Gln His Gly Gln Phe Ser Leu Ala Val Val Ser Leu Asn Ile
            100                 105                 110

Thr Ser Leu Gly Leu Arg Ser Leu Lys Glu Ile Ser Asp Gly Asp Val
        115                 120                 125

Ile Ile Ser Gly Asn Lys Asn Leu Cys Tyr Ala Asn Thr Ile Asn Trp
    130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys His Ala Leu
                165                 170                 175

Cys Ser Pro Glu Gly Cys Trp Gly Pro Glu Pro Arg Asp Cys Val Ser
            180                 185                 190

Cys Arg Asn Val Ser Arg Gly Arg Glu Cys Val Asp Lys Cys Asn Leu
        195                 200                 205
```

```
Leu Glu Gly Glu Pro Arg Glu Phe Val Glu Asn Ser Glu Cys Ile Gln
    210                 215                 220
Cys His Pro Glu Cys Leu Pro Gln Ala Met Asn Ile Thr Cys Thr Gly
225                 230                 235                 240
Arg Gly Pro Asp Asn Cys Ile Gln Cys Ala His Tyr Ile Asp Gly Pro
                245                 250                 255
His Cys Val Lys Thr Cys Pro Ala Gly Val Met Gly Glu Asn Asn Thr
            260                 265                 270
Leu Val Trp Lys Tyr Ala Asp Ala Gly His Val Cys His Leu Cys His
        275                 280                 285
Pro Asn Cys Thr Tyr Gly Cys Thr Gly Pro Gly Leu Glu Gly Cys Pro
    290                 295                 300
Thr Asn Gly Pro Lys Ile Pro Ser Ile Ala Thr Gly Met Val Gly Ala
305                 310                 315                 320
Leu Leu Leu Leu Leu Val Val Ala Leu Gly Ile Gly Leu Phe Met
                325                 330                 335

<210> SEQ ID NO 17
<211> LENGTH: 18
<212> TYPE: PRT
<213> ORGANISM: Artificial Sequence
<220> FEATURE:
<223> OTHER INFORMATION: T2A

<400> SEQUENCE: 17

Glu Gly Arg Gly Ser Leu Leu Thr Cys Gly Asp Val Glu Glu Asn Pro
1               5                   10                  15

Gly Pro

<210> SEQ ID NO 18
<211> LENGTH: 22
<212> TYPE: PRT
<213> ORGANISM: Artificial Sequence
<220> FEATURE:
<223> OTHER INFORMATION: P2A

<400> SEQUENCE: 18

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 19
<211> LENGTH: 19
<212> TYPE: PRT
<213> ORGANISM: Artificial Sequence
<220> FEATURE:
<223> OTHER INFORMATION: P2A

<400> SEQUENCE: 19

Ala Thr Asn Phe Ser Leu Leu Lys Gln Ala Gly Asp Val Glu Glu Asn
1               5                   10                  15

Pro Gly Pro

<210> SEQ ID NO 20
<211> LENGTH: 20
<212> TYPE: PRT
<213> ORGANISM: Artificial Sequence
<220> FEATURE:
<223> OTHER INFORMATION: E2A
```

-continued

```
<400> SEQUENCE: 20

Gln Cys Thr Asn Tyr Ala Leu Leu Lys Leu Ala Gly Asp Val Glu Ser
1               5                   10                  15

Asn Pro Gly Pro
            20

<210> SEQ ID NO 21
<211> LENGTH: 22
<212> TYPE: PRT
<213> ORGANISM: Artificial Sequence
<220> FEATURE:
<223> OTHER INFORMATION: F2A

<400> SEQUENCE: 21

Val Lys Gln Thr Leu Asn Phe Asp Leu Leu Lys Leu Ala Gly Asp Val
1               5                   10                  15

Glu Ser Asn Pro Gly Pro
            20

<210> SEQ ID NO 22
<211> LENGTH: 10
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (5)...(9)
<223> OTHER INFORMATION: SGGGG is repeated 5 times

<400> SEQUENCE: 22

Pro Gly Gly Gly Ser Gly Gly Gly Gly Pro
1               5                   10

<210> SEQ ID NO 23
<211> LENGTH: 17
<212> TYPE: PRT
<213> ORGANISM: Artificial Sequence
<220> FEATURE:
<223> OTHER INFORMATION: Linker

<400> SEQUENCE: 23

Gly Ser Ala Asp Asp Ala Lys Lys Asp Ala Ala Lys Lys Asp Gly Lys
1               5                   10                  15

Ser

<210> SEQ ID NO 24
<211> LENGTH: 66
<212> TYPE: DNA
<213> ORGANISM: Artificial Sequence
<220> FEATURE:
<223> OTHER INFORMATION: GMCSFR alpha chain signal sequence

<400> SEQUENCE: 24
atgcttctcc tggtgacaag ccttctgctc tgtgagttac cacacccagc attcctcctg      60
atccca                                                                66

<210> SEQ ID NO 25
<211> LENGTH: 22
<212> TYPE: PRT
<213> ORGANISM: Artificial Sequence
<220> FEATURE:
<223> OTHER INFORMATION: GMCSFR alpha chain signal sequence

<400> SEQUENCE: 25
```

```
Met Leu Leu Leu Val Thr Ser Leu Leu Leu Cys Glu Leu Pro His Pro
1               5                   10                  15

Ala Phe Leu Leu Ile Pro
            20

<210> SEQ ID NO 26
<211> LENGTH: 18
<212> TYPE: PRT
<213> ORGANISM: Artificial Sequence
<220> FEATURE:
<223> OTHER INFORMATION: CD8 alpha signal peptide

<400> SEQUENCE: 26

Met Ala Leu Pro Val Thr Ala Leu Leu Leu Pro Leu Ala Leu Leu Leu
1               5                   10                  15

His Ala

<210> SEQ ID NO 27
<211> LENGTH: 15
<212> TYPE: PRT
<213> ORGANISM: Artificial Sequence
<220> FEATURE:
<223> OTHER INFORMATION: Hinge

<400> SEQUENCE: 27

Glu Pro Lys Ser Cys Asp Lys Thr His Thr Cys Pro Pro Cys Pro
1               5                   10                  15

<210> SEQ ID NO 28
<211> LENGTH: 12
<212> TYPE: PRT
<213> ORGANISM: Artificial Sequence
<220> FEATURE:
<223> OTHER INFORMATION: Hinge

<400> SEQUENCE: 28

Glu Arg Lys Cys Cys Val Glu Cys Pro Pro Cys Pro
1               5                   10

<210> SEQ ID NO 29
<211> LENGTH: 61
<212> TYPE: PRT
<213> ORGANISM: Artificial Sequence
<220> FEATURE:
<223> OTHER INFORMATION: Hinge

<400> SEQUENCE: 29

Glu Leu Lys Thr Pro Leu Gly Asp Thr His Thr Cys Pro Arg Cys Pro
1               5                   10                  15

Glu Pro Lys Ser Cys Asp Thr Pro Pro Pro Cys Pro Arg Cys Pro Glu
            20                  25                  30

Pro Lys Ser Cys Asp Thr Pro Pro Pro Cys Pro Arg Cys Pro Glu Pro
        35                  40                  45

Lys Ser Cys Asp Thr Pro Pro Pro Cys Pro Arg Cys Pro
    50                  55                  60

<210> SEQ ID NO 30
<211> LENGTH: 12
<212> TYPE: PRT
<213> ORGANISM: Artificial Sequence
<220> FEATURE:
<223> OTHER INFORMATION: Hinge

<400> SEQUENCE: 30
```

```
Glu Ser Lys Tyr Gly Pro Pro Cys Pro Ser Cys Pro
1               5                   10
```

<210> SEQ ID NO 31
<211> LENGTH: 12
<212> TYPE: PRT
<213> ORGANISM: Artificial Sequence
<220> FEATURE:
<223> OTHER INFORMATION: Hinge

<400> SEQUENCE: 31

```
Glu Ser Lys Tyr Gly Pro Pro Cys Pro Pro Cys Pro
1               5                   10
```

<210> SEQ ID NO 32
<211> LENGTH: 9
<212> TYPE: PRT
<213> ORGANISM: Artificial Sequence
<220> FEATURE:
<223> OTHER INFORMATION: Hinge

<400> SEQUENCE: 32

```
Tyr Gly Pro Pro Cys Pro Pro Cys Pro
1               5
```

<210> SEQ ID NO 33
<211> LENGTH: 10
<212> TYPE: PRT
<213> ORGANISM: Artificial Sequence
<220> FEATURE:
<223> OTHER INFORMATION: Hinge

<400> SEQUENCE: 33

```
Lys Tyr Gly Pro Pro Cys Pro Pro Cys Pro
1               5                   10
```

<210> SEQ ID NO 34
<211> LENGTH: 14
<212> TYPE: PRT
<213> ORGANISM: Artificial Sequence
<220> FEATURE:
<223> OTHER INFORMATION: Hinge

<400> SEQUENCE: 34

```
Glu Val Val Val Lys Tyr Gly Pro Pro Cys Pro Pro Cys Pro
1               5                   10
```

<210> SEQ ID NO 35
<211> LENGTH: 11
<212> TYPE: PRT
<213> ORGANISM: Artificial Sequence
<220> FEATURE:
<223> OTHER INFORMATION: FMC63 CDR L1

<400> SEQUENCE: 35

```
Arg Ala Ser Gln Asp Ile Ser Lys Tyr Leu Asn
1               5                   10
```

<210> SEQ ID NO 36
<211> LENGTH: 7
<212> TYPE: PRT
<213> ORGANISM: Artificial Sequence
<220> FEATURE:
<223> OTHER INFORMATION: FMC63 CDR L2

<400> SEQUENCE: 36

```
Ser Arg Leu His Ser Gly Val
1               5
```

<210> SEQ ID NO 37
<211> LENGTH: 9
<212> TYPE: PRT
<213> ORGANISM: Artificial Sequence
<220> FEATURE:
<223> OTHER INFORMATION: FMC63 CDR L3

<400> SEQUENCE: 37

```
Gly Asn Thr Leu Pro Tyr Thr Phe Gly
1               5
```

<210> SEQ ID NO 38
<211> LENGTH: 5
<212> TYPE: PRT
<213> ORGANISM: Artificial Sequence
<220> FEATURE:
<223> OTHER INFORMATION: FMC63 CDR H1

<400> SEQUENCE: 38

```
Asp Tyr Gly Val Ser
1               5
```

<210> SEQ ID NO 39
<211> LENGTH: 16
<212> TYPE: PRT
<213> ORGANISM: Artificial Sequence
<220> FEATURE:
<223> OTHER INFORMATION: FMC63 CDR H2

<400> SEQUENCE: 39

```
Val Ile Trp Gly Ser Glu Thr Thr Tyr Tyr Asn Ser Ala Leu Lys Ser
1               5                   10                  15
```

<210> SEQ ID NO 40
<211> LENGTH: 7
<212> TYPE: PRT
<213> ORGANISM: Artificial Sequence
<220> FEATURE:
<223> OTHER INFORMATION: FMC63 CDR H3

<400> SEQUENCE: 40

```
Tyr Ala Met Asp Tyr Trp Gly
1               5
```

<210> SEQ ID NO 41
<211> LENGTH: 120
<212> TYPE: PRT
<213> ORGANISM: Artificial Sequence
<220> FEATURE:
<223> OTHER INFORMATION: FMC63 VH

<400> SEQUENCE: 41

```
Glu Val Lys Leu Gln Glu Ser Gly Pro Gly Leu Val Ala Pro Ser Gln
1               5                   10                  15

Ser Leu Ser Val Thr Cys Thr Val Ser Gly Val Ser Leu Pro Asp Tyr
                20                  25                  30

Gly Val Ser Trp Ile Arg Gln Pro Pro Arg Lys Gly Leu Glu Trp Leu
            35                  40                  45

Gly Val Ile Trp Gly Ser Glu Thr Thr Tyr Tyr Asn Ser Ala Leu Lys
        50                  55                  60

Ser Arg Leu Thr Ile Ile Lys Asp Asn Ser Lys Ser Gln Val Phe Leu
65                  70                  75                  80
```

```
Lys Met Asn Ser Leu Gln Thr Asp Asp Thr Ala Ile Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Ser Val Thr Val Ser Ser
        115                 120

<210> SEQ ID NO 42
<211> LENGTH: 107
<212> TYPE: PRT
<213> ORGANISM: Artificial Sequence
<220> FEATURE:
<223> OTHER INFORMATION: FMC63 VL

<400> SEQUENCE: 42

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr
            100                 105

<210> SEQ ID NO 43
<211> LENGTH: 245
<212> TYPE: PRT
<213> ORGANISM: Artificial Sequence
<220> FEATURE:
<223> OTHER INFORMATION: FMC63 scFv

<400> SEQUENCE: 43

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Ser Thr Ser Gly
            100                 105                 110

Ser Gly Lys Pro Gly Ser Gly Glu Gly Ser Thr Lys Gly Glu Val Lys
        115                 120                 125

Leu Gln Glu Ser Gly Pro Gly Leu Val Ala Pro Ser Gln Ser Leu Ser
    130                 135                 140

Val Thr Cys Thr Val Ser Gly Val Ser Leu Pro Asp Tyr Gly Val Ser
```

```
                145                 150                 155                 160
Trp Ile Arg Gln Pro Pro Arg Lys Gly Leu Glu Trp Leu Gly Val Ile
                165                 170                 175

Trp Gly Ser Glu Thr Thr Tyr Tyr Asn Ser Ala Leu Lys Ser Arg Leu
                180                 185                 190

Thr Ile Ile Lys Asp Asn Ser Lys Ser Gln Val Phe Leu Lys Met Asn
                195                 200                 205

Ser Leu Gln Thr Asp Asp Thr Ala Ile Tyr Tyr Cys Ala Lys His Tyr
            210                 215                 220

Tyr Tyr Gly Gly Ser Tyr Ala Met Asp Tyr Trp Gly Gln Gly Thr Ser
225                 230                 235                 240

Val Thr Val Ser Ser
                245

<210> SEQ ID NO 44
<211> LENGTH: 11
<212> TYPE: PRT
<213> ORGANISM: Artificial Sequence
<220> FEATURE:
<223> OTHER INFORMATION: SJ25C1 CDR L1

<400> SEQUENCE: 44

Lys Ala Ser Gln Asn Val Gly Thr Asn Val Ala
1               5                   10

<210> SEQ ID NO 45
<211> LENGTH: 7
<212> TYPE: PRT
<213> ORGANISM: Artificial Sequence
<220> FEATURE:
<223> OTHER INFORMATION: SJ25C1 CDR L2

<400> SEQUENCE: 45

Ser Ala Thr Tyr Arg Asn Ser
1               5

<210> SEQ ID NO 46
<211> LENGTH: 9
<212> TYPE: PRT
<213> ORGANISM: Artificial Sequence
<220> FEATURE:
<223> OTHER INFORMATION: SJ25C1 CDR L3

<400> SEQUENCE: 46

Gln Gln Tyr Asn Arg Tyr Pro Tyr Thr
1               5

<210> SEQ ID NO 47
<211> LENGTH: 5
<212> TYPE: PRT
<213> ORGANISM: Artificial Sequence
<220> FEATURE:
<223> OTHER INFORMATION: SJ25C1 CDR H1

<400> SEQUENCE: 47

Ser Tyr Trp Met Asn
1               5

<210> SEQ ID NO 48
<211> LENGTH: 17
<212> TYPE: PRT
<213> ORGANISM: Artificial Sequence
<220> FEATURE:
<223> OTHER INFORMATION: SJ25C1 CDR H2
```

-continued

<400> SEQUENCE: 48

Gln Ile Tyr Pro Gly Asp Gly Asp Thr Asn Tyr Asn Gly Lys Phe Lys
1               5                   10                  15

Gly

<210> SEQ ID NO 49
<211> LENGTH: 13
<212> TYPE: PRT
<213> ORGANISM: Artificial Sequence
<220> FEATURE:
<223> OTHER INFORMATION: SJ25C1 CDR H3

<400> SEQUENCE: 49

Lys Thr Ile Ser Ser Val Val Asp Phe Tyr Phe Asp Tyr
1               5                   10

<210> SEQ ID NO 50
<211> LENGTH: 122
<212> TYPE: PRT
<213> ORGANISM: Artificial Sequence
<220> FEATURE:
<223> OTHER INFORMATION: SJ25C1 VH

<400> SEQUENCE: 50

Glu Val Lys Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Tyr Pro Gly Asp Gly Asp Thr Asn Tyr Asn Gly Lys Phe
    50                  55                  60

Lys Gly Gln Ala Thr Leu Thr Ala Asp Lys Ser Ser Ser Thr Ala Tyr
65                  70                  75                  80

Met Gln Leu Ser Gly Leu Thr Ser Glu Asp Ser Ala Val Tyr Phe Cys
                85                  90                  95

Ala Arg Lys Thr Ile Ser Ser Val Val Asp Phe Tyr Phe Asp Tyr Trp
            100                 105                 110

Gly Gln Gly Thr Thr Val Thr Val Ser Ser
        115                 120

<210> SEQ ID NO 51
<211> LENGTH: 108
<212> TYPE: PRT
<213> ORGANISM: Artificial Sequence
<220> FEATURE:
<223> OTHER INFORMATION: SJ25C1 VL

<400> SEQUENCE: 51

Asp Ile Glu Leu Thr Gln Ser Pro Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Pro Leu Ile
        35                  40                  45

Tyr Ser Ala Thr Tyr Arg Asn Ser Gly Val Pro Asp Arg Phe Thr Gly
    50                  55                  60

Ser Gly Ser Gly Thr Asp Phe Thr Leu Thr Ile Thr Asn Val Gln Ser
65                  70                  75                  80

Lys Asp Leu Ala Asp Tyr Phe Cys Gln Gln Tyr Asn Arg Pro Tyr
            85                  90                  95

Thr Ser Gly Gly Gly Thr Lys Leu Glu Ile Lys Arg
            100                 105

<210> SEQ ID NO 52
<211> LENGTH: 15
<212> TYPE: PRT
<213> ORGANISM: Artificial Sequence
<220> FEATURE:
<223> OTHER INFORMATION: Linker

<400> SEQUENCE: 52

Gly Gly Gly Gly Ser Gly Gly Gly Gly Ser Gly Gly Gly Gly Ser
1               5                   10                  15

<210> SEQ ID NO 53
<211> LENGTH: 245
<212> TYPE: PRT
<213> ORGANISM: Artificial Sequence
<220> FEATURE:
<223> OTHER INFORMATION: SJ25C1 scFv

<400> SEQUENCE: 53

Glu Val Lys Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
            35                  40                  45

Gly Gln Ile Tyr Pro Gly Asp Gly Asp Thr Asn Tyr Asn Gly Lys Phe
        50                  55                  60

Lys Gly Gln Ala Thr Leu Thr Ala Asp Lys Ser Ser Ser Thr Ala Tyr
65                  70                  75                  80

Met Gln Leu Ser Gly Leu Thr Ser Glu Asp Ser Ala Val Tyr Phe Cys
            85                  90                  95

Ala Arg Lys Thr Ile Ser Ser Val Val Asp Phe Tyr Phe Asp Tyr Trp
            100                 105                 110

Gly Gln Gly Thr Thr Val Thr Val Ser Ser Gly Gly Gly Gly Ser Gly
            115                 120                 125

Gly Gly Gly Ser Gly Gly Gly Gly Ser Asp Ile Glu Leu Thr Gln Ser
            130                 135                 140

Pro Lys Phe Met Ser Thr Ser Val Gly Asp Arg Val Ser Val Thr Cys
145                 150                 155                 160

Lys Ala Ser Gln Asn Val Gly Thr Asn Val Ala Trp Tyr Gln Gln Lys
                165                 170                 175

Pro Gly Gln Ser Pro Lys Pro Leu Ile Tyr Ser Ala Thr Tyr Arg Asn
            180                 185                 190

Ser Gly Val Pro Asp Arg Phe Thr Gly Ser Gly Ser Gly Thr Asp Phe
            195                 200                 205

Thr Leu Thr Ile Thr Asn Val Gln Ser Lys Asp Leu Ala Asp Tyr Phe
        210                 215                 220

Cys Gln Gln Tyr Asn Arg Tyr Pro Tyr Thr Ser Gly Gly Gly Thr Lys
225                 230                 235                 240

Leu Glu Ile Lys Arg
            245

```
<210> SEQ ID NO 54
<211> LENGTH: 12
<212> TYPE: PRT
<213> ORGANISM: Artificial Sequence
<220> FEATURE:
<223> OTHER INFORMATION: FMC63 CDR H3

<400> SEQUENCE: 54

His Tyr Tyr Tyr Gly Gly Ser Tyr Ala Met Asp Tyr
1               5                   10

<210> SEQ ID NO 55
<211> LENGTH: 7
<212> TYPE: PRT
<213> ORGANISM: Artificial Sequence
<220> FEATURE:
<223> OTHER INFORMATION: FMC63 CDR L2

<400> SEQUENCE: 55

His Thr Ser Arg Leu His Ser
1               5

<210> SEQ ID NO 56
<211> LENGTH: 9
<212> TYPE: PRT
<213> ORGANISM: Artificial Sequence
<220> FEATURE:
<223> OTHER INFORMATION: FMC63 CDR L3

<400> SEQUENCE: 56

Gln Gln Gly Asn Thr Leu Pro Tyr Thr
1               5

<210> SEQ ID NO 57
<211> LENGTH: 735
<212> TYPE: DNA
<213> ORGANISM: Artificial Sequence
<220> FEATURE:
<223> OTHER INFORMATION: Sequence encoding scFv

<400> SEQUENCE: 57
gacatccaga tgacccagac cacctccagc ctgagcgcca gcctgggcga ccgggtgacc      60
atcagctgcc gggccagcca ggacatcagc aagtacctga actggtatca gcagaagccc     120
gacggcaccg tcaagctgct gatctaccac accagccggc tgcacagcgg cgtgcccagc     180
cggtttagcg gcagcggctc cggcaccgac tacagcctga ccatctccaa cctggaacag     240
gaagatatcg ccacctactt tgccagcag ggcaacacac tgccctacac ctttggcggc      300
ggaacaaagc tggaaatcac cggcagcacc tccggcagcg gcaagcctgg cagcggcgag     360
ggcagcacca agggcgaggt gaagctgcag gaaagcggcc ctggcctggt ggcccccagc     420
cagagcctga gcgtgacctg caccgtgagc ggcgtgagcc tgcccgacta cggcgtgagc     480
tggatccggc agccccccag gaagggcctg aatggctgg gcgtgatctg gggcagcgag      540
accacctact acaacagcgc cctgaagagc cggctgacca tcatcaagga caacagcaag     600
agccaggtgt tcctgaagat gaacagcctg cagaccgacg acaccgccat ctactactgc     660
gccaagcact actactacgg cggcagctac gccatggact actggggcca gggcaccagc     720
gtgaccgtga gcagc                                                      735

<210> SEQ ID NO 58
<211> LENGTH: 5
<212> TYPE: PRT
<213> ORGANISM: Artificial Sequence
```

```
<220> FEATURE:
<223> OTHER INFORMATION: Hinge
<220> FEATURE:
<221> NAME/KEY: VARIANT
<222> LOCATION: (1)...(1)
<223> OTHER INFORMATION: Xaa1 is glycine, cysteine or arginine
<220> FEATURE:
<221> NAME/KEY: VARIANT
<222> LOCATION: (4)...(4)
<223> OTHER INFORMATION: Xaa4 is cysteine or threonine

<400> SEQUENCE: 58

Xaa Pro Pro Xaa Pro
1               5

<210> SEQ ID NO 59
<211> LENGTH: 18
<212> TYPE: PRT
<213> ORGANISM: Artificial Sequence
<220> FEATURE:
<223> OTHER INFORMATION: Linker

<400> SEQUENCE: 59

Gly Ser Thr Ser Gly Ser Gly Lys Pro Gly Ser Gly Glu Gly Ser Thr
1               5                   10                  15

Lys Gly
```

EPIGENETIC ANALYSIS OF CELL THERAPY AND RELATED METHODS

CROSS-REFERENCE TO RELATED APPLICATIONS

This application is a National Stage application under 35 U.S.C. § 371 of International Application No. PCT/US2018/013227, filed on Jan. 10, 2018, which claims priority from U.S. provisional application No. 62/444,802, filed Jan. 10, 2017, entitled "EPIGENETIC ANALYSIS OF CELL THERAPY AND RELATED METHODS," U.S. provisional application No. 62/551,752, filed Aug. 29, 2017, entitled "EPIGENETIC ANALYSIS OF CELL THERAPY AND RELATED METHODS," and U.S. provisional application No. 62/596,662, filed Dec. 8, 2017, entitled "EPIGENETIC ANALYSIS OF CELL THERAPY AND RELATED METHODS," the contents of which are incorporated by reference in their entirety.

INCORPORATION BY REFERENCE OF SEQUENCE LISTING

The present application is being filed along with a Sequence Listing in electronic format. The Sequence Listing is provided as a file entitled 735042009400SeqList.TXT, created Jul. 9, 2019 which is 35,649 bytes in size. The information in the electronic format of the Sequence Listing is incorporated by reference in its entirety.

FIELD

The present disclosure relates in some aspects to a method of identifying genomic region(s) predictive of an outcome of treatment with a cell therapy and/or of a phenotype of function of the cells. In some embodiments, the methods include epigenetic and/or epigenomic analyses of the cells in connection with methods for preparing engineered cells for cell therapy and/or predicting response to a cell therapy, e.g., engineered cells for cell therapy. In some embodiments, the methods include steps to assess, characterize and analyze changes or modifications in an epigenetic property of gene region or regions, such as chromatin accessibility, nucleosome occupancy, histone modification, spatial chromosomal conformation, transcription factor occupancy and/or DNA methylation. In some embodiments, the epigenetic and/or epigenomic analysis includes determining the epigenetic properties of a cell, e.g., an engineered cell for cell therapy.

BACKGROUND

Various strategies are available for preparing and administering cells used in connection with adoptive cell therapy, including methods for preparing genetically engineered T cells or involving administering genetically engineered T cells, such as engineered with antigen receptors, such as CARs. In some aspects, available methods may not be entirely satisfactory. There is a need for additional strategies for preparing cells and for administering cells in connection with adoptive cell therapy. Provided are methods that meet such needs.

SUMMARY

Provided herein are methods of identifying one or more genomic region(s) predictive of an outcome of treatment with a cell therapy, the method that includes: (a) analyzing or determining an epigenetic property of one or more genomic regions of a cell or a population of cells, said cell or population comprised in (i) a first composition of cells to be genetically engineered with a recombinant receptor to produce a second composition that includes the recombinant receptor, or (ii) a second composition of cells that includes the recombinant receptor; and (b) identifying one or more of said one or more genomic regions, of which the epigenetic property, overall across the one or more genomic regions, predicts, indicates or correlates with an outcome of a cell therapy, said cell therapy that includes administering the second composition of cells that includes the recombinant receptor. In some embodiments, the outcome is optionally a complete response, a partial response, progressive disease, a molecularly detectable disease, relapse, durability of response, outcome associated with or indicative of efficacy, or outcome associated with or indicative of toxicity.

Provided herein are methods of identifying one or more genomic region(s) associated with an outcome of treatment with a cell therapy, the method comprising: (a) analyzing or determining an epigenetic property of one or more genomic regions of a cell or a population of cells, said cell or population comprised in (i) a first composition of cells to be genetically engineered with a recombinant receptor to produce a second composition comprising the recombinant receptor, or (ii) a second composition of cells comprising the recombinant receptor; and (b) identifying one or more of the one or more genomic regions, of which the epigenetic property, overall across the one or more genomic regions, predicts, indicates or correlates with an outcome of a cell therapy, said cell therapy comprising administering to a subject or a group of subjects the second composition of cells comprising the recombinant receptor.

In some embodiments, the outcome is an outcome associated with or indicative of efficacy, a response, persistence, a toxicity, or immunogenicity.

Also provided are methods for determining one or more properties or features of a cell composition, the method comprising analyzing or determining an epigenetic property of one or more genomic regions of a T cell composition, said T cell composition enriched for CD4+ primary human T cells and/or CD8+ primary human T cells.

In some embodiments, the cell composition is (i) a first T cell composition of cells to be genetically engineered with a recombinant receptor to produce a second T cell composition comprising the recombinant receptor, or (ii) a second T cell composition of cells comprising the recombinant receptor.

In some embodiments, the method further comprises comparing the epigenetic property for each of the one or more genomic region, individually, to the corresponding epigenetic property of cells from a different cell composition and/or to a reference profile, optionally a reference profile known to indicate or correlate with an attribute or feature of a cell composition.

In some embodiments, the comparison indicates or correlates with the state, phenotype or function of the cells within the cell composition, optionally an activation, effector or memory state; consistency or uniformity of the cells within the cell composition; whether the composition of cells is or is likely to exhibit or produce an outcome when administered to a subject or a group of subjects; the location, abundance or frequency of integration of exogenous nucleic acids; clonality of cells within the cell composition; and/or the proportion or frequency of engineered cells in the cell composition.

Provided herein are methods for determining or identifying an epigenetic property associated with an attribute or feature of a cell composition, the method comprising: (a) determining or measuring a level or degree or relative level or degree of an epigenetic property of one or more genomic regions for a cell or a population of cells comprised in a first cell composition; (b) determining or measuring a level or degree or relative level or degree of said epigenetic property of the one or more genomic regions for a cell or a population of cells comprised in a second cell composition; and (c) comparing the level or degree in (a) and the level or degree in (b), wherein a difference, optionally a significant difference, in the level or degree of the epigenetic property of the one or more of the genomic regions identifies or determines the presence of an epigenetic property indicative of or that correlates with an attribute or feature present in cells of one but not the other of the first and second composition.

In some embodiments, one of the first composition and second composition comprises cells to be genetically engineered with a recombinant receptor and the other of the first composition and second composition comprises the cells engineered to express the recombinant receptor; the first composition and second composition comprise primary cells from different donors, optionally donors that differ based on disease state, severity of disease, or type of disease; the first composition and second composition comprise cells at different stages or steps of a manufacturing process for engineering cells; one of the first composition and second composition comprises cells contacted with an agent to modulate the activity, phenotype or function of the cells and the other of the first and second composition comprises similar cells not so contacted; or one of the first composition and second composition comprises a sample of a cell composition associated with an outcome that occurs or has occurred with the one but not the other of the first and second composition following administration to a subject. In some embodiments, the agent is a polypeptide or protein, a peptide, an antibody, a nucleic acid, a viral vector or viral preparation, or a small molecule compound. In some embodiments, the agent is a stimulatory reagent, optionally anti-CD3/anti-CD28; an immunomodulatory agent, an anti-idiotype antibody or antigen-binding fragment thereof specific to the CAR, an immune checkpoint inhibitor, a modulator of a metabolic pathway, an adenosine receptor antagonist, a kinase inhibitor, an anti-TGFβ antibody or an anti-TGFβR antibody or a cytokine.

In some embodiments, the attribute or feature of the first composition is indicative of a state, phenotype of function, optionally an activation, effector or memory state, phenotype or function; the location, abundance or frequency of integration of exogenous nucleic acids; clonality of cells within the cell composition; the proportion or frequency of engineered cells in the cell composition; and/or whether the composition of cells is or is likely to exhibit or produce an outcome when administered to a subject or a group of subjects.

Provided herein are methods of assessing an attribute or feature of a cell composition, comprising: (a) analyzing an epigenetic property of one or more genomic regions of a cell or population of cells comprised in a cell composition comprising cells engineered with a recombinant receptor and/or cells to be genetically engineered with a recombinant receptor; and (b) comparing the epigenetic property of the one or more genomic region, individually, to a reference profile, wherein the comparison indicates whether the composition of cells is or is likely to exhibit the attribute or feature.

In some embodiments, the attribute or feature is indicative of a state, phenotype of function, optionally an activation, effector or memory state, phenotype or function; the location, abundance or frequency of integration of exogenous nucleic acids; clonality of cells within the cell composition; the proportion or frequency of engineered cells in the cell composition; and/or whether the composition of cells is or is likely to exhibit or produce an outcome when administered to a subject or a group of subjects. In some embodiments, the attribute or feature is whether the composition of cells is or is likely to exhibit or produce an outcome when administered to a subject or a group of subjects and the method is for assessing the cell composition for administration to a subject.

Also provided herein are methods of identifying one or more genomic region(s) predictive of an outcome of treatment with a cell therapy, the method that includes: (a) determining or measuring a level or degree or relative level or degree of an epigenetic property of one or more genomic regions for a cell or a population of cells comprised in a first therapeutic composition; (b) determining or measuring a level or degree or relative level or degree of said epigenetic property of said one or more genomic regions for a cell or a population of cells comprised in second therapeutic composition; (c) comparing the level or degree in (a) and the level or degree in (b) for one or more of the genomic regions.

In some embodiments, the method further includes identifying one or more of the one or more genomic regions in which the level or degree determined or measured in (a) is different, optionally significantly different, as compared to the level or degree determined or measured in (b).

In some embodiments, for each of the plurality of genomic regions, a difference or significant difference between the level or degree detected or measured in (a) and the level or degree detected or measured in (b) indicates that the epigenetic property or degree or level thereof correlates with, predicts, predicts the likelihood or risk of, an outcome that occurs or has occurred with one but not the other of, the first and second therapeutic compositions, wherein the outcome is optionally a complete response, a partial response, progressive disease, a molecularly detectable disease, relapse, durability of response, outcome associated with or indicative of efficacy, or outcome associated with or indicative of toxicity.

In some embodiments, the genomic region includes a genomic locus or gene. In some embodiments, the genomic region includes an open reading frame of a gene. In some embodiments, the epigenetic property is selected from among chromatin accessibility, nucleosome occupancy, histone modification, spatial chromosomal conformation, transcription factor occupancy and DNA methylation. In some embodiments, the epigenetic property is chromatin accessibility. In some embodiments, said epigenetic property includes chromatin accessibility, a level or degree of chromatin accessibility, a relative level or degree of chromatin accessibility, and/or said epigenetic property includes a degree or level of, relative degree or level of, or profile or map of, chromatin accessibility across the genomic region.

In some embodiments, chromatin accessibility is determined by Assay for Transposase Accessible Chromatin with high-throughput sequencing (ATAC-seq) or chromatin immunoprecipitation coupled to high-throughput sequencing (ChIP-seq). In some embodiments, chromatin accessibility is determined by ATAC-seq.

In some embodiments, analyzing the epigenetic property includes generating an epigenetic map showing a profile of sequence reads associated with or indicative of the epigenetic property, optionally sequence reads associated with or indicative of chromatin accessibility, along each of the one or more genomic regions or a subset thereof and/or includes, for each of a plurality of sites or portions along the length of the genomic region, generating one or more sequence reads indicative of an epigenetic readout, optionally chromatin accessibility, at said site or portion, wherein the quantity of said one or more sequence reads indicates a degree or level of said epigenetic property, optionally said chromatin accessibility, at said site or portion.

In some embodiments, said analyzing optionally further includes determining an overall degree or level of said epigenetic readout, optionally determining an overall degree or level of accessibility, over the genomic region. In some embodiments, analyzing the epigenetic property includes determining, measuring or quantitating a value or level of chromatin accessibility across the one or more genomic regions. In some embodiments, analyzing the epigenetic property includes determining, measuring or quantitating a value or level associated with or indicative of the epigenetic property, optionally chromatin accessibility, across the one or more genomic regions or a subset thereof.

In some embodiments, the value or level is or includes determining the fragments per kilobase per million of mapped reads (FPKM) value within each of the one or more genomic regions or a subset thereof. In some embodiments, the value or level is or includes totaling or summing the fragments per kilobase per million of mapped reads (FPKM) value within each of the one or more genomic regions or a subset thereof.

In some embodiments, the step (a) and (b) are performed for a plurality of subjects having each been independently administered a second composition of cells that includes cells engineered with a recombinant receptor.

In some embodiments, for each genomic region or subset thereof, preparing a display that includes the value or level of the sequence reads for each genomic locus mapped to the outcome of the cell therapy for each of the plurality of subjects.

In some embodiments, the display includes a heat map, a scatter plot, a hierarchical clustering and/or a constellation plot. In some embodiments, said identifying said one or more genomic regions includes performing cluster analysis based on outcome of the cell therapy. In some embodiments, said identifying said one or more genomic regions that indicate or correlate with an outcome of the cell therapy includes determining if at least a majority of subjects with the same or similar outcome cluster together in the display. In some embodiments, a genomic region is identified if at least 55%, 60%, 70%, 80%, 90%, 95% or more of the subjects with the same or similar outcome cluster together in the display.

In some embodiments, the whole genome of the cell is analyzed. In some embodiments, a portion of the genome of the cell is analyzed. In some embodiments, the portion of the genome includes one or more genomic regions, optionally one or more genomic loci, associated with or indicative of or likely to be associated with or indicative of the phenotype, the activation state, the strength of an activation signal or the effector function of a cell.

In some embodiments, the outcome of the cell therapy is a response, a toxicity, immunogenicity or a phenotype or function of the cell therapy, a complete response, a partial response, progressive disease, a molecularly detectable disease, relapse, durability of response, outcome associated with or indicative of efficacy, or outcome associated with or indicative of toxicity.

In some embodiments, the response is a complete response, partial response, progressive disease or a molecularly detectable disease.

In some embodiments, the toxicity is cytokine release syndrome (CRS), severe CRS, grade 3 or higher CRS, neurotoxicity, severe neurotoxicity, grade 3 or higher neurotoxicity and/or a cerebral edema. In some embodiments, the toxicity is a dose limiting toxicity (DLT).

In some embodiments, the epigenetic property of from or from about 2 to 50, 2 to 20, 2 to 10, 2 to 5, 5 to 50, 5 to 20, 5 to 10, 10 to 50, 10 to 20 or 20 to 50 genomic regions are analyzed. In some embodiments, a panel that includes two or more of the genomic regions are identified.

In some embodiments, the first composition of cells and second composition of cells comprise primary cells selected or isolated from a subject. In some embodiments, the cell is an immune cell. In some embodiments, the immune cell is a T cell or an NK cell. In some embodiments, the T cells is a CD4+ and/or CD8+ T cells.

In some embodiments, the second composition of cells is analyzed. In some embodiments, the second composition of cells includes a nucleic acid encoding the recombinant receptor.

In some embodiments, the nucleic acid molecule is contained in a viral vector. In some embodiments, the viral vector is an adenovirus, lentivirus, retrovirus, herpesvirus or adeno-associated virus vector.

In some embodiments, the first composition of cells and/or second composition of cells is produced by culturing an input composition in the presence of one or more conditions or agents. In some embodiments, the one or more genomic regions comprise genes involved in or likely to be involved in the activation state or effector state of the cell.

Also provided herein are methods of assessing a cell composition for administration to a subject, that includes: (a) analyzing an epigenetic profile of one or more genomic regions of a cell comprised in a cell composition that includes cells engineered with a recombinant receptor; and (b) comparing the epigenetic profile for each genomic region, individually, to a reference profile, wherein the comparison indicates whether the population of cells is or is likely to exhibit or produce an outcome when administered to a subject.

In some embodiments, the outcome of the cell therapy is a response, a toxicity, immunogenicity or a phenotype or function of the cell therapy, a complete response, a partial response, progressive disease, a molecularly detectable disease, relapse, durability of response, outcome associated with or indicative of efficacy, or outcome associated with or indicative of toxicity. In some embodiments, the response is a complete response or a partial response.

In some embodiments, if the comparison indicates that the cell composition is or is likely to exhibit the outcome, administering the cell composition to the subject.

In some embodiments, if the comparison indicates that the cell composition is not or is not likely to exhibit the outcome, either: (i) administering a cell composition in which the cell composition is altered; (ii) administering the cell composition in which the dose of cells is altered; (iii) administering the cell composition in which the dosage regimen of cells administered to the subject is altered; (iv) administering the cell composition in combination with one or more other therapeutic agents; or (v) not administering the cell composition to the subject.

In some embodiments, prior to administering an altered cell composition, repeating steps (a) and (b) on a cell comprised in the altered cell composition.

In some embodiments, altering the dosing regimen of cells includes administering a second dose of cells to the subject subsequent to administering a first dose of cells to the subject. In some embodiments, the subsequent dose of cells is administered at least 1 week, 2 weeks, 3 weeks, 4 weeks, 2 months, 3 months, 4 months, 5 months, 6 months, 9 months or 12 months after administering the first dose of cells.

In some embodiments, the one or more genomic regions are associated with or indicative of a response to the cell therapy.

In some embodiments, the reference profile includes a threshold value for the epigenetic property for each of the one or more genomic regions or for the overall epigenetic property within the one or more genomic regions.

In some embodiments, the threshold value: is a value or level of the epigenetic property, optionally chromatin accessibility, in the one or more genomic regions in a cell of a cell composition shown to exhibit the outcome when administered to a subject having the same or similar disease or condition; or is an average, median or mean value or level of the epigenetic property, optionally chromatin accessibility, in the one or more genomic regions from a cell of each of a plurality of cell compositions, shown to exhibit the outcome when administered to the subject. In some embodiments, the threshold value includes is the value or level of the epigenetic property in a cell from a normal or healthy subject. In some embodiments, the threshold value includes the value or level of the epigenetic property in a cell that exhibits a naïve or a long-lived memory phenotype.

In some embodiments, the threshold value: is a value or level associated with or indicative of the epigenetic property, optionally chromatin accessibility, in the one or more genomic regions in a cell of a cell composition shown to exhibit the desired outcome when administered to a subject having the same or similar disease or condition; or is an average, median or mean value or level, or is within a standard deviation of the average, median or mean value or level, associated with or indicative of the epigenetic property, optionally chromatin accessibility, in the one or more genomic regions from a cell of each of a plurality of cell compositions that had been individually administered to a group of subjects, wherein each of the subjects of the group went on to shown to exhibit the desired outcome when administered following administration to the subject; or is the value or level associated with or indicative of the epigenetic property in a similar cell composition from a normal or healthy subject.

Also provided herein are methods of assessing a cell culture, that includes: (a) analyzing an epigenetic profile of one or more genomic regions of a cell comprised in an output cell composition, said output composition produced by culturing an input composition in the presence of one or more test agents or conditions; and (b) comparing the epigenetic profile for each genomic region, individually, to a reference profile, wherein the comparison indicates whether the cell is or is likely to exhibit a predetermined phenotype or function.

In some embodiments, the predetermined phenotype or function indicates the effector function or activation state of the cell and/or indicates that the cells exhibit a naïve phenotype or a long-lived memory phenotype.

In some embodiments, the one or more test agents or conditions includes presence or concentration of serum; time in culture; presence or amount of a stimulating agent; the type or extent of a stimulating agent; presence or amount of amino acids; temperature; the source or cell types of the input composition; the ratio or percentage of cell types in the input composition, optionally the CD4+/CD8+ cell ratio; the presence or amount of beads; cell density; static culture; rocking culture; perfusion; the type of viral vector; the vector copy number; the presence of a transduction adjuvant; cell density of the input composition in cryopreservation; the extent of expression of the recombinant receptor; or the presence of a compound to modulate cell phenotype. In some embodiments, the one or more test agents or conditions includes one or more compounds from a library of test compounds.

In some embodiments, the method includes if the comparison indicates that the cell composition is or is likely to have the phenotype or function, selecting the one or more test agent or condition for culturing the cells. In some embodiments, the method includes if the comparison indicates that the cell composition is or is likely not to have the phenotype or function, repeating steps (a) and (b) with one or more further test agent or condition.

In some embodiments, the reference profile includes a threshold value for the epigenetic property for each of the one or more genomic regions or for the overall epigenetic property within the one or more genomic regions.

In some embodiments, the threshold value: is a value or level of the epigenetic property, optionally chromatin accessibility, in the one or more genomic regions in a cell of a reference cell composition shown to exhibit the phenotype or function; or is an average, median or mean value or level of the epigenetic property, optionally chromatin accessibility, in the one or more genomic regions from a cell of each of a plurality of reference cell compositions, shown to exhibit the phenotype or function.

In some embodiments, the reference cell composition has a phenotype indicative of a naïve T cell, a long-lived memory T cell, a central memory T cell (Tcm) or a stem-like memory T cell (Tcsm).

In some embodiments, analyzing the epigenetic property includes determining, measuring or quantitating a value or level of chromatin accessibility across the one or more genomic regions. In some embodiments, analyzing the epigenetic property includes determining, measuring or quantitating a value or level of the sequence reads associated with or indicative of the epigenetic property, optionally chromatin accessibility, in the one or more genomic regions or a subset thereof. In some embodiments, determining, measuring or quantitating a value or level includes determining the fragments per kilobase per million of mapped reads (FPKM) value within each of the one or more genomic regions or a subset thereof. In some embodiments, determining, measuring or quantitating a value or level includes totaling or summing the fragments per kilobase per million of mapped reads (FPKM) value within each of the one or more genomic regions or a subset thereof.

In some embodiments, the one or more genomic regions includes a panel that includes at least 2 to 50, 2 to 20, 2 to 10, 2 to 5, 5 to 50, 5 to 20, 5 to 10, 10 to 50, 10 to 20 or 20 to 50 genomic regions.

In some embodiments, the one or more genomic regions comprise one or more genomic loci associated with or indicative of the effector-like function or activation state of the cell.

In some embodiments, the one or more genomic regions includes a genetic locus selected from the group consisting of Nr4a1, Cblb, Irf4, Tbx21, Eomes, Ifng, Il2ra, Il2, Csf2, Gzmb, Tnfsf10, Gata3, Mir155, Sox21, Ctla4, Lag3, and Pdcd1. In some embodiments, the one or more genomic regions includes a genomic locus selected from the group consisting of Ctla4, Il2ra, Il2, Ifng and Gzmb.

In some embodiments, the genomic region includes a genomic locus or gene. In some embodiments, the genomic region includes an open reading frame of a gene. In some embodiments, the genomic region comprises an intergenic region or a regulatory element. In some embodiments, the genomic region comprises an intron, an exon, a cis-regulatory element, a promoter, an enhancer, an upstream activating sequence (UAS), a 3' untranslated region (UTR), a 5' UTR, a non-coding RNA producing region, a non-coding RNA (ncRNA) gene, a miRNA gene, an siRNA gene, a piRNA gene, a snoRNA gene, a lncRNA gene, a ribosomal RNA (rRNA) gene, a small RNA binding site, a non-coding RNA binding site, a pseudogene, a transcription termination site (TTS), a repeat, a telomeric region, accessible chromatin region, non-accessible chromatin region, open chromatin region and/or heterochromatin region.

In some embodiments, the epigenetic property is selected from among chromatin accessibility, nucleosome occupancy, histone modification, spatial chromosomal conformation, transcription factor occupancy and DNA methylation. In some embodiments, the epigenetic property is chromatin accessibility. In some embodiments, chromatin accessibility is determined by Assay for Transposase Accessible Chromatin with high-throughput sequencing (ATAC-seq) or chromatin immunoprecipitation coupled to high-throughput sequencing (ChIP-seq). In some embodiments, chromatin accessibility is determined by ATAC-seq.

In some embodiments, the assessing the epigenetic property comprises: (1) isolating chromatin from the cells or the population of cells, (2) treating the chromatin with an insertional enzyme complex to generate tagged fragments of genomic DNA, (3) sequencing all or a portion of the tagged fragments to produce a plurality of sequence reads; (4) aligning, filtering and mapping the sequence reads to genomic regions of a genome; and (5) determining or identifying peaks of sequence reads in a plurality of genomic regions for each cell or population of cells. In some embodiments, the analyzing or assessing the epigenetic property further comprises comparing peaks of sequence reads and, optionally identifying peaks of sequence reads that are different between samples from two or more cells or cell compositions. In some embodiments, peaks of sequence reads comprise sequence reads having a peak signal, level or value that is enriched, is above background, and/or is higher compared to sequence reads of a surrounding regions. In some embodiments, the analyzing or assessing the epigenetic property further comprises performing motif analysis, transcription factor occupancy analysis and/or biological pathway analysis of genomic regions identified as containing peaks of sequence reads that are different between samples from two or more cell populations. In some embodiments, the analyzing or assessing the epigenetic property further comprises determining positions of nucleosomes within genomic regions containing peaks of sequence reads.

In some embodiments, the analysis comprises steps for removal of mitochondrial reads and/or additional contaminating sequences based on sequence identity, quality, mapping location, or other sequencing properties of said reads. In some embodiments, the analysis comprises steps for removal of duplicate reads to improve quantitative accuracy. In some embodiments, the analysis comprises steps for separation of sequence reads into subsets representing a specific epigenetic property, optionally chromatin accessibility or chromatin occupancy, wherein the size of the sequenced fragment is used to determine the degree or level to which it represents said epigenetic property.

In some embodiments, analyzing further comprises performing principle component analysis (PCA), biological pathway analysis, gene ontology (GO) analysis and/or motif analysis.

In some embodiments, the cell is obtained from a sample from a subject. In some embodiments, the cell is an immune cell, optionally a T cell, optionally a CD4+ and/or CD8+ T cell.

In some embodiments, the recombinant receptor binds to, recognizes or targets an antigen associated with the disease or condition; and/or the recombinant receptor is a T cell receptor or a functional non-T cell receptor; and/or the recombinant receptor is a chimeric antigen receptor (CAR). In some embodiments, the CAR includes an extracellular antigen-recognition domain that specifically binds to the antigen and an intracellular signaling domain that includes an ITAM, wherein optionally, the intracellular signaling domain includes an intracellular domain of a CD3-zeta (CD3ζ) chain; and/or wherein the CAR further includes a costimulatory signaling region, which optionally includes a signaling domain of CD28 or 4-1BB.

Also provided herein are cell compositions that include a plurality of cells, wherein the level or value of an epigenetic property for one or more genes in a panel is above or below a threshold value in at least 50% of the cells in the composition.

In some embodiments, the level or value is above or below the threshold value in at least 60%, 70%, 75%, 80%, 85%, 90%, 95% or more of the cells in the composition. In some embodiments, the threshold value: is a value or level of the epigenetic property, optionally chromatin accessibility, in the one or more genomic regions in a cell of a reference cell composition shown to exhibit the phenotype or function; or is an average, median or mean value or level of the epigenetic property, optionally chromatin accessibility, in the one or more genomic regions from a cell of each of a plurality of reference cell compositions, shown to exhibit the phenotype or function.

In some embodiments, the reference cell composition has a phenotype indicative of a naïve T cell, a long-lived memory T cell, a central memory T cell (Tcm) or a stem-like memory T cell (Tcsm).

In some embodiments, the panel includes from or from about 2 to 50, 2 to 20, 2 to 10, 2 to 5, 5 to 50, 5 to 20, 5 to 10, 10 to 50, 10 to 20 or 20 to 50 genomic regions.

Also provided herein are methods of assessing transgene integration, the method comprising: determining an epigenetic property of one or more genomic regions comprising a nucleic acid sequence of a transgene, in a cell or a cell composition genetically engineered with a recombinant receptor. In some embodiments, the genetic engineering is carried out by introduction, into one or more cells of a cell composition, of a nucleic acid encoding the recombinant receptor.

In some embodiments, the introduction is by transduction with a viral vector comprising the nucleic acid. In some embodiments, the epigenetic property is chromatin accessibility. In some embodiments, the epigenetic property comprises chromatin accessibility, a level or degree of chromatin accessibility, a relative level or degree of chromatin accessibility, and/or the epigenetic property comprises a degree or level of, relative degree or level of, or profile or map of, chromatin accessibility of the genomic region.

In some embodiments, chromatin accessibility is determined by Assay for Transposase Accessible Chromatin with high-throughput sequencing (ATAC-seq) or chromatin immunoprecipitation coupled to high-throughput sequencing (ChIP-seq). In some embodiments, chromatin accessibility is determined by ATAC-seq.

In some embodiments, the assessing the epigenetic property comprises: (1) isolating chromatin from the cells or the population of cells, (2) treating the chromatin with an insertional enzyme complex to generate tagged fragments of genomic DNA, (3) sequencing all or a portion of the tagged fragments to produce a plurality of sequence reads; (4) aligning, filtering and mapping the sequence reads to genomic regions of a genome; and (5) determining or identifying peaks of sequence reads in a plurality of genomic regions for each cell or population of cells.

In some embodiments, the analyzing or assessing the epigenetic property further comprises determining the peaks of sequence reads that maps to or is corresponds to the nucleic acid sequence of the transgene In some embodiments, peaks of sequence reads comprise sequence reads having a peak signal, level or value that is enriched, is above background, and/or is higher compared to sequence reads of a surrounding regions. In some embodiments, analyzing the epigenetic property comprises generating an epigenetic map showing a profile of sequence reads associated with or indicative of the epigenetic property, optionally sequence reads associated with or indicative of chromatin accessibility, of the genomic region comprising the nucleic acid sequence of the transgene and/or comprises, for the genomic region comprising the nucleic acid sequence of the transgene along the length of the genomic region, generating one or more sequence reads indicative of an epigenetic readout, optionally chromatin accessibility, at said region, wherein the quantity of said one or more sequence reads indicates a degree or level of said epigenetic property, optionally said chromatin accessibility, at said region. In some embodiments, determining the epigenetic property comprises determining, measuring or quantitating a value or level of chromatin accessibility across the genomic region comprising the nucleic acid sequence of the transgene. In some embodiments, determining the epigenetic property comprises determining, measuring or quantitating a value or level associated with or indicative of the epigenetic property, optionally chromatin accessibility, across the genomic region comprising the nucleic acid sequence of the transgene. In some embodiments, the cell composition, optionally the first composition of cells and/or second composition of cells, comprise primary cells obtained from a sample from a subject and/or selected or isolated from a subject.

In some embodiments, the cell is an immune cell. In some embodiments, the immune cell is a T cell or an NK cell. In some embodiments, the T cells is a CD4+ and/or CD8+ T cells.

In some embodiments, the recombinant receptor binds to, recognizes or targets an antigen associated with the disease or condition; and/or the recombinant receptor is a T cell receptor or a functional non-T cell receptor; and/or the recombinant receptor is a chimeric antigen receptor (CAR). In some embodiments, the CAR comprises an extracellular antigen-recognition domain that specifically binds to the antigen and an intracellular signaling domain comprising an ITAM, wherein optionally, the intracellular signaling domain comprises an intracellular domain of a CD3-zeta (CD3ζ) chain; and/or wherein the CAR further comprises a costimulatory signaling region, which optionally comprises a signaling domain of CD28 or 4-1BB.

BRIEF DESCRIPTION OF THE DRAWINGS

FIGS. 6A and 6B show chromatin accessibility of loci associated with strength of signal and effector function as measured by the sum of FPKM over the gene body of each gene for subjects grouped by response.

FIGS. 7A and 7B show results of principal component analysis (PCA) for gene expression (based on RNA-seq results; FIG. 7A) and chromatin accessibility (based on ATAC-seq results; FIG. 7B), in anti-BCMA CAR-expressing T cells generated from 4 different donors (Donors 1-4), stimulated with BCMA-conjugated beads, for 24 hours (24 hr+stim) or 7 days (d7+stim), or cultured without stimulation for 24 hours (24 hr), in the presence or absence of lenalidomide.

FIG. 11 shows motif enrichment analysis, enrichment log p-value, prevalence and transcription factors predicted to bind the motifs for peaks with increased accessibility in the presence of lenalidomide in day 7 cultures.

FIGS. 12A and 12B show exemplary chromatin accessibility profiles on exemplary immune genes (e.g., cell surface markers CD3ε, CD8a, CD8b and CD4) in different cryopreserved CD4+ or CD8+ engineered cell compositions (CDP) or matched samples that had not been subjected to engineering (CMAT); in some cases, CMAT samples were separated by phenotype as naïve T cells ($T_N$), central memory T cells ($T_{CM}$), effector and effector memory T cells ($T_{E+EM}$) or effector memory RA ($T_{EMRA}$).

FIGS. 14B-14D show exemplary differential accessibility peak profiles and quantitation for accessibility peaks at genomic regions near two exemplary immune-related genes (gene 1: FIG. 14B and gene 2: FIG. 14C) in subjects achieving a PD at 3 months, compared to subjects who achieved CR at 3 months. FIG. 14D shows a quantitation of the peaks from subjects who had been administered engineered CAR-T cells, grouped by response outcomes (1 month CR, 3 month CR, 1 month PD, 3 month PD, or PR).

FIGS. 23A and 23B show volcano plots showing peaks with higher or lower accessibility, in subjects based on neurotoxicity (Ntx) or cytokine release syndrome (CRS), for CDP (FIG. 23C) or CMAT (FIG. 23D).

DETAILED DESCRIPTION

Figure 1A:
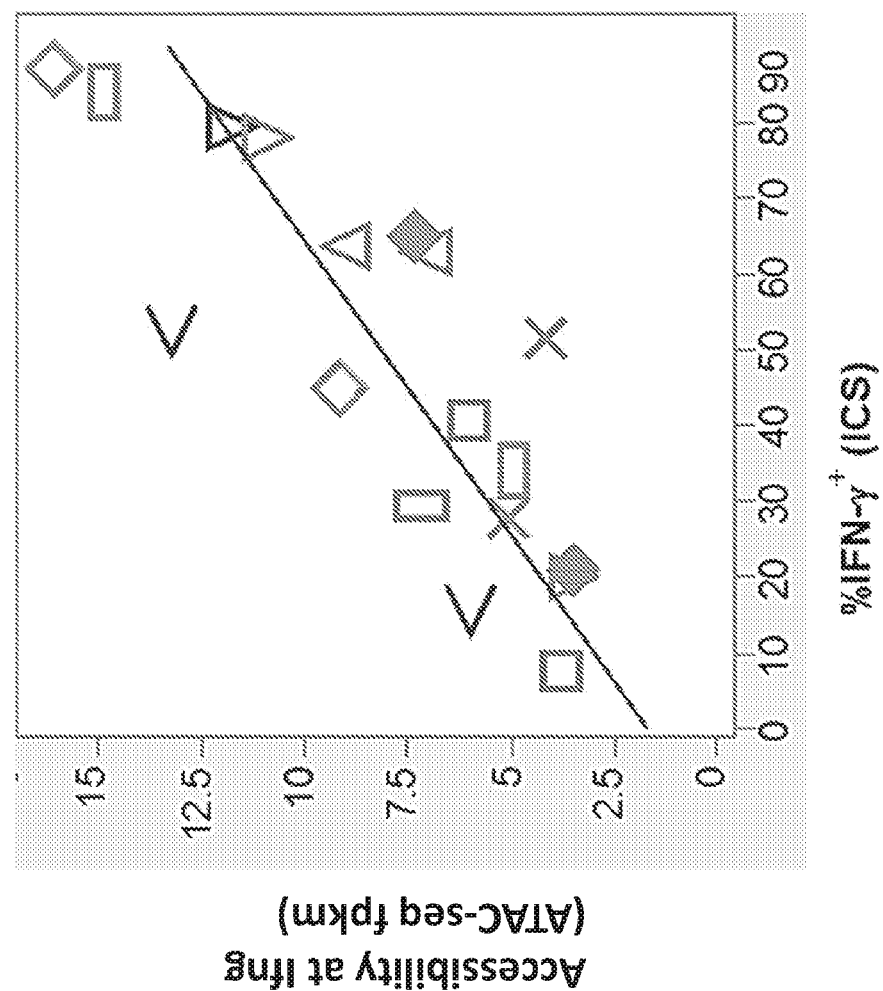
FIG. 1A shows correlation of interferon-gamma (IFNγ) production, as measured by intracellular cytokine staining (ICS) (shown on the x-axis) versus accessibility at the gene encoding IFNγ (Ifng) as determined by ATAC-seq (shown on the y-axis).

I. Methods for Assessing Epigenetic State of Cells

Provided are methods for determining an epigenetic profile or signature for one more genomic regions of a cell or a cell composition, including cell compositions containing primary cells, e.g. T cells, derived from a subject for use in connection with adoptive cell therapy. In some embodiments, the cell compositions include compositions in connection with manufacturing or engineering a cell therapy, including compositions prior to and subsequent to engineering of cells with a recombinant receptor, e.g. a chimeric antigen receptor (CAR). In some aspects, the epigenetic profile or signature and/or one or more epigenetic properties of genomic region(s) of a cell or a cell composition can provide information about certain features or properties of the cells, including those associated with a phenotype, activation state and/or function of the cell or cell composition and/or indicative of, associated with, correlated with and/or predictive of one or more outcomes of treatment with a cell therapy. These methods are based on observations that epigenetic properties, such as chromatin accessibility, of certain genes or genomic regions permits detailed, exquisite and/or comprehensive tracking of features and properties of a cell composition that is not possible with other systems, such as methods that rely on transcription, e.g. RNA sequencing. In some aspects, such epigenetic properties are found to correlate with outcomes, such as disease outcomes, response outcomes, toxicity outcomes and/or phenotype, persistence, activity and/or function of cells. Such correlations are not, in certain aspects, observed using existing methods of analysis, such as methods to assess transcription, protein expression and/or by intracellular staining.

Provided are methods for identifying genomic region(s) that are indicative of, associated with, correlated with, and/or predictive of an outcome, such as an outcome for treatment with a cell therapy, based on epigenetic properties of genomic region(s) and/or as determined from an epigenetic profile for one or more genomic regions. Also provided are methods of assessing cell compositions or cell culture compositions for adoptive cell therapy, based on epigenetic properties of particular genomic region(s).

The provided methods can be used to identify genomic region(s) that are predictive of outcomes of treatment before administration of the adoptive cell therapy. Provided herein are methods of identifying one or more genomic region(s) predictive of an outcome of treatment with a cell therapy. The provided methods can be used to identify an epigenetic profile that is indicative of, associated with, correlated with, and/or predictive of particular outcomes or properties of adoptive cell therapy, e.g., with a desired response and/or safety outcome. In some embodiments, the provided methods can be used to assess one or more properties or features of cells or cell compositions, prior to administration, e.g., by comparing the epigenetic profile to that of another sample, and/or to a reference profile. In some embodiments, the method includes analyzing or determining an epigenetic property of one or more genomic regions of a cell or a population of cells, said cell or population contained in a first composition of cells to be genetically engineered with a recombinant receptor to produce a second composition containing the recombinant receptor, or a second composition of cells containing the recombinant receptor; and identifying one or more of said one or more genomic regions, of which the epigenetic property, overall across the one or more genomic regions, predicts, indicates or correlates with an outcome of a cell therapy, said cell therapy including administering the second composition of cells containing the recombinant receptor.

In some embodiments, the provided methods can be used to measure or quantitate an epigenetic property, such as chromatin accessibility, of genomic regions, e.g., one or more genomic loci, and/or a gene or genes, such as a panel of genes, to provide information about the features or characteristics of cells used in connection with a cell therapy, e.g., CAR+ T cell therapy, including features or characteristics predictive of response to a cell therapy or that are indicative of a desired cell phenotype or function. In some aspects, the provided methods can be used in connection with optimizing or improving cell therapies, including by improving outcomes of the therapy, e.g., response and/or safety outcomes after administration of the cell therapy and/or the quality of the cell therapy.

In some cases, this is an advantageous over existing methods and cell therapies, since responses can be difficult to predict, optimal dosing can be difficult to determine and/or the quality of a cell therapy can be variable. The provided methods can be used to provide better information about the features and characteristics of the engineered cells for adoptive cell therapy prior to administration, such that optimal dosing can be easily and rapidly determined, for increased efficacy and safety of the cell therapy. The provided methods also can be used to identify or characterize cells in connection with manufacturing or engineering a cell therapy, including in connection with the effects of various process parameters (e.g. temperature, culture conditions and other parameters) that can or may affect the phenotype, activity, persistence or function of cells.

In some embodiments, the provided methods can be used for identifying one or more genomic region(s) predictive of an outcome of treatment with a cell therapy, the method including (a) determining or measuring a level or degree or relative level or degree of an epigenetic property of one or more genomic regions for a cell or a population of cells contained in a first therapeutic composition; (b) determining or measuring a level or degree or relative level or degree of said epigenetic property of said one or more genomic regions for a cell or a population of cells contained in second therapeutic composition; and (c) comparing the level or degree in (a) and the level or degree in (b) for one or more of the genomic regions.

In some embodiments, the provided methods can be used for assessing a cell composition for administration to a subject, including analyzing an epigenetic profile of one or more genomic regions of a cell in a cell composition containing cells engineered with a recombinant receptor; and comparing the epigenetic profile for each genomic region, individually, to a reference profile, wherein the comparison indicates whether the population of cells is or is likely to exhibit or produce an outcome when administered to a subject. In some embodiments, the provided methods of assessing a cell culture includes analyzing an epigenetic profile of one or more genomic regions of a cell contained in an output cell composition, said output composition produced by culturing an input composition in the presence of one or more test agents or conditions; and comparing the epigenetic profile for each genomic region, individually, to a reference profile, wherein the comparison indicates whether the cell is or is likely to exhibit a predetermined phenotype, persistence, activity and/or function.

In some embodiments, the provided methods can be used to assess state, quality, consistency, phenotype, clonality, uniformity, characteristics and/or property of cells for cell therapies; to select cells or cell compositions that are indicative of, associated with, correlated with, and/or predictive of particular outcomes or properties of adoptive cell therapy, e.g., with a desired response and/or safety outcome; and/or to modify or alter the dose, types of cells and/or one or more steps or parameters of the engineering process, such that the cell composition for administration can be optimized or improved, based on assessment of the epigenetic properties.

In some aspects, the provided methods can be used to determine the state, quality, consistency, phenotype, clonality, uniformity, characteristics and/or property of the cells, e.g., cells for adoptive cell therapy. In some aspects, the provided methods can be used for cells at one or more stages of engineering, or cell compositions obtained from the subjects before engineering, for purified or selected cell sub-populations at various stages, or cells obtained from the subject after administration of the engineered cells. In some aspects, the methods can be used to assess the state, quality, consistency, phenotype, clonality, uniformity, characteristics and/or property of the cells prior to administration to the subjects, and the results from the analysis methods can be used to select subjects for treatment, determine a treatment regimen, including dosing and frequency and/or additional treatment, and/or modify or change the engineering or manufacturing process to obtain a more desirable cell composition for administration. In some embodiments, the methods can be used to obtain more uniform and predictively potent cell compositions for administration for increased efficacy and/or reduced adverse effects. In some aspects, the provided methods can be used in combination or in conjunction with other methods or assays to characterize the cells in the cell population, e.g., assays to determine cell surface marker expression, persistence, viability and/or expansion of cells, to determine any correlation to such characteristics and/or phenotypes.

In some embodiments, various changes may be made and equivalents may be substituted in the various embodiments. In addition, many modifications may be made to adapt a particular situation, material, composition of matter, process, process act(s) or step(s) to the objective(s), spirit or scope of the various embodiments. In some embodiments, each of the individual variations described and illustrated herein has discrete components and features that may be readily separated from or combined with the features of any of the other several embodiments without departing from the scope or spirit of the various embodiments. All such modifications are intended to be within the scope of claims associated with this disclosure.

II. Epigenetic/Epigenomic Analysis

In any of the provided methods, the epigenetic and/or epigenomic analysis can include steps to assess, characterize and analyze changes or modifications in a gene locus, a plurality of gene loci or genomic loci, a genomic region and/or a genome, such as chromatin accessibility, nucleosome occupancy, histone modification, spatial chromosomal conformation, transcription factor occupancy and/or DNA methylation.

In some aspects, the one or more genomic regions include a genomic locus or a gene. In some aspects, a genomic locus includes a fixed position in the genome, and can include a coding region, an open reading frame of a gene, a non-coding region, an intergenic region or a regulatory element. In some embodiments, one or more genomic regions, loci, elements or intervals include coding regions, non-coding regions, intergenic regions, introns, exons, proximal and distal cis-regulatory regions, promoter regions, enhancer regions, upstream activating sequences (UAS), untranslated regions of a transcript (UTR, e.g., 3'UTR or 5' UTR), non-coding RNA producing regions, non-coding RNA (ncRNA) genes (e.g., miRNA, siRNA, piRNA, snoRNA or lncRNA), ribosomal RNA (rRNA) genes, small RNA binding sites, non-coding RNA binding sites, pseudogenes, transcription termination sites (TTS), repeats, telomeric regions and/or accessible or non-accessible regions (e.g., open chromatin and/or heterochromatin).

In some embodiments, the provided methods involve one or more epigenetic and/or epigenomic analysis step. In some embodiments, the analysis includes a large-scale analysis, e.g., analysis of a plurality of genomic regions, genomic loci, genetic loci or a genome-wide analysis. In some embodiments, the epigenetic and/or epigenomic analysis includes determining the epigenetic properties, state, and/or profile of a cell, e.g., an engineered cell for cell therapy. In some embodiments, the provided methods involve determining the epigenetic/epigenomic properties, state and/or profile of cells or a population or composition of cells. In some embodiments, the methods can involve the use of sequencing, such as large-scale sequencing, e.g., high throughput sequencing or next generation sequencing, to assess the epigenetic/epigenomic property, state and/or profile of cells or cell compositions. In some embodiments, the methods involve aligning and/or filtering the sequences obtained from the assay and/or mapping the sequences to a genome, such as a reference genome. In some aspects, the methods involve determining genomic regions, loci and/or interval where sequences are mapped, such as determining the peaks of sequence reads that are mapped to a particular region, locus and/or interval of the genome.

In some embodiments, the provided methods also involve analyzing the epigenetic/epigenomic properties and/or profile, e.g., by comparing the epigenetic/epigenomic properties and/or profile of a particular cell or cell composition to those of another cell or cell composition. In some embodiments, the provided methods involve various downstream steps or processes for analysis or comparison, e.g., computationally implemented steps, and/or applications of the methods, for assessing one or more properties or characteristics of cells or cell compositions.

In some aspects, exemplary methods for determining or assessing the epigenetic/epigenomic properties, state and/or profile, e.g., using assays such as ATAC-seq, and analysis and/or application thereof, can involve one or more of the following steps: 1) generating ATACseq library; 2) trimming and mapping reads; 3) removing duplicate reads; 4) filtering mitochondrial contamination; 5) filtering for non-nucleosomal fragments; 6) calling accessibility peaks; 7) assembling consensus peak set; 8) counting reads in peaks; 9) clustering samples; and/or 10) performing differential accessibility analysis. In some embodiments, exemplary epigenetic and/or epigenomic analysis includes assessment of the state of the chromatin, e.g., chromatin accessibility, openness or compaction. In some embodiments of the provided methods, epigenetic and/or epigenomic analysis includes assessing chromatin accessibility. In some embodiments, chromatin accessibility analysis is coupled to a step for large-scale sequencing, e.g., high throughput sequencing or next generation sequencing. In some embodiments, the method for assessing chromatin accessibility includes assessment of nucleosome occupancy, histone modification and/or transcription factor occupancy. In some embodiments, chromatin accessibility is determined using DNA insertion elements, DNA-modifying enzymes (e.g., DNase or MNase), and/or antibodies, including fragments thereof. Exemplary assays for epigenetic and/or epigenomic analysis include chromatin immunoprecipitation coupled to high-throughput sequencing (ChIP-seq) to identify protein binding sites of a genome, bisulfite sequencing to determine DNA methylation at base-pair resolution, DNaseI-Seq, Assay for Transposase Accessible Chromatin with high-throughput sequencing (ATAC-seq) to assess open chromatin, and chromosome conformation capture (3C) and related methods, such as chromosome conformation capture-on-chip (4C), chromosome conformation capture carbon copy (5C), Hi-C, 3C-Seq (3C with high-throughput sequencing), 4C-Seq, 5C-Seq and HiC-Seq to determine the spatial organization of chromosomes. In some embodiments, the epigenetic and/or epigenomic analysis includes formaldehyde assisted isolation of regulatory elements with high-throughput sequencing (FAIRE-seq).

A. Determining Epigenetic/Epigenomic Profile

In some embodiments of the provided methods, epigenetic and/or epigenomic analysis, such as determining the epigenetic/epigenomic properties, state and/or profile, includes assessing chromatin accessibility, of genomic regions, loci and/or intervals and/or at a genome-wide level, e.g., throughout a large portion or the entire genome. In some aspects, an epigenetic/epigenomic profile is determined, based on epigenetic/epigenomic properties at one or more genomic regions, loci and/or intervals, and/or at the genome-wide level, of particular cells or cell compositions.

In some embodiments of any of the methods of analysis provided herein, a computer system is used to execute one or more steps, functions, processes or scripts. In some embodiments, the computer system is integrated into and is part of an analysis system, e.g., a liquid handler, a bridge amplification system (e.g. an Illumina cBot), and/or a sequencing system (e.g. an Illumina Genome Analyzer, HiSeq, or MiSeq system). In some embodiments, the computer system is connected to or ported to an analysis system.

1. Chromatin Accessibility Assessment Using ATAC-seq

In some embodiments, the chromatin accessibility is assessed using a DNA insertion element coupled to a high-throughput sequencing method. In some embodiments, chromatin accessibility is assessed using ATAC-seq, for example, such as the methods described in US20160060691, which incorporated by reference in its entirety, and any variations of the methods therein. In some embodiments, exemplary assays for epigenetic and/or epigenomic analysis include those described in, e.g., WO2015102536, WO2015159295, WO2015130968, WO201692070, Dirks et al. Clinical Epigenetics (2016) 8:122, Buenrostro et al., Nat Methods. (2013) 10(12): 1213-1218, Sung et al., Nat Methods. (2016) 13(3): 222-228, which are incorporated by reference in their entirety. In some embodiments, chromatin accessibility assays such as ATAC-seq have advantages such as simplicity of library preparation, short assay timing (results can be obtained within hours, compared to 3-4 days required for certain assays), no requirement for sonication or phenol-chloroform extractions, no requirement for antibodies (eliminating limitations and biases that can be introduced by antibodies), no requirement for sensitive enzymatic digestion (eliminating laborious and sensitive enzymatic titrations), requiring only a very small number of cells as input, and a wide dynamic range. In some embodiments, chromatin accessibility assays such as ATAC-seq have advantages such as providing a more accurate and predictive assessment of the state, quality, consistency, phenotype, characteristics and/or property of the cells (e.g., state of chromatin accessibility throughout the genome) in a composition in a single assay and/or at a single time point, without the requirement of assessing other parameters, such as RNA or protein expression levels, separately.

In some aspects, determining or assessing the epigenetic/epigenomic properties, state and/or profile, e.g., using assays such as ATAC-seq, involve one or more of the following steps: (a) chromatin isolation; (b) tagmentation; (c) sequencing; (d) sequence mapping; and/or (e) peak determination. In some aspects, determining or assessing the epigenetic/epigenomic properties, state and/or profile, e.g., using assays such as ATAC-seq, involve one or more of the following steps: (1) isolating chromatin from the cells or the population of cells, (2) treating the chromatin with an insertional enzyme complex to generate tagged fragments of genomic DNA, (3) sequencing all or a portion of the tagged fragments to produce a plurality of sequence reads; (4) aligning, filtering and mapping the sequence reads to genomic regions of a genome; and/or (5) determining peaks of sequence reads in a plurality of genomic regions for each cell or population of cells.

In some embodiments, the assay for assessing chromatin accessibility, e.g., ATAC-seq, involves one or more of the following steps: (i) washing and lysing cells; (ii) tagmentation; (iii) DNA cleanup; (iv) PCR pre-amplification; (v) quantitative PCR (qPCR) amplification; (vi) PCR n-amplification; (vii) DNA cleanup; (viii) library generation and (ix) sequencing. In some embodiments, assays or steps for quality control are also performed. Exemplary steps for library generation and/or quality control include one or more of the following: (i) genomic DNA isolation and assessment; (ii) size selection to remove residual primers (e.g., using 2% agarose); (iii) DNA cleanup; (iv) qPCR; (v) DNA quantitation; and (vi) dilution and pooling of library. In some embodiments, the libraries generated from the sample are sequenced using high-throughput or next-generation sequencing. In some embodiments, the number of cells required for the methods provided herein is tested using a series of cell dilutions, e.g., samples containing different cell concentrations or cell numbers.

In some embodiments, other parameters or metrics can be used to determine the quality of the sample and the data when performing one or more steps of the method. In some embodiments, parameters or metrics used to determine quality of the samples and the data include number of mapped reads per sample, percentage alignment to the genome of the subject (e.g., human genome), percentage of non-redundant reads, number of unique reads, recovery of known peaks (positive control), qPCR amplification to assess proper tagmentation, nucleosome band assessment of genomic DNA, and/or correlation between repeats or different dilutions.

In some embodiments, the assay for assessing chromatin accessibility, e.g., ATAC-seq, comprises: treating chromatin isolated from a population of cells with an DNA insertion element, e.g., an insertional enzyme complex to produce tagged fragments of genomic DNA. In this step, the chromatin is tagmented (i.e., cleaved and tagged in the same reaction) using an insertional enzyme such as Tn5 or MuA that cleaves the genomic DNA in open regions in the chromatin and adds adaptors to both ends of the fragments. Methods for tagmenting isolated genomic DNA are known in the art (see, e.g., Caruccio Methods Mol. Biol. 2011 733: 241-55; Kaper et al, Proc. Natl. Acad. Sci. 2013 110: 5552-7; Marine et al, Appl. Environ. Microbiol. 2011 77: 8071-9 and US20100120098) and are commercially available, e.g., from Illumina (San Diego, Calif.). Such systems may be readily adapted for use herein. In some cases, the conditions may be adjusted to obtain a desirable level of insertion in the chromatin (e.g., an insertion that occurs, on average, every 50 to 200 base pairs in open regions).

The chromatin used in the assay, e.g., chromatin, which can contain genomic DNA, histones and/or other chromatin-associated factors, from cells, e.g., cells obtained from a subject, may be made by any suitable method. In some embodiments, nuclei may be isolated, lysed, and the chromatin may be further purified, e.g., from the nuclear envelope. In some embodiments, the chromatin may be isolated by contacting isolated nuclei with the reaction buffer. In some embodiments, the isolated nuclei may lyse when it makes contact with the reaction buffer (which comprises insertional enzyme complexes and other necessary reagents), which allows the insertional enzyme complexes access to the chromatin. In some embodiments, the assay includes isolating nuclei from a population of cells; and combining the isolated nuclei with the transposase and adaptors, wherein the combining results in both lysis of the nuclei to release said chromatin and production of the adaptor-tagged fragments of genomic DNA.

After the chromatin has been fragmented and tagged to produce tagged fragments of genomic DNA, at least some of the adaptor tagged fragments are sequenced to produce a plurality of sequence reads. The fragments may be sequenced using any know sequencing method, e.g., a next-generation or high-throughput sequencing method. For example, the fragments may be sequenced using Illumina's reversible terminator method, Roche's pyrosequencing method (454), Life Technologies' sequencing by ligation (the SOLiD platform) or Life Technologies' Ion Torrent platform. Examples of such methods are described, for example, in Margulies et al., Nature 2005 437: 376-80; Ronaghi et al., Analytical Biochemistry 1996 242: 84-9; Shendure et al., Science 2005 309: 1728-32; Imelfort et al., Brief Bioinform. 2009 10:609-18; Fox et al., Methods Mol Biol. 2009; 553:79-108; Appleby et al., Methods Mol Biol. 2009; 513:19-39 and Morozova et al., Genomics. 2008 92:255-64, which are incorporated by reference. Forward and reverse sequencing primer sites that are compatible with a selected next generation sequencing platform can be added to the ends of the fragments during the amplification step. In some embodiments, the fragments may be amplified using PCR primers that hybridize to the tags that have been added to the fragments, where the primer used for PCR have 5' tails that are compatible with a particular sequencing platform. In some cases, the primers used may contain a molecular barcode (an "index") so that different pools can be pooled together before sequencing, and the sequence reads can be traced to a particular sample using the barcode sequence.

In some aspects, the assay includes determining accessibility of a nucleic acid at a site, wherein the nucleic acid is from a cell sample, said assay comprising: inserting a plurality of molecular tags with an insertional enzyme into the nucleic acid and using the molecular tags to determine accessibility at the site. The cell sample can be from a primary source, e.g., a cell from a subject. In some embodiments, the cell sample includes cells from a subject that are selected and/or engineered or modified, e.g., engineered to express a recombinant receptor. The cell sample may consist of a single cell. The cell sample may consist of a finite number of cells (e.g. less than about 500,000 cells).

In some embodiments, the assay further includes the determined accessibility to identify one or more proteins that are bound to the nucleic acid and/or chromatin at a particular locus. In some embodiments, at least one of the proteins is a transcription factor. Additionally, the assay can comprise using the molecular tags to generate an accessibility map of the nucleic acid.

The nucleic acid may be fragmented into a plurality of fragments during the insertion of the molecular tags. In some embodiments, the fragments may be amplified. In some embodiments, the fragments can be sequenced to generate a plurality of sequencing reads. This may be used to determine the accessibility of the nucleic acid at any given site. The fragments may be sequenced using a high-throughput sequencing technique. In some embodiments, the sequencing reads can be normalized based on the sequence insertion preference of the insertional enzyme. The length of the sequenced reads can be used to determine a chromatin state annotation.

The nucleic acid can be bound to a plurality of association molecules. The association molecules can be, for example, proteins, nucleic acids or saccharides. In some embodiments, the association molecules can comprise histones. In other cases, the association molecules can comprise aptamers.

The insertional enzyme can be any enzyme capable of inserting a nucleic acid sequence into a nucleic acid. In some embodiments, the insertional enzyme can insert the nucleic acid sequence into the nucleic acid in a substantially sequence-independent manner. The insertional enzyme can be prokaryotic or eukaryotic. Examples of insertional enzymes include, but are not limited to, transposases, HERMES, and HIV integrase. The transposase can be a Tn transposase (e.g. Tn3, Tn5, Tn7, Tn10, Tn552, Tn903), a MuA transposase, a Vibhar transposase (e.g. from *Vibrio harveyi*), Ac-Ds, Ascot-1, Bs1, Cin4, Copia, En/Spm, F element, hobo, Hsmar1, Hsmar2, IN (HIV), IS1, IS2, IS3, IS4, IS5, IS6, IS10, IS21, IS30, IS50, IS51, IS150, IS256, IS407, IS427, IS630, IS903, IS911, IS982, IS1031, ISL2, L1, Mariner, P element, Tam3, Tc1, Tc3, Tel, THE-1, Tn/O, TnA, Tn3, Tn5, Tn7, Tn10, Tn552, Tn903, Tol1, Tol2, Tn10, Ty1, any prokaryotic transposase, or any transposase related to and/or derived from those listed above. In some embodiments, the transposase is a Tn5 transposase or a derivative thereof.

In some instances, a transposase related to and/or derived from a parent transposase can comprise a peptide fragment with at least about 50%, 55%, 60%, 65%, 70%, 75%, 80%, 85%, 90%, 91%, 92%, 93%, 94%, 95%, 96%, 97%, 98%, or 99% amino acid sequence homology to a corresponding peptide fragment of the parent transposase. The peptide fragment can be at least about 10, 15, 20, 25, 30, 35, 40, 45, 50, 60, 70, 80, 90, 100, 150, 200, 250, 300, 400, or 500 amino acids in length. For example, a transposase derived from Tn5 can comprise a peptide fragment that is 50 amino acids in length and 80% homologous to a corresponding fragment in a parent Tn5 transposase. In some embodiments, the insertion can be facilitated and/or triggered by addition of one or more cations. The cations can be divalent cations such as, for example, $Ca^{2+}$, $Mg^{2+}$ and $Mn^{2+}$.

The molecular tags can comprise sequencing adaptors, locked nucleic acids (LNAs), zip nucleic acids (ZNAs), RNAs, affinity reactive molecules (e.g. biotin, dig), self-complementary molecules, phosphorothioate modifications, azide or alkyne groups. In some embodiments, the sequencing adaptors can further comprise a barcode label. Further, the barcode labels can comprises a unique sequence. The unique sequences can be used to identify the individual insertion events. Any of the tags can further comprise fluorescence tags (e.g. fluorescein, rhodamine, Cy3, Cy5, thiazole orange).

Additionally, the insertional enzyme can further comprise an affinity tag. In some embodiments, the affinity tag can be an antibody. The antibody can bind to, for example, a transcription factor, a modified nucleosome or a modified nucleic acid. Examples of modified nucleic acids include, but are not limited to, methylated or hydroxymethylated DNA. In other cases, the affinity tag can be a single-stranded nucleic acid (e.g. ssDNA, ssRNA). In some examples, the single-stranded nucleic acid can bind to a target nucleic acid. In further cases, the insertional enzyme can further comprise a nuclear localization signal.

In some embodiments, the cells, e.g., cells derived from subjects, can be permeabilized to allow access for the insertional enzyme. The permeabilization can be performed in a way to minimally perturb the nuclei in the cell sample. In some instances, the cell sample can be permeabilized using a permeabilization agent. Examples of permeabilization agents include, but are not limited to, NP40, digitonin, tween, streptolysin, and cationic lipids. In other instances, the cell sample can be permeabilized using hypotonic shock and/or ultrasonication. In other cases, the insertional enzyme can be highly charged, which may allow it to permeabilize through cell membranes.

In some embodiments, the methods include steps for aligning, mapping and/or analyzing large-scale data generated from the assays, e.g. high-throughput sequencing data. In some embodiments, analysis of the generated data include one or more steps of alignments, fixing read mates, removing PCR duplicates, filtering to mapped reads and quality reads and/or filtering out mitochondrial sequences and/or peak calling; and can further include further analysis or application steps, including nucleosome positioning, transposon insertion sites, genome browser visualizations, differential accessibility analysis, motif enrichment, gene ontology (GO) enrichment and/or determining transcription factor occupancy. In some embodiments, other processing steps include de-multiplexing raw data, aligning and filtering, and assessing quality metrics.

In some aspects, the methods include steps for aligning, filtering and mapping the sequence reads to genomic regions of a genome. In some aspects, the methods include steps for determining peaks of sequence reads in a plurality of genomic regions for each cell or population of cells. In some embodiments, any of the methods provided herein further include one or more steps, functions, processes or scripts for aligning, filtering and/or mapping sequence results obtained from one or more steps, functions, processes or scripts of the methods provided herein, e.g., sequences obtained from the epigenetic analysis. In some embodiments, the methods include steps, functions, processes or scripts that are performed computationally, e.g., performed using one or more computer programs and/or via the use of computational algorithms. In some embodiments, also provided are computer systems, computer readable instructions, software, systems and/or devices for carrying out or performing one or more steps of the methods provided herein. In some embodiments, any of the further analysis and/or application steps, such as any described herein, can be performed computationally, e.g., performed using one or more computer programs and/or via the use of computational algorithms.

In some embodiments, the methods involve identification, alignment, filtering, processing, mapping and/or analysis of the sequences obtained from one or more steps of the methods provided herein, e.g., sequence data obtained from the chromatin accessibility analysis, e.g., using ATAC-seq. In some embodiments, identification, alignment, filtering, processing, mapping and/or analysis of the sequences includes procedures for sequence manipulation and alignment procedure used to obtain peaks of signal and/or for performing further analysis and/or application, e.g., identify one or more genomic region(s) in the methods described herein. In some embodiments, the identification, alignment, filtering, processing, mapping and/or analysis of the sequences and/or for performing further analysis and/or application includes any one or more of the exemplary steps, functions, processes or scripts, described herein, sequentially or simultaneously in any order. In some aspects, any of the steps and/or procedures for identification, alignment, filtering, processing, mapping and/or analysis of the sequences and/or for performing further analysis and/or application can be performed using computational scripts, tools and/or processes, and can form an analysis pipeline, e.g., a series or collection of connected steps and/or procedures, e.g., by connecting various computational steps, tools and/or processes. In some aspects, one or more of the steps, functions, processes or scripts can be substituted by similar algorithms, steps, functions, processes or scripts that achieve or carry out a similar function. In some embodiments, the sequential order of one or more steps can be in any order, or any one or more steps, functions, processes or scripts can be performed in parallel.

In some embodiments, the methods of identification, alignment, filtering, processing, mapping and/or analysis of the sequences, e.g., obtained from ATAC-seq, is driven by a set of configuration files, e.g., in YAML format, a human-readable data serialization language. In some embodiments, the configuration files specified general pipeline run parameters, e.g., number of CPU cores used in processing and where output files are uploaded, as well as information for each sample, e.g., sample name and type of sequencing reads in the sample. In some embodiments, the steps and/or methods for identification, alignment, filtering, processing, mapping and/or analysis of the sequences infers, from the configuration provided, the files that needed to be generated, the order of files, and the processing scripts and tools. In some embodiments, each of these steps, functions, processes or scripts can be added to a queue which is distributed out to a set of computing nodes. In some embodiments, during the run, inputs and outputs can be organized into a common folder and file naming structure, and logs can be generated from recording the events during each run. In some embodiments, the methods of analysis include steps, functions, processes or scripts, in a setup or an order.

In some embodiments, the methods of analysis for epigenetic and/or epigenomic properties, states and/or profiles, e.g., as determined from ATAC-seq data, is driven by a set of configuration files, e.g., in a human-readable data serialization language. In some embodiments, the configuration files specified general pipeline run parameters, e.g., number of CPU cores used in processing and where output files are uploaded, as well as information for each sample, e.g., sample name and type of sequencing reads in the sample. In some embodiments, the pipeline infers, from the configuration provided, the files that needed to be generated, the order of files, and the processing scripts and tools. In some embodiments, each of these steps, functions, processes or scripts can be added to a queue which is distributed out to a set of computing nodes. In some embodiments, during the pipeline run, inputs and outputs can be organized into a common folder and file naming structure, and logs can be generated from recording the events during each run. In some embodiments, the methods of analysis include steps, functions, processes or scripts, in a setup or an order.

In some cases, the steps, functions, processes or scripts are branched and are not connected in a linear fashion. In some embodiments, the steps, functions, processes or scripts include steps that are involved in general computational processing or general analysis of next generation sequencing results, e.g., unzipping compressed files, or specific steps that are used for the particular data generation platform used (e.g., particular next generation sequencing platform). In some embodiments, configuration files are read into the pipeline and a directed acyclic graph (DAG) is generated, containing the processing steps, functions, processes or scripts.

Exemplary methods of analysis setup include steps described below. In some embodiments, the steps, functions, processes or scripts, include any one or more of the steps, functions, processes or scripts described.

In some embodiments, one or more of the steps, functions, processes or scripts in the steps and/or methods for identification, alignment, filtering, processing, mapping and/or analysis of the sequences or further analysis and/or application, are automated. In some embodiments, a script, e.g., a Perl script or shell script can be used to invoke any of the various exemplary steps, functions, processes or scripts described herein (see, e.g., Tisdall, Mastering Perl for Bioinformatics, O'Reilly & Associates, Inc., Sebastopol, Calif. 2003; Michael, R., Mastering Unix Shell Scripting, Wiley Publishing, Inc., Indianapolis, Ind. 2003). In some embodiments, the methods of analysis can be embodied wholly or partially in one or more dedicated programs, for example, each optionally written in a compiled language such as C++ then compiled and distributed as a binary. In some embodiments, methods of analysis may be implemented wholly or in part as modules within, or by invoking functionality within, existing sequence analysis platforms. In some embodiments, the methods of analysis include a number of steps, functions, processes or scripts that are all invoked automatically responsive to a single starting queue (e.g., one or a combination of triggering events sourced from human activity, another computer program, or a machine).

In some embodiments, the steps, functions, processes or scripts or any combination of the steps, functions, processes or scripts in the methods of analysis can occur automatically responsive to a queue. The output can be provided in the format of a computer file. In some embodiments, the output is a FASTA file, VCF file, text file, a .bedGraph file or an XML file containing sequence data, such as a sequence of the nucleic acid aligned to a sequence of a reference genome.

In some embodiments, the sequence reads may be analyzed computationally to identify the ends of the fragments (from which the transposon cleavage sites can be inferred). In some embodiments, one end of a fragment can be defined by sequence that is at the beginning of a sequencing read and the other end of the fragment can be defined by sequence that is at the beginning of a second sequencing read, where the first and second sequencing reads were obtained by paired end sequencing (e.g., using Illumina's sequencing platform), e.g. resulting in paired-end reads R1 and R2. The same information can be obtained from examining the beginning and end of longer sequence reads (e.g., having the sequence of both adaptors; one at one end and the other at the other end). In some embodiments, a single sequence read may contain both adaptor sequences, in which case both ends of a fragment (which correspond to two cleavage sites for the two separate transposases) can be inferred from a single sequence read. The lengths of the fragments can be calculated by, e.g., mapping the fragment ends onto the nucleotide sequence of the region of interest, and counting the number of base pairs between those positions. The information used may be obtained using the nucleotide sequences at the beginning and/or the end of a sequence read.

In some embodiments, sequence information corresponding to epigenetic or epigenomic data based on large-scale sequencing, e.g., high throughput sequencing or next generation sequencing, e.g., results from ATAC-seq, which may contain forward (R1) and/or reverse (R2) reads, can contain about or at least about $10^6$, $10^7$, $10^8$, $2\times10^8$, $3\times10^8$, $4\times10^8$, $5\times10^8$, $10^9$, $10^{10}$ or more target polynucleotide reads or clusters, e.g., may comprise about, less than about or more than about $2\times10^6$, $3\times10^6$, $4\times10^6$, $5\times10^6$, $10^7$, $10^8$ or more target polynucleotides or clusters for each sample in the reaction.

In some embodiments, raw data from a high-throughput sequence, which can be in compressed form, can be retrieved, such as from any storage location, e.g. cloud-based storage or downloaded on a computing cluster. Exemplary scripts or tools for retrieving data include get_bcl, e.g. base calls in the form of a .bcl file. In some embodiments, the data from a sequencer run can be decompressed for processing using downstream tools, e.g. using the script untar_bcls. The output sequencing data can be in any of a variety of output data file types or formats, including, but not limited to, *.bcl, *.fasta, *.csfasta, *seq.txt, *qseq.txt, *.fastq, *.sff, *prb.txt, *.sms, *srs and/or *.qv. In some embodiments, one or more processing steps, functions, processes or scripts include converting the format of the sequencing data output from into formats that can be used in further steps of the methods of analysis or for display, e.g., in particular graphical user interface (GUI). For example, a program termed bcl2fastq can be used to convert .bcl raw base call files into compressed FASTQ files. In embodiments involving paired-end runs, each sample has two files, R1 and R2, corresponding to forward and reverse reads (beginning and end of each DNA fragment) respectively.

In some embodiments, raw sequencing counts is normalized for downstream steps. In some embodiments, normalization includes estimating sizing factors and dispersion, and performing a negative binomial generalized linear model fit. In some embodiments, such steps can be assessed using scripts or tools such as DESeq2. In some embodiments, the normalization also includes normalization based on measures such as fraction of reads in peaks (FRiP; showing enrichment of signal, calculated as (number of reads in peaks)/(number of total reads)). In some embodiments, FRiP-normalized counts can be determined (e.g., with variable betaPrior set as true).

In some embodiments, processing steps to retrieve and decompress compressed files generated by any of the steps. In some embodiments, exemplary steps to retrieve compressed files, e.g., compressed FASTQ files and move the files into analysis directories sorted by samples, include a program termed get_data. In some embodiments, exemplary steps to decompress files, e.g., decompressing compressed FASTQ files so they can be processed by downstream tools, including a program termed unzip.

In some aspects, statistics to indicate the quality of the sequences, e.g., overall statistics for sequencing runs, base calling quality, contamination, overclustering, can be generated using scripts or tools, e.g., fastqc.

In some embodiments, sequences identified in one or more sequencing reads for a plurality of clusters are positionally mapped to a reference sequence, e.g., a reference genome. In general, mapping involves placing one sequence along another sequence, iteratively introducing gaps along each sequence, scoring how well the two sequences match, and, in some aspects, repeating for various positions along the reference sequence. The best-scoring match is deemed to be the mapping and represents an inference about the degree of relationship between the sequences. In some embodiments, a reference sequence to which sequencing reads are compared is a reference genome, such as the genome of a member of the same species as the subject. A reference genome may be complete or incomplete. In some embodiments, a reference genome contains only regions containing target polynucleotides. In some embodiments, a reference sequence comprises or consists of a human genome. In some embodiments, a reference sequence comprises or consists of sequences of polynucleotides of one or more organisms other than the subject or from whom a sample is taken. In some embodiments, a reference sequence comprises or consists of a plurality of known sequences, such as all probe sequences used to amplify target polynucleotide sequences (e.g. every sequence B and/or sequence B' for every different target polynucleotide). Sequencing data generated from the extension of one primer (e.g. R1 sequences from forward primer) may be mapped to the same or different reference sequence as sequencing data generated from the extension of another primer (e.g. R2 sequences from reverse primer). Sequencing data generated from the extension of one primer may be mapped to a reference sequence two or more times, with each mapping using a different mapping algorithm. R1 sequences may be mapped independently of R2 sequences.

In some embodiments, exemplary steps for positional mapping of the reads from the sequencing reads, include, e.g., steps, functions, processes or scripts termed get_genome, build_bowtie2_index, Index_genome_fasta and map_atac_reads. Exemplary steps for positional mapping include e.g., steps for fetching appropriate genome files for the specified organism and version from their online sources, such as get_genome; steps for indexing genome files so that reads can be positionally mapped to the genome, using bowtie2_build and/or build_bowtie2_index; steps for building a FASTA index for the downloaded genome files to allow positional access by downstream tools, such as Index_genome_fasta and steps for mapping ATAC-seq sequences reads to the genome to determine their position, using bowtie2 and/or map_atac_reads.

In some embodiments, the reference genome is the human genome. In some embodiments, the reference genome sequence is the NCBI36/hg18 sequence. Alternatively, the reference genome sequence is the GRCh37/hg19. Other sources of public sequence information include GenBank, dbEST, dbSTS, EMBL (the European Molecular Biology Laboratory), and the DDBJ (the DNA Databank of Japan). A number of computer algorithms are available for aligning sequences, including without limitation BLAST (Altschul et al., 1990), BLITZ (MPsrch) (Sturrock & Collins, 1993), FASTA (Person & Lipman, 1988) or BOWTIE (Langmead et al., (2009) Genome Biology 10:R25.1-R25.10).

Other examples of mapping or alignment programs include: BLAT from Kent Informatics (Santa Cruz, Calif.) (Kent, W. J., Genome Research 4: 656-664 (2002)); SOAP2, from Beijing Genomics Institute (Beijing, Conn.) or BGI Americas Corporation (Cambridge, Mass.); Bowtie (Langmead, et al., Genome Biology, 10:R25 (2009)); Efficient Large-Scale Alignment of Nucleotide Databases (ELAND) or the ELANDv2 component of the Consensus Assessment of Sequence and Variation (CASAVA) software (Illumina, San Diego, Calif.); RTG Investigator from Real Time Genomics, Inc. (San Francisco, Calif.); Novoalign from Novocraft (Selangor, Malaysia); Exonerate, European Bioinformatics Institute (Hinxton, UK) (Slater, G., and Birney, E., BMC Bioinformatics 6:31(2005)), Clustal Omega, from University College Dublin (Dublin, Ireland) (Sievers F., et al., Mol Syst Biol 7, article 539 (2011)); ClustalW or ClustalX from University College Dublin (Dublin, Ireland) (Larkin M. A., et al., Bioinformatics, 23, 2947-2948 (2007)); and FASTA, European Bioinformatics Institute (Hinxton, UK) (Pearson W. R., et al., PNAS 85(8):2444-8 (1988); Lipman, D. J., Science 227(4693):1435-41 (1985)). In some embodiments, one end of the clonally expanded copies of the sequences are processed by bioinformatics alignment analysis for the Illumina Genome Analyzer, which uses the ELAND software. In some aspects, the analysis can include steps for genome browser visualizations.

In some embodiments, an output file is generated containing sequence data such as a sequence of the nucleic acid aligned to a sequence of the reference genome. In other embodiments, the output contains coordinates or a string describing one or more mutations in the subject nucleic acid relative to the reference genome and/or other epigenetic or epigenomic data alignments. Alignment strings known include Simple UnGapped Alignment Report (SUGAR), Verbose Useful Labeled Gapped Alignment Report (VULGAR), and Compact Idiosyncratic Gapped Alignment Report (CIGAR) (Ning, Z., et al., Genome Research 11(10): 1725-9 (2001)). In some embodiments, the output is a sequence alignment, such as, for example, a sequence alignment map (SAM) or binary alignment map (BAM) file, comprising a CIGAR string (the SAM format is described, e.g., in Li, et al., The Sequence Alignment/Map format and SAMtools, Bioinformatics, 2009, 25(16):2078-9). In some embodiments, CIGAR displays or includes gapped alignments one-per-line. CIGAR is a compressed pairwise alignment format reported as a CIGAR string.

In some embodiments, aligned sequence files can be converted into a different file format for analysis using downstream tools. In some embodiments, such steps for conversion include steps to convert BAM alignment files into a file format usable by downstream HOMER tools, e.g., using make_homer_tagdir.

In some embodiments, R1 sequence from a cluster comprises forward sequences from a plurality of different target polynucleotides and R2 sequence from a cluster comprises reverse sequences. When each reverse sequence is selected to target a specific target polynucleotide, its sequence and location within the reference sequences (e.g. reference genome) is generally known, and R1 sequences from the same cluster may be expected to fall within an anticipated nucleotide distance. An anticipated nucleotide distance may be based on an average or median fragment length for samples comprising fragmented sample polynucleotides, or an upper threshold distance representing an unlikely fragment length based on such median or average fragment length. Thus, in some embodiments, an R1 sequence that aligns to a position further away than the threshold distance from the R2 sequence from the same cluster may be erroneous and is discarded. In some embodiments, the upper threshold distance along a reference sequence between aligned R1 and R2 sequences from the same cluster, above which sequence reads for a cluster are discarded, is about, or more than about 1,000, 2,500, 5,000, 7,500, 10,000, 12,500, 15,000, 20,000 or more base pairs. In some embodiments, alignments of R1 sequences to non-unique regions of a reference sequence (e.g. a reference genome) are discarded and the sequences re-aligned to a smaller subset of unique sequences within the reference sequence.

In some embodiments, sequencing reads can be duplicative, and duplicative sequences can be removed following an initial positional mapping and/or alignment. When sequencing reads are mapped, duplicative reads may be marked as duplicates by the alignment algorithm. For example, a mark duplicates subroutine within the alignment algorithm examines all of the records in a file of aligned sequences (e.g. a *.BAM file) and decides which reads are duplicates of other reads. In some embodiments, one or more of the two general types of duplicates can exist: optical duplicates, which may be typically caused by defects in the primary analysis software, and PCR duplicates, which may be caused by duplicative PCR reactions.

In some embodiments, the method of analysis involves removal of duplicate reads, e.g., to improve quantitative accuracy. In some embodiments of the methods of analysis, steps, functions, processes or scripts are used to remove duplicative sequences, e.g., to flag and remove duplicate reads arising from PCR amplification bias and cluster miscalling. In some embodiments, such steps can reduce the amount of noise in the datasets. In some embodiments, the steps can include algorithms or programs for proper sorting of naming and indexing of the reads post-mapping, and outputs idxstats files that give mapped counts per chromosome. In some embodiments, exemplary steps to remove duplicates and further indexing include a step for flagging and removing duplicate reads arising from PCR amplification bias and cluster miscalling, to reduce the amount of noise in the datasets, e.g., using a script or tool termed Picard_remove_duplicates. In some aspects, Picard or similar scripts or tools can be used to calculate and visualize the distribution of fragment sizes recovered, e.g., using a script or tool termed atac_insert_size_metrics and calculate statistics about the positional distribution of reads into various types of genomic features, e.g., using a script or tool termed atac_alignment_summary.

In some embodiments, the analysis involves removal of mitochondrial reads and/or additional contaminating sequences based on sequence identity, quality, mapping location, or other sequencing properties of the reads. In some embodiments, the method of analysis involves removal of reads that map to the mitochondrial genome, mitochondrial reads and/or additional contaminating sequences. In some aspects, mitochondrial reads are major contaminants in ATAC-seq libraries that can contribute a large proportion of the sequence reads, e.g., up to 80%, and can reduce the accuracy of downstream steps. In some embodiments, the removal is based on sequence identity, quality, mapping location, or other sequencing properties of the sequencing reads. In some embodiments, exemplary steps for removing mitochondrial reads and/or additional contaminating sequences include steps for filter_mtDNA_reads. In some embodiments, the method of analysis involves retaining and comparing mitochondrial reads.

In some embodiments, analysis involves the separation of sequence reads into subsets representing a specific epigenetic property, e.g. chromatin accessibility or chromatin occupancy. In some embodiments, the size of the sequenced fragment can be used to determine the degree or level to which it represents said property. In some embodiments, the number of reads and/or a normalized number of reads within one or more genomic regions, loci, elements or intervals can be used to determine the degree or level to which it represents said property. In some embodiments, the differences in specific quantity or quality of signal in one or more genomic regions, loci, elements or intervals, can be used to determine the degree or level to which it represents said property.

In some embodiments, analysis involves the shifting of a fixed number of positions of the mapped reads, e.g., about 3, 4, or 5 base pairs, in a specific strand direction, to account for the shift in sequence reads based on the nature of the transposase, e.g., Tn5 transposase, and library preparation. In some embodiments, exemplary steps for shifting read positions include shift_atac_alignments.

In some embodiments, the method of analysis involves assessing or measuring sequence reads of the ATAC-seq fragments. The degree of accessibility of the DNA is associated with more sequence reads of the fragments, such that the signal from sequence reads form peaks that can be detectable or measured, such as by using peak calling tools, scripts or algorithms. In some embodiments, the provided methods include steps for assessing, depicting, or determining peaks of signal, representing DNA in one or more regions of the genome that is accessible. In some aspects, a peak signal of sequence reads is a region with enriched signal, signal above background, or higher signal compared to surrounding regions. In some embodiments, ATAC-seq peaks can be overlaid with a genomic locus region map or a genome map. The identity of a region(s) that are enriched for or depleted of accessibility and/or occupancy signal as measured by quantifying ATAC-seq fragments, e.g. peak signals, can be determined from its position as mapped on the reference genome. The regions can be further categorized into the various regulatory element types—promoters, enhancers, insulators, etc. by integrating further genomic and epigenomic data such as information about histone modifications or evidence for active transcription (Buenrostro et al. (2013) Nature Methods, 10:1213-1218).

In some embodiments, accessible regions, e.g. ATAC-seq fragments, can be between about 5 and about 20,000 bp in size, such as between about 10 and about 10,000 bp, about 50 and about 5,000 bp, about 100 and about 1,000 bp, about 200 and about 900 bp, about 300 and about 800 bp, about 400 and about 700 bp, about 500 and about 600 bp, about 10 and about 500 bp, about 20 and about 400 bp, about 30 and about 300 bp, about 40 and about 200 bp, about 40 and about 100 bp, about 50 and about 100 bp, about 60 and about 100 bp, about 70 and about 100 bp, about 80 and about 100 bp, about 90 and about 100 bp, about 100 and about 500 bp, about 200 and about 500 bp, about 300 and about 500 bp, about 400 and about 500 bp, about 100 and about 400 bp, about 100 and about 300 bp or about 100 and about 200 bp, in size.

In some embodiments, the methods include steps, functions, processes or scripts that can find, determine and/or annotate peaks of signal, e.g. by using peak-calling tools, scripts or algorithms. In some embodiments, peak calling can be carried out on a particular sample and/or present in one or more biological replicates of the sample and/or present in one or more different samples. In some embodiments, peak calling allows discrimination between signal and noise. In some aspects, peak calling can include one or more steps such as estimating fragment length and adjusting read position, identifying local noise, identifying enriched or peak regions and/or estimating false discovery rate (FDR). In some aspects, the called peaks can be broad. In some aspects, the called peaks can be narrow. Any of a variety of peak-calling scripts are available and can be used. In some embodiments, exemplary peak-calling scripts, algorithms or software include MACS, MACS2, Epic, SICER, Bayes-PEak, homer_findPeak, Jmosaics, T-PIC, EDD, GEM or SPP In some aspects, peak-calling is performed using MACS or MACS2. In some embodiments, exemplary peak-calling steps, functions, processes or scripts can include Model-based Analysis of ChIP-Seq (MACS) or MACS2, such as the macs_callpeaks step described herein, for calling accessibility peaks. In some embodiments, the MACS or MACS2 peak calling uses a sample-swapping strategy to estimate the false discovery rate (FDR) by calling both sample peaks over the control and control peaks over the sample. In some embodiments, such peak calling step can scale the larger of a dataset to the smaller of the dataset using total library size, for normalization. In some embodiments, the peaks include genomic regions that are enriched for or depleted of accessibility and/or occupancy signal as measured by quantifying ATAC-seq fragments. In some embodiments, peak regions can be between 10 and 10,000 bp in size. Comparison of peaks between samples may be used downstream to identify active regulatory elements (e.g., associated with specific genes or transcription factors) between conditions and/or be used to identify signatures of specific cell states or predictive of outcome of cell therapy, potency of cell therapy, toxicity and/or other characteristics of the cell composition or culture.

Other exemplary peak-calling steps, functions, processes or scripts can include steps for finding peaks using HOMER, in some embodiments including a script and/or tool identified as homer_findPeaks. In some embodiments, steps to search for motifs, e.g., enriched transcription factor binding motifs shared within the peak sets discovered by MACS and HOMER, can be employed, e.g., using a script or tool termed homer_find_motifs.

After peak calling, other steps, functions, processes or scripts, such as peak annotation steps, such as annotating peaks with additional metadata including the nearest gene they are likely to be associated with, e.g., using homer_annotate_peaks or other annotation strategies, can be used to facilitate further analysis. In some embodiments, other steps for annotation includes retrieving transcriptome annotation files associated with the organism and genome version that the pipeline is running, e.g., using get_gtf_annotation, and/or retrieving subsets of annotations, e.g., annotated transcriptome that only includes protein coding transcripts, e.g., using gtf_coding_transcripts_only.

In some aspects, the methods include generating a consensus set or sets of peaks, e.g., consensus peak accessibility, from common or overlapping peaks present in multiple biological replicates and/or in two or more samples. In some embodiments, exemplary peak-calling scripts, algorithms or software for generating a consensus peak from common or overlapping peaks in two or more samples is DiffBind.

In some embodiments, the provided methods and assay includes making an epigenetic map (also called an epigenetic profile) of a region of the genome of the cells. In some aspects, the epigenetic map depicts the epigenetic state across a plurality of different regions, e.g. coding sequences, intergenic spacers, regulatory regions, e.g. promoters, etc, of the entire genome, a portion of the genome or near or around or within a particular gene or genes. This step may be done by mapping information obtained from the sequence reads to the region. In some embodiments, the sequence reads are analyzed computationally to produce a number of numerical outputs that are mapped to a representation (e.g., a graphical representation) of a region of interest. Exemplary information for mapping include, but are not limited to: (i) cleavage sites for the transposase; (ii) the sizes of the fragments produced; (iii) fragment length; (iii) the positions of sequence reads of a defined range in length; and (iv) sequence read abundance, e.g. peak signal.

In some embodiments, sequence read abundance, i.e., the number of times a particular sequence in a genomic region is represented in the sequence reads, may be calculated. In certain cases, an epigenetic profile or map depicting peak signals of sequence reads, e.g. as determined using peak-calling tools, can be generated. The resultant epigenetic map can provide an analysis of the chromatin in the region of interest. For example, depending on which information is mapped, the map can show one or more of the following: chromatin accessibility along the region; DNA binding protein (e.g., transcription factor) occupancy for a site in the region; nucleosome-free DNA in the region; positioning of nucleosomes along the region; and chromatin states along the region. In some embodiments, the assay further involves measuring global occupancy of a binding site for the DNA binding protein by, e.g., aggregating data for one DNA binding protein over a plurality of sites to which that protein binds. In some instances, the map can also be annotated with sequence information, and information about the sequence (e.g., the positions of promoters, introns, exons, known enhancers, transcriptional start sites, untranslated regions, terminators, etc.) so that the epigenetic information can be viewed in context with the annotation. In some embodiments, computationally implemented scripts or tools can be used to generate epigenetic/epigenomic maps. Exemplary steps include creating genome-wide fragment counts and visualizing the counts on a genome browser. Exemplary scripts or tools that can be utilized include make_homer_ucsc_file, which can create a bedGraph file which allows for genome-wide pileups of fragment counts; and homer_bedgraph_to_bigwig which can convert the bedGraph file to a binary-compressed bigWig file, used by most genome browsers to visualize fragment coverage across the genome.

In some aspects, the analysis includes generating a metric associated with particular elements of a gene. In some aspects, such metrics include accessibility over a promoter of an annotated gene, or over the coding region of an annotated gene. In some aspects, the analysis includes generating a metric such as normalized accessibility count metric for the promoter region of each gene (promoter accessibility). In some embodiments, annotation and generation of metric can be used for further downstream analysis, e.g., comparing epigenetic profiles, clustering and/or biological pathway analysis. In some embodiments, such steps can be computationally implemented using scrips or tools, e.g., to annotate genes and/or regulatory elements. In some embodiments, tools such as ChIPpeakAnno or Homer can be used. In some embodiments, regulatory elements, such as the promoter region, or region including the transcription start site (TSS) can be defined. In some aspects, the TSS can be defined, e.g., as the proximal 500 bp, 1000 bp, 1500 bp, or 2000 bp upstream and 500 bp, 1000 bp, 1500 bp, or 2000 bp downstream of the promoter. In some aspects, the counts can be normalized, e.g., based on FRiP. In some aspects, promoter accessibility can be used as a metric associated with a gene.

In some embodiments, the epigenetic map can provide information regarding active regulatory regions and/or the transcription factors that are bound to the regulatory regions. For example, nucleosome positions can be inferred from the lengths of sequencing reads generated. In some embodiments, transcription factor binding sites can be inferred from the size, distribution and/or position of the sequencing reads generated. In some embodiments, novel transcription factor binding sites can be inferred from sequencing reads generated. In some embodiments, novel transcription factors can be inferred from sequencing reads generated.

In some aspects, if biological or technical replicates were performed, replicates can be evaluated to assess the quality and fidelity of the methods. In some embodiments, replicates can be evaluated using interval analysis. In some embodiments, Venn diagram of common and unique peaks can be used to assess replicates. In some embodiments, counts for each replicate, e.g., log 2 normalized counts, can be plotted on an X-Y plot, and correlation coefficients, e.g., Spearmann correlation, can be calculated to assess replicates.

In some aspects, quality control metrics can be assessed to determine the quality of sequence information and data from the epigenetic/epigenomic analysis. Exemplary control metrics include Fraction of reads in peaks (FRiP), Non-Redundant Fraction (NRF), PCR Bottleneck Coefficient (PBC), Relative strand cross-correlation (RSC), normalized strand cross-correlation (NSC) and Irreproducible Discovery Rate (IDR), determining unmapped, unpaired reads, percent duplication, mtDNA contamination, number of unique peaks, total mapped reads (sequencing depth) and effective sequence depth (redundant vs. nonredundant). In some embodiments, the sequence reads from a sample contain less than 15%, less than 10%, less than 8%, or less than 6% unpaired or unmapped reads. In some aspects, the fraction of duplicate reads can be dependent on input and mtDNA contamination. In some aspects, low mtDNA can also be an indicator of poor enrichment or coincides with an aspirated pellet. In some aspects, the number of total mapped reads (sequencing depth) is at least $10^5$, $10^6$, $10^7$ or $10^8$ or more reads. In some aspects, the effective sequence depth is at least $10^5$, $10^6$, $10^7$ or $10^8$ or more reads. In some aspects, low FRiP can indicate poor enrichment of the samples. In some aspects, the FRiP of the sample is at least 0.05, 0.1, 0.2, 0.3 or more.

2 Samples for Assessment

In some embodiments, the epigenetic and/or epigenomic state is measured, assessed, and/or determined in a sample, such as a sample containing cells or cell compositions. In some embodiments, the sample is a biological sample that is taken, collected, and/or obtained from a subject and/or contains cells that are taken, collected, and/or obtained from a subject. In certain embodiments, the subject has a disease or condition and/or is suspected of having a disease or condition. In some embodiments, subject has received, will receive, or is a candidate to receive a therapy. In some embodiments, the therapy is an administration of a cell therapy and/or an immunotherapy. In certain embodiments, the cell therapy treats and/or is capable of treating the disease or condition. In some embodiments, the cells or cell compositions in the sample contain cells for cell therapy. In some embodiments, the therapy is a cell therapy that contains one or more engineered cells. In some embodiments, the engineered cells express a recombinant receptor. In some embodiments, the recombinant receptor is a chimeric antigen receptor (CAR) or a recombinant T cell receptor (TCR).

In some embodiments, the sample is taken, collected, and/or obtained from a subject who has been, who will be, or is a candidate to be administered a therapy. In some embodiments, the sample is taken, collected, and/or obtained prior to treatment or administration with the therapy, e.g., the cell therapy. In some embodiments, the sample is taken, collected, and/or obtained after treatment or administration with the therapy, e.g., the cell therapy.

In certain embodiments, the sample contains, is taken, is derived, and/or originates from a cell or cell composition. In some embodiments, the cell is contained in the sample. In some embodiments, the sample contains a cell that is taken from, originates from, and/or is derived from a biological sample and/or the same source as the biological sample. In some embodiments, the cell, e.g., a cell from a biological sample and/or from the same source as the biological sample, is one that has been generated in connection with processing and preparing engineered cells, such as for use in adoptive cell therapy and/or those formulated for such use, e.g., in a pharmaceutical composition comprising a pharmaceutically acceptable recipient and/or cryopreservative. In some embodiments, a cell, e.g., a cell from a biological sample and/or from the same source as the biological sample, assessed by the methods, which may in some aspects be a control cell or cells or reference cell or cells.

In some embodiments, cells of the biological sample, and/or of the same source as the biological sample, assessed by the methods and/or compositions provided have been transduced or are to be transduced to contain a heterologous nucleic acid and/or nucleic acid encoding a heterologous protein or other nucleic acid or polypeptide product, e.g., a recombinant protein. In some embodiments the heterologous nucleic acid encodes a binding molecule, such as a recombinant receptor, such as a chimeric antigen receptor (CAR) or transgenic T cell receptor (TCR). In some embodiments, the cell is comprised by populations of such cells, compositions containing such cells and/or enriched for such cells, such as in which cells expressing the binding molecule make up at least 15%, 20%, 25%, 30%, 35%, 40%, 50%, 60%, 70%, 80%, 90%, 91%, 92%, 93%, 94%, 95%, 96%, 97%, 98%, 99%, or more percent of the total cells in the composition or cells of a certain type such as T cells, such as CD8+ and/or CD4+ T cells. In some embodiments, the cells are primary T cells. Among the compositions are pharmaceutical compositions and formulations for administration, such as for adoptive cell therapy.

In some aspects, the sample, e.g., a sample containing the cells, is derived or isolated from blood or a blood-derived sample, or is or is derived from an apheresis or leukapheresis product. Exemplary samples include whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. Samples include, in the context of cell therapy, e.g., adoptive cell therapy, samples from autologous and allogeneic sources.

In some embodiments, the sample includes chromatin preparations from genetically engineered cells expressing the heterologous nucleic acid and/or nucleic acid encoding a heterologous protein or other nucleic acid or polypeptide product, e.g., a human or human-derived recombinant protein. In some embodiments, the cells generally are eukaryotic cells, such as mammalian cells, and typically are human cells. In some embodiments, the cells, e.g., the cells of the sample and/or of the biological sample, are derived from the blood, bone marrow, lymph, or lymphoid organs, are cells of the immune system, such as cells of the innate or adaptive immunity, e.g., myeloid or lymphoid cells, including lymphocytes, typically T cells and/or NK cells. Other exemplary cells include stem cells, such as multipotent and pluripotent stem cells, including induced pluripotent stem cells (iPSCs). In some embodiments, the cells are primary cells, such as those isolated directly from a subject and/or isolated from a subject and frozen.

In some embodiments, the cells are T cells, such as CD4+ T cells and/or CD8+ T cells, and/or natural killer (NK) cells. In some embodiments, the cells are monocytes or granulocytes, e.g., myeloid cells, macrophages, neutrophils, dendritic cells, mast cells, eosinophils, and/or basophils. In some embodiments, the cells or cell compositions include T cells. In some embodiments, the cells or cell compositions include CD4+ cells. In some embodiments, the cells or cell compositions include CD8+ cells.

In some embodiments, the cells and/or reference cells can be from any source. In some embodiments, the cells are isolated or obtained from a subject, e.g., a human subject. In some embodiments, the cell includes a plurality of cells or a population of cells. The cells may be isolated from a soft tissue or from a bodily fluid, or from a cell culture that is grown in vitro. In some embodiments, the chromatin may be isolated from cells from a soft tissue such as brain, adrenal gland, skin, lung, spleen, kidney, liver, spleen, lymph node, bone marrow, bladder stomach, small intestine, large intestine or muscle. In some embodiments, the cells are from a body fluid of a subject, e.g., blood, plasma, saliva, mucous, phlegm, cerebral spinal fluid, pleural fluid, tears, lactal duct fluid, lymph, sputum, cerebrospinal fluid, synovial fluid, urine, amniotic fluid, or semen. In some embodiments, the cells may be obtained from a culture of cells, e.g., a cell line.

In some embodiments, the cells include cells that were previously subject to modification, e.g., genetic engineering. In some embodiments, the cells include cells obtained from a subject that are engineered or modified, e.g., engineered to express a recombinant receptor. In some embodiments, the cells include cells obtained from a subject but have not been subject to genetic engineering. In some embodiments, the cells include cells obtained from a subject, and the methods provided herein can be performed in samples of the cells before or after engineering or modification of the cells. In some embodiments, the cells include cells have been selected or purified from a biological sample from a subject, e.g., blood. In some embodiments, the cells include a subset of cells that express a particular cell surface expression marker.

In some embodiments, the nucleic acid (e.g. genomic DNA, chromosomal DNA) to be assessed is from blood cells, e.g. blood cells from a sample of whole blood or a subpopulation of cells in whole blood. Subpopulations of cells in whole blood include platelets, red blood cells (erythrocytes), platelets and white blood cells (i.e., peripheral blood leukocytes, which are made up of neutrophils, lymphocytes, eosinophils, basophils and monocytes). White blood cells can be further divided into two groups, granulocytes (which are also known as polymorphonuclear leukocytes and include neutrophils, eosinophils and basophils) and mononuclear leukocytes (which include monocytes and lymphocytes). Lymphocytes can be further divided into T cells, B cells and NK cells. Peripheral blood cells are found in the circulating pool of blood and not sequestered within the lymphatic system, spleen, liver, or bone marrow.

In some embodiments, the population of cells may be selected by selection methods such as fluorescence activated cell sorting (FACS) or magnetic activated cell sorting (MACS), from a heterogeneous population of cells, e.g., blood, by known methods using labeled antibodies to cells surface markers. A wide variety of cells can be isolated using these methods, including stem cells, cancer stem cells and subsets of blood cells. Exemplary cells that may be selected from blood by FACS or MACS and exemplary markers used include: T cells (CD3+ CD4+CD8+), B cells (CD19+ CD20+), dendritic cells (CD11c+ CD20+), NK Cell (CD56+), stem cells/precursor cells (CD34+; hematopoietic stem cells only), macrophage/monocytes (CD14+ CD33+), granulocytes (CD66b+), platelet (CD41+ CD61+ CD62+), erythrocytes (CD235a+), enothelial cells (CD146+) and epithelial cells (CD326+). Subsets of these cells can be isolated using antibodies to further cell surface markers.

In some embodiments, the cells, e.g., cells in the sample, such as biological sample, and/or from the same source as the biological sample, include one or more nucleic acids introduced via genetic engineering, and thereby express recombinant or genetically engineered products of such nucleic acids. In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature, including one comprising chimeric combinations of nucleic acids encoding various domains from multiple different cell types.

In some embodiments, the epigenetic and/or epigenomic properties, states and/or profiles can be assessed at any point in the preparation, production, or manufacture of transduced or engineered cells, including cells that are or will be or have been transduced for use in adoptive cell therapy, and post-therapy monitoring of the subject. Exemplary steps for processing cells include steps involved in the isolation, separation, selection, cultivation (e.g., stimulation of the cells, for example, to induce their proliferation and/or activation), transducing, washing, suspension, dilution, concentration, and/or formulation of the cells, including those known and/or described herein. In particular embodiments, the processing steps include transduction of the cells with viral vector particles, where at least a part of the incubation with the viral vector particles is performed in a closed system or chamber to initiate transduction. The methods may further and/or alternatively include other processing steps, such as steps for the isolation, separation, selection, cultivation (e.g., stimulation of the cells, for example, to induce their proliferation and/or activation), washing, suspension, dilution, concentration, and/or formulation of the cells. In some embodiments, the cells or cell composition includes cells that have been subjected to transduction and then cultured, for example at 37° C., for greater than or greater than about 1 day, 2 days or 3 days, such as generally greater than 4 days, 5 days, 6 days, 7 days, 8 days, 9 days, 10 days, 11 days, 12 days, 13 days, 14 days or more.

In some embodiments, the cells or cell composition comprises cells at any stage of a genetic engineering manufacturing process. In some embodiments, the sample contains nucleic acid and/or chromatin preparation derived from cells at any stage of a genetic engineering manufacturing process. For example, the sample may comprise nucleic acid and/or chromatin preparation from cells that have been transduced with a viral vector particle encoding a recombinant and/or heterologous molecule. In some embodiments, the sample contains cells, e.g. autologous or allogeneic cells, engineered by transduction with a heterologous nucleic acid encoding a recombinant antigen receptor (e.g., CAR) and cultured or expanded, such as for use in connection with adoptive cell therapy. In some cases, the sample contains nucleic acid and/or chromatin preparation from such transduced cells that have been cryopreserved, which, some aspects, is referred to as a cryopreserved drug product (CDP). In some cases, the sample contains nucleic acid and/or chromatin preparation from such transduced cells that have been formulated for administration to a subject, which, some aspects, is referred to as a formulated drug product (FDP).

In some embodiments, the sample is obtained from a subject after such subject has received a therapy comprising cells that have been transduced, such as with a viral vector particle encoding a recombinant and/or heterologous molecule, e.g., a CAR. In some embodiments, as a control, the provided methods can be performed on a patient-matched control sample that has not been subjected to transduction and/or genetic engineering, which can be a sample containing the selected or enriched cells to be used for transduction. In some embodiments, such a patient-matched control sample can be a cryopreserved sample, which, in some cases, is referred to as a cryopreserved material (CMAT). In some embodiments, nucleic acid and/or chromatin preparation is isolated from cells. In some cases, the nucleic acid and/or chromatin preparation is isolated from about $1 \times 10^4$, $1 \times 10^5$, $1 \times 10^6$, $1 \times 10^7$, or more cells. In some embodiments, nucleic acid and/or chromatin preparation is isolated from $1 \times 10^6$ cells. In some cases, the nucleic acid and/or chromatin preparation is isolated from all or substantially all of the cells comprised by a sample or selected portion thereof.

In some embodiments, cells are incubated with a cell stimulating agent or agents that is/are a cell-binding agent, such as an antigen-binding reagent, such as antibody, that is able to induce intracellular signaling and/or cell proliferation. In some embodiments, cells are incubated with, including mixed with, anti-CD3/anti-CD28 beads.

In accord with the methods described herein, the sample can be assessed for one or more epigenetic and/or epigenomic properties, e.g., chromatin accessibility profiles as determined by ATAC-seq. In some aspects, the provided methods can be used to assess, evaluate and/or characterize cells and/or cell compositions in the sample, at various stages of engineering, e.g., prior to engineering or after engineering to express a recombinant receptor. In some aspects, the epigenetic and/or epigenomic properties can be used to assess the quality, consistency and/or characteristics of the cells or cell compositions for administration, and/or to identify subjects, prior to receiving a cell therapy, who is likely to exhibit a desired outcome, e.g., respond to the cell therapy and/or who may be at risk of developing a toxicity.

In some embodiments, the sample is taken, collected, and/or obtained prior to engineering of the cells. In some embodiments, the sample is taken, collected, and/or obtained subsequent to engineering of the cells. In some embodiments, the sample is taken, collected, and/or obtained subsequent to treatment or administration with the therapy, e.g., the cell therapy. In accord with methods, kits and articles of manufacture described herein, the sample can be assessed for one or more epigenetic and/or epigenomic properties prior to or after receiving the immunotherapy. In some embodiments, the sample is collected within or about within or about 30 minutes, 1 hours, 2 hours, 3 hours, 4 hours, 5 hours, 6 hours, 8 hours, 10 hours, 12 hours, 14 hours or more prior to engineering the cells, e.g., to express a recombinant receptor. In some embodiments, the sample is collected within or about within or about 30 minutes, 1 hours, 2 hours, 3 hours, 4 hours, 5 hours, 6 hours, 8 hours, 10 hours, 12 hours, 14 hours or more following engineering the cells, e.g., to express a recombinant receptor. In some embodiments, the sample is collected within or within about 30 minutes, 1 hours, 2 hours, 3 hours, 4 hours, 5 hours, 6 hours, 8 hours, 10 hours, 12 hours, 14 hours or more after obtaining a sample, e.g., a blood sample, from the subject. In some embodiments, the sample is collected within or about within or about 30 minutes, 1 hours, 2 hours, 3 hours, 4 hours, 5 hours, 6 hours, 8 hours, 10 hours, 12 hours, 14 hours or more prior to initiation of administration of the immunotherapy, e.g. the cell therapy. In some embodiments, the sample is collected within or about within or about 30 minutes, 1 hours, 2 hours, 3 hours, 4 hours, 5 hours, 6 hours, 8 hours, 10 hours, 12 hours, 14 hours or more following initiation of administration of the immunotherapy, e.g. the cell therapy.

In some aspects, any of the methods provided herein can be used to determine the properties, quality and/or consistency in a cell or cell composition. In some aspects, any of the methods can be used to assess the properties, quality and/or consistency of a cell or cell composition at any one or more of the described time points, e.g., prior to engineering, mid-process of engineering, after engineering, prior to administration, during administration and/or after administration of the cell to the subject.

In some embodiments, the population of cells used in the assay may be composed of any number of cells, e.g., about 500 to about $10^6$ or more cells, about 500 to about 100,000 cells, about 500 to about 50,000 cells, about 500 to about 10,000 cells, about 50 to 1000 cells, about 1 to 500 cells, about 1 to 100 cells, about 1 to 50 cells, or a single cell. In some embodiments, the cell sample includes less than about 1000, 2000, 3000, 4000, 5000, 6000, 7000, 8000, 9000, 10,000, 15,000, 20,000, 25,000, 30,000, 40,000, 50,000, 60,000, 70,000, 80,000, 90,000, 100,000, 120,000, 140,000, 160,000, 180,000, 200,000, 250,000, 300,000, 350,000, 400,000, 450,000, 500,000, 600,000, 700,000, 800,000, 900,000, or 1,000,000 cells. In some embodiments, the cell sample includes more than about 1000, 2000, 3000, 4000, 5000, 6000, 7000, 8000, 9000, 10,000, 15,000, 20,000, 25,000, 30,000, 40,000, 50,000, 60,000, 70,000, 80,000, 90,000, 100,000, 120,000, 140,000, 160,000, 180,000, 200,000, 250, 000, 300,000, 350,000, 400,000, 450,000, 500,000, 600,000, 700,000, 800,000, 900,000, or 1,000,000 cells. In some embodiments, the methods provided herein require relatively fewer cells compared to other methods.

B. Processing and Further Analysis of Epigenetic/Epigenomic Profile

In some embodiments, the provided methods also involve additional processing and/or analysis of one or more aspects of the epigenetic/epigenomic properties and/or profile. In some embodiments, the provide methods include comparing the epigenetic/epigenomic properties and/or profile of a particular cell or cell composition to those of another cell or cell composition, e.g., comparative and/or differential analysis, or generating metrics and counts for normalization or further analysis steps. In some aspects, further processing and/or analysis includes using additional steps to analyze the sequence results, such as nucleosome occupancy analysis.

In some aspects, any one or more of the various additional processing and/or further analysis can be computationally implemented. In some embodiments, processing and/or further analysis can include, e.g., differential accessibility (differential peak) analysis, normalization measures, and assessing nucleosome occupancy/positioning. In some embodiments, the method for analyzing and identifying one or more genomic region(s), e.g., the processing and/or further analysis, can include any one or more of the steps, functions, processes or scripts, described herein, sequentially or simultaneously in any order. One or more of the steps, functions, processes or scripts can be substituted by similar algorithms, steps, functions, processes or scripts that achieve or carry out a similar function. In some embodiments, the sequential order of one or more steps can be in any order, or any one or more steps, functions, processes or scripts can be performed in parallel.

In some embodiments, the one or more of the various processing and/or further analysis can involve identification of one or more genomic region(s), e.g, coding regions, non-coding regions, intergenic regions, untranslated regions, introns, exons, cis-regulatory regions, small RNA binding sites, repeats, telomeric regions and/or accessible or non-accessible regions (e.g., open chromatin and/or heterochromatin), that correlate with an outcome of treatment with a cell therapy and/or that can be used to assess a cell composition or a cell culture, e.g., for administration to a subject. In some embodiments, the one or more genomic region(s) is identified using differences in epigenetic and/or epigenomic profiles of one or more genomic region(s) in two or more samples, e.g., samples from different subjects, from subjects with different outcomes, from subjects receiving different treatment, from different stages of cell engineering, and/or from cells subject to different conditions. In some embodiments, the one or more genomic region(s) include different peaks of signal in the epigenetic and/or epigenomic analysis. In some embodiments, the one or more genomic region(s) include regions showing different statistical parameters or metrics, e.g., mean signal, median signal, sum or total signal over a region, between two or more different samples. In some embodiments, processing and/or further analysis can be used within the framework of the other optional steps of the methods, including thresholding and clustering approaches, predictive modeling and/or differential peak calling.

1. Differential Peak Analysis

In some embodiments, the assays can be used to compare two or more samples. In some embodiments, the assay may comprise analyzing a first population of cells or first cell composition using the assay or analysis methods provided herein to produce a first epigenetic map; and analyzing a second population of cells or a second cell composition using the assay or analysis methods provided herein to produce a second epigenetic map; and comparing the first epigenetic map to the second epigenetic map, e.g., to detect any differences or changes in chromatin accessibility or transcription factor occupancy.

In some aspects, the analysis includes differential analysis, e.g., differential accessibility or differential peak analysis. In some aspects, the analysis includes comparing sequence or signal peaks present in two or more samples, and/or differential enrichment of particular sequence or signal peaks between two or more samples. The two or more samples can include cells from a first population of cells or cell composition and cells from a second population of cells or cell composition. In some aspects, the analysis includes determining peaks that are present in two more samples, and comparing the width and amplitude of the peaks or presence and absence of peaks between two or more samples.

In some embodiments, comparison of peaks between two or more samples, e.g. cell population or cell composition, can be used to identify regions, loci, elements or intervals, e.g., containing active regulatory elements and/or optionally associated with specific genes or transcription factors, that are differentially accessible in samples and/or identify signatures, e.g., signatures of peaks at or near a particular genomic region, element or interval, of specific cell states, or that is correlated with or is predictive of particular outcomes, e.g., outcome of cell therapy.

In some embodiments, differences in peaks can be determined using differential peak calling steps, functions, processes, tools or scripts, such as DESeq2, DiffBind, MAnorm, csaw, DPChIP, BADS, diffReps, DIME, HMCan-diff, ChIPDiff, MMDiff, THOR, POLYPHEMUS, GenoGAM, normR, chromstaR, PePr, ChIPComp, EpiCentr, ODIN, histoneHMM, ImpulseDE2, QChIPat, SICER, MACS2, unique Peaks, ODIN, RSEG, MAnorm, Homer, DBChIP, multiGPS, edgeR and those described in Steinhauser et al. (2016) Briefings in Bioinformatics, 17(6):953-966 or https://omictools.com/peak-calling-category. In some aspects, the methods can be used to identify peaks that exhibit differential accessibility between two or more samples. In some aspects, the methods include computing differentially bound sites from multiple samples using quantative accessibility data. In some aspects, exemplary samples that can be used for differential analysis include different cell compositions or cell types, e.g., CD4+ or CD8+ cells, or cells at different stages of engineering process, e.g., CMAT or CDP, cells from different donors, or cells subject to different treatment, e.g. treatment with drugs or incubation with agents.

In some aspects, differences in peaks can be determined using differential peak calling steps, functions, processes or scripts, such as DiffBind. In some aspects, the analysis step identifies genomic regions, loci and/or intervals that are differently present between two or more samples, and includes processing of peak sets, including overlapping and merging peak sets, counting sequencing reads overlapping intervals in peak sets, and identifying statistically significantly differentially present peak sites based on evidence of differences in read densities. In some embodiments, the analysis step identifies peak overlaps or consensus peaks, e.g., accessibility peaks present in 2 or more samples analyzed. In some embodiments, after overlaps are determined, peaks found in more than two libraries are filtered and sequencing counts are extracted. In some embodiments, measures such as fraction of reads in peaks (FRiP; showing enrichment of signal, calculated as (number of reads in peaks)/(number of total reads)) is calculated.

In some embodiments, differences or changes in peak signal between two or more samples can be determined. In some embodiments, a fold change of peak signal of one sample compared to another sample is determined, such as a control or reference sample, e.g. a sample that has not been treated or a sample that exhibits desired characteristics or outcomes, e.g., any of the reference samples described herein. In some cases, data are transformed and plotted on logarithmic scales. In certain embodiments, the logarithmic transformation is a common log ($\log_{10}(x)$), a natural log (ln(x)) or a binary log ($\log_2(x)$). In some embodiments, the data is plotted as a volcano plot depicting on the x-axis fold change, e.g. log 2 fold change, and on the y-axis the statistical significance, e.g. –log 10 of the p-value.

In some aspects, comparison of peaks between two or more samples can be used to identify active regulatory elements, optionally associated with specific genes or transcription factors, e.g., between samples or conditions and/or be used to identify signatures of specific cell states or predictive of outcomes, such as response or safety outcomes, or other characteristics of the cells or the cell composition.

In some embodiments, analysis steps that include feature selection algorithms can be used to identify regions, loci, elements or intervals that are differentially accessible in samples and/or identify signatures, e.g., signatures of peaks at or near a particular genomic region, element or interval, of specific cell states, or that is correlated with or is predictive of particular outcomes, e.g., outcome of cell therapy.

In some aspects, differential peak analysis can be performed or assessed on a genome-wide scale, or globally throughout the genome, or at particular genomic region, locus and/or interval of interest, e.g., at or near particular genes or gene panel of interest. In some aspects, differential peak analysis can be performed or assessed in a particular panel of genes, e.g., gene associated with cell-type specification, T cell differentiation and/or development, immune cell function, immune phenotype and/or transcription factors, including any gene or panel, set or module of genes described herein.

Any two samples, e.g. cell population or cell composition, can be assessed by the differential accessibility analysis. In some aspects, two or more cell samples, e.g. cell compositions, differ or are likely differ or may differ in one or more property, attribute or feature, such as related to the phenotype or function of the cells, including one or more phenotype or function of T cells, such as T cell activation state, memory phenotype, differentiation state, effector function, cytokine response, production or secretion, cytolytic activity, trafficking or migration ability, persistence or exhaustion, or related to the presence or absence of a transgene, e.g. mediated by viral-based transduction.

In some embodiments, one of the first and second cell sample, e.g. cell composition, is known to be enriched for cells, e.g. more than 75% of such cells, have or are likely to have a naïve phenotype or a long-lived memory phenotype and the other sample, e.g. other cell composition, has an unknown or undetermined memory phenotype. In some embodiments, one of the first and second cell sample, e.g. cell composition, is known to be enriched for cells, e.g. more than 75% of such cells, that are activated and the other sample, e.g. other cell composition, has an unknown or undetermined activation state. In some embodiments, one of the first and second cell sample, e.g. cell composition, is known to be uniform or homogenous or relatively uniform or homogenous, e.g. greater than 85%, 86%, 87%, 88%, 89%, 90%, 91%, 92%, 93%, 94%, 95%, 96%, 97%, 98%, 99% or more of cells in the composition or sample, exhibit one or more property, attributes or features, such as percent of CD4+ cells, CD8+ cells, level of one or more activation marker, memory marker, apoptotic or cell health marker or other marker indicative of a phenotype or function of the cell. In such an example, the other of the cell sample, e.g. cell composition, has an unknown or undetermined uniformity profile for the property, attribute or feature. In some embodiments, one of the first and second sample, e.g. cell composition, is known to have a particular average or mean number of copies of a transgene, e.g. viral vector, per cell (vector copy number (VCN)) and the other of the cell sample, e.g. cell composition, has an unknown or underdetermined VCN. Any number of desired features, attributes or properties of a cell composition can be used in connection with a differential accessibility analysis.

Other exemplary properties or features of a first and second composition include any related to differences in engineering of a cell composition, cell source, disease type or state. In some embodiments, one of the first composition and second composition comprises cells to be genetically engineered with a recombinant receptor and the other of the first composition and second composition comprises the cells engineered to express the recombinant receptor. In some embodiments, different samples, e.g. a first cell composition and second cell composition, comprise primary cells from different donors, optionally donors that differ based on disease state, severity of disease, or type of disease. In some embodiments, different samples, e.g. a first cell composition and a second cell composition, comprise cells at different stages or steps of a manufacturing process for engineering cells. In some embodiments, different samples, e.g. a first cell composition and a second cell composition, comprise cells contacted with an agent to modulate the activity, phenotype or function of the cells and the other of the first and second composition comprises similar cells not so contacted. In such an example, such an agent can include a polypeptide or protein, a peptide, an antibody, a nucleic acid, a viral vector or viral preparation, or a small molecule compound, including, for example, a stimulatory reagent, optionally anti-CD3/anti-CD28; an immunomodulatory agent, an anti-idiotype antibody or antigen-binding fragment thereof specific to the recombinant receptor, e.g. CAR, an immune checkpoint inhibitor, a modulator of a metabolic pathway, an adenosine receptor antagonist, a kinase inhibitor, an anti-TGFβ antibody or an anti-TGFβR antibody or a cytokine.

In some embodiments, the first population of cells and the second or additional population of cells are obtained from the same individual at different times. In other embodiments, the first population of cells and the second or additional population of cells are different populations of cells obtained from tissues or different individuals. In some embodiments, the first population of cells and the second or additional population of cells are obtained from different individuals and/or groups of individuals, e.g., individuals or groups of individuals exhibiting different disease severity, treatment response, treatment outcome, toxicity and/or side effects, physiological response, molecular and/or functional activity of the cells and/or phenotype. In some embodiments, different samples, e.g. a first cell composition and a second cell composition, comprises a sample of a cell composition associated with an outcome that occurs or has occurred with the one but not the other of the first and second composition following administration to a subject.

Exemplary cells for comparison that can be used in the methods include, for example, cells isolated from normal subjects, cells isolated from subjects that have not been subject to engineering, cells isolated from subjects that show complete response, cells isolated from subjects that show durable response, and/or cells isolated from subjects prior to or after a particular treatment. In some embodiments, the cells can be subject to other processes or treatment, e.g. a selection based on cell surface marker expression, or genetic engineering.

In some embodiments, differential peak analysis can be performed, comparing the epigenetic profiles of two or more samples, e.g., two or more test samples or a group of samples. In some embodiments, differential peak analysis can be performed, comparing accessibility profiles of one or more test sample, e.g., cell composition to be tested, to the accessibility profile of one or more reference sample or reference profile, e.g., any reference sample or reference profile described herein, e.g., in Section II.C.1.

2. Normalization Measures and Metrics

In some embodiments, analysis of the sequences and/or peaks from the epigenetic/epigenomic profile includes further processing or analysis of the sequence and/or peak results, e.g., for normalizing or quantitating the results. In some aspects, the analysis includes adopting normalization measures. In some cases, the normalization measures can include generating a metric associated with a gene, e.g., a normalized count per annotated gene. In some embodiments, data from the assays, e.g., chromatin accessibility assays such as ATAC-seq, is further processed or analyzed to determine threshold and/or values, identify loci and/or genes associated with particular outcomes, and/or to compare with results and analyses of other assays. For example, in some embodiments, ATAC-seq peaks can be identified by plotting a frequency, such as a normalized frequency, overlaid with a genomic locus region map or a genome map. In some embodiments, normalized frequency values include FPKM or RPKM. In some embodiments, the term "FPKM" as used herein refers to Fragments Per Kilobase per Million fragments mapped. In some embodiments, the term "RPKM" can refer to Reads Per Kilobase per Million reads mapped. FPKM and RPKM are units to quantify abundance of any genomic feature, such as an exon, transcript, insertion of transposon, histone modification, nucleosome occupancy, DNA methylation, or occupancy of a protein, such as a transcription factor, or any genomic coordinates, determined by the abundance of sequencing reads aligning to it. The FPKM and RPKM measures normalize the abundance by relative length of the genomic unit as well as the total number of reads mapping to it, to facilitate the comparison of abundance levels within and between samples. In some aspects, normalized frequency values include upper quartile (UQ), size factor (SF), counts per million (CPM), Reads Per Kilobase Million (RPKM), Fragments Per Kilobase Million (FPKM) or Transcripts Per Kilobase Million (TPM).

In some embodiments, one or more genomic regions, loci, elements or intervals are selected for analysis. For example, in some embodiments, data from a genomic region, e.g., promoter or enhancer regions, are assessed and/or compared. In some embodiments, data from within or around the coding region of a gene, e.g., gene body, are assessed and/or compared. For example, in some embodiments, the sum of FPKM or RPKM values of the gene body of a gene is assessed and/or compared. In some embodiments, the sum of FPKM or RPKM values are assessed and/or compared, for one or more genomic regions, e.g., genomic loci.

In some embodiments, a pattern of differences compared to a reference value and/or a normalized value, e.g., a higher or lower chromatin accessibility compared to a reference or normalized value, is determined. In some embodiments, the assay includes determining the differences in values, e.g., chromatin accessibility as determined by normalized values, e.g., FPKM or RPKM, at one or more genomic regions, e.g., genomic loci, e.g., a plurality or panel of loci in the genome, are determined and compared. In some embodiments, the plurality or a panel of loci include any of those described herein, or any of those identified using the methods provided herein.

In some embodiments, determining the differences in value at one or more genomic regions, e.g., genomic loci involves determining that the FPKM or RPKM value for the one or more genomic regions, e.g., genomic loci in the nucleic acid obtained from the cancerous biological sample is: i) greater than between a 1 to 20-fold, such as about a 1-fold, 2-fold, 3-fold, 4-fold or 5-fold, change in mean or total FPKM or RPKM value relative to the FPKM or RPKM value of the one or more genomic regions, e.g., genomic loci in the reference nucleic acid obtained from a reference biological sample; and ii) greater than about 10-fold reduction in FPKM or RPKM range relative to the FPKM or RPKM value of the one or more genomic regions, e.g., genomic loci in the reference nucleic acid obtained from obtained from a reference biological sample. For example, in some embodiments, the analysis includes determining the values, e.g., FPKM or RPKM values, for one or more genomic regions, e.g., genomic loci, generating a matrix of sequencing tag counts for the one or more genomic regions, e.g., genomic loci based on any of the assays for epigenetic and/or epigenomic analysis described herein, and determining differences in value compared to a reference value or a normalized value. Then, the analysis further includes clustering analysis, such as hierarchical clustering or principal component analysis (PCA), based on the changes or differences in values in one or more cell populations, e.g., from one or more subjects or cells that were subject to one or more treatments, such as any further or additional analyses described herein.

In some embodiments, the assay includes determining the differences in values, e.g., chromatin accessibility as determined by normalized values, which can be determined using a normalized value adjusted for effective library size. In some embodiments, a negative binomial model can be used to test for differential accessibility. In some embodiments, a difference in peaks, e.g., sequence read peaks between samples from one or more different conditions, in one or more genomic regions, loci, elements or intervals, e.g., genomic loci, can be used to determine differences in the epigenomic and/or epigenetic profile, e.g., differences in chromatin accessibility.

In some embodiments, such normalization measures include calculating a normalized per-gene accessibility value (e.g., normalized FPKM values) representing general accessibility of a gene, using a computationally implemented script or tool, e.g., homer_calculate_per_gene_accessibility_norm. Such calculated metrics or scores can be used for further downstream analyses, e.g., comparing with other samples or correlating with outcomes of cell therapy.

In some embodiments, normalization can also include normalization based on measures such as fraction of reads in peaks (FRiP; showing enrichment of signal, calculated as (number of reads in peaks)/(number of total reads)). In some embodiments, FRiP-normalized counts can be determined for one or more particular genomic regions or intervals.

3. Nucleosome Occupancy Analysis

In some aspects, further processing steps include assessing the nucleosome occupancy or positioning or identifying nucleosome-free regions (NFRs) in the epigenetic/epigenomic profile.

In some embodiments, the peaks contain and/or associated with NFRs (see, e.g., Schep et al., (2015) Genome Research 25:1757-1770). In some aspects, nucleosome-free regions can be associated with transcriptional start sites, promoters or transcription termination sites (see, e.g., Yadon et al., (2010) Mol. Cell. Biol. 30(21):5110-5122) and/or more activated or more differentiated state. In some aspects, NFRs are associated with high genomic accessibility. In some embodiments, peak calling and differential peak analysis can include one or more steps such as filtering sub-nucleosomal reads, finding peaks, counting insertion sites per peak, aggregating promoter and/or transcriptional start site peak signals per gene and/or examining differential accessibility in stably shared peaks. In some aspects, the epigenetic profile includes identifying peaks of differential accessibility, e.g., identifying or determining peaks a difference in peaks, e.g., sequence read peaks between samples from one or more different conditions, in one or more genomic regions, loci, elements or intervals, e.g., genomic loci, can be used to determine differences in the epigenomic and/or epigenetic profile, e.g., differences in chromatin accessibility between samples from one or more different conditions.

In some embodiments, the sequence reads can be placed into groups by length. In some embodiments, some sequences can be annotated as being a nucleosome-free sequence (i.e., a sequence from a fragment that is predicted to be between nucleosomes) based on its size (see, e.g., Schep et al., (2015) Genome Research 25:1757-1770). Reads that are associated with mononucleosomes, dinucleosomes and trinucleosomes can also be identified.

In some embodiments, nucleosome occupancy, nucleosome positioning and/or nucleosome-free region can be determined using steps, functions, processes, tools or scripts, e.g., for separating out particular size of fragments that can represent nucleosome-bound chromatin. In some aspects, fragments of a specific size, e.g., fragments larger than 100 bp, 150 bp, 200 bp, 250 bp or more, can be separated or filtered out filtered out. In some aspects, some of the fragments can represent nucleosome-bound chromatin. In some aspects, exemplary steps for filtering out fragments of a specific size, e.g., larger than 100 bp, 150 bp, 200 bp, 250 bp or more include Filter_nucleosomal_fragments. In some embodiments, such steps can enrich the signal. In some aspects, both filtered and non-filtered reads can be used for further or downstream analyses to infer open and nucleosome-occupied chromatin, respectively. In some embodiments, nucleosome occupancy can be determined using steps, functions, processes, tools or scripts, e.g., for calling nucleosome positions and occupancy using ATAC-Seq data, such as NucleoATAC (see, e.g., Schep et al., (2015) Genome Res. 25(11): 1757-1770).

C. Analysis and Applications

In some embodiments, the provided methods also involve additional applications and/or analysis of one or more aspects of the epigenetic/epigenomic properties and/or profile. In some embodiments, the provide methods include further analysis and/or application steps, such as comparing the epigenetic/epigenomic properties and/or profile of a particular cell or cell composition to those of a reference sample and/or a reference profile. In some aspects, the further analysis and/or application includes determining additional characteristics, properties, and/or states, using additional standards or methods to analyze the sequence results, performing additional downstream analysis, gene subset analysis, biological pathway analysis, transcriptional occupancy analysis, or motif analysis, clustering analysis and/or additional applications, e.g., correlation or association with outcomes of a cell therapy, assessing integration of transgenic sequences, comparing with reference samples and/or reference profiles, and/or assessing phenotype or state or other properties of a cell or a cell composition.

In some aspects, any one or more of the various additional analysis and/or applications can be computationally implemented. In some embodiments, the provided methods involve various downstream steps or processes for analysis or comparison, e.g., computationally implemented steps, and/or applications of the methods, for assessing one or more properties or characteristics of cells or cell compositions. In some embodiments, additional analysis and/or applications can include, e.g., biological pathway analysis, gene ontology (GO) enrichment, motif enrichment, gene subset analysis, transcription factor occupancy, comparison with reference profiles, and/or integration analysis, such as determining transposon insertion sites. In some embodiments, the method for analyzing and identifying one or more genomic region(s), e.g., the further analysis and/or application, can include any one or more of the exemplary steps, functions, processes or scripts, described herein, sequentially or simultaneously in any order. One or more of the steps, functions, processes or scripts can be substituted by similar algorithms, steps, functions, processes or scripts that achieve or carry out a similar function. In some embodiments, the sequential order of one or more steps can be in any order, or any one or more steps, functions, processes or scripts can be performed in parallel.

1. Reference Epigenetic Properly or Profile

In some embodiments, the one or more of the assays, steps and/or procedures described herein can be used to determine the epigenetic and/or epigenomic properties, state and/or profile of particular samples, e.g., particular cells, cell population or cell composition. In some aspects, the methods are used to determine the epigenetic and/or epigenomic properties, state and/or profiles of reference cells or a reference cell composition, or control cells and/or a control cell composition. In some aspects, the one or more of the assays, steps and/or procedures described herein can be used to determine a reference epigenetic property, e.g., a reference epigenetic and/or epigenomic profile. In some aspects, any of such properties or profiles can be used to compare with and/or to assess test samples, e.g., other cells or cell compositions, or test conditions or procedures, e.g., conditions or procedures for generating, manufacturing and/or manipulating cells or cell compositions, e.g., cell compositions for adoptive cell therapy. In some aspects, further analysis and/or application methods or procedures involve comparing epigenetic/epigenomic profiles of test samples with that of the reference sample and/or the reference profile.

In some embodiments, a reference epigenetic property can be determined by identifying an epigenetic property, e.g. by chromatin accessibility analysis, of a reference or control cell sample, population or composition. In some embodiments, the reference or control cell sample exhibits a known attribute or feature or is suspected or likely to have a known attribute or feature, e.g. related to the phenotype or function of the cells, including one or more phenotype or function of T cells, such as T cell activation state, memory phenotype, differentiation state, effector function, cytokine response, production or secretion, cytolytic activity, trafficking or migration ability, persistence or exhaustion, or related to the presence or absence of a transgene, e.g. mediated by viral-based transduction. In some embodiments, the reference or control sample is from a healthy or normal subject.

In some embodiments, the reference sample includes a sample, e.g., cells or cell compositions, derived from subjects who, after administration of the cell therapy, went on to achieve a desired outcome, e.g., a desired response or safety outcome. In some embodiments, the reference sample includes a sample derived from subjects who went on to achieve a partial response (PR) or a complete response (CR), and/or a durable response, after treatment with the cell therapy. In some embodiments, the reference sample is a sample derived from a subject who went on to achieve a desirable safety outcome, e.g., absence of development of toxicity, e.g., cytokine release syndrome (CRS) or neurotoxicity (NT), or absence of development of severe CRS or severe NT. In some embodiments, desired therapeutic outcomes, e.g., response or safety outcomes, include any described in Section III below.

In some aspects, the reference sample can include cells or cell compositions that possess a desired state, quality, consistency, phenotype, characteristics and/or property. For example, in some aspects, a cell composition containing uniform or consistent cells can be desired. In some embodiments, a reference sample can include cells or cell compositions that are known to exhibit consistency and/or uniformity, and/or particular phenotype, state, quality, characteristics and/or property. In some aspects, a reference sample can contain a particular ratio of cells exhibiting particular phenotypes. In some aspects, a reference epigenetic and/or epigenomic profile can be obtained from any of the reference samples described.

In some embodiments, the reference profile includes a collection of epigenetic properties or states at one or more genomic regions, loci and/or intervals, of a reference sample. In some embodiments, the reference profile is a reference epigenetic/epigenomic map. In some embodiments, the reference profile is an epigenetic map that is determined from common peaks of sequence reads from accessibility analysis, optionally chromatin accessibility, among a plurality of cell compositions, e.g. reference cell compositions or samples. In some embodiments, the reference profile is a set of metrics and/or normalized values, e.g., FPKM values or promoter accessibility metrics.

In some embodiments, the reference profile includes a threshold value for the epigenetic property for each of the one or more genomic regions or for the overall epigenetic property within the one or more genomic regions.

In some embodiments, the threshold value: is a value or level of the epigenetic property, optionally chromatin accessibility, in the one or more genomic regions in a cell of a cell composition shown to exhibit the outcome when administered to a subject having the same or similar disease or condition; or is an average, median or mean value or level of the epigenetic property, optionally chromatin accessibility, in the one or more genomic regions from a cell of each of a plurality of cell compositions, shown to exhibit one or more desired outcomes, e.g., when administered to the subject. In some embodiments, the threshold value includes is the value or level of the epigenetic property in a cell from a normal or healthy subject. In some embodiments, the threshold value includes the value or level of the epigenetic property in a cell that exhibits a particular phenotype, e.g., a naïve or a long-lived memory phenotype.

In some embodiments, the provided methods can be used for assessing a cell composition for administration to a subject, including analyzing an epigenetic profile of one or more genomic regions of a cell in a cell composition containing cells engineered with a recombinant receptor; and comparing the epigenetic profile for each genomic region, individually, to a reference profile, wherein the comparison indicates whether the population of cells is or is likely to exhibit or produce an outcome, e.g., desired outcome, when administered to a subject. In some embodiments, the provided methods of assessing a cell culture includes analyzing an epigenetic profile of one or more genomic regions of a cell contained in an output cell composition, said output composition produced by culturing an input composition in the presence of one or more test agents or conditions; and comparing the epigenetic profile for each genomic region, individually, to a reference profile, wherein the comparison indicates whether the cell is or is likely to exhibit a predetermined phenotype, persistence, activity and/or function.

In some embodiments, the comparison is made between epigenetic/epigenomic properties, state and/or profile of one sample, e.g., a test sample, with the epigenetic/epigenomic properties, state and/or profile of a reference sample. In some aspects, the comparison is made with a reference profile. In some embodiments, the reference sample and/or reference profile can be any of those described herein. In some aspects, the reference sample can be a sample from a subject who exhibits a desired outcome, e.g., response outcome or safety outcome, and/or a sample that contains desired properties and/or characteristics.

The methods provided herein may also be used for assessing one or more properties or features of a cell composition, such as consistency, composition, phenotype, function and/or activity of the cell composition. In some aspects, the epigenetic and/or epigenomic profile of a cell composition can be compared to those of a reference sample, e.g., comprising a reference cell composition. In some aspects, the method can be used to select or generate appropriate cell composition for treatment. In some aspects, the assays and analyses described herein can be used to select cells for treatment, e.g., engineered cells for adoptive cell therapy, that are predicted to be more consistent and/or uniform, and/or to exhibit a particular phenotype or composition, and/or is associated with a more consistent, efficacious and/or predictable outcome after administration. In some aspects, The methods provided herein may be used to provide a reliable predictor of efficacy and/or safety of cells for treatment, by selecting cells that exhibit an epigenetic and/or epigenomic properties associated with efficacy and/or safety and/or a more defined, consistent and/or uniform cell composition.

In some embodiments, the provided methods can be used for assessing a cell composition for administration to a subject, including analyzing an epigenetic profile of one or more genomic regions of a cell in a cell composition containing cells engineered with a recombinant receptor; and comparing the epigenetic profile for each genomic region, individually, to a reference profile, wherein the comparison indicates whether the population of cells is or is likely to exhibit or produce an outcome when administered to a subject and/or to produce a consistent, defined and/or uniform cell composition that is associated with an outcome of cell therapy.

In some embodiments, if the comparison indicates that the cell composition is or is likely to exhibit the outcome, e.g., a desired response or safety outcome, the cell composition can be administered to the subject.

In some embodiments, if the comparison indicates that the cell composition is not or is not likely to exhibit an outcome, e.g., a desired response or safety outcome, either: (i) the cell composition can be altered prior to administration; (ii) the dose of the cell composition can be altered prior to administration; (iii) the dosage regimen of the cell composition can be altered prior to administration; (iv) the cell composition can be administered in combination with one or more other therapeutic agents; or (v) the cell composition is not administered to the subject.

In some aspects, the cell composition may be altered prior to administration, based on the results of one or more of the epigenetic/epigenomic analyses. For example, in some aspects, if comparison of the epigenetic/epigenomic profile of a particular cell composition is compared to that of a reference cell composition, and the comparison indicates that the cell composition is not or is not likely to exhibit an outcome, e.g., a desired response or safety outcome, one or more steps or procedures of engineering the cells prior to cell therapy can be modified. In some aspects, such modifications can include culturing the cells engineered with a recombinant receptor and/or cells to be genetically engineered in the presence of one or more test agents or conditions. In some embodiments, the one or more test agents or conditions comprises presence or concentration of serum; time in culture; presence or amount of a stimulating agent; the type or extent of a stimulating agent; presence or amount of amino acids; temperature; the source or cell types of the cell composition; the ratio or percentage of cell types in the cell composition, optionally the CD4+/CD8+ cell ratio; the presence or amount of beads; cell density; static culture; rocking culture; perfusion; the type of viral vector; the vector copy number; the presence of a transduction adjuvant; cell density of the cell composition in cryopreservation; the extent of expression of the recombinant receptor; or the presence of a compound to modulate cell phenotype. In some embodiments, the one or more test agents or conditions comprises one or more compounds from a library of test compounds. In some embodiments, if the comparison indicates that the cell composition is or is likely to have the phenotype or function, the methods also include selecting the one or more test agent or condition for culturing the cells. In some embodiments, if the comparison indicates that the cell composition is or is likely not to have the phenotype or function, the methods can also include repeating epigenetic and/or epigenomic analysis and/or comparison with other samples with one or more further test agent or condition.

The methods provided herein may also be used as a diagnostic (e.g., methods that provide a diagnosis as well as methods that provide a prognosis) and/or to select appropriate subjects and/or cells for treatment. The methods may comprise, e.g., analyzing epigenetic and/or epigenomic features in cells, e.g., cells obtained from a subject, using the assays described herein to produce an epigenetic map; and providing a diagnosis or prognosis based on the epigenetic map and/or further analysis and/or quantitation. For example, the assays and analyses described herein can be used to predict efficacy, complete response, molecular response, durability of response, persistence of cells, expansion of cells safety (lack of or reduced toxicity or adverse effects) and/or lack of immunogenicity of the treatment, e.g., adoptive cell therapy. In some embodiments, the assays and analyses described herein can be used to select agents for treatment, e.g., engineered cells for adoptive cell therapy, that are predicted to be more efficacious and/or safer, e.g., associated with complete response or molecular response. The methods provided herein may be used to provide a reliable predictor of efficacy and/or safety of cells for treatment, by identifying genomic regions, e.g., genomic loci with altered epigenetic and/or epigenomic features, e.g., altered chromatin accessibility, and selecting cells that exhibit an epigenetic and/or epigenomic properties associated with efficacy and/or safety.

In some embodiments, the provided methods can be used for a prognosis, e.g., to determine if a subject for treatment is at risk for recurrence. The methods can be used to identify subjects treated with the cells, e.g., engineered cells, who are likely to experience recurrence of the disease or condition, e.g., cancer, such that they can be offered additional therapeutic options, including additional or altered doses, altered frequency, and/or treatment with additional agents, e.g., other cells expressing a recombinant receptor, chemotherapy, radiation, biological modifiers, inhibitors and other suitable therapies. The methods can be used for predicting long term response to treatment in subjects.

In some embodiments, the provided methods can be used to determine a suitable dosage, frequency, dosage regime and/or course of treatment for a subject having a disease or condition, e.g., a cancer or a tumor. In some embodiments the dosage of treatment, e.g., cells for adoptive cell therapy, can be determined based on the predicted efficacy and/or safety of the cells to be administered. A course of treatment refers to the therapeutic measures taken for a subject after diagnosis or after treatment. For example, a determination of the likelihood for response, toxicity, recurrence, spread, or subject survival, can be used in determining the dosage and extent of treatment and/or any combination therapies to be administered.

In some embodiments, the provided methods can be used to characterize, classify, differentiate, grade, stage, for diagnosis or prognosis of a disease or condition or to select suitable cells for use in treatment, e.g., adoptive cell therapy, characterized by an epigenetic pattern (e.g., a pattern of chromatin accessibility or DNA binding protein occupancy). For example, the method can be used to determine whether the epigenetic map of cells obtained from a subject for engineering and administration, is similar or different compared to the epigenetic map of the same type of cells from a normal subject or a subject who exhibited a robust and/or durable response after adoptive cell therapy, e.g., subjects who exhibited a complete response. The methods can also be used for predicting the susceptibility of an individual to a treatment, e.g., adoptive cell therapy.

2. Biological Pathways, PCA and Other Downstream Analyses

In some aspects, the provided assays and analysis methods can include additional, further or downstream analyses, including combining or applying other genomic or functional analysis steps. In some aspects further or downstream analyses can be used to in combination with the any one or more of the analysis or application steps. In some aspects, exemplary further or downstream analysis steps can include thresholding and clustering approaches, predictive modeling, gene ontology (GO) analysis, motif analysis and/or principal component analysis (PCA). In some aspects, any of the downstream analysis methods can be computationally implemented.

In some aspects, the further or downstream analysis is PCA. In some aspects, PCA can be used to reduce dimensionality of the data and examine general variance in the data, and identify key drivers that contribute to the variation. PCA uses an orthogonal transformation to convert a set of observations of possibly correlated variables into a set of values of linearly uncorrelated variables called principal components. In some aspects, the transformation is defined so that the first principal component has the largest possible variance (e.g., accounts for as much of the variability in the data as possible), and each succeeding component in turn has the highest variance possible under the constraint that it is orthogonal to the preceding components.

In some aspects, the further or downstream analysis can include biological pathways analyses, e.g., including analysis of gene networks, pathways, biological process and molecular functions. In some aspects, an epigenetic property, profile and/or one or more genomic regions, loci and/or intervals identified, can be liked to particular biological processes or pathways, based upon biological, molecular, and/or functional relationships. In some aspects, these relationships are useful for pathway or process based collapsed association methods or inferring the phenotypic influence of particular epigenetic property and/or profiles. Exemplary biological pathways analyses include, but are not limited to: Reactome pathways and gene ontology (GO) biological processes of the nearest gene to provide biological relationships; Disease Ontology utilized to provide phenotypic relationships; and protein domain information and molecular functions (as annotated by Gene Ontology) to provide molecular and functional relationships. Other exemplary biological pathways analysis includes Ingenuity Pathway Analysis (IPA), Pathway Studio pathways analysis, KEGG based analysis, Gene Set Enrichment Analysis (GSEA), Signaling Pathway Impact Analysis (SPIA), EnrichNet, GGEA, Signaling Pathway Impact Analysis (SPIA) and TopoGSA. Exemplary procedures and methods that can be used for biological pathway analysis include Over-Representation Analysis or Enrichment Analysis (ORA), Functional Class Scoring (FCS), and Pathway Topology (PT).

In some aspects, the further or downstream analysis can include clustering analysis, e.g., hierarchical clustering. In some aspects, hierarchical clustering involves creating clusters that have a predetermined ordering from top to bottom or bottom to top. In some aspects, hierarchical clustering can be agglomerative (bottom-up), where each observation starts in its own cluster, and pairs of clusters are merged as one moves up the hierarchy; or divisive (top-down), where all observations start in one cluster, and splits are performed recursively as one moves down the hierarchy. Hierarchical clustering can be used on epigenetic/epigenomic profile at one or more genomic locations, from three or more different samples. In some aspects, hierarchical clustering can be performed based on epigenetic profile of a panel, set or module of genes, e.g., using a metric value for each gene. In some embodiments, hierarchical clustering can identify groups or clusters of samples that show more a similar epigenetic profile to each other compared to samples outside the cluster. In some embodiments, hierarchical clustering can be performed using computationally implemented scripts, tools or software packages, such as JMP or Pheatmap R.

In some aspects, the further or downstream analysis can include motif analysis, e.g., determining repeating or consensus sequence motifs. In some aspects, the further or downstream analysis can include transcription factor binding motif analysis and/or transcription factor occupancy analysis. In some embodiments, transcription factor binding motif analysis can be performed using scripts or tools such as homer_find_motifs. In some aspects, the script or tool can search for enriched transcription factor binding motifs shared within the peak sets determined using methods provided herein.

In some embodiments, the one or more genomic regions, e.g., genomic loci that can be used in the panel of gene loci in characterizing and/or assessing particular cells and/or subjects for treatment can be identified using clustering analysis together with one or more reference samples and/or with one or more different samples. For example, in some embodiments, data from epigenetic and/or epigenomic analysis of cells obtained from subjects that exhibited different outcomes (e.g., some subjects who exhibited complete response and some subjects who exhibited partial response, progressive disease or no response) can be subject to hierarchical clustering or principal component analysis (PCA), to identify particular panel of loci that are associated with desired outcomes (e.g., complete response, reduced toxicity, increased expansion). In some embodiments, cells from subjects with desired outcomes (e.g., complete response, reduced toxicity, increased expansion) are reference samples used for clustering analysis and/or to determine reference values for comparison. In some of these cases, any type of epigenetic and/or epigenomic analysis can be used to identify particular loci that are associated with desired outcomes (e.g., complete response, reduced toxicity, increased expansion). Once the gene locus and/or panel of gene loci are identified, the epigenetic and/or epigenomic properties or pattern of a population of test cells can be determined and compared to the corresponding properties or patterns in samples or groups associated with the desired outcome, and the cells and/or subjects can be selected for treatment, e.g., treatment using adoptive cell therapy. In some embodiments, threshold reference values (e.g., threshold FPKM or RPKM values) for one or more genomic regions, e.g., genomic loci can be determined and used as threshold values to select test cells and/or patients. In some embodiments, the epigenetic and/or epigenomic properties for one or more genomic regions, e.g., genomic loci in the test cells and/or subjects is subject to further clustering analysis, and the cells and/or subjects are selected for treatment if the epigenetic and/or epigenomic properties for the one or more genomic regions, e.g., genomic loci, cluster with reference cells or groups with desired outcomes (e.g., complete response, reduced toxicity, increased expansion).

In some embodiments, clustering analysis can be performed based on average and/or total FPKM or RPKM values for a genomic interval, for one or more genomic regions, e.g., genomic loci. In some embodiments, clustering is performed based on the sum of FPKM or RPKM values over the gene body (e.g., coding region) for one or more genomic regions, e.g., genomic loci. In some embodiments, the clustering analysis is depicted as dendrograms, constellation plots or decision trees. In some embodiments, clustering analysis is performed based on a value, e.g., FPKM or RPKM, at a particular point or a particular interval, e.g., those associated with a coding region or associated with a non-coding region.

In some embodiments, results of the analysis and methods provided herein can be represented or visualized using various plots or graphs. Exemplary plots or graphs include venn diagrams, MA plots (M (log ratio) and A (mean average)), principal component analysis (PCA) plots, boxplots and heatmaps.

In some embodiments, the cells can be subject to additional analysis, e.g., molecular, phenotypic or functional analysis. For example, the cell samples can be analyzed using fluorescence activated cell sorting (FACS) and/or laser capture microdissection (LCM) for phenotypic analysis. In some embodiments, the cell sample and/or nucleic acids may be divided into a plurality of portions. The portions can be divided based on the molecular tags (e.g. fluorescence tags). In some embodiments, the cell sample and/or nucleic acids can be sorted. The sorting can be performed after the molecular tags are inserted into the nucleic acid. The sorting can be performed before the fragments are sequenced. The gene transcription of the cell samples can also be analyzed using techniques such as fluorescence in situ hybridization (FISH). The chromatin accessibility can be correlated with the phenotypical, transcriptional or translational analysis.

In some embodiments, the epigenetic and/or epigenomic analysis can be used in combination with other detection and/or analysis methods, such as transcription analysis, transcriptome analysis, transcription factor occupancy assays, RNAseq, protein expression, proteomic analysis, protein modification analysis, functional activity assays, flow cytometry and/or intracellular cytokine staining. In some embodiments, the correlation between results from one or more epigenetic and/or epigenomic analysis, e.g., ATAC-seq, and other analysis methods, e.g., ChIPseq, RNAseq analysis or intracellular cytokine staining, are determined. In some embodiments, the results from the various assays or analysis methods are strongly correlated, e.g., have a high correlation coefficient. In some embodiments, the results from the various assays or analysis methods are not strongly correlated, e.g., have a low correlation coefficient. In some embodiments, the correlation depends on the gene and/or locus and/or conditions of the experiment. In some embodiments, the method of analysis includes comparing, correlating and/or further analyzing the data obtained, with other data sets, e.g., other epigenetic and/or epigenomic data sets, and/or other phenotypic or physiological data sets. For examples, the method of analysis includes comparing, correlating and/or further analyzing the data obtained, with genome-wide expression data, e.g., RNA-seq data, or genome-wide nucleosome positioning data.

In some embodiments, epigenetic and/or epigenomic analysis includes determination of post-translational histone modification. In some embodiments, the epigenetic analysis includes detection of one or more histone modifications, such as acetylation, methylation, phosphorylation, ubiquitylation, sumoylation and biotinylation of specific residues in histone proteins H1, H2A, H2B, H3 and/or H4.

3. Gene Panel Analysis

In some aspects, any of the analysis methods, including additional, further or downstream analyses, can be performed on one or more selected genomic regions or gene loci. In some aspects, the methods can be performed based on one or more selected genes, such as a subset of genes, panel of genes or module of genes. In some aspects, any of the analysis methods can be used to assess the epigenetic/epigenomic state in genomic regions, genomic loci, at or near a particular gene or a particular panel, module or set of genes, e.g., panel, module or set of genes that are associated with similar activity and/or function and/or co-regulated or co-expressed. In some aspects, analysis can be performed on a pre-selected gene or panel, module or set of genes. In some aspects, analysis can be performed such that genes that exhibit similar epigenetic and/or epigenomic properties, state and/or pattern can be used to identify gene or panel, module or set of genes of interest, e.g., those associated with, correlated with or indicative of an outcome or characteristic, e.g., a desired outcome or characteristic. In some aspects, such panel, module or set of genes can be used to assess the test samples.

In some embodiments, the genomic regions, loci and/or interval for analysis in assessing the epigenetic/epigenomic state in a panel, module or set of genes can include signal at particular elements or portions of a gene, or genomic regions or elements associated with a gene, including an intron, an exon, a cis-regulatory element, a promoter, an enhancer, an upstream activating sequence (UAS), a 3' untranslated region (UTR), a 5' UTR, a non-coding RNA producing region, a non-coding RNA (ncRNA) gene, a miRNA gene, an siRNA gene, a piRNA gene, a snoRNA gene, a lncRNA gene, a ribosomal RNA (rRNA) gene, a small RNA binding site, a non-coding RNA binding site, a pseudogene or a transcription termination site (TTS).

In some embodiments, the one or more genomic regions, e.g., genomic loci, e.g., a panel of gene loci, may be positioned within or adjacent to a gene associated with cell-type specification, T cell differentiation and/or development, or transcription factors. In some embodiments, the one or more genomic regions, e.g., genomic loci are loci encoding biological markers or indicators associated with particular cell phenotypes, e.g., particular immune cell phenotypes or immune cell differentiation markers. For example, in some embodiments, the one or more genomic regions, e.g., genomic loci, e.g., a panel of gene loci, include markers that are associated with T cell differentiation and/or function, e.g., cytokine genes, immunomodulatory protein genes, cell surface markers, apoptosis markers, cell death markers and/or transcriptional regulators. In some embodiments, the one or more genomic regions, e.g., genomic loci, e.g., a panel of gene loci, are associated with particular immune cell phenotypes, such as T cell phenotypes, e.g., naïve T cell phenotypes, initial effector phenotypes, short-term or mid/late effector phenotypes, such as any described in, e.g., Best et al., Nature Immunology (2013) 14, 404-412, which is hereby incorporated by reference. In some embodiments, the subject is human and the gene loci identified are based on the human genome.

In some aspects, analysis based on a panel, module or set of genes, e.g., those that are described as being associated or co-regulated in known pathways or gene groups, can be performed. In some embodiments, the one or more genomic regions, e.g., genomic loci, e.g., a panel of gene loci, include one or more gene selected gene loci related to T cells or activity, stimulation, function and/or particular phenotypes of T cells, e.g., CD8+ T cells, such as any described in, e.g., Best et al., Nature Immunology (2013) 14, 404-412, which is hereby incorporated by reference. For example, in some aspects, a panel, module or set of genes identified as being involved in or indicative of T cell differentiation states, effector function, exhaustion, or specific memory function and/or specific T cell subpopulations can be assessed.

In some embodiments, the one or more genomic regions, e.g., genomic loci, e.g., a panel of gene loci, include one or more immunoregulatory gene loci selected from among: Ifng, Tbet, Lag3, Pd1, Cd25, Foxp3, Il2, Ki67, Tnf, Il13, Il17, Il17a, Foxp and Foxp3. In some embodiments, the one or more genomic regions, e.g., genomic loci, e.g., a panel of gene loci, include one or more loci selected from among: Ifng, Tbx21, Tnf, Il13, Il2ra, Lag3, Il2, Mki67, Il17a, Pdcd1 and Foxp3. In some embodiments, the panel of gene loci includes Ifng and Pdcd1. In some embodiments, the panel of gene loci includes one or more loci associated with initial effector response, such as Ctla4, Il2ra, Ifng, Gzmb and Il2. In some embodiments, the panel of gene loci includes one or more loci associated with cell division, such as Myc, Id3, Egr2, Tnf, Cd69 and Pkm2. In some embodiments, the panel of gene loci includes one or more loci associated with cell cycle and cell division, such as Myb, Hist1h3a, Cdk1 and Ccd45. In some embodiments, the panel of gene loci includes one or more loci associated with naïve and late memory response, such as Sell, Nsg2, Slfn5 and Cnr2. In some embodiments, the panel of gene loci includes one or more loci associated with early effector and late memory, such as Ly6a, Rpl and Snora. In some embodiments, the panel of gene loci includes one or more loci associated with short-term effector response, such as Id2, Cxcr3, Zeb2, Cx3cr1, Klrg1, S1pr5 and Itgam. In some embodiments, the panel of gene loci includes one or more loci associated with memory precursor response, such as Bcl2, Tcf7, Il7r and Foxo3. In some embodiments, the panel of gene loci includes one or more loci associated with naïve cells or late effector response Cxcr6, S1pr4, S1pr1, Klf2 and Klf3. In some embodiments, the panel of gene loci includes one or more loci associated with short-term effector or memory response, such as Prdm1 and Hif2a. In some embodiments, the panel of gene loci includes one or more loci associated with late effector response, such as Tbx21, Prf1, Bhlhe40, Cd44, Klrc2 and Il12rb1. In some embodiments, the panel of gene loci includes one or more loci associated with mid- or late effector response, such as Dmrta1, Bcl2, Edaradd, Prss12, Cnrip1 and Aqp9. In some embodiments, the panel of gene loci includes one or more loci associated with late effector response, such as Unc5a, Xcl1, Yes1, Cdh1, Myo3b, Dock9 and Atn1 In some embodiments, the panel of gene loci includes one or more loci selected from among: Nr4a1, Cblb, Irf4, Tbx21, Eomes, Ifng, Csf2, Gzmb, Tnfsf10, Gata3, Mir155, Sox21, Ctla4, Lag3, Pdcd1 Actb and/or Gapdh. In some embodiments, the panel of gene loci includes housekeeping gene, e.g., Actb or Gapdh, which can be indicative of activation state of the cells.

In some embodiments, the cells are selected for treatment based on the methods provided herein, if the cells for administration, e.g., engineered cells for adoptive cell therapy, exhibit epigenetic and/or epigenomic properties that are different from effector-like T cells. In some embodiments, the subject is selected for treatment with engineered cells if the cells from the subject exhibit epigenetic and/or epigenomic properties that are different from effector-like T cells. For example, the cell and/or subject can be selected for treatment if one or more gene loci associated with effector function of T cells or effector-like phenotype, exhibit relatively lower levels of chromatin accessibility.

4. Transgene Integration Analysis

In some embodiments, the methods can include identifying and/or characterizing integration site(s) of nucleic acid molecules or constructs or transgenes delivered to or introduced into the cell, e.g., constructs introduced into the cell for engineering, for example, to express a recombinant receptor. In some embodiments, one or more sites of integration can be determined based on the nucleic acid sequence, e.g., containing nucleic acid sequences that are adjacent to the integrated construct sequence, obtained from the methods described herein. In some embodiments, the number and location of integration can be determined. In some embodiments, the epigenetic and/or epigenomic profile at the site(s) of nucleic acid integration can be determined. In some embodiments, the nucleic acid molecule or construct for integration include a vector, e.g., a viral vector, a nucleic acid molecule, a transposon and/or a nucleic acid construct that encodes a transgene, e.g., a recombinant receptor. In some embodiments, the methods can include determining the number and/or abundance of the integrated nucleic acid molecule or construct. For example, in some embodiments, the copy number of the nucleic acid, e.g., vector such as a viral vector, or a construct, can be determined, in cells that have been engineered, e.g., in cells engineered to express a recombinant receptor. In some embodiments, the methods include determining level of expression of the encoded gene, e.g., the encoded recombinant receptor.

In some embodiments, the methods can include determining T cell clonality in a plurality or population of T cells, e.g., a plurality of engineered T cells and/or a composition containing a plurality or population of T cells, e.g., a plurality of engineered T cells. In some aspects, the methods can be used to determine clonality in a plurality or population of T cells by determining the epigenetic and/or epigenomic properties and/or the epigenetic and/or epigenomic profile, such as chromatin accessibility, at or around gene loci that encode the T cell receptor (TCR) genes, e.g., genes that encode the variable and/or constant regions of TCR alpha, beta, gamma and/or delta chains. In some aspects, the methods can be used to determine clonality in a plurality or population of T cells by determining the insertion site of a nucleic acid molecule, e.g., nucleic acid sequences encoding a recombinant receptor. In some embodiments, clonality assessment can be used to characterize the plurality or population of T cells, e.g., plurality or population of T cells in a composition. In some aspects, such determination can be used to determine a treatment regimen, e.g., including doses, timing and/or frequency of administration of the engineered cells and/or to determine necessary or favorable modification of culture or process conditions.

D. Exemplary Analysis Scripts

Without wishing to be bound to nomenclature, provided are descriptions of exemplary sequence manipulation and alignment procedures, e.g., scripts referenced herein. This list is not intended to be exhaustive or definitive, rather the scripts listed herein serve as examples of the types of scripts that may be useful for the provided analyses.

In some embodiments, these scripts and/or steps may be performed in parallel and/or are organized in a branched manner, such that multiple steps may be performed at the same time, in any order.

get_bcl: Compressed raw data from a high-throughput sequencer (base calls in the form of a .bcl file) are retrieved from an intermediate storage location (in some embodiments, on cloud-based storage) and downloaded to the computing cluster.

untar_bcls: The data from the sequencer run are decompressed for processing using downstream tools.

bcl2fastq: A software tool bcl2fastq is used to convert the raw base call files into gzip-compressed FASTQ files, containing sequence and metadata for every read in the sequencing run. In exemplary embodiments, for paired-end runs from ATAC-Seq, each sample has two files, R1 and R2, corresponding to forward and reverse reads (beginning and end of each DNA fragment) respectively.

get_data: Compressed FASTQ files from the previous step are retrieved and moved into per-sample analysis directories.

unzip: Compressed FASTQ files are decompressed so that they can be processed by downstream tools.

fastqc: Generates a set of reports on the overall statistics of the sequencing run and base calling quality, as well as potential signs of contamination or overclustering.

get_genome: Fetches the appropriate genome files for the specified organism and version. In some embodiments, this may include from online sources and/or databanks.

build_bowtie2_index: Indexes the genome files so that reads can be positionally mapped to the genome, using a software tool called bowtie2_build.

Index_genome_fasta: Builds a FASTA index for the downloaded genome files to allow positional access by downstream tools.

map_atac_reads: Maps the sequences of the ATAC-seq reads back to the genome to determine their position, using the mapping software bowtie2.

Picard_remove_duplicates: Uses a software suite (e.g. Picard) to flag and remove duplicate reads arising from PCR amplification bias and cluster miscalling, to reduce the amount of noise in the datasets. In some cases, this step can ensure proper sorting naming and indexing of the reads post-mapping, and outputs idxstats files that give mapped counts per chromosome.

atac_insert_size_metrics: Uses software (e.g. Picard) to calculate and visualize the distribution of fragment sizes recovered from the dataset.

atac_alignment_summary: Uses software (e.g. Picard) to calculate statistics related to positional distribution of reads into various types of genomic features.

filter_mtDNA_reads: Filters out mitochondrial DNA.

shift_atac_alignments: Shifts the positions of the mapped fragments to account for the 4 or 5-basepair insertion by the Tn5 transposase during the ATAC-seq library preparation.

Filter_nucleosomal_fragments: Filters out fragments larger than 100 bp. In some embodiments, it is contemplated that these fragments can represent nucleosome-bound chromatin rather than free chromatin. This step is capable of enriching the signal, and both the filtered and non-filtered reads will be used in downstream analyses to infer open and nucleosome-occupied chromatin, respectively.

make_homer_tagdir: Converts BAM alignment files into a file format usable by downstream HOMER tools.

homer_findPeaks: A step that can be employed to find peaks, using HOMER.

homer_find_motifs: Searches for enriched transcription factor binding motifs shared within the peak sets discovered by MACS and HOMER.

homer_annotate_peaks: Annotates peaks with additional metadata including the nearest gene they are likely to be associated with. In some embodiments, this step could be replaced by another annotation strategy.

get_gtf_annotation: Retrieves transcriptome annotation files associated with the organism and genome version that the pipeline is running.

gtf_coding_transcripts_only: Subsets the transcriptome annotation to only protein coding transcripts.

homer_calculate_per_gene_accessibility_norm: Calculates a normalized per-gene accessibility value (e.g., normalized FPKM values) representing general accessibility of a gene.

make_homer_ucsc_file: Creates a .bedGraph file. In some embodiments, this allows for genome-wide pileups of fragment counts.

homer_bedgraph_to_bigwig: Converts the bedGraph file to a binary-compressed bigWig file. In some cases, this file type is used by genome browsers to visualize fragment coverage across the genome.

macs_callpeaks: Uses MACS2 to call accessibility peaks. In some aspects, the peaks include genomic regions that are enriched for or depleted of accessibility and/or occupancy signal as measured by quantifying ATAC-seq fragments. In some embodiments, the peak regions can be between 10 and 10,000 bp in size. Comparison of peaks between samples may be used downstream to identify active regulatory elements (optionally associated with specific genes or transcription factors) between conditions and/or be used to identify signatures of specific cell states or predictive of outcome of cell therapy, performance of cell therapy, toxicity and/or other characteristics of the cell composition or culture.

nucleoatac_run: Runs NucleoATAC, a tool capable of calling and counting transposase insertion sites within peak regions as well as output summary tables on the data from previous steps.

Additional downstream analyses can be used within the framework of the analysis pipeline, including thresholding and clustering approaches, predictive modeling and/or differential peak calling.

III. Therapeutic Outcomes

In some embodiments of the provided methods, the epigenetic properties (e.g. chromatin accessibility) of the genome of the population of cells, such as a population of cells that is comprised in a composition of cells to be genetically engineered with a recombinant receptor or that has been genetically engineered with a recombinant receptor, is or can be correlated with the occurrence of an outcome of treatment of a cell therapy in accord with the provided methods.

In some embodiments of the provided methods, the epigenetic properties (e.g. chromatin accessibility) of the genome of the population of cells, such as a population of cells that is comprised in a composition of cells to be genetically engineered with a recombinant receptor or that has been genetically engineered with a recombinant receptor, can be predictive of and/or diagnose or detect the likelihood of the occurrence of an outcome of treatment of a cell therapy in accord with the provided methods.

In some embodiments, the subject has been, is receiving or will be receiving a therapy, such as a cell therapy, for example, for treating a disease or condition in a subject. For example, in some embodiments, the cell therapy is an adoptive cell therapy, including a therapy involving administration of cells expressing chimeric receptors specific for a disease or disorder of interest, such as chimeric antigen receptors (CARs) and/or other recombinant antigen receptors, as well as other adoptive immune cells and adoptive T cell therapies. In some embodiments, the adoptive cell therapy includes administration of a dose of cells expressing a recombinant receptor, such as a CAR or other recombinant antigen receptor. In some embodiments, chimeric receptors, such chimeric antigen receptor, contain one or more domains that combine a ligand-binding domain (e.g. antibody or antibody fragment) that provides specificity for a desired antigen (e.g., tumor antigen) with intracellular signaling domains. In some embodiments, the intracellular signaling domain is an activating intracellular domain portion, such as a T cell activating domain, providing a primary activation signal. In some embodiments, the intracellular signaling domain contains or additionally contains a costimulatory signaling domain to facilitate effector functions. In some embodiments, chimeric receptors when genetically engineered into immune cells can modulate T cell activity, and, in some cases, can modulate T cell differentiation or homeostasis, thereby resulting in genetically engineered cells with improved longevity, survival and/or persistence in vivo, such as for use in adoptive cell therapy methods.

A. Toxicity Outcome

In some embodiments, a toxic outcome in a subject to administration of a therapeutic agent (e.g. CAR T-cells) can be assessed or monitored. In some embodiments, the toxic outcome is or is associated with the presence of a toxic event, such as cytokine release syndrome (CRS), severe CRS (sCRS), macrophage activation syndrome, tumor lysis syndrome, fever of at least at or about 38 degrees Celsius for three or more days and a plasma level of C-reactive protein (CRP) of at least at or about 20 mg/dL, neurotoxicity and/or severe neurotoxicity. In some embodiments, the toxic outcome is a sign, or symptom, particular signs, and symptoms and/or quantities or degrees thereof which presence or absence may specify a particular extent, severity or level of toxicity in a subject. It is within the level of a skilled artisan to specify or determine a particular sign, symptom and/or quantities or degrees thereof that are related to an undesired toxic outcome of a therapeutic agent (e.g. CAR-T cells).

In some embodiments, the toxic outcome is an indicator associated with the toxic event. In some embodiments, the toxic outcome is the presence or absence of one or more biomarkers or the presence of absence of a level of one or more biomarkers. In some embodiments, the biomarker is a molecule present in the serum or other bodily fluid or tissue indicative of cytokine-release syndrome (CRS), severe CRS or CRS-related outcomes. In some embodiments, the biomarker is a molecule present in the serum or other bodily fluid or tissue indicative of neurotoxicity or severe neurotoxicity.

In some embodiments, the subject exhibits toxicity or a toxic outcome if a toxic event, such as CRS-related outcomes, e.g. if a serum level of an indicator of CRS or other biochemical indicator of the toxicity is more than at or about 10 times, more than at or about 15 times, more than at or about 20 times, more than at or about 25 times, more than at or about 50 times, more than at or about 75 times, more than at or about 100 times, more than at or about 125 times, more than at or about 150 times, more than at or about 200 times, or more than at or about 250 times the baseline or pre-treatment level, such as the serum level of the indicator immediately prior to administration of the first dose of the therapeutic agent.

In some aspects, the toxic outcome is or is associated with or indicative of cytokine release syndrome (CRS) or severe CRS (sCRS). CRS, e.g., sCRS, can occur in some cases following adoptive T cell therapy and administration to subjects of other biological products. See Davila et al., Sci Transl Med 6, 224ra25 (2014); Brentjens et al., Sci. Transl. Med. 5, 177ra38 (2013); Grupp et al., N. Engl. J. Med. 368, 1509-1518 (2013); and Kochenderfer et al., Blood 119, 2709-2720 (2012); Xu et al., Cancer Letters 343 (2014) 172-78.

Typically, CRS is caused by an exaggerated systemic immune response mediated by, for example, T cells, B cells, NK cells, monocytes, and/or macrophages. Such cells may release a large amount of inflammatory mediators such as cytokines and chemokines. Cytokines may trigger an acute inflammatory response and/or induce endothelial organ damage, which may result in microvascular leakage, heart failure, or death. Severe, life-threatening CRS can lead to pulmonary infiltration and lung injury, renal failure, or disseminated intravascular coagulation. Other severe, life-threatening toxicities can include cardiac toxicity, respiratory distress, neurologic toxicity and/or hepatic failure.

In the context of administering CAR-expressing cells, CRS typically occurs 6-20 days after infusion of cells that express a CAR. See Xu et al., Cancer Letters 343 (2014) 172-78. In some cases, CRS occurs less than 6 days or more than 20 days after CAR T cell infusion. The incidence and timing of CRS may be related to baseline cytokine levels or tumor burden at the time of infusion. Commonly, CRS involves elevated serum levels of interferon (IFN)-γ, tumor necrosis factor (TNF)-α, and/or interleukin (IL)-2. Other cytokines that may be rapidly induced in CRS are IL-1β, IL-6, IL-8, and IL-10.

Exemplary signs or symptoms associated with CRS include fever, rigors, chills, hypotension, dyspnea, acute respiratory distress syndrome (ARDS), encephalopathy, aspartate transaminase (AST)/alanine transaminase (ALT) elevation, renal failure, cardiac disorders, hypoxia, neurologic disturbances, and death. Neurological complications include delirium, seizure-like activity, confusion, word-finding difficulty, aphasia, and/or becoming obtunded. Other CRS-related signs or outcomes include fatigue, nausea, headache, seizure, tachycardia, myalgias, rash, acute vascular leak syndrome, liver function impairment, and renal failure. In some aspects, CRS is associated with an increase in one or more factors such as serum-ferritin, d-dimer, aminotransferases, lactate dehydrogenase and triglycerides, or with hypofibrinogenemia or hepatosplenomegaly.

In some embodiments, signs or symptoms associated with CRS include one or more of: persistent fever, e.g., fever of a specified temperature, e.g., greater than at or about 38 degrees Celsius, for two or more, e.g., three or more, e.g., four or more days or for at least three consecutive days; fever greater than at or about 38 degrees Celsius; elevation of cytokines (e.g. IFNγ or IL-6); and/or at least one clinical sign of toxicity, such as hypotension (e.g., as measured by at least one intravenous vasoactive pressor); hypoxia (e.g., plasma oxygen ($PO_2$) levels of less than at or about 90%); and/or one or more neurologic disorders (including mental status changes, obtundation, and seizures).

Exemplary CRS-related outcomes include increased or high serum levels of one or more factors, including cytokines and chemokines and other factors associated with CRS. Exemplary outcomes further include increases in synthesis or secretion of one or more of such factors. Such synthesis or secretion can be by the T cell or a cell that interacts with the T cell, such as an innate immune cell or B cell.

In some embodiments, one or more inflammatory markers, e.g., cytokines or chemokines are monitored before, during, or after CAR treatment. In some aspects, the one or more cytokines or chemokines include IFN-γ, TNF-α, IL-2, IL-1β, IL-6, IL-7, IL-8, IL-10, IL-12, sIL-2Rα, granulocyte macrophage colony stimulating factor (GM-CSF), or macrophage inflammatory protein (MIP). In some embodiments, IFN-γ, TNF-α, and IL-6 are monitored.

In some embodiments, the presence of one or more biomarkers is indicative of the grade of, severity or extent of a toxic event, such as CRS or neurotoxicity. In some embodiments, the toxic outcome is a particular grade, severity or extent of a toxic event, such as a particular grade, severity or extent of CRS or neurotoxicity. In some embodiments, the presence of a toxic event about a certain grade, severity or extent can be a dose-limiting toxicity. In some embodiments, the absence of a toxic event or the presence of a toxic event below a certain grade, severity or extent can indicate the absence of a dose-limiting toxicity.

CRS criteria that appear to correlate with the onset of CRS to predict which patients are more likely to be at risk for developing sCRS have been developed (see Davila et al. Science translational medicine. 2014; 6(224):224ra25). Factors include fevers, hypoxia, hypotension, neurologic changes, elevated serum levels of inflammatory cytokines whose treatment-induced elevation can correlate well with both pretreatment tumor burden and sCRS symptoms. Other guidelines on the diagnosis and management of CRS are known (see e.g., Lee et al, Blood. 2014; 124(2):188-95). In some embodiments, the criteria reflective of CRS grade are those detailed in Table 1 below.

TABLE 1

Exemplary Grading Criteria for CRS

| Grade | Description of Symptoms |
|---|---|
| 1<br>Mild | Not life-threatening, require only symptomatic treatment such as antipyretics and anti-emetics (e.g., fever, nausea, fatigue, headache, myalgias, malaise) |
| 2<br>Moderate | Require and respond to moderate intervention:<br>　Oxygen requirement <40%, or<br>　Hypotension responsive to fluids or low dose of a single vasopressor, or<br>　Grade 2 organ toxicity (by CTCAE v4.0) |
| 3<br>Severe | Require and respond to aggressive intervention:<br>　Oxygen requirement ≥40%, or<br>　Hypotension requiring high dose of a single vasopressor (e.g., norepinephrine ≥20 μg/kg/min, dopamine ≥10 μg/kg/min, phenylephrine ≥200 μg/kg/min, or epinephrine ≥10 μg/kg/min), or<br>　Hypotension requiring multiple vasopressors (e.g., vasopressin + one of the above agents, or combination vasopressors equivalent to ≥20 μg/kg/min norepinephrine), or<br>　Grade 3 organ toxicity or Grade 4 transaminitis (by CTCAE v4.0) |
| 4<br>Life-threatening | Life-threatening:<br>　Requirement for ventilator support, or<br>　Grade 4 organ toxicity (excluding transaminitis) |
| 5<br>Fatal | Death |

In some embodiments, the toxic outcome is severe CRS. In some embodiments, the toxic outcome is the absence of severe CRS (e.g. moderate or mild CRS). In some embodiments, severe CRS includes CRS with a grade of 3 or greater, such as set forth in Table 1. In some embodiments, severe CRS includes CRS with a grade of 2 or higher, such as grades 2, 3, 4 or 5 CRS.

In some embodiments, the level of the toxic outcome, e.g. the CRS-related outcome, e.g. the serum level of an indicator of CRS, is measured by ELISA. In some embodiments, fever and/or levels of C-reactive protein (CRP) can be measured. In some embodiments, subjects with a fever and a CRP≥15 mg/dL may be considered high-risk for developing severe CRS. In some embodiments, the CRS-associated serum factors or CRS-related outcomes include an increase in the level and/or concentration of inflammatory cytokines and/or chemokines, including Flt-3L, fracktalkine, granulocyte macrophage colony stimulating factor (GM-CSF), interleukin-1 beta (IL-1β), IL-2, IL-5, IL-6, IL-7, IL-8, IL-10, IL-12, interferon gamma (IFN-γ), macrophage inflammatory protein (MIP)-1, MIP-1, sIL-2Rα, or tumor necrosis factor alpha (TNFα). In some embodiments, the factor or outcome includes C reactive protein (CRP). In addition to being an early and easily measurable risk factor for CRS, CRP also is a marker for cell expansion. In some embodiments, subjects that are measured to have high levels of CRP, such as ≥15 mg/dL, have CRS. In some embodiments, subjects that are measured to have high levels of CRP do not have CRS. In some embodiments, a measure of CRS includes a measure of CRP and another factor indicative of CRS.

In some aspects, the toxic outcome is or is associated with neurotoxicity. In some embodiments, signs or symptoms associated with a clinical risk of neurotoxicity include confusion, delirium, expressive aphasia, obtundation, myoclonus, lethargy, altered mental status, convulsions, seizure-like activity, seizures (optionally as confirmed by electroencephalogram (EEG)), elevated levels of beta amyloid (Aβ), elevated levels of glutamate, and elevated levels of oxygen radicals. In some embodiments, neurotoxicity is graded based on severity (e.g., using a Grade 1-5 scale (see, e.g., Guido Cavaletti & Paola Marmiroli *Nature Reviews Neurology* 6, 657-666 (December 2010); National Cancer Institute—Common Toxicity Criteria version 4.03 (NCI-CTCAE v4.03). In some embodiments, a subject is deemed to develop "severe neurotoxicity" in response to or secondary to administration of a cell therapy or dose of cells thereof, if, following administration, the subject displays symptoms that limit self-care (e.g. bathing, dressing and undressing, feeding, using the toilet, taking medications) from among: 1) symptoms of peripheral motor neuropathy, including inflammation or degeneration of the peripheral motor nerves; 2) symptoms of peripheral sensory neuropathy, including inflammation or degeneration of the peripheral sensory nerves, dysesthesia, such as distortion of sensory perception, resulting in an abnormal and unpleasant sensation, neuralgia, such as intense painful sensation along a nerve or a group of nerves, and/or paresthesia, such as functional disturbances of sensory neurons resulting in abnormal cutaneous sensations of tingling, numbness, pressure, cold and warmth in the absence of stimulus. In some embodiments, severe neurotoxicity includes neurotoxicity with a grade of 3 or greater, such as set forth in Table 2. In some embodiments, severe neurotoxicity includes neurotoxicity with a grade of 2 or higher, such as grades 2, 3, 4 or 5 neurotoxicity.

TABLE 2

Exemplary Grading Criteria for neurotoxicity

| Grade | Description of Symptoms |
|---|---|
| 1<br>Asymptomatic or Mild | Mild or asymptomatic symptoms |
| 2<br>Moderate | Presence of symptoms that limit instrumental activities of daily living (ADL), such as preparing meals, shopping for groceries or clothes, using the telephone, managing money |
| 3<br>Severe | Presence of symptoms that limit self-care ADL, such as bathing, dressing and undressing, feeding self, using the toilet, taking medications |
| 4<br>Life-threatening | Symptoms that are life-threatening, requiring urgent intervention |
| 5<br>Fatal | Death |

In some embodiments, the toxic outcome is a dose-limiting toxicity. In some embodiments, the toxic outcome is the absence of a dose-limiting toxicity. In some embodiments, a dose-limiting toxicity (DLT) is defined as any grade 3 or higher toxicity as assessed by any known or published guidelines for assessing the particular toxicity, such as any described herein and including the National Cancer Institute (NCI) Common Terminology Criteria for Adverse Events (CTCAE) version 4.0.

B. Response Outcome

In some embodiments, the therapeutic outcome is a response or efficacy outcome of the cell therapy, a toxicity outcome of the cell therapy, an immunogenic response to the cell therapy or is another characteristic or feature of the cell therapy (e.g. persistence or expansion of the cells in subject). In certain embodiments, the therapeutic outcome is a therapeutic or prophylactic efficacy outcome of the cell therapy. In some embodiments, the response outcome of the cell therapy includes efficacy outcome at particular dose. In some aspects, the therapeutic outcome of the cell therapy includes the dose of the cell therapy that is needed to achieve a response. In some aspects, persistence and/or expansion of the cells are assessed.

In some embodiments, the response outcome in a subject to administration of the cell therapy can be monitored or assessed. In some embodiments, the response outcome of the cell therapy is a complete response (CR). In some embodiments, response outcome is assessed by monitoring the disease burden in the subject. In some embodiments, the presence of no response, a partial response or a clinical or complete response can be assessed. In some embodiments, the response outcome of the cell therapy is durability of response.

In some embodiments, a partial response (PR) or complete response (CR) is one in which the therapeutic agent reduces or prevents the expansion or burden of the disease or condition in the subject. For example, where the disease or condition is a tumor, reduced disease burden exists or is present if there is a reduction in the tumor size, bulk, metastasis, percentage of blasts in the bone marrow or molecularly detectable cancer and/or an improvement prognosis or survival or other symptom associated with tumor burden compared to prior to treatment with the therapeutic agent (e.g. CAR T cells).

In some aspects, response rates in subjects, such as subjects with NHL, are based on the Lugano criteria. (Cheson et al., (2014) JCO 32(27):3059-3067; Johnson et al., (2015) Radiology 2:323-338; Cheson, B. D. (2015) Chin Clin Oncol 4(1):5). In some aspects, response assessment utilizes any of clinical, hematologic, and/or molecular methods. In some aspects, response assessed using the Lugano criteria involves the use of positron emission tomography (PET)-computed tomography (CT) and/or CT as appropriate. PET-CT evaluations may further comprise the use of fluorodeoxyglucose (FDG) for FDG-avid lymphomas. In some aspects, where PET-CT will be used to assess response in FDG-avid histologies, a 5-point scale may be used. In some respects, the 5-point scale comprises the following criteria: 1, no uptake above background; 2, uptake≤mediastinum; 3, uptake>mediastinum but ≤liver; 4, uptake moderately>liver; 5, uptake markedly higher than liver and/or new lesions; X, new areas of uptake unlikely to be related to lymphoma.

In some aspects, a complete response as described using the Lugano criteria involves a complete metabolic response and a complete radiologic response at various measureable sites. In some aspects, these sites include lymph nodes and extralymphatic sites, wherein a CR is described as a score of 1, 2, or 3 with or without a residual mass on the 5-point scale, when PET-CT is used. In some aspects, in Waldeyer's ring or extranodal sites with high physiologic uptake or with activation within spleen or marrow (e.g., with chemotherapy or myeloid colony-stimulating factors), uptake may be greater than normal mediastinum and/or liver. In this circumstance, complete metabolic response may be inferred if uptake at sites of initial involvement is no greater than surrounding normal tissue even if the tissue has high physiologic uptake. In some aspects, response is assessed in the lymph nodes using CT, wherein a CR is described as no extralymphatic sites of disease and target nodes/nodal masses must regress to ≤1.5 cm in longest transverse diameter of a lesion (LDi). Further sites of assessment include the bone marrow wherein PET-CT-based assessment should indicate a lack of evidence of FDG-avid disease in marrow and a CT-based assessment should indicate a normal morphology, which if indeterminate should be IHC negative. Further sites may include assessment of organ enlargement, which should regress to normal. In some aspects, nonmeasured lesions and new lesions are assessed, which in the case of CR should be absent (Cheson et al., (2014) JCO 32(27): 3059-3067; Johnson et al., (2015) Radiology 2:323-338; Cheson, B. D. (2015) Chin Clin Oncol 4(1):5).

In some aspects, a partial response (PR) as described using the Lugano criteria involves a partial metabolic and/or radiological response at various measureable sites. In some aspects, these sites include lymph nodes and extralymphatic sites, wherein a PR is described as a score of 4 or 5 with reduced uptake compared with baseline and residual mass(es) of any size, when PET-CT is used. At interim, such findings can indicate responding disease. At the end of treatment, such findings can indicate residual disease. In some aspects, response is assessed in the lymph nodes using CT, wherein a PR is described as ≥50% decrease in sum of product dimensions (SPD) of up to 6 target measureable nodes and extranodal sites. If a lesion is too small to measure on CT, 5 mm×5 mm is assigned as the default value; if the lesion is no longer visible, the value is 0 mm×0 mm; for a node>5 mm×5 mm, but smaller than normal, actual measurements are used for calculation. Further sites of assessment include the bone marrow wherein PET-CT-based assessment should indicate residual uptake higher than uptake in normal marrow but reduced compared with baseline (diffuse uptake compatible with reactive changes from chemotherapy allowed). In some aspects, if there are persistent focal changes in the marrow in the context of a nodal response, consideration should be given to further evaluation with MRI or biopsy, or an interval scan. In some aspects, further sites may include assessment of organ enlargement, where the spleen must have regressed by >50% in length beyond normal. In some aspects, nonmeasured lesions and new lesions are assessed, which in the case of PR should be absent/normal, regressed, but no increase. No response/stable disease (SD) or progressive disease (PD) can also be measured using PET-CT and/or CT based assessments. (Cheson et al., (2014) JCO 32(27):3059-3067; Johnson et al., (2015) Radiology 2:323-338; Cheson, B. D. (2015) Chin Clin Oncol 4(1):5).

In some respects, progression-free survival (PFS) is described as the length of time during and after the treatment of a disease, such as cancer, that a subject lives with the disease but it does not get worse. In some aspects, objective response (OR) is described as a measurable response. In some aspects, objective response rate (ORR) is described as the proportion of patients who achieved CR or PR. In some aspects, overall survival (OS) is described as the length of time from either the date of diagnosis or the start of treatment for a disease, such as cancer, that subjects diagnosed with the disease are still alive. In some aspects, event-free survival (EFS) is described as the length of time after treatment for a cancer ends that the subject remains free of certain complications or events that the treatment was intended to prevent or delay. These events may include the return of the cancer or the onset of certain symptoms, such as bone pain from cancer that has spread to the bone, or death.

In some embodiments, the measure of duration of response (DOR) includes the time from documentation of tumor response to disease progression. In some embodiments, the parameter for assessing response can include durable response, e.g., response that persists after a period of time from initiation of therapy and/or long-lasting positive response to therapy. In some embodiments, durable response is indicated by the response rate at approximately 1, 2, 3, 4, 5, 6, 7, 8, 9, 10, 11, 12, 18 or 24 months after initiation of therapy. In some embodiments, the response is durable for greater than 3 months or greater than 6 months. In some embodiments, durable response is response measured at month 3 after administration of therapy, e.g., a 3-month response. In some embodiments, durable response is response measured at month 6 after administration of therapy, e.g., a 6-month response.

In some aspects, the RECIST criteria is used to determine objective tumor response; in some aspects, in solid tumors. (Eisenhauer et al., European Journal of Cancer 45 (2009) 228-247.) In some aspects, the RECIST criteria is used to determine objective tumor response for target lesions. In some respects, a complete response as determined using RECIST criteria is described as the disappearance of all target lesions and any pathological lymph nodes (whether target or non-target) must have reduction in short axis to <10 mm. In other aspects, a partial response as determined using RECIST criteria is described as at least a 30% decrease in the sum of diameters of target lesions, taking as reference the baseline sum diameters. In other aspects, progressive disease (PD) is described as at least a 20% increase in the sum of diameters of target lesions, taking as reference the smallest sum on study (this includes the baseline sum if that is the smallest on study). In addition to the relative increase of 20%, the sum must also demonstrate an absolute increase of at least 5 mm (in some aspects the appearance of one or more new lesions is also considered progression). In other aspects, stable disease (SD) is described as neither sufficient shrinkage to qualify for PR nor sufficient increase to qualify for PD, taking as reference the smallest sum diameters while on study.

In some embodiments, the disease or condition is a tumor and a reduction in disease burden is a reduction in tumor size. In some embodiments, the disease burden reduction is indicated by a reduction in one or more factors, such as load or number of disease cells in the subject or fluid or organ or tissue thereof, the mass or volume of a tumor, or the degree or extent of metastases. In some embodiments, disease burden, e.g. tumor burden, can be assessed or monitored for the extent of morphological disease and/or minimal residual disease.

In some embodiments, the burden of a disease or condition in the subject is detected, assessed, or measured. Disease burden may be detected in some aspects by detecting the total number of disease or disease-associated cells, e.g., tumor cells, in the subject, or in an organ, tissue, or bodily fluid of the subject, such as blood or serum. In some embodiments, disease burden, e.g. tumor burden, is assessed by measuring the mass of a solid tumor and/or the number or extent of metastases. In some aspects, survival of the subject, survival within a certain time period, extent of survival, presence or duration of event-free or symptom-free survival, or relapse-free survival, is assessed. In some embodiments, any symptom of the disease or condition is assessed. In some embodiments, the measure of disease or condition burden is specified.

In some embodiments, disease burden can encompass a total number of cells of the disease in the subject or in an organ, tissue, or bodily fluid of the subject, such as the organ or tissue of the tumor or another location, e.g., which would indicate metastasis. For example, tumor cells may be detected and/or quantified in the blood or bone marrow in the context of certain hematological malignancies.

Disease burden can include, in some embodiments, the mass of a tumor, the number or extent of metastases and/or the percentage of blast cells present in the bone marrow.

In some embodiments, a subject has leukemia. The extent of disease burden can be determined by assessment of residual leukemia in blood or bone marrow.

In some aspects, response rates in subjects, such as subjects with chronic lymphocytic leukemia (CLL), are based on the International Workshop on Chronic Lymphocytic Leukemia (IWCLL) response criteria (Hallek, et al., Blood 2008, Jun. 15; 111(12): 5446-5456). In some aspects, these criteria are described as follows: complete remission (CR), which in some aspects requires the absence of peripheral blood clonal lymphocytes by immunophenotyping, absence of lymphadenopathy, absence of hepatomegaly or splenomegaly, absence of constitutional symptoms and satisfactory blood counts; complete remission with incomplete marrow recovery (CRi), which in some aspects is described as CR above, but without normal blood counts; partial remission (PR), which in some aspects is described as ≥50% fall in lymphocyte count, ≥50% reduction in lymphadenopathy or ≥50% reduction in liver or spleen, together with improvement in peripheral blood counts; progressive disease (PD), which in some aspects is described as ≥50% rise in lymphocyte count to ≥5×10$^9$/L, ≥50% increase in lymphadenopathy, ≥50% increase in liver or spleen size, Richter's transformation, or new cytopenias due to CLL; and stable disease, which in some aspects is described as not meeting criteria for CR, CRi, PR or PD.

In some embodiments, the subjects exhibits a CR or OR if, within 1 month of the administration of the dose of cells, lymph nodes in the subject are less than at or about 20 mm in size, less than at or about 10 mm in size or less than at or about 10 mm in size.

In some embodiments, an index clone of the CLL is not detected in the bone marrow of the subject (or in the bone marrow of greater than 50%, 60%, 70%, 80%, 90% or more of the subjects treated according to the methods. In some embodiments, an index clone of the CLL is assessed by IgH deep sequencing. In some embodiments, the index clone is not detected at a time that is at or about or at least at or about 1, 2, 3, 4, 5, 6, 12, 18 or 24 months following the administration of the cells.

In some embodiments, a response outcome exists if there is a reduction in the percent of blasts in the bone marrow compared to the percent of blasts in the bone marrow prior to treatment with the therapeutic agent. In some embodiments, reduction of disease burden exists if there is a decrease or reduction of at least or at least about 20%, 30%, 40%, 50%, 60%, 70%, 80%, 90%, 95% or more in the number or percentage of blasts in the bone marrow compared to the number or percent of blasts in the bone marrow prior to treatment.

In some embodiments, the subject exhibits a response if the subject does not exhibit morphologic disease (non-morphological disease) or does not exhibit substantial morphologic disease. In some embodiments, a subject exhibits morphologic disease if there are greater than or equal to 5% blasts in the bone marrow, for example, as detected by light microscopy. In some embodiments, a subject exhibits complete or clinical remission if there are less than 5% blasts in the bone marrow.

In some embodiments, a subject exhibits reduced or decreased disease burden if they exhibited morphological disease prior to treatment and exhibit complete remission (e.g., fewer than 5% blasts in bone marrow) with or without molecular disease (e.g., minimum residual disease (MRD) that is molecularly detectable, e.g., as detected by flow cytometry or quantitative PCR) after treatment. In some embodiments, a subject exhibits reduced or decreased disease burden if they exhibited molecular disease prior to treatment and do not exhibit molecular disease after treatment.

In some embodiments, a subject may exhibit complete remission, but a small proportion of morphologically undetectable (by light microscopy techniques) residual leukemic cells are present. A subject is said to exhibit minimum residual disease (MRD) if the subject exhibits less than 5% blasts in the bone marrow and exhibits molecularly detectable cancer. In some embodiments, molecularly detectable cancer can be assessed using any of a variety of molecular techniques that permit sensitive detection of a small number of cells.

In some embodiments, the response outcome of the cell therapy is a molecular response outcome. In some aspects, such techniques include PCR assays, which can determine unique Ig/T-cell receptor gene rearrangements or fusion transcripts produced by chromosome translocations. In some embodiments, flow cytometry can be used to identify cancer cell based on leukemia-specific immunophenotypes. In some embodiments, molecular detection of cancer can detect as few as 1 leukemia or blast cell in 100,000 normal cells or 1 leukemia or blast cell in 10,000 normal cells. In some embodiments, a subject exhibits minimum residual disease (MRD) that is molecularly detectable if at least or greater than 1 leukemia cell in 100,000 cells is detected, such as by PCR or flow cytometry.

In some embodiments, the disease burden of a subject is molecularly undetectable or MRD$^-$, such that, in some cases, no leukemia cells are able to be detected in the subject using PCR or flow cytometry techniques.

In some embodiments the response outcome is the absence of a CR or the presence of a complete response (CR) in which the subject achieves or exhibits minimal residual disease or molecular detectable disease status. In some embodiments, the response outcome is the presence of a CR with molecularly detectable disease or the presence of a CR without molecularly detectable disease. In some embodiments, subjects are assessed for disease burden using methods as described herein, such as methods that assess blasts in bone marrow or molecular disease by flow cytometry or qPCR methods.

In some embodiments of the methods provided herein, response is determined by complete response (CR) and/or objective response (OR); and/or the subject exhibits CR, OR, lymph nodes of less than at or about 20 mm in size, within 1 month of the administration of the dose of cells; and/or an index clone of the disease or condition, such as the CLL or NHL, is not detected in the bone marrow of the subject (or in the bone marrow of greater than 50% of subjects treated according to the methods), optionally as assessed by IgH deep sequencing, optionally at a time that is at or about or at least at or about 1, 2, 3, 4, 5, 6, 12, 18, or 24 months following the administration of the cell dose.

In some aspects, toxic outcomes and/or presence or absence of a host immune response are assessed. In some embodiments, the response outcome of the cell therapy is a lack of immune response. In some embodiments, the information about toxic outcome and response outcome can be jointly assessed in a subject, such as assessed in parallel or at around the same time or substantially the same time, and used to inform the dosing decisions or adaptive treatments of subjects.

In some embodiments, the toxic outcome or response outcome is present and/or can be assessed or monitored. In some embodiments, the toxic outcome and response outcome are monitored at a time at which a toxicity outcome and a response outcome are present. In some embodiments, the time at which a toxic outcome or response outcome is assessed is within or within about a period of time in which a symptom of toxicity or efficacy is detectable in a subject or at such time in which an adverse outcome associated with non-response or toxicity is not detectable in the subject. In some embodiments, the time period is near or substantially near to when the toxic outcome and/or response outcome has peaked in the subject.

In some embodiments, the toxic outcome or response outcome is present or can be assessed or monitored at such time period where only a single dose of the therapeutic agent is administered. In the context of adoptive cell therapy, administration of a given "dose" encompasses administration of the given amount or number of cells as a single composition and/or single uninterrupted administration, e.g., as a single injection or continuous infusion, and also encompasses administration of the given amount or number of cells as a split dose, provided in multiple individual compositions or infusions, over a specified period of time, which is no more than 3 days. Thus, in some contexts, the first dose is a single or continuous administration of the specified number of cells, given or initiated at a single point in time. In some contexts, however, the first dose is administered in multiple injections or infusions over a period of no more than three days, such as once a day for three days or for two days or by multiple infusions over a single day period.

The term "split dose" refers to a dose that is split so that it is administered over more than one day. This type of dosing is encompassed by the present methods and is considered to be a single dose.

As used herein, "first dose" is used to describe the timing of a given dose, which, in some cases can be the only dose or can be followed by one or more repeat or additional doses. The term does not necessarily imply that the subject has never before received a dose of a therapeutic agent even that the subject has not before received a dose of the same or substantially the same therapeutic agent.

In some embodiments, the toxic outcome and response outcome can be assessed by monitoring one or more symptoms or events associated with a toxic outcome and one or more symptoms or events associated with a response outcome.

IV. Engineering Cells for Adoptive Cell Therapy

In some embodiments, the provided methods can be used to assess cells for adoptive cell therapy. In any of the provided methods, the epigenetic and/or epigenomic analysis of cells for cell therapy can include steps to assess and analyze changes or modifications in a genomic locus or a genome, such as chromatin accessibility, nucleosome occupancy, histone modification, spatial chromosomal conformation, transcription factor occupancy and/or DNA methylation. In some embodiments, the provided methods involve one or more epigenetic and/or epigenomic analysis step of the cells. In some aspects, the epigenetic and/or epigenomic analysis is performed prior to genetic engineering of the cells. In some cases, the epigenetic and/or epigenomic analysis is performed after the cells have been genetically engineered with a recombinant receptor.

In some embodiments, the analysis includes a large-scale analysis, e.g., analysis of a plurality of genetic loci or a genome-wide analysis of the cells. In some embodiments, the epigenetic and/or epigenomic analysis includes determining the epigenetic properties of a cell, e.g., an engineered cell for cell therapy. In some embodiments, the cell therapy is a T cell therapy, for example, a tumor infiltrating lymphocytic (TIL) therapy, a transgenic TCR therapy or a chimeric antigen receptor (CAR)-expressing T cell therapy.

A. Cells

The cells generally are eukaryotic cells, such as mammalian cells, and typically are human cells, e.g., those derived from human subjects and engineered, for example, to express the recombinant receptors. In some embodiments, the cells are derived from the blood, bone marrow, lymph, or lymphoid organs, are cells of the immune system, such as cells of the innate or adaptive immunity, e.g., myeloid or lymphoid cells, including lymphocytes, typically T cells and/or NK cells. Other exemplary cells include stem cells, such as multipotent and pluripotent stem cells, including induced pluripotent stem cells (iPSCs). The cells typically are primary cells, such as those isolated directly from a subject and/or isolated from a subject and frozen. In some embodiments, the cells include one or more subsets of T cells or other cell types, such as whole T cell populations, CD4+ cells, CD8+ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion properties, and/or degree of differentiation. With reference to the subject to be treated, the cells may be allogeneic and/or autologous. Among the methods include off-the-shelf methods. In some aspects, such as for off-the-shelf technologies, the cells are pluripotent and/or multipotent, such as stem cells, such as induced pluripotent stem cells (iPSCs). In some embodiments, the methods include isolating cells from the subject, preparing, processing, culturing, and/or engineering them, and re-introducing them into the same subject, before or after cryopreservation.

Among the sub-types and subpopulations of T cells and/or of CD4+ and/or of CD8+ T cells are naïve T ($T_N$) cells, effector T cells ($T_{EFF}$), memory T cells and sub-types thereof, such as stem cell memory T ($T_{SCM}$), central memory T ($T_{CM}$), effector memory T ($T_{EM}$), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells.

In some embodiments, the cells are natural killer (NK) cells. In some embodiments, the cells are monocytes or granulocytes, e.g., myeloid cells, macrophages, neutrophils, dendritic cells, mast cells, eosinophils, and/or basophils.

In some embodiments, the cells include one or more nucleic acids introduced via genetic engineering, and thereby express recombinant or genetically engineered products of such nucleic acids. In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature, including one comprising chimeric combinations of nucleic acids encoding various domains from multiple different cell types.

B. Preparation of Cells for Engineering

In some embodiments, preparation of the engineered cells includes one or more culture and/or preparation steps. The cells for introduction of the nucleic acid encoding the transgenic receptor such as the CAR, may be isolated from a sample, such as a biological sample, e.g., one obtained from or derived from a subject. In some embodiments, the subject from which the cell is isolated is one having the disease or condition or in need of a cell therapy or to which cell therapy will be administered. The subject in some embodiments is a human in need of a particular therapeutic intervention, such as the adoptive cell therapy for which cells are being isolated, processed, and/or engineered.

Accordingly, the cells in some embodiments are primary cells, e.g., primary human cells. The samples include tissue, fluid, and other samples taken directly from the subject, as well as samples resulting from one or more processing steps, such as separation, centrifugation, genetic engineering (e.g. transduction with viral vector), washing, and/or incubation. The biological sample can be a sample obtained directly from a biological source or a sample that is processed. Biological samples include, but are not limited to, body fluids, such as blood, plasma, serum, cerebrospinal fluid, synovial fluid, urine and sweat, tissue and organ samples, including processed samples derived therefrom.

In some aspects, the sample from which the cells are derived or isolated is blood or a blood-derived sample, or is or is derived from an apheresis or leukapheresis product. Exemplary samples include whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. Samples include, in the context of cell therapy, e.g., adoptive cell therapy, samples from autologous and allogeneic sources.

In some aspects, the cells of the second dose are derived from the same apheresis product as the cells of the first dose. In some embodiments, the cells of multiple doses, e.g., first, second, third, and so forth, are derived from the same apheresis product.

In other embodiments, the cells of the second (or other subsequent) dose are derived from an apheresis product that is distinct from that from which the cells of the first (or other prior) dose are derived.

In some embodiments, the cells are derived from cell lines, e.g., T cell lines. The cells in some embodiments are obtained from a xenogeneic source, for example, from mouse, rat, non-human primate, and pig.

In some embodiments, isolation of the cells includes one or more preparation and/or non-affinity based cell separation steps. In some examples, cells are washed, centrifuged, and/or incubated in the presence of one or more reagents, for example, to remove unwanted components, enrich for desired components, lyse or remove cells sensitive to particular reagents. In some examples, cells are separated based on one or more property, such as density, adherent properties, size, sensitivity and/or resistance to particular components.

In some examples, cells from the circulating blood of a subject are obtained, e.g., by apheresis or leukapheresis. The samples, in some aspects, contain lymphocytes, including T cells, monocytes, granulocytes, B cells, other nucleated white blood cells, red blood cells, and/or platelets, and in some aspects contains cells other than red blood cells and platelets.

In some embodiments, the blood cells collected from the subject are washed, e.g., to remove the plasma fraction and to place the cells in an appropriate buffer or media for subsequent processing steps. In some embodiments, the cells are washed with phosphate buffered saline (PBS). In some embodiments, the wash solution lacks calcium and/or magnesium and/or many or all divalent cations. In some aspects, a washing step is accomplished a semi-automated "flow-through" centrifuge (for example, the Cobe 2991 cell processor, Baxter) according to the manufacturer's instructions. In some aspects, a washing step is accomplished by tangential flow filtration (TFF) according to the manufacturer's instructions. In some embodiments, the cells are resuspended in a variety of biocompatible buffers after washing, such as, for example, $Ca^{++}/Mg^{++}$ free PBS. In certain embodiments, components of a blood cell sample are removed and the cells directly resuspended in culture media.

In some embodiments, the methods include density-based cell separation methods, such as the preparation of white blood cells from peripheral blood by lysing the red blood cells and centrifugation through a Percoll or Ficoll gradient.

In some embodiments, the isolation methods include the separation of different cell types based on the expression or presence in the cell of one or more specific molecules, such as surface markers, e.g., surface proteins, intracellular markers, or nucleic acid. In some embodiments, any known method for separation based on such markers may be used. In some embodiments, the separation is affinity- or immunoaffinity-based separation. For example, the isolation in some aspects includes separation of cells and cell populations based on the cells' expression or expression level of one or more markers, typically cell surface markers, for example, by incubation with an antibody or binding partner that specifically binds to such markers, followed generally by washing steps and separation of cells having bound the antibody or binding partner, from those cells having not bound to the antibody or binding partner.

Such separation steps can be based on positive selection, in which the cells having bound the reagents are retained for further use, and/or negative selection, in which the cells having not bound to the antibody or binding partner are retained. In some examples, both fractions are retained for further use. In some aspects, negative selection can be particularly useful where no antibody is available that specifically identifies a cell type in a heterogeneous population, such that separation is best carried out based on markers expressed by cells other than the desired population.

The separation need not result in 100% enrichment or removal of a particular cell population or cells expressing a particular marker. For example, positive selection of or enrichment for cells of a particular type, such as those expressing a marker, refers to increasing the number or percentage of such cells, but need not result in a complete absence of cells not expressing the marker. Likewise, negative selection, removal, or depletion of cells of a particular type, such as those expressing a marker, refers to decreasing the number or percentage of such cells, but need not result in a complete removal of all such cells.

In some examples, multiple rounds of separation steps are carried out, where the positively or negatively selected fraction from one step is subjected to another separation step, such as a subsequent positive or negative selection. In some examples, a single separation step can deplete cells expressing multiple markers simultaneously, such as by incubating cells with a plurality of antibodies or binding partners, each specific for a marker targeted for negative selection. Likewise, multiple cell types can simultaneously be positively selected by incubating cells with a plurality of antibodies or binding partners expressed on the various cell types.

For example, in some aspects, specific subpopulations of T cells, such as cells positive or expressing high levels of one or more surface markers, e.g., $CD28^+$, $CD62L^+$, $CCR7^+$, $CD27^+$, $CD127^+$, $CD4^+$, $CD8^+$, $CD45RA^+$, and/or $CD45RO^+$ T cells, are isolated by positive or negative selection techniques.

For example, $CD3^+$, $CD28^+$ T cells can be positively selected using anti-CD3/anti-CD28 conjugated magnetic beads (e.g., DYNABEADS® M-450 CD3/CD28 T Cell Expander).

In some embodiments, isolation is carried out by enrichment for a particular cell population by positive selection, or depletion of a particular cell population, by negative selection. In some embodiments, positive or negative selection is accomplished by incubating cells with one or more antibodies or other binding agent that specifically bind to one or more surface markers expressed or expressed (marker$^+$) at a relatively higher level (marker$^{high}$) on the positively or negatively selected cells, respectively.

In some embodiments, T cells are separated from a PBMC sample by negative selection of markers expressed on non-T cells, such as B cells, monocytes, or other white blood cells, such as CD14. In some aspects, a $CD4^+$ or $CD8^+$ selection step is used to separate $CD4^+$ helper and $CD8^+$ cytotoxic T cells. Such $CD4^+$ and $CD8^+$ populations can be further sorted into sub-populations by positive or negative selection for markers expressed or expressed to a relatively higher degree on one or more naive, memory, and/or effector T cell subpopulations.

In some embodiments, $CD8^+$ cells are further enriched for or depleted of naive, central memory, effector memory, and/or central memory stem cells, such as by positive or negative selection based on surface antigens associated with the respective subpopulation. In some embodiments, enrichment for central memory T ($T_{CM}$) cells is carried out to increase efficacy, such as to improve long-term survival, expansion, and/or engraftment following administration, which in some aspects is particularly robust in such subpopulations. See Terakura et al. (2012) Blood. 1:72-82; Wang et al. (2012) *J Immunother.* 35(9):689-701. In some embodiments, combining $T_{CM}$-enriched $CD8^+$ T cells and $CD4^+$ T cells further enhances efficacy.

In embodiments, memory T cells are present in both $CD62L^+$ and $CD62L^-$ subsets of $CD8^+$ peripheral blood lymphocytes. PBMC can be enriched for or depleted of $CD62L^-CD8^+$ and/or $CD62L^+CD8^+$ fractions, such as using anti-CD8 and anti-CD62L antibodies.

In some embodiments, the enrichment for central memory T ($T_{CM}$) cells is based on positive or high surface expression of CD45RO, CD62L, CCR7, CD28, CD3, and/or CD127; in some aspects, it is based on negative selection for cells expressing or highly expressing CD45RA and/or granzyme B. In some aspects, isolation of a CD8$^+$ population enriched for $T_{CM}$ cells is carried out by depletion of cells expressing CD4, CD14, CD45RA, and positive selection or enrichment for cells expressing CD62L. In one aspect, enrichment for central memory T ($T_{CM}$) cells is carried out starting with a negative fraction of cells selected based on CD4 expression, which is subjected to a negative selection based on expression of CD14 and CD45RA, and a positive selection based on CD62L. Such selections in some aspects are carried out simultaneously and in other aspects are carried out sequentially, in either order. In some aspects, the same CD4 expression-based selection step used in preparing the CD8$^+$ cell population or subpopulation, also is used to generate the CD4$^+$ cell population or subpopulation, such that both the positive and negative fractions from the CD4-based separation are retained and used in subsequent steps of the methods, optionally following one or more further positive or negative selection steps.

In a particular example, a sample of PBMCs or other white blood cell sample is subjected to selection of CD4$^+$ cells, where both the negative and positive fractions are retained. The negative fraction then is subjected to negative selection based on expression of CD14 and CD45RA or CD19, and positive selection based on a marker characteristic of central memory T cells, such as CD62L or CCR7, where the positive and negative selections are carried out in either order.

CD4$^+$ T helper cells are sorted into naïve, central memory, and effector cells by identifying cell populations that have cell surface antigens. CD4$^+$ lymphocytes can be obtained by standard methods. In some embodiments, naive CD4$^+$ T lymphocytes are CD45RO$^-$, CD45RA$^+$, CD62L$^+$, CD4$^+$ T cells. In some embodiments, central memory CD4$^+$ cells are CD62L$^+$ and CD45RO$^+$. In some embodiments, effector CD4$^+$ cells are CD62L$^-$ and CD45RO$^-$.

In one example, to enrich for CD4$^+$ cells by negative selection, a monoclonal antibody cocktail typically includes antibodies to CD14, CD20, CD11b, CD16, HLA-DR, and CD8. In some embodiments, the antibody or binding partner is bound to a solid support or matrix, such as a magnetic bead or paramagnetic bead, to allow for separation of cells for positive and/or negative selection. For example, in some embodiments, the cells and cell populations are separated or isolated using immunomagnetic (or affinitymagnetic) separation techniques (reviewed in Methods in Molecular Medicine, vol. 58: Metastasis Research Protocols, Vol. 2: Cell Behavior In Vitro and In Vivo, p 17-25 Edited by: S. A. Brooks and U. Schumacher© Humana Press Inc., Totowa, NJ).

In some aspects, the sample or composition of cells to be separated is incubated with small, magnetizable or magnetically responsive material, such as magnetically responsive particles or microparticles, such as paramagnetic beads (e.g., such as Dynalbeads or MACS beads). The magnetically responsive material, e.g., particle, generally is directly or indirectly attached to a binding partner, e.g., an antibody, that specifically binds to a molecule, e.g., surface marker, present on the cell, cells, or population of cells that it is desired to separate, e.g., that it is desired to negatively or positively select.

In some embodiments, the magnetic particle or bead comprises a magnetically responsive material bound to a specific binding member, such as an antibody or other binding partner. There are many well-known magnetically responsive materials used in magnetic separation methods. Suitable magnetic particles include those described in Molday, U.S. Pat. No. 4,452,773, and in European Patent Specification EP 452342 B, which are hereby incorporated by reference. Colloidal sized particles, such as those described in Owen U.S. Pat. No. 4,795,698, and Liberti et al., U.S. Pat. No. 5,200,084 are other examples.

The incubation generally is carried out under conditions whereby the antibodies or binding partners, or molecules, such as secondary antibodies or other reagents, which specifically bind to such antibodies or binding partners, which are attached to the magnetic particle or bead, specifically bind to cell surface molecules if present on cells within the sample.

In some aspects, the sample is placed in a magnetic field, and those cells having magnetically responsive or magnetizable particles attached thereto will be attracted to the magnet and separated from the unlabeled cells. For positive selection, cells that are attracted to the magnet are retained; for negative selection, cells that are not attracted (unlabeled cells) are retained. In some aspects, a combination of positive and negative selection is performed during the same selection step, where the positive and negative fractions are retained and further processed or subject to further separation steps.

In certain embodiments, the magnetically responsive particles are coated in primary antibodies or other binding partners, secondary antibodies, lectins, enzymes, or streptavidin. In certain embodiments, the magnetic particles are attached to cells via a coating of primary antibodies specific for one or more markers. In certain embodiments, the cells, rather than the beads, are labeled with a primary antibody or binding partner, and then cell-type specific secondary antibody- or other binding partner (e.g., streptavidin)-coated magnetic particles, are added. In certain embodiments, streptavidin-coated magnetic particles are used in conjunction with biotinylated primary or secondary antibodies.

In some embodiments, the magnetically responsive particles are left attached to the cells that are to be subsequently incubated, cultured and/or engineered; in some aspects, the particles are left attached to the cells for administration to a patient. In some embodiments, the magnetizable or magnetically responsive particles are removed from the cells. Methods for removing magnetizable particles from cells are known and include, e.g., the use of competing non-labeled antibodies, and magnetizable particles or antibodies conjugated to cleavable linkers. In some embodiments, the magnetizable particles are biodegradable.

In some embodiments, the affinity-based selection is via magnetic-activated cell sorting (MACS) (Miltenyi Biotec, Auburn, CA). Magnetic Activated Cell Sorting (MACS) systems are capable of high-purity selection of cells having magnetized particles attached thereto. In certain embodiments, MACS operates in a mode wherein the non-target and target species are sequentially eluted after the application of the external magnetic field. That is, the cells attached to magnetized particles are held in place while the unattached species are eluted. Then, after this first elution step is completed, the species that were trapped in the magnetic field and were prevented from being eluted are freed in some manner such that they can be eluted and recovered. In certain embodiments, the non-target cells are labelled and depleted from the heterogeneous population of cells.

In certain embodiments, the isolation or separation is carried out using a system, device, or apparatus that carries out one or more of the isolation, cell preparation, separation, processing, incubation, culture, and/or formulation steps of the methods. In some aspects, the system is used to carry out each of these steps in a closed or sterile environment, for example, to minimize error, user handling and/or contamination. In one example, the system is a system as described in International Patent Application, Publication Number WO2009/072003, or US 20110003380 A1.

In some embodiments, the system or apparatus carries out one or more, e.g., all, of the isolation, processing, engineering, and formulation steps in an integrated or self-contained system, and/or in an automated or programmable fashion. In some aspects, the system or apparatus includes a computer and/or computer program in communication with the system or apparatus, which allows a user to program, control, assess the outcome of, and/or adjust various aspects of the processing, isolation, engineering, and formulation steps.

In some aspects, the separation and/or other steps is carried out using CliniMACS system (Miltenyi Biotec), for example, for automated separation of cells on a clinical-scale level in a closed and sterile system. Components can include an integrated microcomputer, magnetic separation unit, peristaltic pump, and various pinch valves. The integrated computer in some aspects controls all components of the instrument and directs the system to perform repeated procedures in a standardized sequence. The magnetic separation unit in some aspects includes a movable permanent magnet and a holder for the selection column. The peristaltic pump controls the flow rate throughout the tubing set and, together with the pinch valves, ensures the controlled flow of buffer through the system and continual suspension of cells.

The CliniMACS system in some aspects uses antibody-coupled magnetizable particles that are supplied in a sterile, non-pyrogenic solution. In some embodiments, after labelling of cells with magnetic particles the cells are washed to remove excess particles. A cell preparation bag is then connected to the tubing set, which in turn is connected to a bag containing buffer and a cell collection bag. The tubing set consists of pre-assembled sterile tubing, including a pre-column and a separation column, and are for single use only. After initiation of the separation program, the system automatically applies the cell sample onto the separation column. Labelled cells are retained within the column, while unlabeled cells are removed by a series of washing steps. In some embodiments, the cell populations for use with the methods described herein are unlabeled and are not retained in the column. In some embodiments, the cell populations for use with the methods described herein are labeled and are retained in the column. In some embodiments, the cell populations for use with the methods described herein are eluted from the column after removal of the magnetic field, and are collected within the cell collection bag.

In certain embodiments, separation and/or other steps are carried out using the CliniMACS Prodigy® system (Miltenyi Biotec). The CliniMACS Prodigy® system in some aspects is equipped with a cell processing unity that permits automated washing and fractionation of cells by centrifugation. The CliniMACS Prodigy® system can also include an onboard camera and image recognition software that determines the optimal cell fractionation endpoint by discerning the macroscopic layers of the source cell product. For example, peripheral blood is automatically separated into erythrocytes, white blood cells and plasma layers. The CliniMACS Prodigy® system can also include an integrated cell cultivation chamber which accomplishes cell culture protocols such as, e.g., cell differentiation and expansion, antigen loading, and long-term cell culture. Input ports can allow for the sterile removal and replenishment of media and cells can be monitored using an integrated microscope. See, e.g., Klebanoff et al. (2012) *J Immunother.* 35(9): 651-660, Terakura et al. (2012) Blood. 1:72-82, and Wang et al. (2012) J Immunother. 35(9):689-701.

In some embodiments, a cell population described herein is collected and enriched (or depleted) via flow cytometry, in which cells stained for multiple cell surface markers are carried in a fluidic stream. In some embodiments, a cell population described herein is collected and enriched (or depleted) via preparative scale (FACS)-sorting. In certain embodiments, a cell population described herein is collected and enriched (or depleted) by use of microelectromechanical systems (MEMS) chips in combination with a FACS-based detection system (see, e.g., WO 2010/033140, Cho et al. (2010) *Lab Chip* 10, 1567-1573; and Godin et al. (2008) J Biophoton. 1(5):355-376. In both cases, cells can be labeled with multiple markers, allowing for the isolation of well-defined T cell subsets at high purity.

In some embodiments, the antibodies or binding partners are labeled with one or more detectable marker, to facilitate separation for positive and/or negative selection. For example, separation may be based on binding to fluorescently labeled antibodies. In some examples, separation of cells based on binding of antibodies or other binding partners specific for one or more cell surface markers are carried in a fluidic stream, such as by fluorescence-activated cell sorting (FACS), including preparative scale (FACS) and/or microelectromechanical systems (MEMS) chips, e.g., in combination with a flow-cytometric detection system. Such methods allow for positive and negative selection based on multiple markers simultaneously.

In some embodiments, the preparation methods include steps for freezing, e.g., cryopreserving, the cells, either before or after isolation, incubation, and/or engineering. In some embodiments, the freeze and subsequent thaw step removes granulocytes and, to some extent, monocytes in the cell population. In some embodiments, the cells are suspended in a freezing solution, e.g., following a washing step to remove plasma and platelets. Any of a variety of known freezing solutions and parameters in some aspects may be used. One example involves using PBS containing 20% DMSO and 8% human serum albumin (HSA), or other suitable cell freezing media. This is then diluted 1:1 with media so that the final concentration of DMSO and HSA are 10% and 4%, respectively. The cells are generally then frozen to −80° C. at a rate of 1° per minute and stored in the vapor phase of a liquid nitrogen storage tank.

In some embodiments, the cells are incubated and/or cultured prior to or in connection with genetic engineering. The incubation steps can include culture, cultivation, stimulation, activation, and/or propagation. In some embodiments, the compositions or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for the introduction of a recombinant antigen receptor.

The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells.

In some embodiments, the stimulating conditions or agents include one or more agent, e.g., ligand, which is capable of activating an intracellular signaling domain of a TCR complex. In some aspects, the agent turns on or initiates TCR/CD3 intracellular signaling cascade in a T cell. Such agents can include antibodies, such as those specific for a TCR, e.g. anti-CD3. In some embodiments, the stimulating conditions include one or more agent, e.g. ligand, which is capable of stimulating a costimulatory receptor, e.g., anti-CD28. In some embodiments, such agents and/or ligands may be, bound to solid support such as a bead, and/or one or more cytokines. Optionally, the expansion method may further comprise the step of adding anti-CD3 and/or anti CD28 antibody to the culture medium (e.g., at a concentration of at least about 0.5 ng/ml). In some embodiments, the stimulating agents include IL-2, IL-15 and/or IL-7. In some aspects, the IL-2 concentration is at least about 10 units/mL.

In some aspects, incubation is carried out in accordance with techniques such as those described in U.S. Pat. No. 6,040,177 to Riddell et al., Klebanoff et al. (2012) J Immunother. 35(9): 651-660, Terakura et al. (2012) Blood. 1:72-82, and/or Wang et al. (2012) J Immunother. 35(9):689-701.

In some embodiments, the T cells are expanded by adding to a culture-initiating composition feeder cells, such as non-dividing peripheral blood mononuclear cells (PBMC), (e.g., such that the resulting population of cells contains at least about 5, 10, 20, or 40 or more PBMC feeder cells for each T lymphocyte in the initial population to be expanded); and incubating the culture (e.g. for a time sufficient to expand the numbers of T cells). In some aspects, the non-dividing feeder cells can comprise gamma-irradiated PBMC feeder cells. In some embodiments, the PBMC are irradiated with gamma rays in the range of about 3000 to 3600 rads to prevent cell division. In some aspects, the feeder cells are added to culture medium prior to the addition of the populations of T cells.

In some embodiments, the stimulating conditions include temperature suitable for the growth of human T lymphocytes, for example, at least about 25 degrees Celsius, generally at least about 30 degrees, and generally at or about 37 degrees Celsius. Optionally, the incubation may further comprise adding non-dividing EBV-transformed lymphoblastoid cells (LCL) as feeder cells. LCL can be irradiated with gamma rays in the range of about 6000 to 10,000 rads. The LCL feeder cells in some aspects is provided in any suitable amount, such as a ratio of LCL feeder cells to initial T lymphocytes of at least about 10:1.

In embodiments, antigen-specific T cells, such as antigen-specific CD4+ and/or CD8+ T cells, are obtained by stimulating naive or antigen specific T lymphocytes with antigen. For example, antigen-specific T cell lines or clones can be generated to cytomegalovirus antigens by isolating T cells from infected subjects and stimulating the cells in vitro with the same antigen.

In some embodiments, any one or more conditions or agents in connection with culturing or processing cells can be altered or tested and assessed for their effect on the phenotype or function or characteristic of the cells as determined by epigenetic analysis, such as chromatin accessibility, in accord with the provided methods. In some embodiments, an agent or condition can be added to a culture of cells, and a cell can be assessed for an epigenetic property of a genomic region or regions indicative of the phenotype or function of the cells. In some embodiments, a gene or a panel of genes indicative of identifying naïve cells or long-lived memory cells are assessed. In some embodiments, a gene or panel of genes indicative of effector-life functions of cells, such as effector cells or effector memory cells, are assessed. Exemplary of such genes are provided.

C. Recombinant Receptors Expressed by the Cells

The cells generally express recombinant receptors. The receptors may include antigen receptors, such as functional non-TCR antigen receptors, including chimeric antigen receptors (CARs), and other antigen-binding receptors such as transgenic T cell receptors (TCRs). The receptors may also include other chimeric receptors, such as receptors binding to particular ligands and having transmembrane and/or intracellular signaling domains similar to those present in a CAR. Among the receptors are antigen receptors and receptors containing one or more component thereof. The recombinant receptors may include chimeric receptors, such as those containing ligand-binding domains or binding fragments thereof and intracellular signaling domains or regions, functional non-TCR antigen receptors, chimeric antigen receptors (CARs), and T cell receptors (TCRs), such as recombinant or transgenic TCRs, chimeric autoantibody receptor (CAAR) and components of any of the foregoing. The recombinant receptor, such as a CAR, generally includes the extracellular antigen (or ligand) binding domain linked to one or more intracellular signaling components, in some aspects via linkers and/or transmembrane domain(s).

1. Chimeric Antigen Receptors (CARs)

In some embodiments, engineered cells, such as T cells, express a CAR with specificity for a particular antigen (or marker or ligand), such as an antigen expressed on the surface of a particular cell type. In some embodiments, the antigen is a polypeptide. In some embodiments, it is a carbohydrate or other molecule. In some embodiments, the antigen is selectively expressed or overexpressed on cells of the disease or condition, e.g., the tumor or pathogenic cells, as compared to normal or non-targeted cells or tissues. In other embodiments, the antigen is expressed on normal cells and/or is expressed on the engineered cells.

In particular embodiments, the recombinant receptor, such as chimeric receptor, contains an intracellular signaling region, which includes a cytoplasmic signaling domain or region (also interchangeably called an intracellular signaling domain or region), such as a cytoplasmic (intracellular) region capable of inducing a primary activation signal in a T cell, for example, a cytoplasmic signaling domain or region of a T cell receptor (TCR) component (e.g. a cytoplasmic signaling domain or region of a zeta chain of a CD3-zeta (CD3ζ) chain or a functional variant or signaling portion thereof) and/or that comprises an immunoreceptor tyrosine-based activation motif (ITAM).

In some embodiments, the chimeric receptor further contains an extracellular ligand-binding domain that specifically binds to a ligand (e.g. antigen) antigen. In some embodiments, the chimeric receptor is a CAR that contains an extracellular antigen-recognition domain that specifically binds to an antigen. In some embodiments, the ligand, such as an antigen, is a protein expressed on the surface of cells. In some embodiments, the CAR is a TCR-like CAR and the antigen is a processed peptide antigen, such as a peptide antigen of an intracellular protein, which, like a TCR, is recognized on the cell surface in the context of a major histocompatibility complex (MHC) molecule.

Exemplary antigen receptors, including CARs, and methods for engineering and introducing such receptors into cells, include those described, for example, in international patent application publication numbers WO200014257, WO2013126726, WO2012/129514, WO2014031687, WO2013/166321, WO2013/071154, WO2013/123061 U.S.

patent application publication numbers US2002131960, US2013287748, US20130149337, U.S. Pat. Nos. 6,451,995, 7,446,190, 8,252,592, 8,339,645, 8,398,282, 7,446,179, 6,410,319, 7,070,995, 7,265,209, 7,354,762, 7,446,191, 8,324,353, and 8,479,118, and European patent application number EP2537416, and/or those described by Sadelain et al., Cancer Discov. 2013 April; 3(4): 388-398; Davila et al. (2013) PLoS ONE 8(4): e61338; Turtle et al., Curr. Opin. Immunol., 2012 October; 24(5): 633-39; Wu et al., Cancer, 2012 Mar. 18(2): 160-75. In some aspects, the antigen receptors include a CAR as described in U.S. Pat. No. 7,446,190, and those described in International Patent Application Publication No.: WO/2014055668 A1. Examples of the CARs include CARs as disclosed in any of the aforementioned publications, such as WO2014031687, U.S. Pat. Nos. 8,339,645, 7,446,179, US 2013/0149337, U.S. Pat. Nos. 7,446,190, 8,389,282, Kochenderfer et al., 2013, Nature Reviews Clinical Oncology, 10, 267-276 (2013); Wang et al. (2012) J. Immunother. 35(9): 689-701; and Brentjens et al., Sci Transl Med. 2013 5(177). See also International Patent Publication No.: WO2014031687, U.S. Pat. Nos. 8,339,645, 7,446,179, 7,446,190, and 8,389,282, and U.S. patent application Publication No. US 2013/0149337. Among the chimeric receptors are chimeric antigen receptors (CARs). The chimeric receptors, such as CARs, generally include an extracellular antigen binding domain, such as a portion of an antibody molecule, generally a variable heavy (VH) chain region and/or variable light (VL) chain region of the antibody, e.g., an scFv antibody fragment.

In some embodiments, the CAR is constructed with a specificity for a particular antigen (or marker or ligand), such as an antigen expressed in a particular cell type to be targeted by adoptive therapy, e.g., a cancer marker, and/or an antigen intended to induce a dampening response, such as an antigen expressed on a normal or non-diseased cell type. Thus, the CAR typically includes in its extracellular portion one or more antigen binding molecules, such as one or more antigen-binding fragment, domain, or portion, or one or more antibody variable domains, and/or antibody molecules. In some embodiments, the CAR includes an antigen-binding portion or portions of an antibody molecule, such as a single-chain antibody fragment (scFv) derived from the variable heavy (VH) and variable light (VL) chains of a monoclonal antibody (mAb).

In some embodiments, the antibody or antigen-binding portion thereof is expressed on cells as part of a recombinant receptor, such as an antigen receptor. Among the antigen receptors are functional non-TCR antigen receptors, such as chimeric antigen receptors (CARs). Generally, a CAR containing an antibody or antigen-binding fragment that exhibits TCR-like specificity directed against peptide-MHC complexes also may be referred to as a TCR-like CAR. In some embodiments, the extracellular antigen binding domain specific for an MHC-peptide complex of a TCR-like CAR is linked to one or more intracellular signaling components, in some aspects via linkers and/or transmembrane domain(s). In some embodiments, such molecules can typically mimic or approximate a signal through a natural antigen receptor, such as a TCR, and, optionally, a signal through such a receptor in combination with a costimulatory receptor.

In some embodiments, the recombinant receptor, such as a chimeric receptor (e.g. CAR), includes a ligand-binding domain that binds, such as specifically binds, to an antigen (or a ligand). Among the antigens targeted by the chimeric receptors are those expressed in the context of a disease, condition, or cell type to be targeted via the adoptive cell therapy. Among the diseases and conditions are proliferative, neoplastic, and malignant diseases and disorders, including cancers and tumors, including hematologic cancers, cancers of the immune system, such as lymphomas, leukemias, and/or myelomas, such as B, T, and myeloid leukemias, lymphomas, and multiple myelomas.

In some embodiments, the antigen (or a ligand) is a polypeptide. In some embodiments, it is a carbohydrate or other molecule. In some embodiments, the antigen (or a ligand) is selectively expressed or overexpressed on cells of the disease or condition, e.g., the tumor or pathogenic cells, as compared to normal or non-targeted cells or tissues. In other embodiments, the antigen is expressed on normal cells and/or is expressed on the engineered cells.

In some embodiments, the CAR contains an antibody or an antigen-binding fragment (e.g. scFv) that specifically recognizes an antigen, such as an intact antigen, expressed on the surface of a cell.

In some embodiments, the antigen (or a ligand) is a tumor antigen or cancer marker. In some embodiments, the antigen (or a ligand) the antigen is or includes αvβ6 integrin (avb6 integrin), B cell maturation antigen (BCMA), B7-H3, B7-H6, carbonic anhydrase 9 (CA9, also known as CAIX or G250), a cancer-testis antigen, cancer/testis antigen$_{1B}$ (CTAG, also known as NY-ESO-1 and LAGE-2), carcinoembryonic antigen (CEA), a cyclin, cyclin A2, C-C Motif Chemokine Ligand 1 (CCL-1), CD19, CD20, CD22, CD23, CD24, CD30, CD33, CD38, CD44, CD44v6, CD44v7/8, CD123, CD138, CD171, epidermal growth factor protein (EGFR), truncated epidermal growth factor protein (tEGFR), type III epidermal growth factor receptor mutation (EGFR vIII), epithelial glycoprotein 2 (EPG-2), epithelial glycoprotein 40 (EPG-40), ephrinB2, ephrine receptor A2 (EPHa2), estrogen receptor, Fc receptor like 5 (FCRL5; also known as Fc receptor homolog 5 or FCRH5), fetal acetylcholine receptor (fetal AchR), a folate binding protein (FBP), folate receptor alpha, ganglioside GD2, O-acetylated GD2 (OGD2), ganglioside GD3, glycoprotein 100 (gp100), G Protein Coupled Receptor κD (GPCR5D), Her2/neu (receptor tyrosine kinase erb-B2), Her3 (erb-B3), Her4 (erb-B4), erbB dimers, Human high molecular weight-melanoma-associated antigen (HMW-MAA), hepatitis B surface antigen, Human leukocyte antigen A1 (HLA-A1), Human leukocyte antigen A2 (HLA-A2), IL-22 receptor alpha (IL-22Ra), IL-13 receptor alpha 2 (IL-13Ra2), kinase insert domain receptor (kdr), kappa light chain, L1 cell adhesion molecule (L1-CAM), CE7 epitope of L1-CAM, Leucine Rich Repeat Containing 8 Family Member A (LRRC8A), Lewis Y, Melanoma-associated antigen (MAGE)-A1, MAGE-A3, MAGE-A6, mesothelin, c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), Receptor Tyrosine Kinase Like Orphan Receptor 1 (ROR1), survivin, Trophoblast glycoprotein (TPBG also known as 5T4), tumor-associated glycoprotein 72 (TAG72), vascular endothelial growth factor receptor (VEGFR), vascular endothelial growth factor receptor 2 (VEGFR2), Wilms Tumor 1 (WT-1), a pathogen-specific antigen, or an antigen associated with a universal tag, and/or biotinylated molecules, and/or molecules expressed by HIV, HCV, HBV or other pathogens. Antigens targeted by the receptors in some embodiments include antigens associated with a B cell malignancy, such as any of a number of known B cell marker. In some embodiments, the antigen is or includes CD20, CD19, CD22, ROR1, CD45, CD21, CD5, CD33, Igkappa, Iglambda, CD79a, CD79b or CD30.

In some embodiments, the antigen is or includes a pathogen-specific or pathogen-expressed antigen. In some embodiments, the antigen is a viral antigen (such as a viral antigen from HIV, HCV, HBV, etc.), bacterial antigens, and/or parasitic antigens.

In some embodiments, the antibody or an antigen-binding fragment (e.g. scFv) that specifically recognizes an antigen, such as CD19.

In some embodiments the scFv and/or $V_H$ domains is derived from FMC63. FMC63 generally refers to a mouse monoclonal IgG1 antibody raised against Nalm-1 and -16 cells expressing CD19 of human origin (Ling, N. R., et al. (1987). *Leucocyte typing III.* 302). The FMC63 antibody comprises CDRH1 and H2 set forth in SEQ ID NOS: 38, 39 respectively, and CDRH3 set forth in SEQ ID NOS: 40 or 54 and CDRL1 set forth in SEQ ID NOS: 35 and CDR L2 36 or 55 and CDR L3 sequences 37 or 56. The FMC63 antibody comprises the heavy chain variable region ($V_H$) comprising the amino acid sequence of SEQ ID NO: 41 and the light chain variable region ($V_L$) comprising the amino acid sequence of SEQ ID NO: 42. In some embodiments, the svFv comprises a variable light chain containing the CDRL1 sequence of SEQ ID NO:35, a CDRL2 sequence of SEQ ID NO:36, and a CDRL3 sequence of SEQ ID NO:37 and/or a variable heavy chain containing a CDRH1 sequence of SEQ ID NO:38, a CDRH2 sequence of SEQ ID NO:39, and a CDRH3 sequence of SEQ ID NO:40. In some embodiments, the scFv comprises a variable heavy chain region of FMC63 set forth in SEQ ID NO:41 and a variable light chain region of FMC63 set forth in SEQ ID NO:42. In some embodiments, the variable heavy and variable light chain are connected by a linker. In some embodiments, the linker is set forth in SEQ ID NO:59. In some embodiments, the scFv comprises, in order, a $V_H$, a linker, and a $V_L$. In some embodiments, the scFv comprises, in order, a $V_L$, a linker, and a $V_H$. In some embodiments, the svFc is encoded by a sequence of nucleotides set forth in SEQ ID NO:57 or a sequence that e$_H$ibits at least 85%, 86%, 87%, 88%, 89%, 90%, 91%, 92%, 93%, 94%, 95%, 96%, 97%, 98%, or 99% sequence identity to SEQ ID NO:57. In some embodiments, the scFv comprises the sequence of amino acids set forth in SEQ ID NO:43 or a sequence that e$_H$ibits at least 85%, 86%, 87%, 88%, 89%, 90%, 91%, 92%, 93%, 94%, 95%, 96%, 97%, 98%, or 99% sequence identity to SEQ ID NO:43.

In some embodiments the scFv is derived from SJ25C1. SJ25C1 is a mouse monoclonal IgG1 antibody raised against Nalm-1 and -16 cells expressing CD19 of human origin (Ling, N. R., et al. (1987). *Leucocyte typing III.* 302). The SJ25C1 antibody comprises CDRH1, H2 and H3 set forth in SEQ ID NOS: 47-49, respectively, and CDRL1, L2 and L3 sequences set forth in SEQ ID NOS: 44-46, respectively. The SJ25C1 antibody comprises the heavy chain variable region ($V_H$) comprising the amino acid sequence of SEQ ID NO: 50 and the light chain variable region ($V_L$) comprising the amino acid sequence of SEQ ID NO: 51. In some embodiments, the svFv comprises a variable light chain containing the CDRL1 sequence of SEQ ID NO:44, a CDRL2 sequence of SEQ ID NO: 45, and a CDRL3 sequence of SEQ ID NO:46 and/or a variable heavy chain containing a CDRH1 sequence of SEQ ID NO:47, a CDRH2 sequence of SEQ ID NO:48, and a CDRH3 sequence of SEQ ID NO:49. In some embodiments, the scFv comprises a variable heavy chain region of SJ25C1 set forth in SEQ ID NO:50 and a variable light chain region of SJ25C1 set forth in SEQ ID NO:51. In some embodiments, the variable heavy and variable light chain are connected by a linker. In some embodiments, the linker is set forth in SEQ ID NO:52. In some embodiments, the scFv comprises, in order, a $V_H$, a linker, and a $V_L$. In some embodiments, the scFv comprises, in order, a $V_L$, a linker, and a $V_H$. In some embodiments, the scFv comprises the sequence of amino acids set forth in SEQ ID NO:53 or a sequence that e$_H$ibits at least 85%, 86%, 87%, 88%, 89%, 90%, 91%, 92%, 93%, 94%, 95%, 96%, 97%, 98%, or 99% sequence identity to SEQ ID NO:53.

In some embodiments, the CAR contains a TCR-like antibody, such as an antibody or an antigen-binding fragment (e.g. scFv) that specifically recognizes an intracellular antigen, such as a tumor-associated antigen, presented on the cell surface as a MHC-peptide complex. In some embodiments, an antibody or antigen-binding portion thereof that recognizes an MHC-peptide complex can be expressed on cells as part of a recombinant receptor, such as an antigen receptor. Among the antigen receptors are functional non-TCR antigen receptors, such as chimeric antigen receptors (CARs). Generally, a CAR containing an antibody or antigen-binding fragment that exhibits TCR-like specificity directed against peptide-MHC complexes also may be referred to as a TCR-like CAR.

Reference to "Major histocompatibility complex" (MHC) refers to a protein, generally a glycoprotein, that contains a polymorphic peptide binding site or binding groove that can, in some cases, complex with peptide antigens of polypeptides, including peptide antigens processed by the cell machinery. In some cases, MHC molecules can be displayed or expressed on the cell surface, including as a complex with peptide, i.e. MHC-peptide complex, for presentation of an antigen in a conformation recognizable by an antigen receptor on T cells, such as a TCRs or TCR-like antibody. Generally, MHC class I molecules are heterodimers having a membrane spanning α chain, in some cases with three α domains, and a non-covalently associated β(2 microglobulin. Generally, MHC class II molecules are composed of two transmembrane glycoproteins, α and β, both of which typically span the membrane. An MHC molecule can include an effective portion of an MHC that contains an antigen binding site or sites for binding a peptide and the sequences necessary for recognition by the appropriate antigen receptor. In some embodiments, MHC class I molecules deliver peptides originating in the cytosol to the cell surface, where a MHC-peptide complex is recognized by T cells, such as generally CD8$^+$ T cells, but in some cases CD4+ T cells. In some embodiments, MHC class II molecules deliver peptides originating in the vesicular system to the cell surface, where they are typically recognized by CD4$^+$ T cells. Generally, MHC molecules are encoded by a group of linked loci, which are collectively termed H-2 in the mouse and human leukocyte antigen (HLA) in humans. Hence, typically human MHC can also be referred to as human leukocyte antigen (HLA).

The term "MHC-peptide complex" or "peptide-MHC complex" or variations thereof, refers to a complex or association of a peptide antigen and an MHC molecule, such as, generally, by non-covalent interactions of the peptide in the binding groove or cleft of the MHC molecule. In some embodiments, the MHC-peptide complex is present or displayed on the surface of cells. In some embodiments, the MHC-peptide complex can be specifically recognized by an antigen receptor, such as a TCR, TCR-like CAR or antigen-binding portions thereof.

In some embodiments, a peptide, such as a peptide antigen or epitope, of a polypeptide can associate with an MHC molecule, such as for recognition by an antigen receptor. Generally, the peptide is derived from or based on a fragment of a longer biological molecule, such as a polypeptide or protein. In some embodiments, the peptide typically is about 8 to about 24 amino acids in length. In some embodiments, a peptide has a length of from or from about 9 to 22 amino acids for recognition in the MHC Class II complex. In some embodiments, a peptide has a length of from or from about 8 to 13 amino acids for recognition in the MHC Class I complex. In some embodiments, upon recognition of the peptide in the context of an MHC molecule, such as MHC-peptide complex, the antigen receptor, such as TCR or TCR-like CAR, produces or triggers an activation signal to the T cell that induces a T cell response, such as T cell proliferation, cytokine production, a cytotoxic T cell response or other response.

In some embodiments, a TCR-like antibody or antigen-binding portion, are known or can be produced by known methods (see e.g. US Published Application Nos. US 2002/0150914; US 2003/0223994; US 2004/0191260; US 2006/0034850; US 2007/00992530; US20090226474; US20090304679; and International PCT Publication No. WO 03/068201).

In some embodiments, an antibody or antigen-binding portion thereof that specifically binds to a MHC-peptide complex, can be produced by immunizing a host with an effective amount of an immunogen containing a specific MHC-peptide complex. In some cases, the peptide of the MHC-peptide complex is an epitope of antigen capable of binding to the MHC, such as a tumor antigen, for example a universal tumor antigen, myeloma antigen or other antigen as described below. In some embodiments, an effective amount of the immunogen is then administered to a host for eliciting an immune response, wherein the immunogen retains a three-dimensional form thereof for a period of time sufficient to elicit an immune response against the three-dimensional presentation of the peptide in the binding groove of the MHC molecule. Serum collected from the host is then assayed to determine if desired antibodies that recognize a three-dimensional presentation of the peptide in the binding groove of the MHC molecule is being produced. In some embodiments, the produced antibodies can be assessed to confirm that the antibody can differentiate the MHC-peptide complex from the MHC molecule alone, the peptide of interest alone, and a complex of MHC and irrelevant peptide. The desired antibodies can then be isolated.

In some embodiments, an antibody or antigen-binding portion thereof that specifically binds to an MHC-peptide complex can be produced by employing antibody library display methods, such as phage antibody libraries. In some embodiments, phage display libraries of mutant Fab, scFv or other antibody forms can be generated, for example, in which members of the library are mutated at one or more residues of a CDR or CDRs. See e.g. US published application No. US20020150914, US2014/0294841; and Cohen C J. et al. (2003) *J Mol. Recogn.* 16:324-332.

The term "antibody" herein is used in the broadest sense and includes polyclonal and monoclonal antibodies, including intact antibodies and functional (antigen-binding) antibody fragments, including fragment antigen binding (Fab) fragments, F(ab')$_2$ fragments, Fab' fragments, Fv fragments, recombinant IgG (rIgG) fragments, variable heavy chain (V$_H$) regions capable of specifically binding the antigen, single chain antibody fragments, including single chain variable fragments (scFv), and single domain antibodies (e.g., sdAb, sdFv, nanobody) fragments. The term encompasses genetically engineered and/or otherwise modified forms of immunoglobulins, such as intrabodies, peptibodies, chimeric antibodies, fully human antibodies, humanized antibodies, and heteroconjugate antibodies, multispecific, e.g., bispecific, antibodies, diabodies, triabodies, and tetrabodies, tandem di-scFv, tandem tri-scFv. Unless otherwise stated, the term "antibody" should be understood to encompass functional antibody fragments thereof. The term also encompasses intact or full-length antibodies, including antibodies of any class or sub-class, including IgG and sub-classes thereof, IgM, IgE, IgA, and IgD.

In some embodiments, the antigen-binding proteins, antibodies and antigen binding fragments thereof specifically recognize an antigen of a full-length antibody. In some embodiments, the heavy and light chains of an antibody can be full-length or can be an antigen-binding portion (a Fab, F(ab')2, Fv or a single chain Fv fragment (scFv)). In other embodiments, the antibody heavy chain constant region is chosen from, e.g., IgG1, IgG2, IgG3, IgG4, IgM, IgA1, IgA2, IgD, and IgE, particularly chosen from, e.g., IgG1, IgG2, IgG3, and IgG4, more particularly, IgG1 (e.g., human IgG1). In another embodiment, the antibody light chain constant region is chosen from, e.g., kappa or lambda, particularly kappa.

Among the provided antibodies are antibody fragments. An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; variable heavy chain (V$_H$) regions, single-chain antibody molecules such as scFvs and single-domain V$_H$ single antibodies; and multispecific antibodies formed from antibody fragments. In particular embodiments, the antibodies are single-chain antibody fragments comprising a variable heavy chain region and/or a variable light chain region, such as scFvs.

The term "variable region" or "variable domain" refers to the domain of an antibody heavy or light chain that is involved in binding the antibody to antigen. The variable domains of the heavy chain and light chain (V$_H$ and V$_L$, respectively) of a native antibody generally have similar structures, with each domain comprising four conserved framework regions (FRs) and three CDRs. (See, e.g., Kindt et al. Kuby Immunology, 6th ed., W.H. Freeman and Co., page 91 (2007). A single V$_H$ or V$_L$ domain may be sufficient to confer antigen-binding specificity. Furthermore, antibodies that bind a particular antigen may be isolated using a V$_H$ or V$_L$ domain from an antibody that binds the antigen to screen a library of complementary V$_L$ or V$_H$ domains, respectively. See, e.g., Portolano et al., J. Immunol. 150:880-887 (1993); Clarkson et al., Nature 352:624-628 (1991).

Single-domain antibodies are antibody fragments comprising all or a portion of the heavy chain variable domain or all or a portion of the light chain variable domain of an antibody. In certain embodiments, a single-domain antibody is a human single-domain antibody. In some embodiments, the CAR comprises an antibody heavy chain domain that specifically binds the antigen, such as a cancer marker or cell surface antigen of a cell or disease to be targeted, such as a tumor cell or a cancer cell, such as any of the target antigens described herein or known.

Antibody fragments can be made by various techniques, including but not limited to proteolytic digestion of an intact antibody as well as production by recombinant host cells. In some embodiments, the antibodies are recombinantly-produced fragments, such as fragments comprising arrangements that do not occur naturally, such as those with two or more antibody regions or chains joined by synthetic linkers, e.g., peptide linkers, and/or that are may not be produced by enzyme digestion of a naturally-occurring intact antibody. In some embodiments, the antibody fragments are scFvs.

A "humanized" antibody is an antibody in which all or substantially all CDR amino acid residues are derived from non-human CDRs and all or substantially all FR amino acid residues are derived from human FRs. A humanized antibody optionally may include at least a portion of an antibody constant region derived from a human antibody. A "humanized form" of a non-human antibody, refers to a variant of the non-human antibody that has undergone humanization, typically to reduce immunogenicity to humans, while retaining the specificity and affinity of the parental non-human antibody. In some embodiments, some FR residues in a humanized antibody are substituted with corresponding residues from a non-human antibody (e.g., the antibody from which the CDR residues are derived), e.g., to restore or improve antibody specificity or affinity.

Thus, in some embodiments, the chimeric antigen receptor, including TCR-like CARs, includes an extracellular portion containing an antibody or antibody fragment. In some embodiments, the antibody or fragment includes an scFv. In some aspects, the chimeric antigen receptor includes an extracellular portion containing the antibody or fragment and an intracellular signaling region. In some embodiments, the intracellular signaling region comprises an intracellular signaling domain. In some embodiments, the intracellular signaling domain is or comprises a primary signaling domain, a signaling domain that is capable of inducing a primary activation signal in a T cell, a signaling domain of a T cell receptor (TCR) component, and/or a signaling domain comprising an immunoreceptor tyrosine-based activation motif (ITAM).

In some embodiments, the recombinant receptor such as the CAR, such as the antibody portion thereof, further includes a spacer, which may be or include at least a portion of an immunoglobulin constant region or variant or modified version thereof, such as a hinge region, e.g., an IgG4 hinge region, and/or a $C_H1/C_L$ and/or Fc region. In some embodiments, the recombinant receptor further comprises a spacer and/or a hinge region. In some embodiments, the constant region or portion is of a human IgG, such as IgG4 or IgG1. In some aspects, the portion of the constant region serves as a spacer region between the antigen-recognition component, e.g., scFv, and transmembrane domain. The spacer can be of a length that provides for increased responsiveness of the cell following antigen binding, as compared to in the absence of the spacer. Exemplary spacers, e.g., hinge regions, include those described in international patent application publication number WO2014031687. In some examples, the spacer is or is about 12 amino acids in length or is no more than 12 amino acids in length. Exemplary spacers include those having at least about 10 to 229 amino acids, about 10 to 200 amino acids, about 10 to 175 amino acids, about 10 to 150 amino acids, about 10 to 125 amino acids, about 10 to 100 amino acids, about 10 to 75 amino acids, about 10 to 50 amino acids, about 10 to 40 amino acids, about 10 to 30 amino acids, about 10 to 20 amino acids, or about 10 to 15 amino acids, and including any integer between the endpoints of any of the listed ranges. In some embodiments, a spacer region has about 12 amino acids or less, about 119 amino acids or less, or about 229 amino acids or less. Exemplary spacers include IgG4 hinge alone, IgG4 hinge linked to CH2 and CH3 domains, or IgG4 hinge linked to the CH3 domain. Exemplary spacers include, but are not limited to, those described in Hudecek et al. (2013) Clin. Cancer Res., 19:3153, Hudecek et al. (2015) Cancer Immunol Res. 3(2): 125-135 or international patent application publication number WO2014031687, U.S. Pat. No. 8,822,647 or published app. No. US2014/0271635. In some embodiments, the constant region or portion is of a human IgG, such as IgG4 or IgG1. In some embodiments, the spacer has the sequence set forth in SEQ ID NO: 1, and is encoded by the sequence set forth in SEQ ID NO: 2. In some embodiments, the spacer has the sequence set forth in SEQ ID NO: 3. In some embodiments, the spacer has the sequence set forth in SEQ ID NO: 4.

In some aspects, the spacer is a polypeptide spacer that (a) comprises or consists of all or a portion of an immunoglobulin hinge or a modified version thereof or comprises about 15 amino acids or less, and does not comprise a CD28 extracellular region or a CD8 extracellular region, (b) comprises or consists of all or a portion of an immunoglobulin hinge, optionally an IgG4 hinge, or a modified version thereof and/or comprises about 15 amino acids or less, and does not comprise a CD28 extracellular region or a CD8 extracellular region, or (c) is at or about 12 amino acids in length and/or comprises or consists of all or a portion of an immunoglobulin hinge, optionally an IgG4, or a modified version thereof; or (d) consists or comprises the sequence of amino acids set forth in SEQ ID NOS: 1, 3-5, 27-34 or 58, or a variant of any of the foregoing having at least 85%, 86%, 87%, 88%, 89%, 90%, 91%, 92%, 93%, 94%, 95%, 96%, 97%, 98%, 99% or more sequence identity thereto, or (e) comprises or consists of the formula $X_1PPX_2P$, where $X_1$ is glycine, cysteine or arginine and $X_2$ is cysteine or threonine.

In some embodiments, the constant region or portion is of IgD. In some embodiments, the spacer has the sequence set forth in SEQ ID NO: 5. In some embodiments, the spacer has a sequence of amino acids that exhibits at least or at least about 85%, 86%, 87%, 88%, 89%, 90%, 91%, 92%, 93%, 94%, 95%, 96%, 97%, 98%, 99% or more sequence identity to any of SEQ ID NOS: 1, 3, 4 and 5.

This antigen recognition domain generally is linked to one or more intracellular signaling components, such as signaling components that mimic activation through an antigen receptor complex, such as a TCR complex, in the case of a CAR, and/or signal via another cell surface receptor. The signal may be immunostimulatory and/or costimulatory in some embodiments. In some embodiments, it may be suppressive, e.g., immunosuppressive. Thus, in some embodiments, the antigen-binding component (e.g., antibody) is linked to one or more transmembrane and intracellular signaling domains and/or regions. In some embodiments, the transmembrane domain is fused to the extracellular domain. In one embodiment, a transmembrane domain that naturally is associated with one of the domains in the receptor, e.g., CAR, is used. In some instances, the transmembrane domain is selected or modified by amino acid substitution to avoid binding of such domains to the transmembrane domains of the same or different surface membrane proteins to minimize interactions with other members of the receptor complex.

The transmembrane domain in some embodiments is derived either from a natural or from a synthetic source. Where the source is natural, the domain in some aspects is derived from any membrane-bound or transmembrane protein. Transmembrane regions include those derived from (i.e. comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154 and/or transmembrane regions containing functional variants thereof such as those retaining a substantial portion of the structural, e.g., transmembrane, properties thereof. In some embodiments, the transmembrane domain is a transmembrane domain derived from CD4, CD28, or CD8, e.g., CD8alpha, or functional variant thereof. The transmembrane domain in some embodiments is synthetic. In some aspects, the synthetic transmembrane domain comprises predominantly hydrophobic residues such as leucine and valine. In some aspects, a triplet of phenylalanine, tryptophan and valine will be found at each end of a synthetic transmembrane domain. In some embodiments, the linkage is by linkers, spacers, and/or transmembrane domain(s).

Among the intracellular signaling domains are those that mimic or approximate a signal through a natural antigen receptor, a signal through such a receptor in combination with a costimulatory receptor, and/or a signal through a costimulatory receptor alone. In some embodiments, a short oligo- or polypeptide linker, for example, a linker of between 2 and 10 amino acids in length, such as one containing glycines and serines, e.g., glycine-serine doublet, is present and forms a linkage between the transmembrane domain and the cytoplasmic signaling domain of the CAR.

The receptor, e.g., the CAR, generally includes at least one intracellular signaling component or components. In some embodiments, the receptor includes an intracellular component of a TCR complex, such as a TCR CD3 chain that mediates T-cell activation and cytotoxicity, e.g., CD3 zeta chain. Thus, in some aspects, the antigen-binding portion is linked to one or more cell signaling modules. In some embodiments, cell signaling modules include CD3 transmembrane domain, CD3 intracellular signaling domains, and/or other CD transmembrane domains. In some embodiments, the receptor, e.g., CAR, further includes a portion of one or more additional molecules such as Fc receptor γ, CD8, CD4, CD25, or CD16. For example, in some aspects, the CAR or other chimeric receptor includes a chimeric molecule between CD3-zeta (CD3-ζ) or Fc receptor γ and CD8, CD4, CD25 or CD16.

In some embodiments, upon ligation of the CAR or other chimeric receptor, the cytoplasmic domain or intracellular signaling domain and/or region of the receptor activates at least one of the normal effector functions or responses of the immune cell, e.g., T cell engineered to express the CAR. For example, in some contexts, the CAR induces a function of a T cell such as cytolytic activity or T-helper activity, such as secretion of cytokines or other factors. In some embodiments, a truncated portion of an intracellular signaling domain of an antigen receptor component or costimulatory molecule is used in place of an intact immunostimulatory chain, for example, if it transduces the effector function signal. In some embodiments, the intracellular signaling domain and/or region or domains include the cytoplasmic sequences of the T cell receptor (TCR), and in some aspects also those of co-receptors that in the natural context act in concert with such receptors to initiate signal transduction following antigen receptor engagement, and/or any derivative or variant of such molecules, and/or any synthetic sequence that has the same functional capability.

In the context of a natural TCR, full activation generally requires not only signaling through the TCR, but also a costimulatory signal. Thus, in some embodiments, to promote full activation, a component for generating secondary or co-stimulatory signal is also included in the CAR. In other embodiments, the CAR does not include a component for generating a costimulatory signal. In some aspects, an additional CAR is expressed in the same cell and provides the component for generating the secondary or costimulatory signal.

T cell activation is in some aspects described as being mediated by two classes of cytoplasmic signaling sequences: those that initiate antigen-dependent primary activation through the TCR (primary cytoplasmic signaling sequences), and those that act in an antigen-independent manner to provide a secondary or co-stimulatory signal (secondary cytoplasmic signaling sequences). In some aspects, the CAR includes one or both of such signaling components.

In some aspects, the CAR includes a primary cytoplasmic signaling sequence derived from a signaling molecule or domain that promotes primary activation of a TCR complex in a natural setting. Primary cytoplasmic signaling sequences that act in a stimulatory manner may contain signaling motifs which are known as immunoreceptor tyrosine-based activation motifs or ITAMs. Examples of ITAM containing primary cytoplasmic signaling sequences include those derived from the TCR or CD3 zeta chain, FcR gamma, CD3 gamma, CD3 delta and CD3 epsilon or FcR beta. In some embodiments, cytoplasmic signaling molecule(s) in the CAR contain(s) a cytoplasmic signaling domain, portion thereof, or sequence derived from CD3 zeta.

In some embodiments, the CAR includes a signaling domain and/or transmembrane portion of a costimulatory receptor, such as CD28, 4-1BB, OX40, DAP10, and ICOS. In some aspects, the same CAR includes both the activating and costimulatory components.

In some embodiments, the activating domain is included within one CAR, whereas the costimulatory component is provided by another CAR recognizing another antigen, present on the same cell. In some embodiments, the CARs include activating or stimulatory CARs, costimulatory CARs, both expressed on the same cell (see WO2014/055668). In some aspects, the cells include one or more stimulatory or activating CAR and/or a costimulatory CAR. In some embodiments, the cells further include inhibitory CARs (iCARs, see Fedorov et al., Sci. Transl. Medicine, 5(215) (December, 2013), such as a CAR recognizing an antigen other than the one associated with and/or specific for the disease or condition whereby an activating signal delivered through the disease-targeting CAR is diminished or inhibited by binding of the inhibitory CAR to its ligand, e.g., to reduce off-target effects.

In some embodiments, the intracellular signaling component of the recombinant receptor, such as CAR, comprises a CD3 zeta intracellular domain and a costimulatory signaling region. In certain embodiments, the intracellular signaling domain comprises a CD28 transmembrane and signaling domain linked to a CD3 (e.g., CD3-zeta) intracellular domain. In some embodiments, the intracellular signaling domain comprises a chimeric CD28 and CD137 (4-1BB, TNFRSF9) co-stimulatory domains, linked to a CD3 zeta intracellular domain.

In some embodiments, the CAR encompasses one or more, e.g., two or more, costimulatory domains and an activation domain, e.g., primary activation domain, in the cytoplasmic portion. Exemplary CARs include intracellular components of CD3-zeta, CD28, and 4-1BB.

In some embodiments, the CAR or other antigen receptor further includes a marker, such as a cell surface marker, which may be used to confirm transduction or engineering of the cell to express the receptor, such as a truncated version of a cell surface receptor, such as truncated EGFR (tEGFR).

In some aspects, the marker includes all or part (e.g., truncated form) of CD34, a NGFR, or epidermal growth factor receptor (e.g., tEGFR). In some embodiments, the nucleic acid encoding the marker is operably linked to a polynucleotide encoding for a linker sequence, such as a cleavable linker sequence, e.g., T2A. For example, a marker, and optionally a linker sequence, can be any as disclosed in published patent application No. WO2014031687. For example, the marker can be a truncated EGFR (tEGFR) that is, optionally, linked to a linker sequence, such as a T2A cleavable linker sequence. In some embodiments, the marker is a molecule, e.g., cell surface protein, not naturally found on T cells or not naturally found on the surface of T cells, or a portion thereof.

In some embodiments, the molecule is a non-self molecule, e.g., non-self protein, i.e., one that is not recognized as "self" by the immune system of the host into which the cells will be adoptively transferred.

In some embodiments, the marker serves no therapeutic function and/or produces no effect other than to be used as a marker for genetic engineering, e.g., for selecting cells successfully engineered. In other embodiments, the marker may be a therapeutic molecule or molecule otherwise exerting some desired effect, such as a ligand for a cell to be encountered in vivo, such as a costimulatory or immune checkpoint molecule to enhance and/or dampen responses of the cells upon adoptive transfer and encounter with ligand.

In some cases, CARs are referred to as first, second, and/or third generation CARs. In some aspects, a first generation CAR is one that solely provides a CD3-chain induced signal upon antigen binding; in some aspects, a second-generation CARs is one that provides such a signal and costimulatory signal, such as one including an intracellular signaling domain from a costimulatory receptor such as CD28 or CD137; in some aspects, a third generation CAR is one that includes multiple costimulatory domains of different costimulatory receptors.

In some embodiments, the chimeric antigen receptor includes an extracellular portion containing an antigen-binding domain, such as an antibody or antigen-binding antibody fragment, such as an scFv or Fv. In some aspects, the chimeric antigen receptor includes an extracellular portion containing the antibody or fragment and an intracellular signaling domain. In some embodiments, the antibody or fragment includes an scFv or a single-domain $V_H$ antibody and the intracellular domain contains an ITAM. In some aspects, the intracellular signaling domain includes a signaling domain of a zeta chain of a CD3-zeta (CD3ζ) chain. In some embodiments, the chimeric antigen receptor includes a transmembrane domain linking the extracellular domain and the intracellular signaling domain. In some aspects, the transmembrane domain contains a transmembrane portion of CD28. In some embodiments, the chimeric antigen receptor contains an intracellular domain of a T cell costimulatory molecule. The extracellular domain and transmembrane domain can be linked directly or indirectly. In some embodiments, the extracellular domain and transmembrane are linked by a spacer, such as any described herein. In some embodiments, the receptor contains extracellular portion of the molecule from which the transmembrane domain is derived, such as a CD28 extracellular portion. In some embodiments, the chimeric antigen receptor contains an intracellular domain derived from a T cell costimulatory molecule or a functional variant thereof, such as between the transmembrane domain and intracellular signaling domain. In some aspects, the T cell costimulatory molecule is CD28 or 41BB.

For example, in some embodiments, the CAR contains an antibody, e.g., an antibody fragment, a transmembrane domain that is or contains a transmembrane portion of CD28 or a functional variant thereof, and an intracellular signaling domain containing a signaling portion of CD28 or functional variant thereof and a signaling portion of CD3 zeta or functional variant thereof. In some embodiments, the CAR contains an antibody, e.g., antibody fragment, a transmembrane domain that is or contains a transmembrane portion of CD28 or a functional variant thereof, and an intracellular signaling domain containing a signaling portion of a 4-1BB or functional variant thereof and a signaling portion of CD3 zeta or functional variant thereof. In some such embodiments, the receptor further includes a spacer containing a portion of an Ig molecule, such as a human Ig molecule, such as an Ig hinge, e.g. an IgG4 hinge, such as a hinge-only spacer.

In some embodiments, the transmembrane domain of the receptor, e.g., the CAR is a transmembrane domain of human CD28 or variant thereof, e.g., a 27-amino acid transmembrane domain of a human CD28 (Accession No.: P10747.1), or is a transmembrane domain that comprises the sequence of amino acids set forth in SEQ ID NO: 8 or a sequence of amino acids that exhibits at least or at least about 85%, 86%, 87%, 88%, 89%, 90%, 91%, 92%, 93%, 94%, 95%, 96%, 97%, 98%, 99% or more sequence identity to SEQ ID NO:8; in some embodiments, the transmembrane-domain containing portion of the recombinant receptor comprises the sequence of amino acids set forth in SEQ ID NO: 9 or a sequence of amino acids having at least or at least about 85%, 86%, 87%, 88%, 89%, 90%, 91%, 92%, 93%, 94%, 95%, 96%, 97%, 98%, 99% or more sequence identity thereto.

In some embodiments, the intracellular signaling region comprises an intracellular costimulatory signaling domain of human CD28 or functional variant or portion thereof, such as a 41 amino acid domain thereof and/or such a domain with an LL to GG substitution at positions 186-187 of a native CD28 protein. In some embodiments, the intracellular signaling domain can comprise the sequence of amino acids set forth in SEQ ID NO: 10 or 11 or a sequence of amino acids that exhibits at least or at least about 85%, 86%, 87%, 88%, 89%, 90%, 91%, 92%, 93%, 94%, 95%, 96%, 97%, 98%, 99% or more sequence identity to SEQ ID NO: 10 or 11. In some embodiments, the intracellular region comprises an intracellular costimulatory signaling domain of 4-1BB or functional variant or portion thereof, such as a 42-amino acid cytoplasmic domain of a human 4-1BB (Accession No. Q07011.1) or functional variant or portion thereof, such as the sequence of amino acids set forth in SEQ ID NO: 12 or a sequence of amino acids that exhibits at least or at least about 85%, 86%, 87%, 88%, 89%, 90%, 91%, 92%, 93%, 94%, 95%, 96%, 97%, 98%, 99% or more sequence identity to SEQ ID NO: 12.

In some embodiments, the intracellular signaling region comprises a human CD3 chain, optionally a CD3 zeta stimulatory signaling domain or functional variant thereof, such as an 112 AA cytoplasmic domain of isoform 3 of human CD3ζ (Accession No.: P20963.2) or a CD3 zeta signaling domain as described in U.S. Pat. No. 7,446,190 or 8,911,993. In some embodiments, the intracellular signaling region comprises the sequence of amino acids set forth in SEQ ID NO: 13, 14 or 15 or a sequence of amino acids that exhibits at least or at least about 85%, 86%, 87%, 88%, 89%, 90%, 91%, 92%, 93%, 94%, 95%, 96%, 97%, 98%, 99% or more sequence identity to SEQ ID NO: 13, 14 or 15.

In some aspects, the spacer contains only a hinge region of an IgG, such as only a hinge of IgG4 or IgG1, such as the hinge only spacer set forth in SEQ ID NO:1. In other embodiments, the spacer is an Ig hinge, e.g., and IgG4 hinge, linked to a $C_H2$ and/or $C_H3$ domains. In some embodiments, the spacer is an Ig hinge, e.g., an IgG4 hinge, linked to $C_H2$ and $C_H3$ domains, such as set forth in SEQ ID NO:3. In some embodiments, the spacer is an Ig hinge, e.g., an IgG4 hinge, linked to a $C_H3$ domain only, such as set forth in SEQ ID NO:4. In some embodiments, the spacer is or comprises a glycine-serine rich sequence or other flexible linker such as known flexible linkers.

In some embodiments, the chimeric antigen receptor contains an intracellular domain of a T cell costimulatory molecule. In some aspects, the T cell costimulatory molecule is CD28 or 41BB.

For example, in some embodiments, the CAR includes an antibody such as an antibody fragment, including scFvs, a spacer, such as a spacer containing a portion of an immunoglobulin molecule, such as a hinge region and/or one or more constant regions of a heavy chain molecule, such as an Ig-hinge containing spacer, a transmembrane domain containing all or a portion of a CD28-derived transmembrane domain, a CD28-derived intracellular signaling domain, and a CD3 zeta signaling domain. In some embodiments, the CAR includes an antibody or fragment, such as scFv, a spacer such as any of the Ig-hinge containing spacers, a CD28-derived transmembrane domain, a 4-1BB-derived intracellular signaling domain, and a CD3 zeta-derived signaling domain.

In some embodiments, nucleic acid molecules encoding such CAR constructs further includes a sequence encoding a T2A ribosomal skip element and/or a tEGFR sequence, e.g., downstream of the sequence encoding the CAR. In some embodiments, T cells expressing an antigen receptor (e.g. CAR) can also be generated to express a truncated EGFR (EGFRt) as a non-immunogenic selection epitope (e.g. by introduction of a construct encoding the CAR and EGFRt separated by a T2A ribosome switch to express two proteins from the same construct), which then can be used as a marker to detect such cells (see e.g. U.S. Pat. No. 8,802,374).

The terms "polypeptide" and "protein" are used interchangeably to refer to a polymer of amino acid residues, and are not limited to a minimum length. Polypeptides, including the provided receptors and other polypeptides, e.g., linkers or peptides, may include amino acid residues including natural and/or non-natural amino acid residues. The terms also include post-expression modifications of the polypeptide, for example, glycosylation, sialylation, acetylation, and phosphorylation. In some aspects, the polypeptides may contain modifications with respect to a native or natural sequence, as long as the protein maintains the desired activity. These modifications may be deliberate, as through site-directed mutagenesis, or may be accidental, such as through mutations of hosts which produce the proteins or errors due to PCR amplification.

2. T Cell Receptors (TCRs)

In some embodiments, engineered cells, such as T cells, are provided that express a T cell receptor (TCR) or antigen-binding portion thereof that recognizes an peptide epitope or T cell epitope of a target polypeptide, such as an antigen of a tumor, viral or autoimmune protein.

In some embodiments, a "T cell receptor" or "TCR" is a molecule that contains a variable α and β chains (also known as TCRα and TCRβ, respectively) or a variable γ and δ chains (also known as TCRα and TCRβ, respectively), or antigen-binding portions thereof, and which is capable of specifically binding to a peptide bound to an MHC molecule. In some embodiments, the TCR is in the αβ form. Typically, TCRs that exist in αβ and γδ forms are generally structurally similar, but T cells expressing them may have distinct anatomical locations or functions. A TCR can be found on the surface of a cell or in soluble form. Generally, a TCR is found on the surface of T cells (or T lymphocytes) where it is generally responsible for recognizing antigens bound to major histocompatibility complex (MHC) molecules.

Unless otherwise stated, the term "TCR" should be understood to encompass full TCRs as well as antigen-binding portions or antigen-binding fragments thereof. In some embodiments, the TCR is an intact or full-length TCR, including TCRs in the αβ form or γδ form. In some embodiments, the TCR is an antigen-binding portion that is less than a full-length TCR but that binds to a specific peptide bound in an MHC molecule, such as binds to an MHC-peptide complex. In some cases, an antigen-binding portion or fragment of a TCR can contain only a portion of the structural domains of a full-length or intact TCR, but yet is able to bind the peptide epitope, such as MHC-peptide complex, to which the full TCR binds. In some cases, an antigen-binding portion contains the variable domains of a TCR, such as variable α chain and variable β chain of a TCR, sufficient to form a binding site for binding to a specific MHC-peptide complex. Generally, the variable chains of a TCR contain complementarity determining regions involved in recognition of the peptide, MHC and/or MHC-peptide complex.

In some embodiments, the variable domains of the TCR contain hypervariable loops, or complementarity determining regions (CDRs), which generally are the primary contributors to antigen recognition and binding capabilities and specificity. In some embodiments, a CDR of a TCR or combination thereof forms all or substantially all of the antigen-binding site of a given TCR molecule. The various CDRs within a variable region of a TCR chain generally are separated by framework regions (FRs), which generally display less variability among TCR molecules as compared to the CDRs (see, e.g., Jores et al., Proc. Nat'l Acad. Sci. U.S.A. 87:9138, 1990; Chothia et al., EMBO J. 7:3745, 1988; see also Lefranc et al., Dev. Comp. Immunol. 27:55, 2003). In some embodiments, CDR3 is the main CDR responsible for antigen binding or specificity, or is the most important among the three CDRs on a given TCR variable region for antigen recognition, and/or for interaction with the processed peptide portion of the peptide-MHC complex. In some contexts, the CDR1 of the alpha chain can interact with the N-terminal part of certain antigenic peptides. In some contexts, CDR1 of the beta chain can interact with the C-terminal part of the peptide. In some contexts, CDR2 contributes most strongly to or is the primary CDR responsible for the interaction with or recognition of the MHC portion of the MHC-peptide complex. In some embodiments, the variable region of the β-chain can contain a further hypervariable region (CDR4 or HVR4), which generally is involved in superantigen binding and not antigen recognition (Kotb (1995) Clinical Microbiology Reviews, 8:411-426).

In some embodiments, a TCR also can contain a constant domain, a transmembrane domain and/or a short cytoplasmic tail (see, e.g., Janeway et al., Immunobiology: The Immune System in Health and Disease, 3rd Ed., Current Biology Publications, p. 4:33, 1997). In some aspects, each chain of the TCR can possess one N-terminal immunoglobulin variable domain, one immunoglobulin constant domain, a transmembrane region, and a short cytoplasmic tail at the C-terminal end. In some embodiments, a TCR is associated with invariant proteins of the CD3 complex involved in mediating signal transduction.

In some embodiments, a TCR chain contains one or more constant domain. For example, the extracellular portion of a given TCR chain (e.g., α-chain or β-chain) can contain two immunoglobulin-like domains, such as a variable domain (e.g., Vα or Vβ; typically amino acids 1 to 116 based on Kabat numbering Kabat et al., "Sequences of Proteins of Immunological Interest, US Dept. Health and Human Services, Public Health Service National Institutes of Health, 1991, 5th ed.) and a constant domain (e.g., α-chain constant domain or Cα, typically positions 117 to 259 of the chain based on Kabat numbering or β chain constant domain or $C_\beta$, typically positions 117 to 295 of the chain based on Kabat) adjacent to the cell membrane. For example, in some cases, the extracellular portion of the TCR formed by the two chains contains two membrane-proximal constant domains, and two membrane-distal variable domains, which variable domains each contain CDRs. The constant domain of the TCR may contain short connecting sequences in which a cysteine residue forms a disulfide bond, thereby linking the two chains of the TCR. In some embodiments, a TCR may have an additional cysteine residue in each of the α and β chains, such that the TCR contains two disulfide bonds in the constant domains.

In some embodiments, the TCR chains contain a transmembrane domain. In some embodiments, the transmembrane domain is positively charged. In some cases, the TCR chain contains a cytoplasmic tail. In some cases, the structure allows the TCR to associate with other molecules like CD3 and subunits thereof. For example, a TCR containing constant domains with a transmembrane region may anchor the protein in the cell membrane and associate with invariant subunits of the CD3 signaling apparatus or complex. The intracellular tails of CD3 signaling subunits (e.g. CD3γ, CD3δ, CD3ε and CD3ζ chains) contain one or more immunoreceptor tyrosine-based activation motif or ITAM that are involved in the signaling capacity of the TCR complex.

In some embodiments, the TCR may be a heterodimer of two chains α and β (or optionally γ and δ) or it may be a single chain TCR construct. In some embodiments, the TCR is a heterodimer containing two separate chains (α and β chains or γ and δ chains) that are linked, such as by a disulfide bond or disulfide bonds.

In some embodiments, the TCR can be generated from a known TCR sequence(s), such as sequences of Vα,β chains, for which a substantially full-length coding sequence is readily available. Methods for obtaining full-length TCR sequences, including V chain sequences, from cell sources are well known. In some embodiments, nucleic acids encoding the TCR can be obtained from a variety of sources, such as by polymerase chain reaction (PCR) amplification of TCR-encoding nucleic acids within or isolated from a given cell or cells, or synthesis of publicly available TCR DNA sequences.

In some embodiments, the TCR is obtained from a biological source, such as from cells such as from a T cell (e.g. cytotoxic T cell), T-cell hybridomas or other publicly available source. In some embodiments, the T-cells can be obtained from in vivo isolated cells. In some embodiments, the TCR is a thymically selected TCR. In some embodiments, the TCR is a neoepitope-restricted TCR. In some embodiments, the T-cells can be a cultured T-cell hybridoma or clone. In some embodiments, the TCR or antigen-binding portion thereof or antigen-binding fragment thereof can be synthetically generated from knowledge of the sequence of the TCR.

In some embodiments, the TCR is generated from a TCR identified or selected from screening a library of candidate TCRs against a target polypeptide antigen, or target T cell epitope thereof. TCR libraries can be generated by amplification of the repertoire of Vα and Vβ from T cells isolated from a subject, including cells present in PBMCs, spleen or other lymphoid organ. In some cases, T cells can be amplified from tumor-infiltrating lymphocytes (TILs). In some embodiments, TCR libraries can be generated from CD4+ or CD8+ cells. In some embodiments, the TCRs can be amplified from a T cell source of a normal of healthy subject, i.e. normal TCR libraries. In some embodiments, the TCRs can be amplified from a T cell source of a diseased subject, i.e. diseased TCR libraries. In some embodiments, degenerate primers are used to amplify the gene repertoire of Vα and Vβ, such as by RT-PCR in samples, such as T cells, obtained from humans. In some embodiments, scTv libraries can be assembled from naïve Vα and Vβ libraries in which the amplified products are cloned or assembled to be separated by a linker. Depending on the source of the subject and cells, the libraries can be HLA allele-specific. Alternatively, in some embodiments, TCR libraries can be generated by mutagenesis or diversification of a parent or scaffold TCR molecule. In some aspects, the TCRs are subjected to directed evolution, such as by mutagenesis, e.g., of the α or β chain. In some aspects, particular residues within CDRs of the TCR are altered. In some embodiments, selected TCRs can be modified by affinity maturation. In some embodiments, antigen-specific T cells may be selected, such as by screening to assess CTL activity against the peptide. In some aspects, TCRs, e.g. present on the antigen-specific T cells, may be selected, such as by binding activity, e.g., particular affinity or avidity for the antigen.

In some embodiments, the genetically engineered antigen receptors include recombinant T cell receptors (TCRs) and/or TCRs cloned from naturally occurring T cells. In some embodiments, a high-affinity T cell clone for a target antigen (e.g., a cancer antigen) is identified, isolated from a patient, and introduced into the cells. In some embodiments, the TCR clone for a target antigen has been generated in transgenic mice engineered with human immune system genes (e.g., the human leukocyte antigen system, or HLA). See, e.g., tumor antigens (see, e.g., Parkhurst et al. (2009) Clin Cancer Res. 15:169-180 and Cohen et al. (2005) J Immunol. 175:5799-5808. In some embodiments, phage display is used to isolate TCRs against a target antigen (see, e.g., Varela-Rohena et al. (2008) Nat Med. 14:1390-1395 and Li (2005) Nat Biotechnol. 23:349-354.

In some embodiments, the TCR or antigen-binding portion thereof is one that has been modified or engineered. In some embodiments, directed evolution methods are used to generate TCRs with altered properties, such as with higher affinity for a specific MHC-peptide complex. In some embodiments, directed evolution is achieved by display methods including, but not limited to, yeast display (Holler et al. (2003) Nat Immunol, 4, 55-62; Holler et al. (2000) Proc Natl Acad Sci USA, 97, 5387-92), phage display (Li et al. (2005) Nat Biotechnol, 23, 349-54), or T cell display (Chervin et al. (2008) J Immunol Methods, 339, 175-84). In some embodiments, display approaches involve engineering, or modifying, a known, parent or reference TCR. For example, in some cases, a wild-type TCR can be used as a template for producing mutagenized TCRs in which in one or more residues of the CDRs are mutated, and mutants with an desired altered property, such as higher affinity for a desired target antigen, are selected.

In some embodiments, peptides of a target polypeptide for use in producing or generating a TCR of interest are known or can be readily identified by a skilled artisan. In some embodiments, peptides suitable for use in generating TCRs or antigen-binding portions can be determined based on the presence of an HLA-restricted motif in a target polypeptide of interest, such as a target polypeptide described below. In some embodiments, peptides are identified using available computer prediction models. In some embodiments, for predicting MHC class I binding sites, such models include, but are not limited to, ProPred1 (Singh and Raghava (2001) Bioinformatics 17(12):1236-1237, and SYFPEITHI (see Schuler et al. (2007) Immunoinformatics Methods in Molecular Biology, 409(1): 75-93 2007). In some embodiments, the MHC-restricted epitope is HLA-A0201, which is expressed in approximately 39-46% of all Caucasians and therefore, represents a suitable choice of MHC antigen for use preparing a TCR or other MHC-peptide binding molecule.

HLA-A0201-binding motifs and the cleavage sites for proteasomes and immune-proteasomes using computer prediction models are known. For predicting MHC class I binding sites, such models include, but are not limited to, ProPred1 (described in more detail in Singh and Raghava, ProPred: prediction of HLA-DR binding sites. BIOINFORMATICS 17(12):1236-1237 2001), and SYFPEITHI (see Schuler et al. SYFPEITHI, Database for Searching and T-Cell Epitope Prediction. in Immunoinformatics Methods in Molecular Biology, vol 409(1): 75-93 2007).

In some embodiments, the TCR or antigen binding portion thereof may be a recombinantly produced natural protein or mutated form thereof in which one or more property, such as binding characteristic, has been altered. In some embodiments, a TCR may be derived from one of various animal species, such as human, mouse, rat, or other mammal. A TCR may be cell-bound or in soluble form. In some embodiments, for purposes of the provided methods, the TCR is in cell-bound form expressed on the surface of a cell.

In some embodiments, the TCR is a full-length TCR. In some embodiments, the TCR is an antigen-binding portion. In some embodiments, the TCR is a dimeric TCR (dTCR). In some embodiments, the TCR is a single-chain TCR (sc-TCR). In some embodiments, a dTCR or scTCR have the structures as described in WO 03/020763, WO 04/033685, WO2011/044186.

In some embodiments, the TCR contains a sequence corresponding to the transmembrane sequence. In some embodiments, the TCR does contain a sequence corresponding to cytoplasmic sequences. In some embodiments, the TCR is capable of forming a TCR complex with CD3. In some embodiments, any of the TCRs, including a dTCR or scTCR, can be linked to signaling domains that yield an active TCR on the surface of a T cell. In some embodiments, the TCR is expressed on the surface of cells.

In some embodiments a dTCR contains a first polypeptide wherein a sequence corresponding to a TCR α chain variable region sequence is fused to the N terminus of a sequence corresponding to a TCR α chain constant region extracellular sequence, and a second polypeptide wherein a sequence corresponding to a TCR β chain variable region sequence is fused to the N terminus a sequence corresponding to a TCR β chain constant region extracellular sequence, the first and second polypeptides being linked by a disulfide bond. In some embodiments, the bond can correspond to the native inter-chain disulfide bond present in native dimeric αβ TCRs. In some embodiments, the interchain disulfide bonds are not present in a native TCR. For example, in some embodiments, one or more cysteines can be incorporated into the constant region extracellular sequences of dTCR polypeptide pair. In some cases, both a native and a non-native disulfide bond may be desirable. In some embodiments, the TCR contains a transmembrane sequence to anchor to the membrane.

In some embodiments, a dTCR contains a TCR α chain containing a variable α domain, a constant α domain and a first dimerization motif attached to the C-terminus of the constant α domain, and a TCR β chain comprising a variable α domain, a constant β domain and a first dimerization motif attached to the C-terminus of the constant β domain, wherein the first and second dimerization motifs easily interact to form a covalent bond between an amino acid in the first dimerization motif and an amino acid in the second dimerization motif linking the TCR α chain and TCR β chain together.

In some embodiments, the TCR is a scTCR. Typically, a scTCR can be generated using methods known, See e.g., Soo Hoo, W. F. et al. PNAS (USA) 89, 4759 (1992); Wülfing, C. and Plückthun, A., J. Mol. Biol. 242, 655 (1994); Kurucz, I. et al. PNAS (USA) 90 3830 (1993); International published PCT Nos. WO 96/13593, WO 96/18105, WO99/60120, WO99/18129, WO 03/020763, WO2011/044186; and Schlueter, C. J. et al. J. Mol. Biol. 256, 859 (1996). In some embodiments, a scTCR contains an introduced non-native disulfide interchain bond to facilitate the association of the TCR chains (see e.g. International published PCT No. WO 03/020763). In some embodiments, a scTCR is a non-disulfide linked truncated TCR in which heterologous leucine zippers fused to the C-termini thereof facilitate chain association (see e.g. International published PCT No. WO99/60120). In some embodiments, a scTCR contain a TCRα variable domain covalently linked to a TCRβ variable domain via a peptide linker (see e.g., International published PCT No. WO99/18129).

In some embodiments, a scTCR contains a first segment constituted by an amino acid sequence corresponding to a TCR α chain variable region, a second segment constituted by an amino acid sequence corresponding to a TCR β chain variable region sequence fused to the N terminus of an amino acid sequence corresponding to a TCR β chain constant domain extracellular sequence, and a linker sequence linking the C terminus of the first segment to the N terminus of the second segment.

In some embodiments, a scTCR contains a first segment constituted by an α chain variable region sequence fused to the N terminus of an α chain extracellular constant domain sequence, and a second segment constituted by a β chain variable region sequence fused to the N terminus of a sequence β chain extracellular constant and transmembrane sequence, and, optionally, a linker sequence linking the C terminus of the first segment to the N terminus of the second segment.

In some embodiments, a scTCR contains a first segment constituted by a TCR β chain variable region sequence fused to the N terminus of a β chain extracellular constant domain sequence, and a second segment constituted by an α chain variable region sequence fused to the N terminus of a sequence α chain extracellular constant and transmembrane sequence, and, optionally, a linker sequence linking the C terminus of the first segment to the N terminus of the second segment.

In some embodiments, the linker of a scTCRs that links the first and second TCR segments can be any linker capable of forming a single polypeptide strand, while retaining TCR binding specificity. In some embodiments, the linker sequence may, for example, have the formula -P-AA-P- wherein P is proline and AA represents an amino acid sequence wherein the amino acids are glycine and serine. In some embodiments, the first and second segments are paired so that the variable region sequences thereof are orientated for such binding. Hence, in some cases, the linker has a sufficient length to span the distance between the C terminus of the first segment and the N terminus of the second segment, or vice versa, but is not too long to block or reduces bonding of the scTCR to the target ligand. In some embodiments, the linker can contain from or from about 10 to 45 amino acids, such as 10 to 30 amino acids or 26 to 41 amino acids residues, for example 29, 30, 31 or 32 amino acids. In some embodiments, the linker has the formula -PGGG-(SGGGG)$_5$-P- wherein P is proline, G is glycine and S is serine (SEQ ID NO:22). In some embodiments, the linker has the sequence GSADDAKKDAAKKDGKS (SEQ ID NO:23)

In some embodiments, the scTCR contains a covalent disulfide bond linking a residue of the immunoglobulin region of the constant domain of the α chain to a residue of the immunoglobulin region of the constant domain of the β chain. In some embodiments, the interchain disulfide bond in a native TCR is not present. For example, in some embodiments, one or more cysteines can be incorporated into the constant region extracellular sequences of the first and second segments of the scTCR polypeptide. In some cases, both a native and a non-native disulfide bond may be desirable.

In some embodiments of a dTCR or scTCR containing introduced interchain disulfide bonds, the native disulfide bonds are not present. In some embodiments, the one or more of the native cysteines forming a native interchain disulfide bonds are substituted to another residue, such as to a serine or alanine. In some embodiments, an introduced disulfide bond can be formed by mutating non-cysteine residues on the first and second segments to cysteine. Exemplary non-native disulfide bonds of a TCR are described in published International PCT No. WO2006/000830.

In some embodiments, the TCR or antigen-binding fragment thereof exhibits an affinity with an equilibrium binding constant for a target antigen of between or between about 10-5 and 10-12 M and all individual values and ranges therein. In some embodiments, the target antigen is an MHC-peptide complex or ligand.

In some embodiments, nucleic acid or nucleic acids encoding a TCR, such as α and β chains, can be amplified by PCR, cloning or other suitable means and cloned into a suitable expression vector or vectors. The expression vector can be any suitable recombinant expression vector, and can be used to transform or transfect any suitable host. Suitable vectors include those designed for propagation and expansion or for expression or both, such as plasmids and viruses.

In some embodiments, the vector can be a vector of the pUC series (Fermentas Life Sciences), the pBluescript series (Stratagene, LaJolla, Calif.), the pET series (Novagen, Madison, Wis.), the pGEX series (Pharmacia Biotech, Uppsala, Sweden), or the pEX series (Clontech, Palo Alto, Calif.). In some cases, bacteriophage vectors, such as λ610, λGT11, λZapII (Stratagene), λEMBL4, and λNM1149, also can be used. In some embodiments, plant expression vectors can be used and include pBI01, pBI101.2, pBI101.3, pBI121 and pBIN19 (Clontech). In some embodiments, animal expression vectors include pEUK-Cl, pMAM and pMAM-neo (Clontech). In some embodiments, a viral vector is used, such as a retroviral vector.

In some embodiments, the recombinant expression vectors can be prepared using standard recombinant DNA techniques. In some embodiments, vectors can contain regulatory sequences, such as transcription and translation initiation and termination codons, which are specific to the type of host (e.g., bacterium, fungus, plant, or animal) into which the vector is to be introduced, as appropriate and taking into consideration whether the vector is DNA- or RNA-based. In some embodiments, the vector can contain a nonnative promoter operably linked to the nucleotide sequence encoding the TCR or antigen-binding portion (or other MHC-peptide binding molecule). In some embodiments, the promoter can be a non-viral promoter or a viral promoter, such as a cytomegalovirus (CMV) promoter, an SV40 promoter, an RSV promoter, and a promoter found in the long-terminal repeat of the murine stem cell virus. Other known promoters also are contemplated.

In some embodiments, after the T-cell clone is obtained, the TCR alpha and beta chains are isolated and cloned into a gene expression vector. In some embodiments, the TCR alpha and beta genes are linked via a picornavirus 2A ribosomal skip peptide so that both chains are coexpression. In some embodiments, genetic transfer of the TCR is accomplished via retroviral or lentiviral vectors, or via transposons (see, e.g., Baum et al. (2006) Molecular Therapy: The Journal of the American Society of Gene Therapy. 13:1050-1063; Frecha et al. (2010) Molecular Therapy: The Journal of the American Society of Gene Therapy. 18:1748-1757; and Hackett et al. (2010) Molecular Therapy: The Journal of the American Society of Gene Therapy. 18:674-683.

In some embodiments, to generate a vector encoding a TCR, the α and β chains are PCR amplified from total cDNA isolated from a T cell clone expressing the TCR of interest and cloned into an expression vector. In some embodiments, the α and β chains are cloned into the same vector. In some embodiments, the α and β chains are cloned into different vectors. In some embodiments, the generated α and β chains are incorporated into a retroviral, e.g. lentiviral, vector.

3. Chimeric Auto-Antibody Receptor (CAAR)

In some embodiments, the recombinant receptor is a chimeric autoantibody receptor (CAAR). In some embodiments, the CAAR is specific for an autoantibody. In some embodiments, a cell expressing the CAAR, such as a T cell engineered to express a CAAR, can be used to specifically bind to and kill autoantibody-expressing cells, but not normal antibody expressing cells. In some embodiments, CAAR-expressing cells can be used to treat an autoimmune disease associated with expression of self-antigens, such as autoimmune diseases. In some embodiments, CAAR-expressing cells can target B cells that ultimately produce the autoantibodies and display the autoantibodies on their cell surfaces, mark these B cells as disease-specific targets for therapeutic intervention. In some embodiments, CAAR-expressing cells can be used to efficiently targeting and killing the pathogenic B cells in autoimmune diseases by targeting the disease-causing B cells using an antigen-specific chimeric autoantibody receptor. In some embodiments, the recombinant receptor is a CAAR, such as any described in U.S. Patent Application Pub. No. US 2017/0051035.

In some embodiments, the CAAR comprises an autoantibody binding domain, a transmembrane domain, and an intracellular signaling region. In some embodiments, the intracellular signaling region comprises an intracellular signaling domain. In some embodiments, the intracellular signaling domain is or comprises a primary signaling domain, a signaling domain that is capable of inducing a primary activation signal in a T cell, a signaling domain of a T cell receptor (TCR) component, and/or a signaling domain comprising an immunoreceptor tyrosine-based activation motif (ITAM). In some embodiments, the intracellular signaling region comprises a secondary or costimulatory signaling region (secondary intracellular signaling regions).

In some embodiments, the autoantibody binding domain comprises an autoantigen or a fragment thereof. The choice of autoantigen can depend upon the type of autoantibody being targeted. For example, the autoantigen may be chosen because it recognizes an autoantibody on a target cell, such as a B cell, associated with a particular disease state, e.g. an autoimmune disease, such as an autoantibody-mediated autoimmune disease. In some embodiments, the autoimmune disease includes pemphigus vulgaris (PV). Exemplary autoantigens include desmoglein 1 (Dsg1) and Dsg3.

4. Multi-Targeting

In some embodiments, the cells and methods include multi-targeting strategies, such as expression of two or more genetically engineered receptors on the cell, each recognizing the same of a different antigen and typically each including a different intracellular signaling component. Such multi-targeting strategies are described, for example, in International Patent Application Publication No: WO 2014055668 A1 (describing combinations of activating and costimulatory CARs, e.g., targeting two different antigens present individually on off-target, e.g., normal cells, but present together only on cells of the disease or condition to be treated) and Fedorov et al., Sci. Transl. Medicine, 5(215) (December, 2013) (describing cells expressing an activating and an inhibitory CAR, such as those in which the activating CAR binds to one antigen expressed on both normal or non-diseased cells and cells of the disease or condition to be treated, and the inhibitory CAR binds to another antigen expressed only on the normal cells or cells which it is not desired to treat).

For example, in some embodiments, the cells include a receptor expressing a first genetically engineered antigen receptor (e.g., CAR or TCR) which is capable of inducing an activating or stimulating signal to the cell, generally upon specific binding to the antigen recognized by the first receptor, e.g., the first antigen. In some embodiments, the cell further includes a second genetically engineered antigen receptor (e.g., CAR or TCR), e.g., a chimeric costimulatory receptor, which is capable of inducing a costimulatory signal to the immune cell, generally upon specific binding to a second antigen recognized by the second receptor. In some embodiments, the first antigen and second antigen are the same. In some embodiments, the first antigen and second antigen are different.

In some embodiments, the first and/or second genetically engineered antigen receptor (e.g. CAR or TCR) is capable of inducing an activating or stimulating signal to the cell. In some embodiments, the receptor includes an intracellular signaling component containing ITAM or ITAM-like motifs. In some embodiments, the activation induced by the first receptor involves a signal transduction or change in protein expression in the cell resulting in initiation of an immune response, such as ITAM phosphorylation and/or initiation of ITAM-mediated signal transduction cascade, formation of an immunological synapse and/or clustering of molecules near the bound receptor (e.g. CD4 or CD8, etc.), activation of one or more transcription factors, such as NF-κB and/or AP-1, and/or induction of gene expression of factors such as cytokines, proliferation, and/or survival.

In some embodiments, the first and/or second receptor includes intracellular signaling domains of costimulatory receptors such as CD28, CD137 (4-1BB), OX40, and/or ICOS. In some embodiments, the first and second receptor include an intracellular signaling domain of a costimulatory receptor that are different. In one embodiment, the first receptor contains a CD28 costimulatory signaling region and the second receptor contain a 4-1BB co-stimulatory signaling region or vice versa.

In some embodiments, the first and/or second receptor includes both an intracellular signaling domain containing ITAM or ITAM-like motifs and an intracellular signaling domain of a costimulatory receptor.

In some embodiments, the first receptor contains an intracellular signaling domain containing ITAM or ITAM-like motifs and the second receptor contains an intracellular signaling domain of a costimulatory receptor. The costimulatory signal in combination with the activating or stimulating signal induced in the same cell is one that results in an immune response, such as a robust and sustained immune response, such as increased gene expression, secretion of cytokines and other factors, and T cell mediated effector functions such as cell killing.

In some embodiments, neither ligation of the first receptor alone nor ligation of the second receptor alone induces a robust immune response. In some aspects, if only one receptor is ligated, the cell becomes tolerized or unresponsive to antigen, or inhibited, and/or is not induced to proliferate or secrete factors or carry out effector functions. In some such embodiments, however, when the plurality of receptors are ligated, such as upon encounter of a cell expressing the first and second antigens, a desired response is achieved, such as full immune activation or stimulation, e.g., as indicated by secretion of one or more cytokine, proliferation, persistence, and/or carrying out an immune effector function such as cytotoxic killing of a target cell.

In some embodiments, the two receptors induce, respectively, an activating and an inhibitory signal to the cell, such that binding by one of the receptor to its antigen activates the cell or induces a response, but binding by the second inhibitory receptor to its antigen induces a signal that suppresses or dampens that response. Examples are combinations of activating CARs and inhibitory CARs or iCARs. Such a strategy may be used, for example, in which the activating CAR binds an antigen expressed in a disease or condition but which is also expressed on normal cells, and the inhibitory receptor binds to a separate antigen which is expressed on the normal cells but not cells of the disease or condition.

In some embodiments, the multi-targeting strategy is employed in a case where an antigen associated with a particular disease or condition is expressed on a non-diseased cell and/or is expressed on the engineered cell itself, either transiently (e.g., upon stimulation in association with genetic engineering) or permanently. In such cases, by requiring ligation of two separate and individually specific antigen receptors, specificity, selectivity, and/or efficacy may be improved.

In some embodiments, the plurality of antigens, e.g., the first and second antigens, are expressed on the cell, tissue, or disease or condition being targeted, such as on the cancer cell. In some aspects, the cell, tissue, disease or condition is multiple myeloma or a multiple myeloma cell. In some embodiments, one or more of the plurality of antigens generally also is expressed on a cell which it is not desired to target with the cell therapy, such as a normal or non-diseased cell or tissue, and/or the engineered cells themselves. In such embodiments, by requiring ligation of multiple receptors to achieve a response of the cell, specificity and/or efficacy is achieved.

D. Compositions and Formulations

In some embodiments, the engineered cells are provided by the methods described herein which include epigenetic and/or epigenomic analysis. In some embodiments, the cells, such as cells genetically engineered with a recombinant receptor (e.g. CAR-T cells) are provided as compositions, including pharmaceutical compositions and formulations, such as unit dose form compositions including the number of cells for administration in a given dose or fraction thereof. The pharmaceutical compositions and formulations generally include one or more optional pharmaceutically acceptable carrier or excipient. In some embodiments, the composition includes at least one additional therapeutic agent.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

In some aspects, the choice of carrier is determined in part by the particular cell and/or by the method of administration. Accordingly, there are a variety of suitable formulations. For example, the pharmaceutical composition can contain preservatives. Suitable preservatives may include, for example, methylparaben, propylparaben, sodium benzoate, and benzalkonium chloride. In some aspects, a mixture of two or more preservatives is used. The preservative or mixtures thereof are typically present in an amount of about 0.0001% to about 2% by weight of the total composition. Carriers are described, e.g., by Remington's Pharmaceutical Sciences 16th edition, Osol, A. Ed. (1980). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Buffering agents in some aspects are included in the compositions. Suitable buffering agents include, for example, citric acid, sodium citrate, phosphoric acid, potassium phosphate, and various other acids and salts. In some aspects, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

The formulations can include aqueous solutions. The formulation or composition may also contain more than one active ingredient useful for the particular indication, disease, or condition being treated with the cells, preferably those with activities complementary to the cells, where the respective activities do not adversely affect one another. Such active ingredients are suitably present in combination in amounts that are effective for the purpose intended. Thus, in some embodiments, the pharmaceutical composition further includes other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, and/or vincristine.

The pharmaceutical composition in some embodiments contains the cells in amounts effective to treat or prevent the disease or condition, such as a therapeutically effective or prophylactically effective amount. Therapeutic or prophylactic efficacy in some embodiments is monitored by periodic assessment of treated subjects. The desired dosage can be delivered by a single bolus administration of the cells, by multiple bolus administrations of the cells, or by continuous infusion administration of the cells.

The cells and compositions may be administered using standard administration techniques, formulations, and/or devices. Administration of the cells can be autologous or heterologous. For example, immunoresponsive cells or progenitors can be obtained from one subject, and administered to the same subject or a different, compatible subject. Peripheral blood derived immunoresponsive cells or their progeny (e.g., in vivo, ex vivo or in vitro derived) can be administered via localized injection, including catheter administration, systemic injection, localized injection, intravenous injection, or parenteral administration. When administering a therapeutic composition (e.g., a pharmaceutical composition containing a genetically modified immunoresponsive cell), it will generally be formulated in a unit dosage injectable form (solution, suspension, emulsion).

Formulations include those for oral, intravenous, intraperitoneal, subcutaneous, pulmonary, transdermal, intramuscular, intranasal, buccal, sublingual, or suppository administration. In some embodiments, the cell populations are administered parenterally. The term "parenteral," as used herein, includes intravenous, intramuscular, subcutaneous, rectal, vaginal, and intraperitoneal administration. In some embodiments, the cells are administered to the subject using peripheral systemic delivery by intravenous, intraperitoneal, or subcutaneous injection.

Compositions in some embodiments are provided as sterile liquid preparations, e.g., isotonic aqueous solutions, suspensions, emulsions, dispersions, or viscous compositions, which may in some aspects be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol) and suitable mixtures thereof.

Sterile injectable solutions can be prepared by incorporating the cells in a solvent, such as in admixture with a suitable carrier, diluent, or excipient such as sterile water, physiological saline, glucose, dextrose, or the like. The compositions can contain auxiliary substances such as wetting, dispersing, or emulsifying agents (e.g., methylcellulose), pH buffering agents, gelling or viscosity enhancing additives, preservatives, flavoring agents, and/or colors, depending upon the route of administration and the preparation desired. Standard texts may in some aspects be consulted to prepare suitable preparations.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, and sorbic acid. Prolonged absorption of the injectable pharmaceutical form can be brought about by the use of agents delaying absorption, for example, aluminum monostearate and gelatin.

The formulations to be used for in vivo administration are generally sterile. Sterility may be readily accomplished, e.g., by filtration through sterile filtration membranes.

V. Methods of Administration

In some embodiments, the provided methods generally involve administering doses of cells expressing recombinant molecules such as recombinant receptors, such as CARs, other chimeric receptors, or other antigen receptors, such as transgenic TCRs, to subjects having a disease or condition, such as a disease or condition a component of which is specifically recognized by and/or treated by the recombinant molecules, e.g., receptors. In some embodiments, the cells are analyzed using the methods provided for assessing epigenetics and/or epigenomics. In some aspects, the epigenetic and/or epigenomic analysis can be performed on the cells before and/or after genetic engineering. The administrations generally effect an improvement in one or more symptoms of the disease or condition and/or treat or prevent the disease or condition or symptom thereof.

The disease or condition that is treated can be any in which expression of an antigen is associated with and/or involved in the etiology of a disease condition or disorder, e.g. causes, exacerbates or otherwise is involved in such disease, condition, or disorder. Exemplary diseases and conditions can include diseases or conditions associated with malignancy or transformation of cells (e.g. cancer), autoimmune or inflammatory disease, or an infectious disease, e.g. caused by a bacterial, viral or other pathogen. Exemplary antigens, which include antigens associated with various diseases and conditions that can be treated, are described herein. In particular embodiments, the chimeric antigen receptor or transgenic TCR specifically binds to an antigen associated with the disease or condition.

Among the diseases, conditions, and disorders are tumors, including solid tumors, hematologic malignancies, and melanomas, and including localized and metastatic tumors, infectious diseases, such as infection with a virus or other pathogen, e.g., HIV, HCV, HBV, CMV, HPV, and parasitic disease, and autoimmune and inflammatory diseases. In some embodiments, the disease, disorder or condition is a tumor, cancer, malignancy, neoplasm, or other proliferative disease or disorder. Such diseases include but are not limited to leukemia, lymphoma, e.g., chronic lymphocytic leukemia (CLL), ALL, non-Hodgkin's lymphoma, acute myeloid leukemia, multiple myeloma, refractory follicular lymphoma, mantle cell lymphoma, indolent B cell lymphoma, B cell malignancies, cancers of the colon, lung, liver, breast, prostate, ovarian, skin, melanoma, bone, and brain cancer, ovarian cancer, epithelial cancers, renal cell carcinoma, pancreatic adenocarcinoma, Hodgkin lymphoma, cervical carcinoma, colorectal cancer, glioblastoma, neuroblastoma, Ewing sarcoma, medulloblastoma, osteosarcoma, synovial sarcoma, and/or mesothelioma.

In some embodiments, the disease or condition is a tumor and the subject has a large tumor burden prior to the administration of the first dose, such as a large solid tumor or a large number or bulk of disease-associated, e.g., tumor, cells. In some aspects, the subject has a high number of metastases and/or widespread localization of metastases. In some aspects, the tumor burden in the subject is low and the subject has few metastases. In some embodiments, the size or timing of the doses is determined by the initial disease burden in the subject. For example, whereas in some aspects the subject may be administered a relatively low number of cells in the first dose, in context of lower disease burden the dose may be higher.

In some embodiments, the disease or condition is an infectious disease or condition, such as, but not limited to, viral, retroviral, bacterial, and protozoal infections, immunodeficiency, Cytomegalovirus (CMV), Epstein-Barr virus (EBV), adenovirus, BK polyomavirus. In some embodiments, the disease or condition is an autoimmune or inflammatory disease or condition, such as arthritis, e.g., rheumatoid arthritis (RA), Type I diabetes, systemic lupus erythematosus (SLE), inflammatory bowel disease, psoriasis, scleroderma, autoimmune thyroid disease, Grave's disease, Crohn's disease, multiple sclerosis, asthma, and/or a disease or condition associated with transplant.

In some embodiments, the antigen associated with the disease or disorder is or includes an antigen selected from the group consisting of αvβ6 integrin (avb6 integrin), B cell maturation antigen (BCMA), B7-H3, B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C-C Motif Chemokine Ligand 1 (CCL-1), CD19, CD20, CD22, CD23, CD24, CD30, CD33, CD38, CD44, CD44v6, CD44v7/8, CD123, CD138, CD171, epidermal growth factor protein (EGFR), truncated epidermal growth factor protein (tEGFR), type III epidermal growth factor receptor mutation (EGFR vIII), epithelial glycoprotein 2 (EPG-2), epithelial glycoprotein 40 (EPG-40), ephrinB2, ephrine receptor A2 (EPHa2), estrogen receptor, Fc receptor like 5 (FCRL5; also known as Fc receptor homolog 5 or FCRH5), fetal acetylcholine receptor (fetal AchR), a folate binding protein (FBP), folate receptor alpha, fetal acetylcholine receptor, ganglioside GD2, O-acetylated GD2 (OGD2), ganglioside GD3, glycoprotein 100 (gp100), G Protein Coupled Receptor 5D (GPCR5D), Her2/neu (receptor tyrosine kinase erbB2), Her3 (erb-B3), Her4 (erb-B4), erbB dimers, Human high molecular weight-melanoma-associated antigen (HMW-MAA), hepatitis B surface antigen, Human leukocyte antigen A1 (HLA-A1), Human leukocyte antigen A2 (HLA-A2), IL-22 receptor alpha (IL-22Ra), IL-13 receptor alpha 2 (IL-13Ra2), kinase insert domain receptor (kdr), kappa light chain, L1 cell adhesion molecule (L1CAM), CE7 epitope of L1-CAM, Leucine Rich Repeat Containing 8 Family Member A (LRRC8A), Lewis Y, Melanoma-associated antigen (MAGE)-A1, MAGE-A3, MAGE-A6, mesothelin, c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), Receptor Tyrosine Kinase Like Orphan Receptor 1 (ROR1), survivin, Trophoblast glycoprotein (TPBG also known as 5T4), tumor-associated glycoprotein 72 (TAG72), vascular endothelial growth factor receptor (VEGFR), vascular endothelial growth factor receptor 2 (VEGFR2), Wilms Tumor 1 (WT-1), a pathogen-specific or pathogen-expressed antigen, or an antigen associated with a universal tag, and/or biotinylated molecules, and/or molecules expressed by HIV, HCV, HBV or other pathogens.

As used herein, "treatment" (and grammatical variations thereof such as "treat" or "treating") refers to complete or partial amelioration or reduction of a disease or condition or disorder, or a symptom, adverse effect or outcome, or phenotype associated therewith. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. The terms do not imply necessarily complete curing of a disease or complete elimination of any symptom or effect(s) on all symptoms or outcomes.

As used herein, "delaying development of a disease" means to defer, hinder, slow, retard, stabilize, suppress and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

"Preventing," as used herein, includes providing prophylaxis with respect to the occurrence or recurrence of a disease in a subject that may be predisposed to the disease but has not yet been diagnosed with the disease. In some embodiments, the provided cells and compositions are used to delay development of a disease or to slow the progression of a disease.

As used herein, to "suppress" a function or activity is to reduce the function or activity when compared to otherwise same conditions except for a condition or parameter of interest, or alternatively, as compared to another condition. For example, cells that suppress tumor growth reduce the rate of growth of the tumor compared to the rate of growth of the tumor in the absence of the cells.

An "effective amount" of an agent, e.g., a pharmaceutical formulation, cells, or composition, in the context of administration, refers to an amount effective, at dosages/amounts and for periods of time necessary, to achieve a desired result, such as a therapeutic or prophylactic result.

A "therapeutically effective amount" of an agent, e.g., a pharmaceutical formulation or cells, refers to an amount effective, at dosages and for periods of time necessary, to achieve a desired therapeutic result, such as for treatment of a disease, condition, or disorder, and/or pharmacokinetic or pharmacodynamic effect of the treatment. The therapeutically effective amount may vary according to factors such as the disease state, age, sex, and weight of the subject, and the populations of cells administered. In some embodiments, the provided methods involve administering the cells and/or compositions at effective amounts, e.g., therapeutically effective amounts.

A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount. In the context of lower tumor burden, the prophylactically effective amount in some aspects will be higher than the therapeutically effective amount.

Methods for administration of cells for adoptive cell therapy are known and may be used in connection with the provided methods and compositions. For example, adoptive T cell therapy methods are described, e.g., in US Patent Application Publication No. 2003/0170238 to Gruenberg et al; U.S. Pat. No. 4,690,915 to Rosenberg; Rosenberg (2011) Nat Rev Clin Oncol. 8(10):577-85). See, e.g., Themeli et al. (2013) Nat Biotechnol. 31(10): 928-933; Tsukahara et al. (2013) Biochem Biophys Res Commun 438(1): 84-9; Davila et al. (2013) PLoS ONE 8(4): e61338.

In some embodiments, the cell therapy, e.g., adoptive cell therapy, e.g., adoptive T cell therapy, is carried out by autologous transfer, in which the cells are isolated and/or otherwise prepared from the subject who is to receive the cell therapy, or from a sample derived from such a subject. Thus, in some aspects, the cells are derived from a subject, e.g., patient, in need of a treatment and the cells, following isolation and processing are administered to the same subject.

In some embodiments, the cell therapy, e.g., adoptive cell therapy, e.g., adoptive T cell therapy, is carried out by allogeneic transfer, in which the cells are isolated and/or otherwise prepared from a subject other than a subject who is to receive or who ultimately receives the cell therapy, e.g., a first subject. In such embodiments, the cells then are administered to a different subject, e.g., a second subject, of the same species. In some embodiments, the first and second subjects are genetically identical. In some embodiments, the first and second subjects are genetically similar. In some embodiments, the second subject expresses the same HLA class or supertype as the first subject.

The cells can be administered by any suitable means, for example, by bolus infusion, by injection, e.g., intravenous or subcutaneous injections, intraocular injection, periocular injection, subretinal injection, intravitreal injection, transseptal injection, subscleral injection, intrachoroidal injection, intracameral injection, subconjectval injection, subconjuntival injection, sub-Tenon's injection, retrobulbar injection, peribulbar injection, or posterior juxtascleral delivery. In some embodiments, they are administered by parenteral, intrapulmonary, and intranasal, and, if desired for local treatment, intralesional administration. Parenteral infusions include intramuscular, intravenous, intraarterial, intraperitoneal, intrathoracic, intracranial, or subcutaneous administration. In some embodiments, a given dose is administered by a single bolus administration of the cells. In some embodiments, it is administered by multiple bolus administrations of the cells, for example, over a period of no more than 3 days, or by continuous infusion administration of the cells.

For the prevention or treatment of disease, the appropriate dosage may depend on the type of disease to be treated, the type of cells or recombinant receptors, the severity and course of the disease, whether the cells are administered for preventive or therapeutic purposes, previous therapy, the subject's clinical history and response to the cells, and the discretion of the attending physician. The compositions and cells are in some embodiments suitably administered to the subject at one time or over a series of treatments.

In some embodiments, the cells are administered as part of a combination treatment, such as simultaneously with or sequentially with, in any order, another therapeutic intervention, such as an antibody or engineered cell or receptor or other agent, such as a cytotoxic or therapeutic agent. Thus, the cells in some embodiments are co-administered with one or more additional therapeutic agents or in connection with another therapeutic intervention, either simultaneously or sequentially in any order. In some contexts, the cells are co-administered with another therapy sufficiently close in time such that the cell populations enhance the effect of one or more additional therapeutic agents, or vice versa. In some embodiments, the cells are administered prior to the one or more additional therapeutic agents. In some embodiments, the cells are administered after the one or more additional therapeutic agents. In some embodiments, the one or more additional agents includes a cytokine, such as IL-2 or other cytokine, for example, to enhance persistence. In some embodiments, the methods comprise administration of a chemotherapeutic agent, e.g., a conditioning chemotherapeutic agent, for example, to reduce tumor burden prior to the dose administrations.

Preconditioning subjects with immunodepleting (e.g., lymphodepleting) therapies in some aspects can improve the effects of adoptive cell therapy (ACT).

Thus, in some embodiments, the methods include administering a preconditioning agent, such as a lymphodepleting or chemotherapeutic agent, such as cyclophosphamide, fludarabine, or combinations thereof, to a subject prior to the initiation of the cell therapy. For example, the subject may be administered a preconditioning agent at least 2 days prior, such as at least 3, 4, 5, 6, or 7 days prior, to the initiation of the cell therapy. In some embodiments, the subject is administered a preconditioning agent no more than 7 days prior, such as no more than 6, 5, 4, 3, or 2 days prior, to the initiation of the cell therapy.

In some embodiments, the subject is preconditioned with cyclophosphamide at a dose between or between about 20 mg/kg and 100 mg/kg, such as between or between about 40 mg/kg and 80 mg/kg. In some aspects, the subject is preconditioned with or with about 60 mg/kg of cyclophosphamide. In some embodiments, the cyclophosphamide can be administered in a single dose or can be administered in a plurality of doses, such as given daily, every other day or every three days. In some embodiments, the cyclophosphamide is administered once daily for one or two days. In some embodiments, where the lymphodepleting agent comprises cyclophosphamide, the subject is administered cyclophosphamide at a dose between or between about 100 mg/m$^2$ and 500 mg/m$^2$, such as between or between about 200 mg/m$^2$ and 400 mg/m$^2$, or 250 mg/m$^2$ and 350 mg/m$^2$, inclusive. In some instances, the subject is administered about 300 mg/m$^2$ of cyclophosphamide. In some embodiments, the cyclophosphamide can be administered in a single dose or can be administered in a plurality of doses, such as given daily, every other day or every three days. In some embodiments, cyclophosphamide is administered daily, such as for 1-5 days, for example, for 3 to 5 days. In some instances, the subject is administered about 300 mg/m$^2$ of cyclophosphamide, daily for 3 days, prior to initiation of the cell therapy.

In some embodiments, where the lymphodepleting agent comprises fludarabine, the subject is administered fludarabine at a dose between or between about 1 mg/m$^2$ and 100 mg/m$^2$, such as between or between about 10 mg/m$^2$ and 75 mg/m$^2$, 15 mg/m$^2$ and 50 mg/m$^2$, 20 mg/m$^2$ and 40 mg/m$^2$, or 24 mg/m$^2$ and 35 mg/m$^2$, inclusive. In some instances, the subject is administered about 30 mg/m$^2$ of fludarabine. In some embodiments, the fludarabine can be administered in a single dose or can be administered in a plurality of doses, such as given daily, every other day or every three days. In some embodiments, fludarabine is administered daily, such as for 1-5 days, for example, for 3 to 5 days. In some instances, the subject is administered about 30 mg/m$^2$ of fludarabine, daily for 3 days, prior to initiation of the cell therapy.

In some embodiments, the lymphodepleting agent comprises a combination of agents, such as a combination of cyclophosphamide and fludarabine. Thus, the combination of agents may include cyclophosphamide at any dose or administration schedule, such as those described herein, and fludarabine at any dose or administration schedule, such as those described herein. For example, in some aspects, the subject is administered 60 mg/kg (~2 g/m$^2$) of cyclophosphamide and 3 to 5 doses of 25 mg/m$^2$ fludarabine prior to the first or subsequent dose.

Once the cells are administered to the subject (e.g., human), the biological activity of the engineered cell populations in some aspects is measured by any of a number of known methods. Parameters to assess include specific binding of an engineered or natural T cell or other immune cell to antigen, in vivo, e.g., by imaging, or ex vivo, e.g., by ELISA or flow cytometry. In certain embodiments, the ability of the engineered cells to destroy target cells can be measured using any suitable method known in the art, such as cytotoxicity assays described in, for example, Kochenderfer et al., J. Immunotherapy, 32(7): 689-702 (2009), and Herman et al. J. Immunological Methods, 285(1): 25-40 (2004). In certain embodiments, the biological activity of the cells also can be measured by assaying expression and/or secretion of certain cytokines, such as CD 107a, IFNγ, IL-2, and TNF. In some aspects the biological activity is measured by assessing clinical outcome, such as reduction in tumor burden or load. In some aspects, toxic outcomes, persistence and/or expansion of the cells, and/or presence or absence of a host immune response, are assessed.

In certain embodiments, engineered cells are modified in any number of ways, such that their therapeutic or prophylactic efficacy is increased. For example, the engineered CAR or TCR expressed by the population can be conjugated either directly or indirectly through a linker to a targeting moiety. The practice of conjugating compounds, e.g., the CAR or TCR, to targeting moieties is known in the art. See, for instance, Wadwa et al., J. Drug Targeting 3: 1 1 1 (1995), and U.S. Pat. No. 5,087,616.

In some embodiments, the cells are administered as part of a combination treatment, such as simultaneously with or sequentially with, in any order, another therapeutic intervention, such as an antibody or engineered cell or receptor or agent, such as a cytotoxic or therapeutic agent. The cells in some embodiments are co-administered with one or more additional therapeutic agents or in connection with another therapeutic intervention, either simultaneously or sequentially in any order. In some contexts, the cells are co-administered with another therapy sufficiently close in time such that the cell populations enhance the effect of one or more additional therapeutic agents, or vice versa. In some embodiments, the cells are administered prior to the one or more additional therapeutic agents. In some embodiments, the cells are administered after the one or more additional therapeutic agents. In some embodiments, the one or more additional agent includes a cytokine, such as IL-2, for example, to enhance persistence.

A. Dosing

In some embodiments, a dose of cells is administered to subjects in accord with the provided methods, and/or with the provided articles of manufacture or compositions. In some embodiments, the size or timing of the doses is determined as a function of the particular disease or condition in the subject. In some cases, the size or timing of the doses for a particular disease in view of the provided description may be empirically determined.

In some embodiments, the dose of cells comprises between at or about $2\times10^5$ of the cells/kg and at or about $2\times10^6$ of the cells/kg, such as between at or about $4\times10^5$ of the cells/kg and at or about $1\times10^6$ of the cells/kg or between at or about $6\times10^5$ of the cells/kg and at or about $8\times10^5$ of the cells/kg. In some embodiments, the dose of cells comprises no more than $2\times10^5$ of the cells (e.g. antigen-expressing, such as CAR-expressing cells) per kilogram body weight of the subject (cells/kg), such as no more than at or about $3\times10^5$ cells/kg, no more than at or about $4\times10^5$ cells/kg, no more than at or about $5\times10^5$ cells/kg, no more than at or about $6\times10^5$ cells/kg, no more than at or about $7\times10^5$ cells/kg, no more than at or about $8\times10^5$ cells/kg, no more than at or about $9\times10^5$ cells/kg, no more than at or about $1\times10^6$ cells/kg, or no more than at or about $2\times10^6$ cells/kg. In some embodiments, the dose of cells comprises at least or at least about or at or about $2\times10^5$ of the cells (e.g. antigen-expressing, such as CAR-expressing cells) per kilogram body weight of the subject (cells/kg), such as at least or at least about or at or about $3\times10^5$ cells/kg, at least or at least about or at or about $4\times10^5$ cells/kg, at least or at least about or at or about $5\times10^5$ cells/kg, at least or at least about or at or about $6\times10^5$ cells/kg, at least or at least about or at or about $7\times10^5$ cells/kg, at least or at least about or at or about $8\times10^5$ cells/kg, at least or at least about or at or about $9\times10^5$ cells/kg, at least or at least about or at or about $1\times10^6$ cells/kg, or at least or at least about or at or about $2\times10^6$ cells/kg.

In the context of adoptive cell therapy, administration of a given "dose" encompasses administration of the given amount or number of cells as a single composition and/or single uninterrupted administration, e.g., as a single injection or continuous infusion, and also encompasses administration of the given amount or number of cells as a split dose, provided in multiple individual compositions or infusions, over a specified period of time, which is no more than 3 days. Thus, in some contexts, the dose is a single or continuous administration of the specified number of cells, given or initiated at a single point in time. In some contexts, however, the dose is administered in multiple injections or infusions over a period of no more than three days, such as once a day for three days or for two days or by multiple infusions over a single day period.

Thus, in some aspects, the cells are administered in a single pharmaceutical composition.

In some embodiments, the cells are administered in a plurality of compositions, collectively containing the cells of a single dose.

Thus, one or more of the doses in some aspects may be administered as a split dose. For example, in some embodiments, the dose may be administered to the subject over 2 days or over 3 days. Exemplary methods for split dosing include administering 25% of the dose on the first day and administering the remaining 75% of the dose on the second day. In other embodiments 33% of the dose may be administered on the first day and the remaining 67% administered on the second day. In some aspects, 10% of the dose is administered on the first day, 30% of the dose is administered on the second day, and 60% of the dose is administered on the third day. In some embodiments, the split dose is not spread over more than 3 days.

In some embodiments, multiple doses are given, in some aspects using the same timing guidelines as those with respect to the timing between the first and second doses, e.g., by administering a first and multiple subsequent doses, with each subsequent dose given at a point in time that is greater than about 28 days after the administration of the first or prior dose.

In certain embodiments, the cells, or individual populations of sub-types of cells, are administered to the subject at a range of about one million to about 100 billion cells and/or that amount of cells per kilogram of body weight, such as, e.g., 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), such as about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), and in some cases about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells) or any value in between these ranges and/or per kilogram of body weight. Dosages may vary depending on attributes particular to the disease or disorder and/or patient and/or other treatments.

In some embodiments, the dose of genetically engineered cells comprises from or from about $1\times10^5$ to $5\times10^8$ total CAR-expressing T cells, $1\times10^5$ to $2.5\times10^8$ total CAR-expressing T cells, $1\times10^5$ to $1\times10^8$ total CAR-expressing T cells, $1\times10^5$ to $5\times10^7$ total CAR-expressing T cells, $1\times10^5$ to $2.5\times10^7$ total CAR-expressing T cells, $1\times10^5$ to $1\times10^7$ total CAR-expressing T cells, $1\times10^5$ to $5\times10^6$ total CAR-expressing T cells, $1\times10^5$ to $2.5\times10^6$ total CAR-expressing T cells, $1\times10^5$ to $1\times10^6$ total CAR-expressing T cells, $1\times10^6$ to $5\times10^8$ total CAR-expressing T cells, $1\times10^6$ to $2.5\times10^8$ total CAR-expressing T cells, $1\times10^6$ to $1\times10^8$ total CAR-expressing T cells, $1\times10^6$ to $5\times10^7$ total CAR-expressing T cells, $1\times10^6$ to $2.5\times10^7$ total CAR-expressing T cells, $1\times10^6$ to $1\times10^7$ total CAR-expressing T cells, $1\times10^6$ to $5\times10^6$ total CAR-expressing T cells, $1\times10^6$ to $2.5\times10^6$ total CAR-expressing T cells, $2.5\times10^6$ to $5\times10^8$ total CAR-expressing T cells, $2.5\times10^6$ to $2.5\times10^8$ total CAR-expressing T cells, $2.5\times10^6$ to $1\times10^8$ total CAR-expressing T cells, $2.5\times10^6$ to $5\times10^7$ total CAR-expressing T cells, $2.5\times10^6$ to $2.5\times10^7$ total CAR-expressing T cells, $2.5\times10^6$ to $1\times10^7$ total CAR-expressing T cells, $2.5\times10^6$ to $5\times10^6$ total CAR-expressing T cells, $5\times10^6$ to $5\times10^8$ total CAR-expressing T cells, $5\times10^6$ to $2.5\times10^8$ total CAR-expressing T cells, $5\times10^6$ to $1\times10^8$ total CAR-expressing T cells, $5\times10^6$ to $5\times10^7$ total CAR-expressing T cells, $5\times10^6$ to $2.5\times10^7$ total CAR-expressing T cells, $5\times10^6$ to $1\times10^7$ total CAR-expressing T cells, $1\times10^7$ to $5\times10^8$ total CAR-expressing T cells, $1\times10^7$ to $2.5\times10^8$ total CAR-expressing T cells, $1\times10^7$ to $1\times10^8$ total CAR-expressing T cells, $1\times10^7$ to $5\times10^7$ total CAR-expressing T cells, $1\times10^7$ to $2.5\times10^7$ total CAR-expressing T cells, $2.5\times10^7$ to $5\times10^8$ total CAR-expressing T cells, $2.5\times10^7$ to $2.5\times10^8$ total CAR-expressing T cells, $2.5\times10^7$ to $1\times10^8$ total CAR-expressing T cells, $2.5\times10^7$ to $5\times10^7$ total CAR-expressing T cells, $5\times10^7$ to $5\times10^8$ total CAR-expressing T cells, $5\times10^7$ to $2.5\times10^8$ total CAR-expressing T cells, $5\times10^7$ to $1\times10^8$ total CAR-expressing T cells, $1\times10^8$ to $5\times10^8$ total CAR-expressing T cells, $1\times10^8$ to $2.5\times10^8$ total CAR-expressing T cells, or $2.5\times10^8$ to $5\times10^8$ total CAR-expressing T cells.

In some embodiments, the dose of genetically engineered cells comprises at least or at least about $1\times10^5$ CAR-expressing cells, at least or at least about $2.5\times10^5$ CAR-expressing cells, at least or at least about $5\times10^5$ CAR-expressing cells, at least or at least about $1\times10^6$ CAR-expressing cells, at least or at least about $2.5\times10^6$ CAR-expressing cells, at least or at least about $5\times10^6$ CAR-expressing cells, at least or at least about $1\times10^7$ CAR-expressing cells, at least or at least about $2.5\times10^7$ CAR-expressing cells, at least or at least about $5\times10^7$ CAR-expressing cells, at least or at least about $1\times10^8$ CAR-expressing cells, at least or at least about $2.5\times10^8$ CAR-expressing cells, or at least or at least about $5\times10^8$ CAR-expressing cells.

In some embodiments, the cell therapy comprises administration of a dose comprising a number of cell from or from about $1\times10^5$ to $5\times10^8$ total recombinant receptor-expressing cells, total T cells, or total peripheral blood mononuclear cells (PBMCs), from or from about $5\times10^5$ to $1\times10^7$ total recombinant receptor-expressing cells, total T cells, or total peripheral blood mononuclear cells (PBMCs) or from or from about $1\times10^6$ to $1\times10^7$ total recombinant receptor-expressing cells, total T cells, or total peripheral blood mononuclear cells (PBMCs), each inclusive. In some embodiments, the cell therapy comprises administration of a dose of cells comprising a number of cells at least or at least about $1\times10^5$ total recombinant receptor-expressing cells, total T cells, or total peripheral blood mononuclear cells (PBMCs), such at least or at least $1\times10^6$, at least or at least about $1\times10^7$, at least or at least about $1\times10^8$ of such cells. In some embodiments, the number is with reference to the total number of CD3+ or CD8+, in some cases also recombinant receptor-expressing (e.g. CAR+) cells. In some embodiments, the cell therapy comprises administration of a dose comprising a number of cell from or from about $1\times10^5$ to $5\times10^8$ CD3+ or CD8+ total T cells or CD3+ or CD8+ recombinant receptor-expressing cells, from or from about $5\times10^5$ to $1\times10^7$ CD3+ or CD8+ total T cells or CD3+ or CD8+ recombinant receptor-expressing cells, or from or from about $1\times10^6$ to $1\times10^7$ CD3+ or CD8+ total T cells or CD3+ or CD8+ recombinant receptor-expressing cells, each inclusive. In some embodiments, the cell therapy comprises administration of a dose comprising a number of cell from or from about $1\times10^5$ to $5\times10^8$ total CD3+/CAR+ or CD8+/CAR+ cells, from or from about $5\times10^5$ to $1\times10^7$ total CD3+/CAR+ or CD8+/CAR+ cells, or from or from about $1\times10^6$ to $1\times10^7$ total CD3+/CAR+ or CD8+/CAR+ cells, each inclusive.

In some embodiments, the T cells of the dose include CD4+ T cells, CD8+ T cells or CD4+ and CD8+ T cells.

In some embodiments, for example, where the subject is human, the CD8+ T cells of the dose, including in a dose including CD4+ and CD8+ T cells, includes between about $1\times10^6$ and $5\times10^8$ total recombinant receptor (e.g., CAR)-expressing CD8+ cells, e.g., in the range of about $5\times10^6$ to $1\times10^8$ such cells, such cells $1\times10^7$, $2.5\times10^7$, $5\times10^7$, $7.5\times10^7$, $1\times10^8$, or $5\times10^8$ total such cells, or the range between any two of the foregoing values. In some embodiments, the patient is administered multiple doses, and each of the doses or the total dose can be within any of the foregoing values. In some embodiments, the dose of cells comprises the administration of from or from about $1\times10^7$ to $0.75\times10^8$ total recombinant receptor-expressing CD8+ T cells, $1\times10^7$ to $2.5\times10^7$ total recombinant receptor-expressing CD8+ T cells, from or from about $1\times10^7$ to $0.75\times10^8$ total recombinant receptor-expressing CD8+ T cells, each inclusive. In some embodiments, the dose of cells comprises the administration of or about $1\times10^7$, $2.5\times10^7$, $5\times10^7$ $7.5\times10^7$, $1\times10^8$, or $5\times10^8$ total recombinant receptor-expressing CD8+ T cells.

In some embodiments, the dose of cells, e.g., recombinant receptor-expressing T cells, is administered to the subject as a single dose or is administered only one time within a period of two weeks, one month, three months, six months, 1 year or more.

In some embodiments, the dose contains a number of cells, number of recombinant receptor (e.g., CAR)-expressing cells, number of T cells, or number of peripheral blood mononuclear cells (PBMCs) in the range from about $10^5$ to about $10^6$ of such cells per kilogram body weight of the subject, and/or a number of such cells that is no more than about $10^5$ or about $10^6$ such cells per kilogram body weight of the subject. For example, in some embodiments, the first or subsequent dose includes less than or no more than at or about $1\times10^5$, at or about $2\times10^5$, at or about $5\times10^5$, or at or about $1\times10^6$ of such cells per kilogram body weight of the subject. In some embodiments, the first dose includes at or about $1\times10^5$, at or about $2\times10^5$, at or about $5\times10^5$, or at or about $1\times10^6$ of such cells per kilogram body weight of the subject, or a value within the range between any two of the foregoing values. In particular embodiments, the numbers and/or concentrations of cells refer to the number of recombinant receptor (e.g., CAR)-expressing cells. In other embodiments, the numbers and/or concentrations of cells refer to the number or concentration of all cells, T cells, or peripheral blood mononuclear cells (PBMCs) administered.

In some embodiments, for example, where the subject is a human, the dose includes fewer than about $1\times10^8$ total recombinant receptor (e.g., CAR)-expressing cells, T cells, or peripheral blood mononuclear cells (PBMCs), e.g., in the range of about $1\times10^6$ to $1\times10^8$ such cells, such as $2\times10^6$, $5\times10^6$, $1\times10^7$, $5\times10^7$, or $1\times10^8$ or total such cells, or the range between any two of the foregoing values.

In some embodiments, the dose contains fewer than about $1\times10^8$ total recombinant receptor (e.g., CAR)-expressing cells, T cells, or peripheral blood mononuclear cells (PBMCs) cells per m² of the subject, e.g., in the range of about $1\times10^6$ to $1\times10^8$ such cells per m² of the subject, such as $2\times10^6$, $5\times10^6$, $1\times10^7$, $5\times10^7$, or $1\times10^8$ such cells per m² of the subject, or the range between any two of the foregoing values.

In certain embodiments, the number of cells, recombinant receptor (e.g., CAR)-expressing cells, T cells, or peripheral blood mononuclear cells (PBMCs) in the dose is greater than about $1\times10^6$ such cells per kilogram body weight of the subject, e.g., $2\times10^6$, $3\times10^6$, $5\times10^6$, $1\times10^7$, $5\times10^7$, $1\times10^8$, $1\times10^9$, or $1\times10^{10}$ such cells per kilogram of body weight and/or, $1\times10^8$, or $1\times10^9$, $1\times10^{10}$ such cells per m² of the subject or total, or the range between any two of the foregoing values.

In some aspects, the size of the dose is determined based on one or more criteria such as response of the subject to prior treatment, e.g. chemotherapy, disease burden in the subject, such as tumor load, bulk, size, or degree, extent, or type of metastasis, stage, and/or likelihood or incidence of the subject developing toxic outcomes, e.g., CRS, macrophage activation syndrome, tumor lysis syndrome, neurotoxicity, and/or a host immune response against the cells and/or recombinant receptors being administered.

In some aspects, the size of the dose is determined by the burden of the disease or condition in the subject. For example, in some aspects, the number of cells administered in the dose is determined based on the tumor burden that is present in the subject immediately prior to administration of the initiation of the dose of cells. In some embodiments, the size of the first and/or subsequent dose is inversely correlated with disease burden. In some aspects, as in the context of a large disease burden, the subject is administered a low number of cells, for example less than about $1 \times 10^6$ cells per kilogram of body weight of the subject. In other embodiments, as in the context of a lower disease burden, the subject is administered a larger number of cells, such as more than about $1 \times 10^6$ cells per kilogram body weight of the subject.

In some aspects, results of the assessment of epigenetic properties, e.g., profiles from ATAC-seq analysis, can be used to determine a treatment regimen, e.g., including doses, timing and/or frequency of administration of the engineered cells. In some aspects, the characteristics and/or properties of the cell composition, such as an engineered cell composition or a pre-engineering cell composition obtained from a subject, as determined using methods described herein, can be used to select subjects for treatment and/or determine the appropriate dose for treatment. In some embodiments, the methods described herein can be used to assess clinical doses of cells in the administered composition.

VI. Kits and Article of Manufacture

Also provided are kits and articles of manufacture, such as those containing reagents for performing the methods provided herein, e.g., reagents for assessing the epigenetic properties at one or more genomic regions, e.g., genomic loci in cells, e.g., cells for engineering. In some embodiments, the kits also include reagents for assessing other parameter or performing additional epigenetic and/or epigenomic analysis for one or more genomic regions, e.g., genomic loci.

In some embodiments, provided are kits that comprise a nucleic acid, an insertional enzyme and an insertion element, wherein: the insertion element can comprise a nucleic acid comprising a predetermined sequence and the insertional enzyme can further comprise an affinity tag. In some embodiments, the kits further comprise association molecules, e.g., proteins (e.g. histones) or nucleic acids (e.g. aptamers) that associate with the nucleic acids. In some embodiments, the affinity tag can be an antibody. In some embodiments, the antibody can bind a transcription factor, modified nucleosome and/or modified nucleic acids. Examples of modified nucleic acids include, but are not limited to, methylated or hydroxymethylated DNA. The affinity tag can also be a single-stranded nucleic acid (e.g. ssDNA, ssRNA). In some embodiments, the single-stranded nucleic acid can be bound to a target nucleic acid. In some instances, the insertional enzyme can further comprise a nuclear localization signal.

In some embodiments, the kits further comprise: (a) reagents for isolating nuclei from a population of cells; (b) transposase and transposon tags, and (c) transposase reaction buffer, wherein the components of the kit are configured such that, combining the reaction buffer, transposase and adaptors with nuclei in vitro results in both lysis of the nuclei to release chromatin and production of adaptor-tagged fragments of genomic DNA.

In some embodiments, the kit can comprise: (a) a cell lysis buffer; (b) an insertional enzyme comprising an affinity tag; and (c) an insertion element comprising a nucleic acid, wherein said nucleic acid comprises a predetermined sequence. The insertional enzyme can be, for example, a transposase. The insertional enzyme can also comprise two or more enzymatic moieties that are linked together.

In some embodiments, the kit optionally contains other components, for example: PCR primers, PCR reagents such as polymerase, buffer, nucleotides, reagents for additional assays, e.g., intracellular cytokine staining, flow cytometry, chromatin immunoprecipitation and/or additional epigenetic and/or epigenomic analysis. In some embodiments, the reagents for additional assays include components for performing an in vitro assay to measure the expression or level of particular molecules. In some cases, the in vitro assay is an immunoassay, an aptamer-based assay, a histological or cytological assay, or an mRNA expression level assay. In some embodiments, the in vitro assay is selected from among an enzyme linked immunosorbent assay (ELISA), immunoblotting, immunoprecipitation, radioimmunoassay (RIA), immunostaining, flow cytometry assay, surface plasmon resonance (SPR), chemiluminescence assay, lateral flow immunoassay, inhibition assay and avidity assay. In some aspects, the reagent is a binding reagent that specifically binds the molecules. In some cases, the binding reagent is an antibody or antigen-binding fragment thereof, an aptamer or a nucleic acid probe. The various components of the kit may be present in separate containers or certain compatible components may be precombined into a single container. In some embodiments, the kits further contain instructions for using the components of the kit to practice the provided methods.

VII. Definitions

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

As used herein, the singular forms "a," "an," and "the" include plural referents unless the context clearly dictates otherwise. For example, "a" or "an" means "at least one" or "one or more." It is understood that aspects and variations described herein include "consisting" and/or "consisting essentially of" aspects and variations.

The term "about" as used herein refers to the usual error range for the respective value readily known to the skilled person in this technical field. Reference to "about" a value or parameter herein includes (and describes) embodiments that are directed to that value or parameter per se. For example, description referring to "about X" includes description of "X".

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

As used herein, a composition refers to any mixture of two or more products, substances, or compounds, including cells. It may be a solution, a suspension, liquid, powder, a paste, aqueous, non-aqueous or any combination thereof.

As used herein, a statement that a cell or population of cells is "positive" for a particular marker refers to the detectable presence on or in the cell of a particular marker, typically a surface marker. When referring to a surface marker, the term refers to the presence of surface expression as detected by flow cytometry, for example, by staining with an antibody that specifically binds to the marker and detecting said antibody, wherein the staining is detectable by flow cytometry at a level substantially above the staining detected carrying out the same procedure with an isotype-matched control under otherwise identical conditions and/or at a level substantially similar to that for cell known to be positive for the marker, and/or at a level substantially higher than that for a cell known to be negative for the marker.

As used herein, a statement that a cell or population of cells is "negative" for a particular marker refers to the absence of substantial detectable presence on or in the cell of a particular marker, typically a surface marker. When referring to a surface marker, the term refers to the absence of surface expression as detected by flow cytometry, for example, by staining with an antibody that specifically binds to the marker and detecting said antibody, wherein the staining is not detected by flow cytometry at a level substantially above the staining detected carrying out the same procedure with an isotype-matched control under otherwise identical conditions, and/or at a level substantially lower than that for cell known to be positive for the marker, and/or at a level substantially similar as compared to that for a cell known to be negative for the marker.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

As used herein, a "subject" is a mammal, such as a human or other animal, and typically is human.

VIII. Exemplary Embodiments

Among the provided embodiments are:

1. A method of identifying one or more genomic region(s) predictive of an outcome of treatment with a cell therapy, the method comprising:
   (a) analyzing or determining an epigenetic property of one or more genomic regions of a cell or a population of cells, said cell or population comprised in (i) a first composition of cells to be genetically engineered with a recombinant receptor to produce a second composition comprising the recombinant receptor, or (ii) a second composition of cells comprising the recombinant receptor; and
   (b) identifying one or more of said one or more genomic regions, of which the epigenetic property, overall across the one or more genomic regions, predicts, indicates or correlates with an outcome of a cell therapy, said cell therapy comprising administering the second composition of cells comprising the recombinant receptor.

2. The method of embodiment 1, wherein the outcome is optionally a complete response, a partial response, progressive disease, a molecularly detectable disease, relapse, durability of response, outcome associated with or indicative of efficacy, or outcome associated with or indicative of toxicity.

3. A method of identifying one or more genomic region(s) predictive of an outcome of treatment with a cell therapy, the method comprising:
   (a) determining or measuring a level or degree or relative level or degree of an epigenetic property of one or more genomic regions for a cell or a population of cells comprised in a first therapeutic composition;
   (b) determining or measuring a level or degree or relative level or degree of said epigenetic property of said one or more genomic regions for a cell or a population of cells comprised in second therapeutic composition;
   (c) comparing the level or degree in (a) and the level or degree in (b) for one or more of the genomic regions.

4. The method of embodiment 3, further comprising identifying one or more of the one or more genomic regions in which the level or degree determined or measured in (a) is different, optionally significantly different, as compared to the level or degree determined or measured in (b).

5. The method of embodiment 3 or embodiment 4, wherein, for each of the plurality of genomic regions, a difference or significant difference between the level or degree detected or measured in (a) and the level or degree detected or measured in (b) indicates that the epigenetic property or degree or level thereof correlates with, predicts, predicts the likelihood or risk of, an outcome that occurs or has occurred with one but not the other of, the first and second therapeutic compositions, wherein the outcome is optionally a complete response, a partial response, progressive disease, a molecularly detectable disease, relapse, durability of response, outcome associated with or indicative of efficacy, or outcome associated with or indicative of toxicity.

6. The method of any of embodiments 1-5, wherein the genomic region comprises a genomic locus or gene.

7. The method of embodiment 1 or embodiment 2, wherein the genomic region comprises an open reading frame of a gene.

8. The method of any of embodiments 1-7, wherein the epigenetic property is selected from among chromatin accessibility, nucleosome occupancy, histone modification, spatial chromosomal conformation, transcription factor occupancy and DNA methylation.

9. The method of any of embodiments 1-8, wherein the epigenetic property is chromatin accessibility.

10. The method of any of embodiments 1-9, wherein:
said epigenetic property comprises chromatin accessibility, a level or degree of chromatin accessibility, a relative level or degree of chromatin accessibility, and/or
said epigenetic property comprises a degree or level of, relative degree or level of, or profile or map of, chromatin accessibility across the genomic region.

11. The method of any of embodiments 8-10, wherein chromatin accessibility is determined by Assay for Transposase Accessible Chromatin with high-throughput sequencing (ATAC-seq) or chromatin immunoprecipitation coupled to high-throughput sequencing (ChIP-seq).

12. The method of any of embodiments 8-11, wherein chromatin accessibility is determined by ATAC-seq.

13. The method of any of embodiments 1-12, wherein analyzing the epigenetic property comprises generating an epigenetic map showing a profile of sequence reads associated with or indicative of the epigenetic property, optionally sequence reads associated with or indicative of chromatin accessibility, along each of the one or more genomic regions or a subset thereof and/or
comprises, for each of a plurality of sites or portions along the length of the genomic region, generating one or more sequence reads indicative of an epigenetic readout, optionally chromatin accessibility, at said site or portion, wherein the quantity of said one or more sequence reads indicates a degree or level of said epigenetic property, optionally said chromatin accessibility, at said site or portion.

14. The method of embodiment 13, wherein said analyzing optionally further comprises determining an overall degree or level of said epigenetic readout, optionally determining an overall degree or level of accessibility, over the genomic region.

15. The method of any of embodiments 1-14, wherein analyzing the epigenetic property comprises determining, measuring or quantitating a value or level of chromatin accessibility across the one or more genomic regions.

16. The method of any of embodiments 1-14, wherein analyzing the epigenetic property comprises determining, measuring or quantitating a value or level associated with or indicative of the epigenetic property, optionally chromatin accessibility, across the one or more genomic regions or a subset thereof.

17. The method of embodiment 15 or embodiment 16, wherein the value or level is or comprises determining the fragments per kilobase per million of mapped reads (FPKM) value within each of the one or more genomic regions or a subset thereof.

18. The method of any of embodiments 15-17, wherein the value or level is or comprises totaling or summing the fragments per kilobase per million of mapped reads (FPKM) value within each of the one or more genomic regions or a subset thereof.

19. The method of any of embodiments 1-18, wherein step (a) and (b) are performed for a plurality of subjects having each been independently administered a second composition of cells comprising cells engineered with a recombinant receptor.

20. The method of any of embodiments 16-19, wherein, for each genomic region or subset thereof, preparing a display comprising the value or level of the sequence reads for each genomic locus mapped to the outcome of the cell therapy for each of the plurality of subjects.

21. The method of embodiment 20, wherein the display comprises a heat map, a scatter plot, a hierarchical clustering and/or a constellation plot.

22. The method of embodiment 20 or embodiment 21, wherein said identifying said one or more genomic regions comprises performing cluster analysis based on outcome of the cell therapy.

23. The method of embodiment 20 or embodiment 21, wherein said identifying said one or more genomic regions that indicate or correlate with an outcome of the cell therapy comprises determining if at least a majority of subjects with the same or similar outcome cluster together in the display.

24. The method of embodiment 23, wherein a genomic region is identified if at least 55%, 60%, 70%, 80%, 90%, 95% or more of the subjects with the same or similar outcome cluster together in the display.

25. The method of any of embodiments 1-24, wherein the whole genome of the cell is analyzed.

26. The method of any of embodiments 1-24, wherein a portion of the genome of the cell is analyzed.

27. The method of embodiment 26, wherein the portion of the genome comprises one or more genomic regions, optionally one or more genomic loci, associated with or indicative of or likely to be associated with or indicative of the phenotype, the activation state, the strength of an activation signal or the effector function of a cell.

28. The method of any of embodiments 1-27, wherein the outcome of the cell therapy is a response, a toxicity, immunogenicity or a phenotype or function of the cell therapy, a complete response, a partial response, progressive disease, a molecularly detectable disease, relapse, durability of response, outcome associated with or indicative of efficacy, or outcome associated with or indicative of toxicity.

29. The method of embodiment 28, wherein the response is a complete response, partial response, progressive disease or a molecularly detectable disease.

30. The method of embodiment 28, wherein the toxicity is cytokine release syndrome (CRS), severe CRS, grade 3 or higher CRS, neurotoxicity, severe neurotoxicity, grade 3 or higher neurotoxicity and/or a cerebral edema.

31. The method of embodiment 28 or embodiment 30, wherein the toxicity is a dose limiting toxicity (DLT).

32. The method of any of embodiments 1-31, wherein the epigenetic property of from or from about 2 to 50, 2 to 20, 2 to 10, 2 to 5, 5 to 50, 5 to 20, 5 to 10, 10 to 50, 10 to 20 or 20 to 50 genomic regions are analyzed.

33. The method of any of embodiments 1-32, wherein a panel comprising two or more of the genomic regions are identified.

34. The method of any of embodiments 1-33, wherein the first composition of cells and second composition of cells comprise primary cells selected or isolated from a subject.

35. The method of any of embodiments 1-34, wherein the cell is an immune cell.

36. The method of any of embodiments 1-35, wherein the immune cell is a T cell or an NK cell.

37. The method of any of embodiments 1-36, wherein the T cells is a CD4+ and/or CD8+ T cells.

38. The method of any of embodiments 1-37, wherein the second composition of cells is analyzed.

39. The method of any of embodiments 1-38, wherein the second composition of cells comprises a nucleic acid encoding the recombinant receptor.

40. The method of embodiment 39, wherein the nucleic acid molecule is contained in a viral vector.

41. The method of embodiment 40, wherein the viral vector is an adenovirus, lentivirus, retrovirus, herpesvirus or adeno-associated virus vector.

42. The method of any of embodiments 1-41, wherein the first composition of cells and/or second composition of cells is produced by culturing an input composition in the presence of one or more conditions or agents.

43. The method of any of embodiments 1-42, wherein the one or more genomic regions comprise genes involved in or likely to be involved in the activation state or effector state of the cell.

44. A method of assessing a cell composition for administration to a subject, comprising:
(a) analyzing an epigenetic profile of one or more genomic regions of a cell comprised in a cell composition comprising cells engineered with a recombinant receptor; and
(b) comparing the epigenetic profile for each genomic region, individually, to a reference profile, wherein the comparison indicates whether the population of cells is or is likely to exhibit or produce an outcome when administered to a subject.

45. The method of embodiment 44, wherein the outcome of the cell therapy is a response, a toxicity, immunogenicity or a phenotype or function of the cell therapy, a complete response, a partial response, progressive disease, a molecularly detectable disease, relapse, durability of response, outcome associated with or indicative of efficacy, or outcome associated with or indicative of toxicity.

46. The method of embodiment 45, wherein the response is a complete response or a partial response.

47. The method of any of embodiments 44-46, wherein if the comparison indicates that the cell composition is or is likely to exhibit the outcome, administering the cell composition to the subject.

48. The method of embodiment 47, wherein if the comparison indicates that the cell composition is not or is not likely to exhibit the outcome, either:
(i) administering a cell composition in which the cell composition is altered;
(ii) administering the cell composition in which the dose of cells is altered;
(iii) administering the cell composition in which the dosage regimen of cells administered to the subject is altered;
(iv) administering the cell composition in combination with one or more other therapeutic agents; or
(v) not administering the cell composition to the subject.

49. The method of embodiment 48, wherein, prior to administering an altered cell composition, repeating steps (a) and (b) on a cell comprised in the altered cell composition.

50. The method of embodiment 49, wherein altering the dosing regimen of cells comprises administering a second dose of cells to the subject subsequent to administering a first dose of cells to the subject.

51. The method of embodiment 50, wherein the subsequent dose of cells is administered at least 1 week, 2 weeks, 3 weeks, 4 weeks, 2 months, 3 months, 4 months, 5 months, 6 months, 9 months or 12 months after administering the first dose of cells.

52. The method of any of embodiments 44-51, wherein the one or more genomic regions are associated with or indicative of a response to the cell therapy.

53. The method of any of embodiments 44-52, wherein the reference profile comprises a threshold value for the epigenetic property for each of the one or more genomic regions or for the overall epigenetic property within the one or more genomic regions.

54. The method of embodiment 53, wherein the threshold value:
is a value or level of the epigenetic property, optionally chromatin accessibility, in the one or more genomic regions in a cell of a cell composition shown to exhibit the outcome when administered to a subject having the same or similar disease or condition; or
is an average, median or mean value or level of the epigenetic property, optionally chromatin accessibility, in the one or more genomic regions from a cell of each of a plurality of cell compositions, shown to exhibit the outcome when administered to the subject.

55. The method of any of embodiments 44-54, wherein the threshold value comprises is the value or level of the epigenetic property in a cell from a normal or healthy subject.

56. The method of any of embodiments 44-55, wherein the threshold value comprises the value or level of the epigenetic property in a cell that exhibits a naïve or a long-lived memory phenotype.

57. A method of assessing a cell culture, comprising:
(a) analyzing an epigenetic profile of one or more genomic regions of a cell comprised in an output cell composition, said output composition produced by culturing an input composition in the presence of one or more test agents or conditions; and
(b) comparing the epigenetic profile for each genomic region, individually, to a reference profile, wherein the comparison indicates whether the cell is or is likely to exhibit a predetermined phenotype or function.

58. The method of embodiment 57, wherein the predetermined phenotype or function indicates the effector function or activation state of the cell and/or indicates that the cells exhibit a naïve phenotype or a long-lived memory phenotype.

59. The method of embodiment 57 or embodiment 58, wherein the one or more test agents or conditions comprises presence or concentration of serum; time in culture; presence or amount of a stimulating agent; the type or extent of a stimulating agent; presence or amount of amino acids; temperature; the source or cell types of the input composition; the ratio or percentage of cell types in the input composition, optionally the CD4+/CD8+ cell ratio; the presence or amount of beads; cell density; static culture; rocking culture; perfusion; the type of viral vector; the vector copy number; the presence of a transduction adjuvant; cell density of the input composition in cryopreservation; the extent of expression of the recombinant receptor; or the presence of a compound to modulate cell phenotype.

60. The method of embodiment 58 or embodiment 59, wherein the one or more test agents or conditions comprises one or more compounds from a library of test compounds.

61. The method of any of embodiments 57-60, comprising if the comparison indicates that the cell composition is or is likely to have the phenotype or function, selecting the one or more test agent or condition for culturing the cells.

62. The method of any of embodiments 57-60, comprising if the comparison indicates that the cell composition is or is likely not to have the phenotype or function, repeating steps (a) and (b) with one or more further test agent or condition.

63. The method of any of embodiments 57-62, wherein the reference profile comprises a threshold value for the epigenetic property for each of the one or more genomic regions or for the overall epigenetic property within the one or more genomic regions.

64. The method of embodiment 63, wherein the threshold value:
is a value or level of the epigenetic property, optionally chromatin accessibility, in the one or more genomic regions in a cell of a reference cell composition shown to exhibit the phenotype or function; or
is an average, median or mean value or level of the epigenetic property, optionally chromatin accessibility, in the one or more genomic regions from a cell of each of a plurality of reference cell compositions, shown to exhibit the phenotype or function.

65. The method of embodiment 64, wherein the reference cell composition has a phenotype indicative of a naïve T cell, a long-lived memory T cell, a central memory T cell (Tcm) or a stem-like memory T cell (Tcsm).

66. The method of any of embodiments 44-65, wherein analyzing the epigenetic property comprises determining, measuring or quantitating a value or level of chromatin accessibility across the one or more genomic regions.

67. The method of any of embodiments 44-66, wherein analyzing the epigenetic property comprises determining, measuring or quantitating a value or level of the sequence reads associated with or indicative of the epigenetic property, optionally chromatin accessibility, in the one or more genomic regions or a subset thereof.

68. The method of embodiment 66 or embodiment 67, wherein determining, measuring or quantitating a value or level comprises determining the fragments per kilobase per million of mapped reads (FPKM) value within each of the one or more genomic regions or a subset thereof.

69. The method of any of embodiments 66-68, wherein determining, measuring or quantitating a value or level comprises totaling or summing the fragments per kilobase per million of mapped reads (FPKM) value within each of the one or more genomic regions or a subset thereof.

70. The method of any of embodiments 1-69, wherein the one or more genomic regions comprises a panel comprising at least 2 to 50, 2 to 20, 2 to 10, 2 to 5, 5 to 50, 5 to 20, 5 to 10, 10 to 50, 10 to 20 or 20 to 50 genomic regions.

71. The method of any of embodiments 27-70, wherein the one or more genomic regions comprise one or more genomic loci associated with or indicative of the effector-like function or activation state of the cell.

72. The method of any of embodiments 27-71, wherein the one or more genomic regions comprises a genetic locus selected from the group consisting of Nr4a1, Cblb, Irf4, Tbx21, Eomes, Ifng, Il2ra, Il2, Csf2, Gzmb, Tnfsf10, Gata3, Mir155, Sox21, Ctla4, Lag3, and Pdcd1.

73. The method of any of embodiments 27-72, wherein the one or more genomic regions comprises a genomic locus selected from the group consisting of Ctla4, Il2ra, Il2, Ifng and Gzmb.

74. The method of any of embodiments 27-73, wherein the genomic region comprises a genomic locus or gene.

75. The method of any of embodiments 27-74, wherein the genomic region comprises an open reading frame of a gene.

76. The method of any of embodiments 27-75, wherein the epigenetic property is selected from among chromatin accessibility, nucleosome occupancy, histone modification, spatial chromosomal conformation, transcription factor occupancy and DNA methylation.

77. The method of any of embodiments 27-76, wherein the epigenetic property is chromatin accessibility.

78. The method of embodiment 77, wherein chromatin accessibility is determined by Assay for Transposase Accessible Chromatin with high-throughput sequencing (ATAC-seq) or chromatin immunoprecipitation coupled to high-throughput sequencing (ChIP-seq).

79. The method of embodiment 77 or embodiment 78, wherein chromatin accessibility is determined by ATAC-seq.

80. The method of any of embodiments 1-79, wherein the cell is obtained from a sample from a subject.

81. The method of embodiment 80, wherein the cell is an immune cell, optionally a T cell, optionally a CD4+ and/or CD8+ T cell.

82. The method of any of embodiments 1-81, wherein:
the recombinant receptor binds to, recognizes or targets an antigen associated with the disease or condition; and/or
the recombinant receptor is a T cell receptor or a functional non-T cell receptor; and/or
the recombinant receptor is a chimeric antigen receptor (CAR).

83. The method of embodiment 82, wherein:
the CAR comprises an extracellular antigen-recognition domain that specifically binds to the antigen and an intracellular signaling domain comprising an ITAM, wherein optionally, the intracellular signaling domain comprises an intracellular domain of a CD3-zeta (CD3ζ) chain; and/or wherein the CAR further comprises a costimulatory signaling region, which optionally comprises a signaling domain of CD28 or 4-1BB.

84. A cell composition, comprising a plurality of cells, wherein the level or value of an epigenetic property for one or more genes in a panel is above or below a threshold value in at least 50% of the cells in the composition.

85. The cell composition of embodiment 84, wherein the level or value is above or below the threshold value in at least 60%, 70%, 75%, 80%, 85%, 90%, 95% or more of the cells in the composition.

86. The cell composition of embodiment 84 or embodiment 85, wherein the threshold value:
is a value or level of the epigenetic property, optionally chromatin accessibility, in the one or more genomic regions in a cell of a reference cell composition shown to exhibit the phenotype or function; or
is an average, median or mean value or level of the epigenetic property, optionally chromatin accessibility, in the one or more genomic regions from a cell of each of a plurality of reference cell compositions, shown to exhibit the phenotype or function.

87. The cell composition of any of embodiments 84-86, wherein the reference cell composition has a phenotype indicative of a naïve T cell, a long-lived memory T cell, a central memory T cell (Tcm) or a stem-like memory T cell (Tcsm).

88. The composition of any of embodiments 84-87, wherein the panel comprises from or from about 2 to 50, 2 to 20, 2 to 10, 2 to 5, 5 to 50, 5 to 20, 5 to 10, 10 to 50, 10 to 20 or 20 to 50 genomic regions.

89. A method of identifying one or more genomic region(s) associated with an outcome of treatment with a cell therapy, the method comprising:

(a) analyzing or determining an epigenetic property of one or more genomic regions of a cell or a population of cells, said cell or population comprised in (i) a first composition of cells to be genetically engineered with a recombinant receptor to produce a second composition comprising the recombinant receptor, or (ii) a second composition of cells comprising the recombinant receptor; and (b) identifying one or more of the one or more genomic regions, of which the epigenetic property, overall across the one or more genomic regions, predicts, indicates or correlates with an outcome of a cell therapy, said cell therapy comprising administering to a subject or a group of subjects the second composition of cells comprising the recombinant receptor.

90. The method of embodiment 89, wherein the outcome is an outcome associated with or indicative of efficacy, a response, persistence, a toxicity, or immunogenicity.

91. The method of embodiment 90, wherein the outcome is a response, and the response is a complete response, a partial response, progressive disease, a molecularly detectable disease, relapse, or durability of response.

92. The method of 90, wherein the outcome is a toxicity and the toxicity is cytokine release syndrome (CRS), severe CRS, grade 3 or higher CRS, neurotoxicity, severe neurotoxicity, grade 3 or higher neurotoxicity and/or a cerebral edema.

93. The method of embodiment 90 or embodiment 92, wherein the toxicity is a dose limiting toxicity (DLT).

94. The method of any of embodiments 89-93, wherein:
the first composition is enriched for CD4+ primary human T cells and/or CD8+ primary human T cells; and/or
the second composition is enriched for CD4+ primary human T cells and/or CD8+ primary human T cells.

95. A method for determining one or more properties or features of a cell composition, the method comprising analyzing or determining an epigenetic property of one or more genomic regions of a T cell composition, said T cell composition enriched for CD4+ primary human T cells and/or CD8+ primary human T cells.

96. The method of embodiment 95, wherein the cell composition is (i) a first T cell composition of cells to be genetically engineered with a recombinant receptor to produce a second T cell composition comprising the recombinant receptor, or (ii) a second T cell composition of cells comprising the recombinant receptor.

97. The method of any of embodiments 84-96, wherein:
the cell composition comprises greater than or greater than about 70%, greater than or greater than about 75%, greater than or greater than about 80%, greater than or greater than about 85%, greater than or greater than about 90%, greater than or greater than about 95% or greater than or greater than about 98% CD4+ and/or CD8+ primary human T cells; and/or
the cell composition consists essentially of CD4+ and/or CD8+ primary human T cells.

98. The method of embodiment 95-97, further comprising comparing the epigenetic property for each of the one or more genomic region, individually, to the corresponding epigenetic property of cells from a different cell composition and/or to a reference profile, optionally a reference profile known to indicate or correlate with an attribute or feature of a cell composition.

99. The method of embodiment 98, wherein the comparison indicates or correlates with the state, phenotype or function of the cells within the cell composition, optionally an activation, effector or memory state; consistency or uniformity of the cells within the cell composition; whether the composition of cells is or is likely to exhibit or produce an outcome when administered to a subject or a group of subjects; the location, abundance or frequency of integration of exogenous nucleic acids; clonality of cells within the cell composition; and/or the proportion or frequency of engineered cells in the cell composition.

100. A method for determining or identifying an epigenetic property associated with an attribute or feature of a cell composition, the method comprising:

(a) determining or measuring a level or degree or relative level or degree of an epigenetic property of one or more genomic regions for a cell or a population of cells comprised in a first cell composition;

(b) determining or measuring a level or degree or relative level or degree of said epigenetic property of the one or more genomic regions for a cell or a population of cells comprised in a second cell composition; and (c) comparing the level or degree in (a) and the level or degree in (b), wherein a difference, optionally a significant difference, in the level or degree of the epigenetic property of the one or more of the genomic regions identifies or determines the presence of an epigenetic property indicative of or that correlates with an attribute or feature present in cells of one but not the other of the first and second composition.

101. The method of embodiment 100, wherein:
one of the first composition and second composition comprises cells to be genetically engineered with a recombinant receptor and the other of the first composition and second composition comprises the cells engineered to express the recombinant receptor;
the first composition and second composition comprise primary cells from different donors, optionally donors that differ based on disease state, severity of disease, or type of disease;
the first composition and second composition comprise cells at different stages or steps of a manufacturing process for engineering cells;
one of the first composition and second composition comprises cells contacted with an agent to modulate the activity, phenotype or function of the cells and the other of the first and second composition comprises similar cells not so contacted; or
one of the first composition and second composition comprises a sample of a cell composition associated with an outcome that occurs or has occurred with the one but not the other of the first and second composition following administration to a subject.

102. The method of embodiment 101, wherein the agent is a polypeptide or protein, a peptide, an antibody, a nucleic acid, a viral vector or viral preparation, or a small molecule compound.

103. The method of embodiment 101 or embodiment 102, wherein the agent is a stimulatory reagent, optionally anti-CD3/anti-CD28; an immunomodulatory agent, an anti-idiotype antibody or antigen-binding fragment thereof specific to the CAR, an immune checkpoint inhibitor, a modulator of a metabolic pathway, an adenosine receptor antagonist, a kinase inhibitor, an anti-TGFβ antibody or an anti-TGFβR antibody or a cytokine.

104. The method of any of embodiments 100-103, wherein the attribute or feature of the first composition is indicative of a state, phenotype of function, optionally an activation, effector or memory state, phenotype or function; the location, abundance or frequency of integration of exogenous nucleic acids; clonality of cells within the cell composition; the proportion or frequency of engineered cells in the cell composition; and/or whether the composition of cells is or is likely to exhibit or produce an outcome when administered to a subject or a group of subjects.

105. The method of embodiment 100 or embodiment 104, wherein the outcome is an outcome associated with or indicative of efficacy, a response, persistence, a toxicity, or immunogenicity.

106. The method of embodiment 105, wherein the outcome is a response, and the response is a complete response, a partial response, progressive disease, a molecularly detectable disease, relapse, or durability of response.

107. The method of 106, wherein the outcome is a toxicity and the toxicity is cytokine release syndrome (CRS), severe CRS, grade 3 or higher CRS, neurotoxicity, severe neurotoxicity, grade 3 or higher neurotoxicity and/or a cerebral edema.

108. The method of embodiment 106 or embodiment 107, wherein the toxicity is a dose limiting toxicity (DLT).

109. The method of any of embodiments 1100-108 that is repeated a plurality of times.

110. The method of embodiment 109, wherein an epigenetic property is identified or determined that is present in a majority of one but not the other of the first and second composition.

111. A method of assessing an attribute or feature of a cell composition, comprising:
（a) analyzing an epigenetic property of one or more genomic regions of a cell or population of cells comprised in a cell composition comprising cells engineered with a recombinant receptor and/or cells to be genetically engineered with a recombinant receptor; and
(b) comparing the epigenetic property of the one or more genomic region, individually, to a reference profile, wherein the comparison indicates whether the composition of cells is or is likely to exhibit the attribute or feature.

112. The method of embodiment 111, wherein the attribute or feature is indicative of a state, phenotype of function, optionally an activation, effector or memory state, phenotype or function; the location, abundance or frequency of integration of exogenous nucleic acids; clonality of cells within the cell composition; the proportion or frequency of engineered cells in the cell composition; and/or whether the composition of cells is or is likely to exhibit or produce an outcome when administered to a subject or a group of subjects.

113. The method of embodiment 113 or embodiment 112, wherein the attribute or feature is whether the composition of cells is or is likely to exhibit or produce an outcome when administered to a subject or a group of subjects and the method is for assessing the cell composition for administration to a subject.

114. The method of embodiment 112 or embodiment 113, wherein the outcome is an outcome associated with or indicative of efficacy, a response, persistence, a toxicity, or immunogenicity.

115. The method of embodiment 114, wherein the outcome is a response, and the response is a complete response, a partial response, progressive disease, a molecularly detectable disease, relapse, or durability of response.

116. The method of 115, wherein the outcome is a toxicity and the toxicity is cytokine release syndrome (CRS), severe CRS, grade 3 or higher CRS, neurotoxicity, severe neurotoxicity, grade 3 or higher neurotoxicity and/or a cerebral edema.

117. The method of embodiment 115 or embodiment 116, wherein the toxicity is a dose limiting toxicity (DLT).

118. The method of any of embodiments 111-117, wherein if the comparison indicates that the cell composition is or is likely to exhibit a desired outcome, administering the cell composition to the subject.

119. The method of any of embodiments 111-118, wherein if the comparison indicates that the cell composition is not or is not likely to exhibit a desired outcome, either:
(i) administering a cell composition in which the cell composition is altered;
(ii) administering the cell composition in which the dose of cells is altered;
(iii) administering the cell composition in which the dosage regimen of cells administered to the subject is altered;
(iv) administering the cell composition in combination with one or more other therapeutic agents; or
(v) not administering the cell composition to the subject.

120. The method of embodiment 118 or embodiment 119, wherein the desired outcome is a complete response, partial response, or durable response and/or is a grade 3 or lower neurotoxicty or grade 1 or grade 2 neurotoxicty, is a grade 3 or lower CRS, or is grade 1 or grade 2 CRS, or does not include any grade of neurotoxicity or any grade of CRS.

121. The method of embodiment 119 or embodiment 120, wherein the cell composition is altered by altering one or more agents or conditions in one or more steps for engineering the cells in the cell composition.

122. The method of embodiment 121, wherein the one or more agents or conditions is selected from presence or concentration of serum; time in culture; presence or amount of a stimulating agent; the type or extent of a stimulating agent; presence or amount of amino acids; temperature; the source or cell types of the cell composition; the ratio or percentage of cell types in the cell composition, optionally the CD4+/CD8+ cell ratio; the presence or amount of beads; cell density; static culture; rocking culture; perfusion; the type of viral vector; the vector copy number; the presence of a transduction adjuvant; cell density of the cell composition in cryopreservation; the extent of expression of the recombinant receptor; or the presence of a compound to modulate cell phenotype.

123. The method of embodiment 121 or embodiment 122, wherein, prior to administering an altered cell composition, repeating steps (a) and (b) on a cell comprised in the altered cell composition.

124. The method of embodiment 123, wherein altering the dosing regimen of cells comprises administering a second dose of cells to the subject subsequent to administering a first dose of cells to the subject.

125. The method of embodiment 124, wherein the subsequent dose of cells is administered at least 1 week, 2 weeks, 3 weeks, 4 weeks, 2 months, 3 months, 4 months, 5 months, 6 months, 9 months or 12 months after administering the first dose of cells.

126. The method of any of embodiments 111-125, wherein the reference profile comprises a threshold value for the epigenetic property for each of the one or more genomic regions or for the overall epigenetic property within the one or more genomic regions.

127. The method of embodiment 126, wherein the threshold value:
is a value or level associated with or indicative of the epigenetic property, optionally chromatin accessibility, in the one or more genomic regions in a cell of a cell composition shown to exhibit the desired outcome when administered to a subject having the same or similar disease or condition;

is an average, median or mean value or level, or is within a standard deviation of the average, median or mean value or level, associated with or indicative of the epigenetic property, optionally chromatin accessibility, in the one or more genomic regions from a cell of each of a plurality of cell compositions that had been individually administered to a group of subjects, wherein each of the subjects of the group went on to exhibit the desired outcome following administration; or is the value or level associated with or indicative of the epigenetic property in a similar cell composition from a normal or healthy subject.

128. The method of any of embodiments 111-125, wherein:

the comparison comprises differential accessibility analysis; and/or the reference profile comprises a reference epigenetic map comprising peaks of sequence reads within the one or more genomic regions.

129. The method of embodiment 128, wherein:

the reference epigenetic map is determined from accessibility analysis, optionally chromatin accessibility, of a cell composition shown to exhibit the desired outcome following administration of the cell or cell composition to a subject having the same or similar disease or condition;

the reference epigenetic map is a determined from common peaks of sequence reads from accessibility analysis, optionally chromatin accessibility, among a plurality of cell compositions that had been individually administered to a group of subjects, wherein each of the subjects of the group went on to exhibit the desired outcome following administration; or the reference epigenetic map is determined from accessibility analysis, optionally chromatin accessibility of a similar cell composition from a normal or healthy subject.

130. A method of assessing a cell composition, comprising:

(a) analyzing an epigenetic property of one or more genomic regions of a cell comprised in an output cell composition, said output composition produced by culturing an input composition in the presence of one or more test agents or conditions, and/or of a cell comprised in the input composition; and (b) comparing the epigenetic property of the one or more genomic region, individually, to a reference profile, wherein the comparison indicates whether the cell is or is likely to exhibit a predetermined feature or attribute.

131. The method of embodiment 130, wherein the predetermined feature or attribute is the state, phenotype or function of cells within the composition, the consistency or uniformity of the cells within the cell composition, the location, abundance or frequency of integration of exogenous nucleic acids, clonality of cells within the cell composition and/or the proportion or frequency of engineered cells in the cell composition.

132. The method of embodiment 131, wherein the predetermined phenotype or attribute is a state, phenotype or function that indicates the effector function or activation state of the cell and/or indicates that the cells exhibit a naïve phenotype or a long-lived memory phenotype.

133. The method of embodiment 131 or embodiment 132, wherein the one or more test agents or conditions comprises presence or concentration of serum; time in culture; presence or amount of a stimulating agent; the type or extent of a stimulating agent; presence or amount of amino acids; temperature; the source or cell types of the input composition; the ratio or percentage of cell types in the input composition, optionally the CD4+/CD8+ cell ratio; the presence or amount of beads; cell density; static culture; rocking culture; perfusion; the type of viral vector; the vector copy number; the presence of a transduction adjuvant; cell density of the input composition in cryopreservation; the extent of expression of the recombinant receptor; or the presence of a compound to modulate cell phenotype.

134. The method of any of embodiments 131-133, wherein the one or more test agents or conditions comprises one or more compounds from a library of test compounds.

135. The method of any of embodiments 131-134, comprising if the comparison indicates that the cell composition is or is likely to have a desired feature or attribute, selecting the one or more test agent or condition for culturing the cells and/or selecting the cell composition for administration to a subject.

136. The method of any of embodiments 131-134, comprising if the comparison indicates that the cell composition is or is likely not to have a desired feature or attribute, repeating steps (a) and (b) with one or more further test agent or condition.

137. The method of any of embodiments 131-136, wherein the reference profile comprises a threshold value for the epigenetic property for each of the one or more genomic regions or for the overall epigenetic property within the one or more genomic regions.

138. The method of embodiment 137, wherein the threshold value:

is a value or level associated with or indicative of the epigenetic property, optionally chromatin accessibility, in the one or more genomic regions in a cell of a cell composition known to exhibit the desired attribute or feature;

is an average, median or mean value or level, or is within a standard deviation of the average, median or mean value or level, associated with or indicative of the epigenetic property, optionally chromatin accessibility, in the one or more genomic regions from a cell of each of a plurality of cell compositions known to exhibit the desired attribute or feature.

139. The method of any of embodiments 131-136, wherein:

the comparison comprises differential accessibility analysis; and/or the reference profile comprises a reference epigenetic map comprising peaks of sequence reads within the one or more genomic regions.

140. The method of embodiment 139, wherein:

the reference epigenetic map is determined from accessibility analysis, optionally chromatin accessibility, of a cell composition known to exhibit the desired attribute or feature;

the reference epigenetic map is a determined from common peaks of sequence reads from accessibility analysis, optionally chromatin accessibility, among a plurality of cell compositions known to exhibit the desired attribute or feature.

141. The method of any of embodiments 131-140, wherein the desired outcome or feature is a phenotype or function indicative of a naïve T cell, a long-lived memory T cell, a central memory T cell (Tcm) or a stem-like memory T cell (Tcsm).

142. The method of any of embodiments 89-141, wherein the genomic region comprises a genomic locus or gene.

143. The method of any of embodiments 89-142, a wherein the genomic region comprises a coding region, an open reading frame of a gene, a non-coding region, an intergenic region or a regulatory element.

144. The method of any of embodiments 89-143, wherein the genomic region comprises an open reading frame of a gene.

145. The method of any of embodiments 89-143, wherein the genomic region comprises an intergenic region or a regulatory element.

146. The method of any of embodiments 89-143 and 145, wherein the genomic region comprises an intron, an exon, a cis-regulatory element, a promoter, an enhancer, an upstream activating sequence (UAS), a 3' untranslated region (UTR), a 5' UTR, a non-coding RNA producing region, a non-coding RNA (ncRNA) gene, a miRNA gene, an siRNA gene, a piRNA gene, a snoRNA gene, a lncRNA gene, a ribosomal RNA (rRNA) gene, a small RNA binding site, a non-coding RNA binding site, a pseudogene, a transcription termination site (TTS), a repeat, a telomeric region, accessible chromatin region, non-accessible chromatin region, open chromatin region and/or heterochromatin region.

147. The method of any of embodiments 89-146, wherein the epigenetic property is selected from among chromatin accessibility, nucleosome occupancy, histone modification, spatial chromosomal conformation, transcription factor occupancy and DNA methylation.

148. The method of any of embodiments 89-147, wherein the epigenetic property is chromatin accessibility.

149. The method of any of embodiments 89-148, wherein:
the epigenetic property comprises chromatin accessibility, a level or degree of chromatin accessibility, a relative level or degree of chromatin accessibility, and/or
the epigenetic property comprises a degree or level of, relative degree or level of, or profile or map of, chromatin accessibility of the genomic region.

150. The method of any of embodiments 147-149, wherein chromatin accessibility is determined by Assay for Transposase Accessible Chromatin with high-throughput sequencing (ATAC-seq) or chromatin immunoprecipitation coupled to high-throughput sequencing (ChIP-seq).

151. The method of any of embodiments 147-150, wherein chromatin accessibility is determined by ATAC-seq.

152. The method of any of embodiments 147-151, wherein the assessing the epigenetic property comprises:
(1) isolating chromatin from the cells or the population of cells,
(2) treating the chromatin with an insertional enzyme complex to generate tagged fragments of genomic DNA,
(3) sequencing all or a portion of the tagged fragments to produce a plurality of sequence reads;
(4) aligning, filtering and mapping the sequence reads to genomic regions of a genome; and
(5) determining or identifying peaks of sequence reads in a plurality of genomic regions for each cell or population of cells.

153. The method of embodiment 152, wherein the analyzing or assessing the epigenetic property further comprises comparing peaks of sequence reads and, optionally identifying peaks of sequence reads that are different between samples from two or more cells or cell compositions.

154. The method of embodiment 152 or embodiment 153, wherein peaks of sequence reads comprise sequence reads having a peak signal, level or value that is enriched, is above background, and/or is higher compared to sequence reads of a surrounding regions.

155. The method of any of embodiments 152-154, wherein the analyzing or assessing the epigenetic property further comprises performing motif analysis, transcription factor occupancy analysis and/or biological pathway analysis of genomic regions identified as containing peaks of sequence reads that are different between samples from two or more cell populations.

156. The method of any of embodiments 152-155, wherein the analyzing or assessing the epigenetic property further comprises determining positions of nucleosomes within genomic regions containing peaks of sequence reads.

157. The method of any of embodiments 89-156, wherein analyzing the epigenetic property comprises generating an epigenetic map showing a profile of sequence reads associated with or indicative of the epigenetic property, optionally sequence reads associated with or indicative of chromatin accessibility, along each of the one or more genomic regions or a subset thereof and/or
comprises, for each of a plurality of sites or portions along the length of the genomic region, generating one or more sequence reads indicative of an epigenetic readout, optionally chromatin accessibility, at said site or portion, wherein the quantity of said one or more sequence reads indicates a degree or level of said epigenetic property, optionally said chromatin accessibility, at said site or portion.

158. The method of embodiment 157, wherein said analyzing optionally further comprises determining an overall degree or level of said epigenetic property, optionally determining an overall degree or level of accessibility, over the genomic region.

159. The method of any of embodiments 89-158, wherein analyzing the epigenetic property comprises determining, measuring or quantitating a value or level of chromatin accessibility across the one or more genomic regions.

160. The method of any of embodiments 89-159, wherein analyzing the epigenetic property comprises determining, measuring or quantitating a value or level associated with or indicative of the epigenetic property, optionally chromatin accessibility, across the one or more genomic regions or a subset thereof.

161. The method of embodiment 127, 138, 159 or embodiment 160, wherein the value or level is or comprises determining the fragments per kilobase per million of mapped reads (FPKM) value within each of the one or more genomic regions or a subset thereof.

162. The method of any of embodiments 127, 138 and 159-161, wherein the value or level is or comprises totaling or summing the fragments per kilobase per million of mapped reads (FPKM) value within each of the one or more genomic regions or a subset thereof.

163. The method of any of embodiments 89-162, wherein the analysis comprises steps for removal of mitochondrial reads and/or additional contaminating sequences based on sequence identity, quality, mapping location, or other sequencing properties of said reads.

164. The method of any of embodiments 89-163, wherein the analysis comprises steps for removal of duplicate reads to improve quantitative accuracy.

165. The method of any of embodiments 89-164, wherein the analysis comprises steps for separation of sequence reads into subsets representing a specific epigenetic property, optionally chromatin accessibility or chromatin occupancy, wherein the size of the sequenced fragment is used to determine the degree or level to which it represents said epigenetic property.

166. The method of any of embodiments 89-94 and 142-165, wherein the step (a) and (b) are performed on cell compositions from a plurality of subjects having each been independently administered a second composition of cells comprising cells engineered with a recombinant receptor.

167. The method of any of embodiments 89-94 and 142-166, wherein, for each genomic region or subset thereof, preparing a display comprising the value or level of the sequence reads for each genomic locus mapped to the outcome of the cell therapy for each of the plurality of subjects.

168. The method of embodiment 167, wherein the display comprises a heat map, a scatter plot, a hierarchical clustering and/or a constellation plot.

169. The method of embodiment any of embodiments 89-169 and 142-169, wherein said identifying said one or more genomic regions comprises performing cluster analysis based on outcome of the cell therapy.

170. The method of embodiment 89-169 and 142-169, wherein said identifying said one or more genomic regions that indicate or correlate with an outcome of the cell therapy comprises determining if at least a majority of subjects with the same or similar outcome cluster together in the display.

171. The method of embodiment 170, wherein a genomic region is identified if at least 55%, 60%, 70%, 80%, 90%, 95% or more of the subjects with the same or similar outcome cluster together in the display.

172. The method of any of embodiments 89-171, wherein the whole genome of the cell is analyzed.

173. The method of any of embodiments 89-172, wherein a portion of the genome of the cell is analyzed.

174. The method of embodiment 173, wherein the portion of the genome comprises one or more genomic regions, optionally one or more genomic loci, associated with or indicative of or likely to be associated with or indicative of the phenotype, the activation state, the strength of an activation signal or the effector function of a cell.

175. The method of any of embodiments 89-174, wherein said analyzing further comprises performing principle component analysis (PCA), biological pathway analysis, gene ontology (GO) analysis and/or motif analysis.

176. The method of embodiment 175, wherein the analysis comprises biological pathway analysis and/or gene subset analysis of one or more genomic regions associated with a T cell memory phenotype, T cell activation state, effector function, cytokine response, trafficking, persistence or exhaustion.

177. The method of any of embodiments 174-176, wherein the one or more genomic regions comprise one or more genomic loci associated with or indicative of the effector-like function or activation state of the cell.

178. The method of any of any of embodiments 174-177, wherein the one or more genomic regions comprises a genetic locus selected from the group consisting of Nr4a1, Cblb, Irf4, Tbx21, Eomes, Ifng, Il2ra, Il2, Csf2, Gzmb, Tnfsf10, Gata3, Mir155, Sox21, Ctla4, Lag3, and Pdcd1.

179. The method of any of embodiments 174-178, wherein the one or more genomic regions comprises a genomic locus selected from the group consisting of Ctla4, Il2ra, Il2, Ifng and Gzmb.

180. The method of any of embodiments 89-180, wherein:
the epigenetic property of from or from about 2 to 50, 2 to 20, 2 to 10, 2 to 5, 5 to 50, 5 to 20, 5 to 10, 10 to 50, 10 to 20 or 20 to 50 genomic regions are analyzed; or
the epigenetic property of at least 2, 3, 5, 6, 7, 8, 9, 10, 15, 20, 30, 40, 50, 60, 70, 80. 90. 100, 200, 300, 400, 500 or more genomic regions are analyzed; or
the epigenetic property of only one genomic region is analyzed.

181. The method of any of embodiments 89-180, wherein a panel comprising two or more of the genomic regions are identified.

182. A method of assessing transgene integration, the method comprising: determining an epigenetic property of one or more genomic regions comprising a nucleic acid sequence of a transgene, in a cell or a cell composition genetically engineered with a recombinant receptor.

183. The method of embodiment 182, wherein the genetic engineering is carried out by introduction, into one or more cells of a cell composition, of a nucleic acid encoding the recombinant receptor.

184. The method of embodiment 183, wherein the introduction is by transduction with a viral vector comprising the nucleic acid.

185. The method of any of embodiments 182-184, wherein the epigenetic property is chromatin accessibility.

186. The method of any of embodiments 182-185, wherein:
the epigenetic property comprises chromatin accessibility, a level or degree of chromatin accessibility, a relative level or degree of chromatin accessibility, and/or
the epigenetic property comprises a degree or level of, relative degree or level of, or profile or map of, chromatin accessibility of the genomic region.

187. The method of any of embodiments 182-186, wherein chromatin accessibility is determined by Assay for Transposase Accessible Chromatin with high-throughput sequencing (ATAC-seq) or chromatin immunoprecipitation coupled to high-throughput sequencing (ChIP-seq).

188. The method of any of embodiments 182-187, wherein chromatin accessibility is determined by ATAC-seq.

189. The method of any of embodiments 188, wherein the assessing the epigenetic property comprises:
(1) isolating chromatin from the cells or the population of cells,
(2) treating the chromatin with an insertional enzyme complex to generate tagged fragments of genomic DNA,
(3) sequencing all or a portion of the tagged fragments to produce a plurality of sequence reads;
(4) aligning, filtering and mapping the sequence reads to genomic regions of a genome; and
(5) determining or identifying peaks of sequence reads in a plurality of genomic regions for each cell or population of cells.

190. The method of embodiment 189, wherein the analyzing or assessing the epigenetic property further comprises determining the peaks of sequence reads that maps to or is corresponds to the nucleic acid sequence of the transgene 191. The method of any of embodiments 182-190, wherein peaks of sequence reads comprise sequence reads having a peak signal, level or value that is enriched, is above background, and/or is higher compared to sequence reads of a surrounding regions.

192. The method of any of embodiments 182-191, wherein analyzing the epigenetic property comprises generating an epigenetic map showing a profile of sequence reads associated with or indicative of the epigenetic property, optionally sequence reads associated with or indicative of chromatin accessibility, of the genomic region comprising the nucleic acid sequence of the transgene and/or comprises, for the genomic region comprising the nucleic acid sequence of the transgene along the length of the genomic region, generating one or more sequence reads indicative of an epigenetic readout, optionally chromatin accessibility, at said region, wherein the quantity of said one or more sequence reads indicates a degree or level of said epigenetic property, optionally said chromatin accessibility, at said region.

193. The method of any of embodiments 182-192, wherein determining the epigenetic property comprises determining, measuring or quantitating a value or level of chromatin accessibility across the genomic region comprising the nucleic acid sequence of the transgene.

194. The method of any of embodiments 182-193, wherein determining the epigenetic property comprises determining, measuring or quantitating a value or level associated with or indicative of the epigenetic property, optionally chromatin accessibility, across the genomic region comprising the nucleic acid sequence of the transgene.

195. The method of any of embodiments 89-194, wherein the cell composition, optionally the first composition of cells and/or second composition of cells, comprise primary cells obtained from a sample from a subject and/or selected or isolated from a subject.

196. The method of any of embodiments 89-195, wherein the cell is an immune cell.

197. The method of any of embodiments 89-196, wherein the immune cell is a T cell or an NK cell.

198. The method of any of embodiments 89-197, wherein the T cells is a CD4+ and/or CD8+ T cells.

199. The method of any of embodiments 89-198, wherein:
the recombinant receptor binds to, recognizes or targets an antigen associated with the disease or condition; and/or
the recombinant receptor is a T cell receptor or a functional non-T cell receptor; and/or
the recombinant receptor is a chimeric antigen receptor (CAR).

200. The method of embodiment 199, wherein:
the CAR comprises an extracellular antigen-recognition domain that specifically binds to the antigen and an intracellular signaling domain comprising an ITAM, wherein optionally, the intracellular signaling domain comprises an intracellular domain of a CD3-zeta (CD3ζ) chain; and/or wherein the CAR further comprises a costimulatory signaling region, which optionally comprises a signaling domain of CD28 or 4-1BB.

IX. Examples

The following examples are included for illustrative purposes only and are not intended to limit the scope of the invention.

Example 1: Sample Preparation and Analysis of CAR T Cell Chromatin Accessibility by ATAC-Seq Compositions of CD4+/CD8+ T cells genetically engineered with a chimeric antigen receptor were assessed for chromatin accessibility using assay for transposase-accessible chromatin using sequencing (ATAC-Seq).

CD4+ and/or CD8+ T cells were isolated by immunoaffinity-based enrichment from leukapheresis of human Peripheral Blood Mononuclear Cells (PBMC). The isolated CD4+/CD8+ T cells were activated and transduced with a viral vector encoding an anti-CD19 CAR. The viral vector construct further encoded a truncated EGFR (EGFRt), which served as a surrogate marker for CAR expression; the EGFRt-coding region was separated from the CAR sequence by a T2A skip sequence. After transduction, cells were expanded in culture and frozen by cryopreservation. A total of 43 cryopreserved engineered cell compositions (CDP) from 19 subjects were prepared. CD4+/CD8+ cell compositions matched to 18 of the subjects, but which were not subjected to the genetic engineering, also were cryopreserved (CMAT) and assessed. In some cases, CMAT samples were separated by phenotype as naïve T cells ($T_N$), central memory T cells ($T_{CM}$), effector and effector memory T cells ($T_{E+EM}$) or effector memory RA ($T_{EMRA}$) for analysis. To generate libraries for ATAC-Seq analysis, cells were thawed, washed and lysed. DNA was then fragmented and tagged ("tagmented") using an enzyme (Tn5 transposase) which mediates both the fragmentation of double-stranded DNA and ligates synthetic oligonucleotides to the DNA fragments. The samples were then cleaned using a column followed by five cycles of PCR amplification and column purification. qPCR amplification was performed on samples and normal amplification was observed on all samples, indicative of successfully tagmented DNA. Successful library generation was qualitatively determined based on nucleosome banding. Agilent D1000 electrophoresis profiles were run on size-selected DNA for library size distribution which was used as a correction factor for quantification. Size selection removed residual primers and primer-dimers that may interfere with sequencing. qPCR dilutions were then made and libraries were pooled for sequencing. After sequencing, the DNA was aligned to a reference genome (Langmead et al. Genome Biol. (2009) 10:R25). Sequence data were analyzed for quality using various sequencing metrics, including metrics for total mapped reads, % alignment to genome, non-redundant fractions (redundancy), mitochondrial DNA contamination, effective sequence depth, as well as genome-wide accessibility peaks and fragments of reads in peaks (FRiP). It was observed that on average across libraries generated using the methods described above, >97% of reads aligned to the reference genome.

Additional processing steps to ensure quality of the data was performed including filtering out reads that failed quality checks, removing duplicates, and fixing read mates. Nucleosome positioning, transposon insertion sites, and transcription factor occupancy were identified and the data was visualized using a genome browser (U.S. Patent Application Publication Number US 20160060691).

Peak calling was performed to identify sequence reads with accessible chromatin. To quantify chromatin accessibility, in some studies Fragments Per Kilobase per Million fragments mapped (FPKM) was determined within each gene body and in others peak accessibility was calculated based on FRiP-normalized sequencing tag counts with DESeq2 software. In all cases common and unique peaks were identified by interval analysis, then quantification and/or differential accessibility was performed by downstream interrogation of gene body FPKM values or FRIP-normalized peak counts. These count metrics were used for direct correlation with other assays, input into gene module analysis or interrogated for differences between various groups of interest. Including subsequent studies, approximately 450 ATAC-seq libraries have been sequenced.

Example 2: Assessment of Markers of T Cells by Flow Cytometry and ATAC-Seq

ATAC-Seq was used to assess the chromatin accessibility of genes associated with T cell activation state or response in a cell composition containing genetically engineered cells and was compared to protein expression of the same genes by intracellular cytokine staining (ICS; in some cases referred to as intracellular flow cytometry). Genetically engineered human T cells expressing anti-CD19 CARs, produced as described in Example 1, were thawed. For assessment of protein markers by flow cytometry, cells were re-stimulated in culture with phorbol myristate acetate (PMA)/Ionomycin in the presence of Golgi inhibitor, and assessed by flow cytometry. For measuring chromatin accessibility of the genes, the genetically engineered cells, without further re-stimulation, were assessed by ATAC-seq as outlined in Example 1.

Figure 1B:
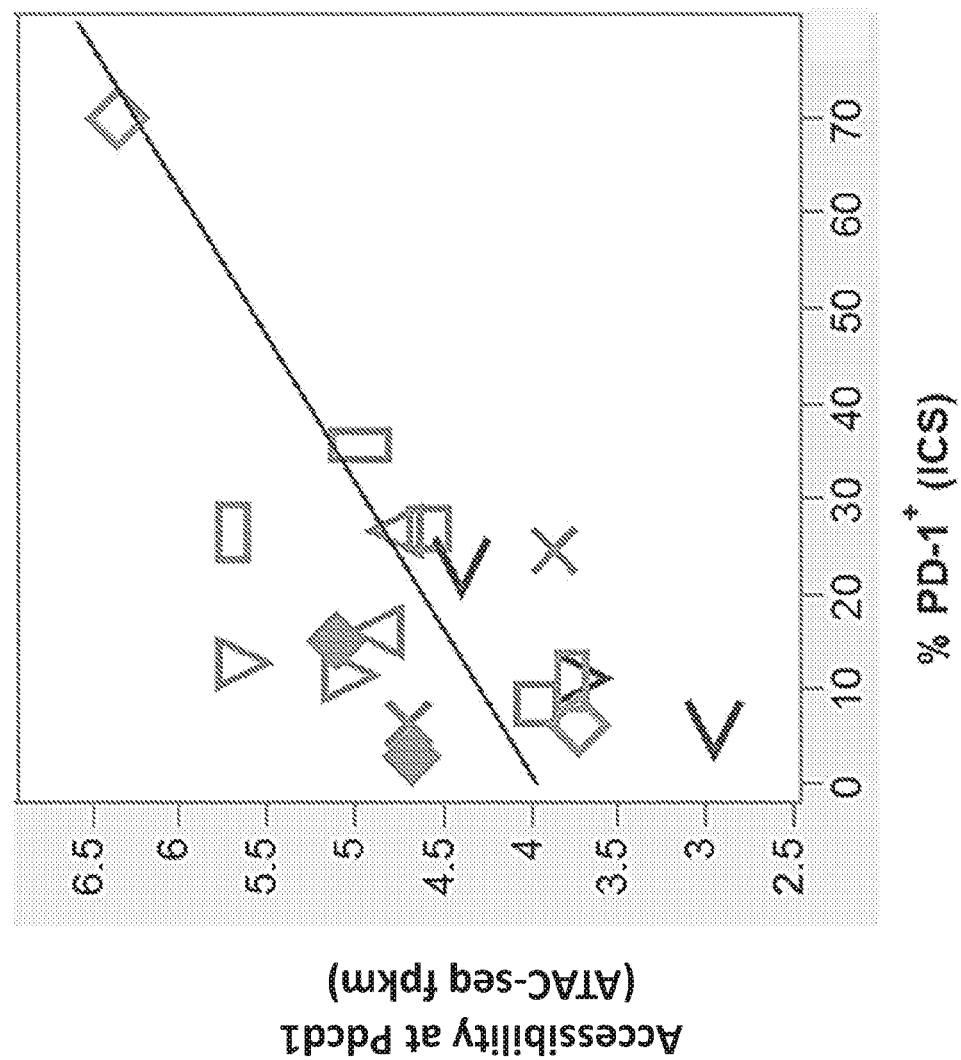
FIG. 1B shows correlation of programmed cell death protein 1 (PD-1) production, as measured by ICS (shown on the x-axis) versus accessibility at the gene encoding PD1 (Pdcd1) as determined by ATAC-seq (shown on the y-axis).

Table E1 provides the p value for correlation of each marker as determined using multivariate correlations. FIGS. 1A and 1B show a representative correlation of interferon-gamma (IFNγ) and programmed cell death protein 1 (PD-1) production, respectively, as measured by ICS (shown on the x-axis) versus accessibility at the gene encoding each protein (Ifng and Pdcd1, respectively) as determined by ATAC-seq (shown on the y-axis). As shown in Table 1, there was not a statistically significant correlation between the extent of chromatin accessibility and protein expression of many of the assessed T cell markers, although expression of certain cytokine markers did exhibit a significant correlation to chromatin accessibility.

TABLE E1

ATAC-seq vs ICS initial multivariate correlations

| Cytokine | P value |
| --- | --- |
| IFN-g | p < 0.0001 |
| IL-13 | p = 0.0002 |
| PD-1 | p = 0.018 |
| Tbet | p = 0.05 |
| CD25 | p = 0.106 |
| IL-2 | p = 0.104 |
| Lag3 | p = 0.171 |
| KI-67 | p = 0.123 |
| TNF | p = 0.249 |
| Annexin V | p = 0.342 |
| Foxp3 | p = 0.491 |

Figure 1C:
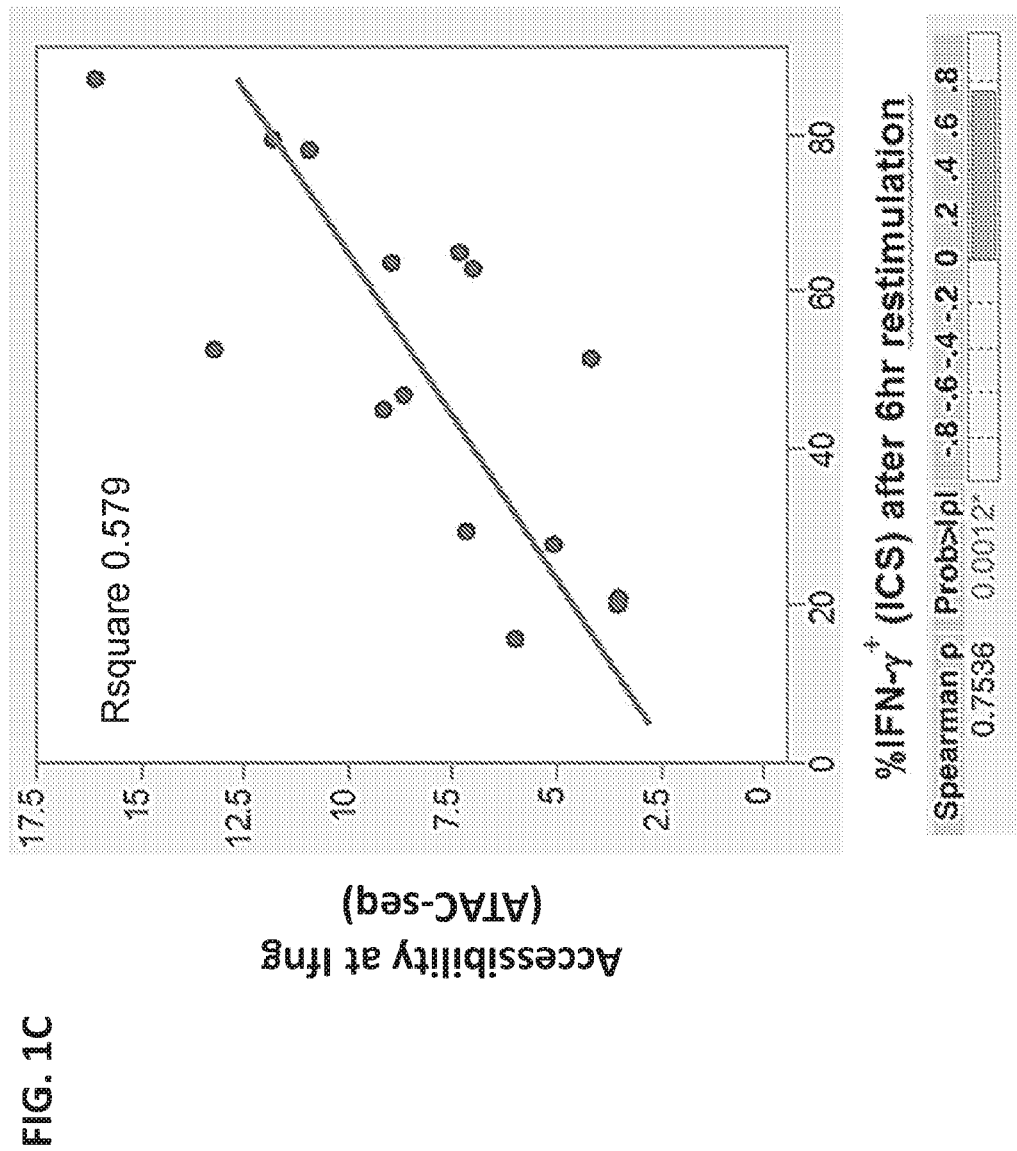
FIG. 1C shows correlation of the % cells producing IFNγ after re-stimulation, as measured by ICS (shown on the x-axis) versus accessibility at the gene encoding IFNγ (Ifng) as determined by ATAC-seq (shown on the y-axis).
Figure 1D:
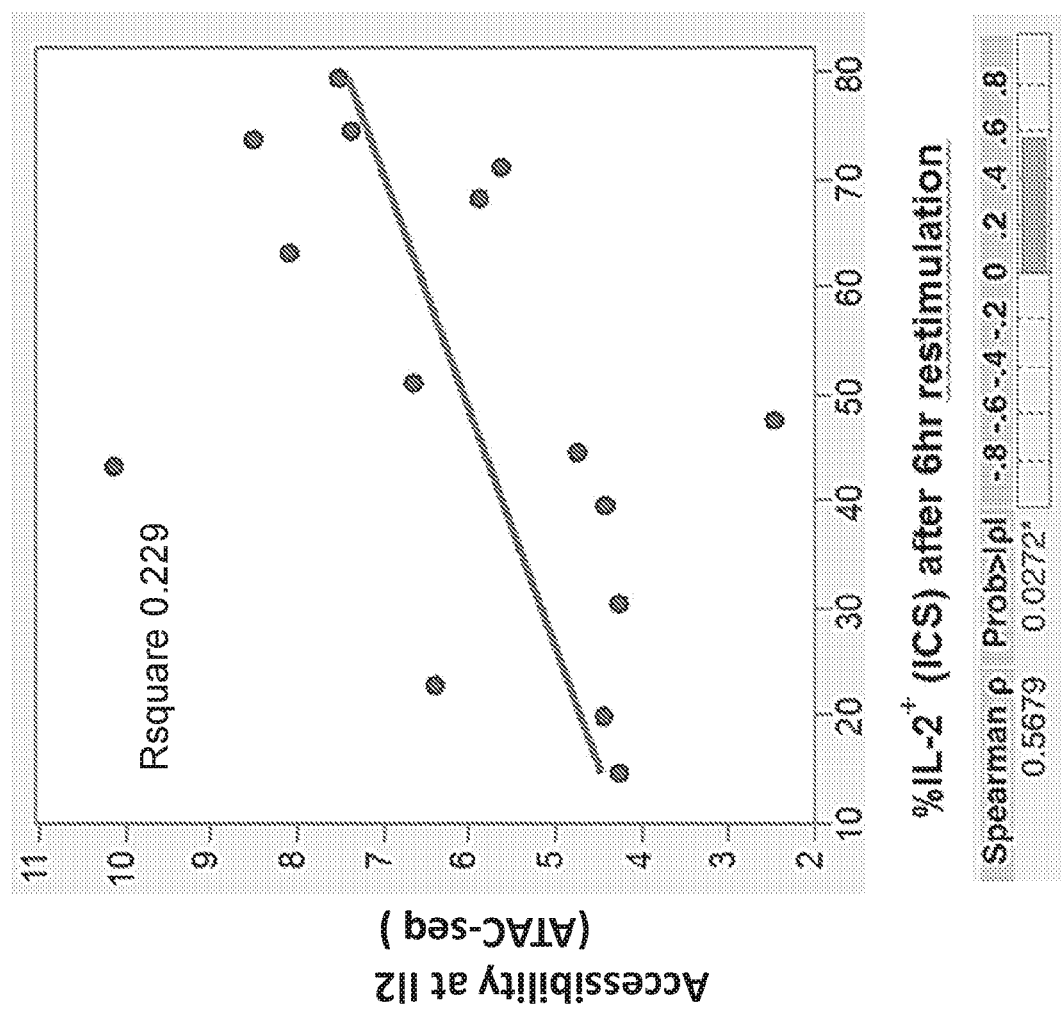
FIG. 1D of the % cells producing Interleukin 2 (IL-2) after re-stimulation, as measured by ICS (shown on the x-axis) versus accessibility at the gene encoding IL-2 (Il2) as determined by ATAC-seq (shown on the y-axis).

In another study, ATAC-seq was performed generally as described above to assess chromatin accessibility at the gene encoding IFNγ and IL-2 (Ifng and Il2, respectively). Production of IFNγ and IL-2 were assessed by ICS following a 6-hour re-stimulation with phorbol myristate acetate (PMA)/Ionomycin. As shown in FIG. 1C, chromatin accessibility at the gene encoding IFNγ correlated with the production of IFNγ as measured by ICS, with an $R^2$ value of 0.579, Spearman's rank correlation (ρ) of 0.7536, and a prob>|ρ| of 0.0012. As shown in FIG. 1D, chromatin accessibility at the gene encoding IL-2 correlated with production of IL-2, with an $R^2$ value of 0.229, Spearman's rank correlation (ρ) of 0.5679, and a prob>|ρ| of 0.0272.

The results in Table E1 and FIGS. 1A-1D are consistent with the finding that in some cases, accessibility of chromatin for a given gene can be predictive of and/or correlate with the expression of the gene or other outcomes following activation of the cells.

Figure 2:
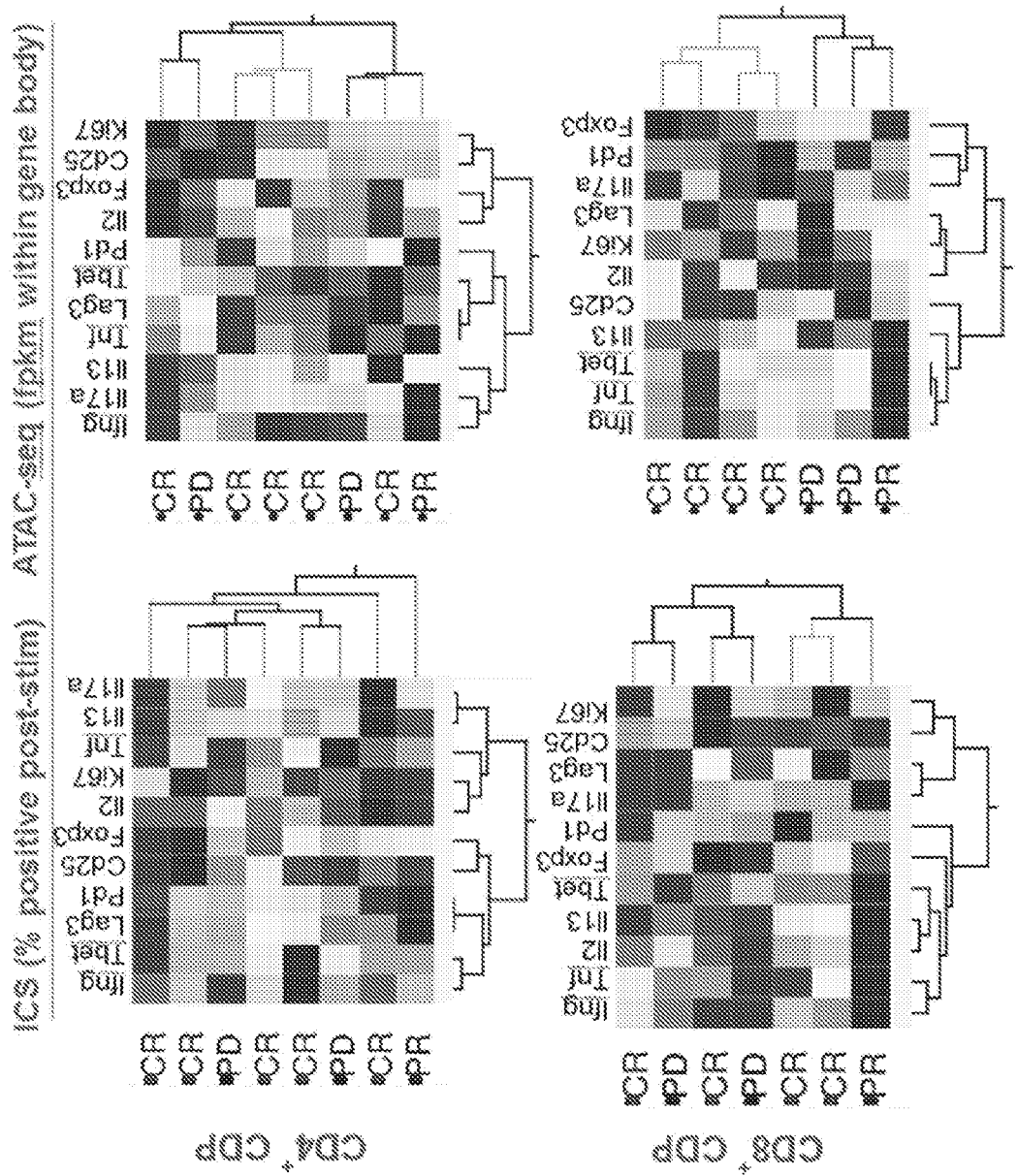
FIG. 2 shows protein expression by intracellular cytokine staining (ICS) of select genes in CD4+ or CD8+ T cells of an engineered T cell composition (left panels) or chromatin accessibility of genes as measured by ATAC-seq in CD4+ or CD8+ in the same engineered T cell compositions (right panels), each correlated to response outcome following administration of the cell therapy to a subject.

ICS and ATAC-seq were used to assess immunophenotype (protein expression or chromatin accessibility, respectively) of exemplary T cell markers in CD4+ cells or CD8+ cells obtained from a CDP sample containing engineered T cells that had been administered to an autologous subject for treating a B cell malignancy using the methods described above. The results of the ICS and ATAC-seq were independently further correlated with the response outcome of the subject to treatment with the autologous engineered cells (complete response (CR), progressive disease (PD), or partial response (PR)). The level of cytokine accessibility for the representative genes or the level of protein expression by ICS was determined and displayed in a hierarchial cluster and annotated by the response outcome. As a control, the levels of T cell markers in normal donor (ND) cells also were assessed by ICS and ATAC-Seq. FIG. 2 shows the response clustering on immunophenotyping data of CD4+ CDP samples and CD8+ CDP samples. As shown in FIG. 2, cytokine production as measured by ATAC-seq in CD8+ CDP samples was correlated to response outcome. No correlation to response outcome was observed by ICS.

Example 3: Whole Genome Assessment of Chromatin Accessibility by ATAC-Seq

Whole genome analysis using ATAC-seq was performed on a thawed CD8+ cells from a CDP containing genetically engineered human T cells expressing anti-CD19 CARs produced as described above in Example 1. The results of the ATAC-seq were independently further correlated with the response outcome of the subjects to treatment with the autologous engineered cells based on whether the treatment resulted in complete response (CR), progressive disease (PD) or a partial response (PR). The asterisk indicates a subject who converted from CR to PD at three months after initiation of the dose of cells. Whole genome analysis of normal donor (ND) CD8+ cells also was assessed by ATAC-seq. Hierarchial clustering was performed based on differences in chromatin accessibility for each gene, as calculated by the sum of FPKM over the gene body of each gene, which was scaled low (blue) to high (red) for each gene.

Figure 3A:
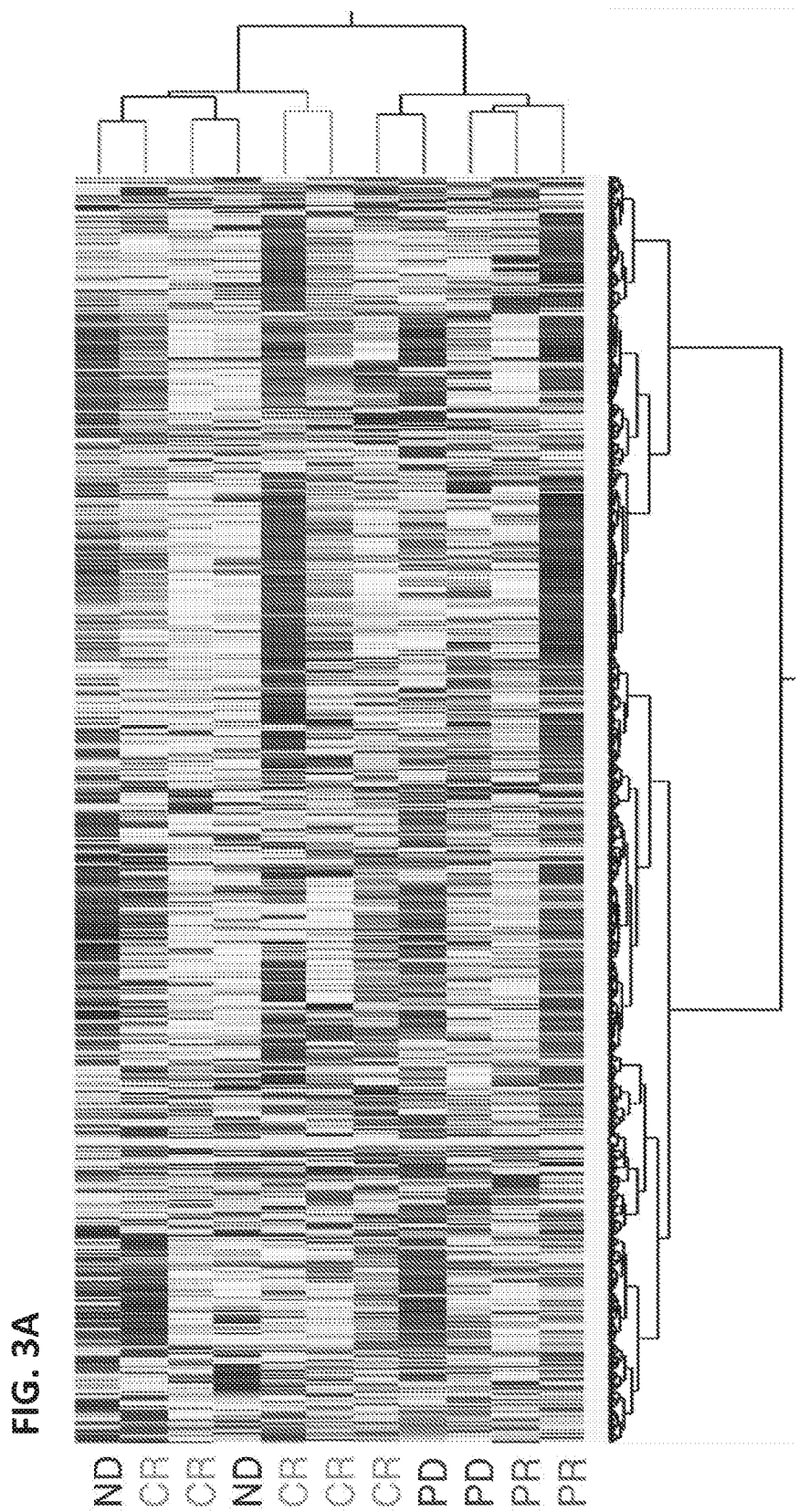
FIG. 3A shows the results of a whole genome analysis using ATAC-seq performed on CD8+ cells from a T cell composition containing genetically engineered human T cells expressing anti-CD19 CARs. Each column represents hierarchical clustering based on differences in chromatin accessibility for each gene, as calculated by the sum of FPKM over the gene body of each gene, shown as low (blue) or high (red). Subjects were categorized by response groups, including subjects who showed evidence of complete response (CR), progressive disease (PD) or partial response (PR). Chromatin accessibility results by ATAC-seq also are shown from CD8+ cells from a normal donor (ND). The asterisk indicates a subject who converted from CR to PD at three months.
Figure 3B:
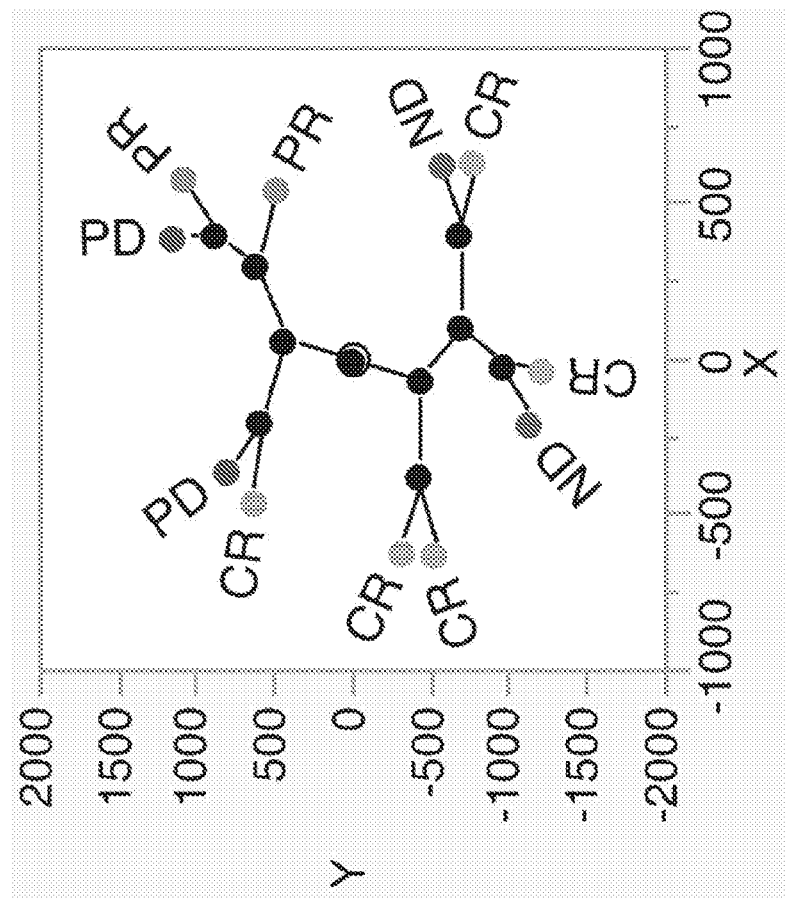
FIG. 3B shows a clustering decision tree (constellation plot) showing CD8+ CDP clustering observed on whole genome ATAC-seq data by response groups.

A representative whole genome analysis of chromatin accessibility for a plurality of genes in cells from a CDP from each of 9 subjects that had been administered the autologous CDP is shown in FIG. 3A. FIG. 3B shows a clustering decision tree (constellation plot) showing CD8+ CDP clustering observed on ATAC-seq data by response groups (the CR patient that clustered with the PR and PD samples converted to a PD at 3 months.)

Figure 4A:
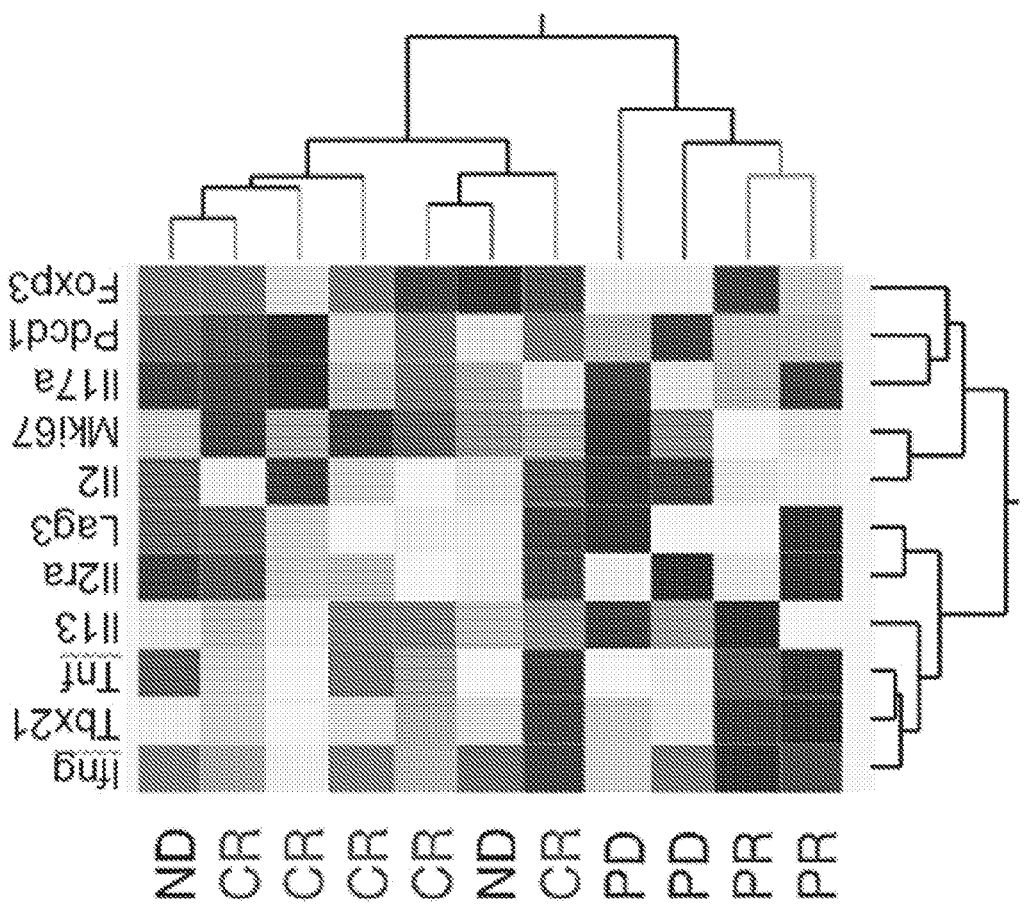
FIG. 4A shows the results of an analysis using ATAC-seq for a subset of targeted panel of genes from the whole genome sequencing data performed on CD8+ cells from a CDP containing genetically engineered human T cells expressing anti-CD19 CARs.
Figure 4B:
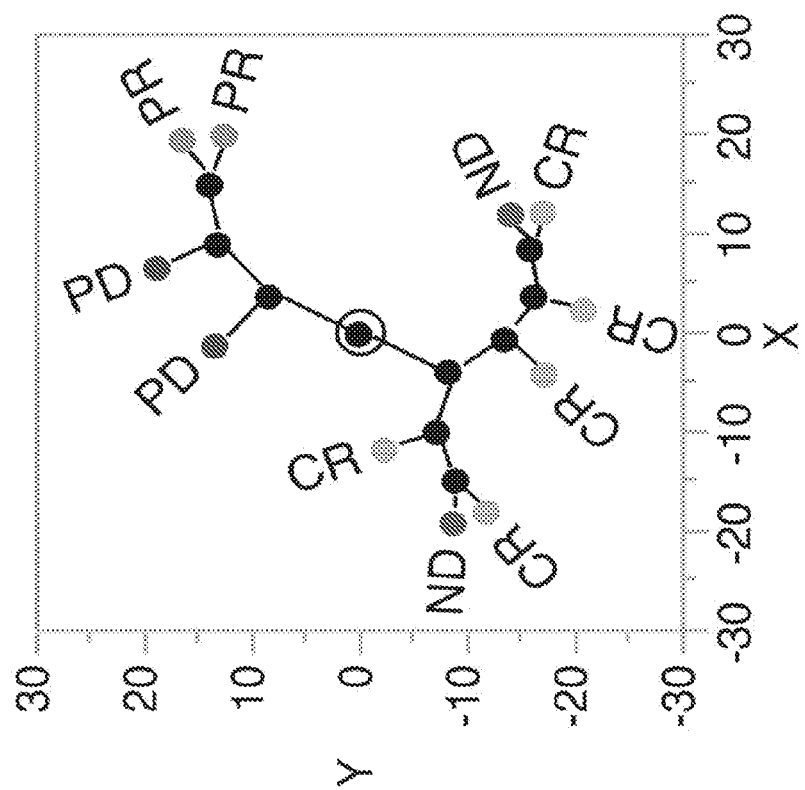
FIG. 4B shows a clustering decision tree (constellation plot) for chromatin accessibility based on ATAC-seq data of specific genes in CD8+ cells obtained from a CDP by response groups.

A select subset of targeted panel of genes from above was further analyzed and represented in FIG. 4A as a hierarchial cluster and FIG. 4B as a constellation plot. Similar to above, CD8+ CDP clustering for the specific genes indicated was observed on ATAC-seq data by response groups.

Figure 5A:
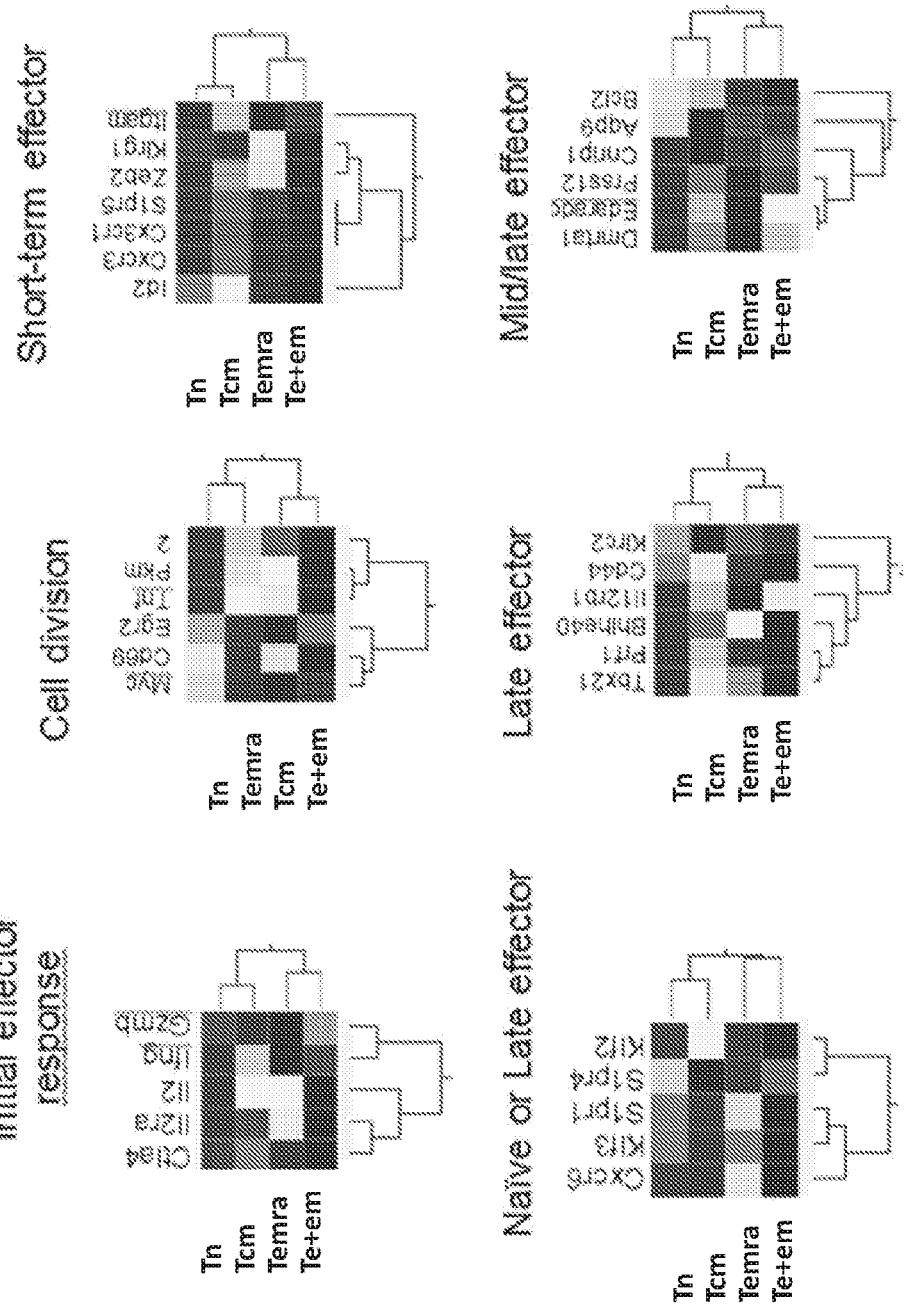
FIG. 5A shows chromatin accessibility by ATAC-seq (represented as relative values of the sum of FPKM over the gene body of each gene) of genes that are indicative of effector cell phenotype in cryopreserved FACS-purified CD4+/CD8+ cell compositions (CMAT) which were not subjected to the genetic engineering.

Example 4: Assessment of Chromatin Accessibility in CD8+ CAR T Cells by ATAC-Seq Cyropreserved CMAT samples, containing T cells obtained from subjects but not engineered with an anti-CD19 CAR, were separated based on phenotype into naïve T cells ($T_N$), central memory T cells ($T_{CM}$), effector cells and effector memory T cells ($T_{E+EM}$) or effector memory RA ($T_{EMRA}$). Cells from each subset were assessed for chromatin accessibility of each of six panel of genes that represented selected gene subsets from memory CD8+ T cell modules identified by the Immgen Consortium (Best et al., Nature Immunology (2013) 14:404-412). Hierarchial clustering was performed based on differences in chromatin accessibility for each gene, as calculated by the sum of FPKM over the gene body of each gene, which was scaled low (blue) to high (red) for each gene. The signature profile of chromatin accessibility for each gene panel for the assessed cell types is shown in FIG. 5A. The results demonstrated that chromatin accessibility of these panels of gene subsets are indicative of the phenotypic effector-like state of the cells.

Figure 5B:
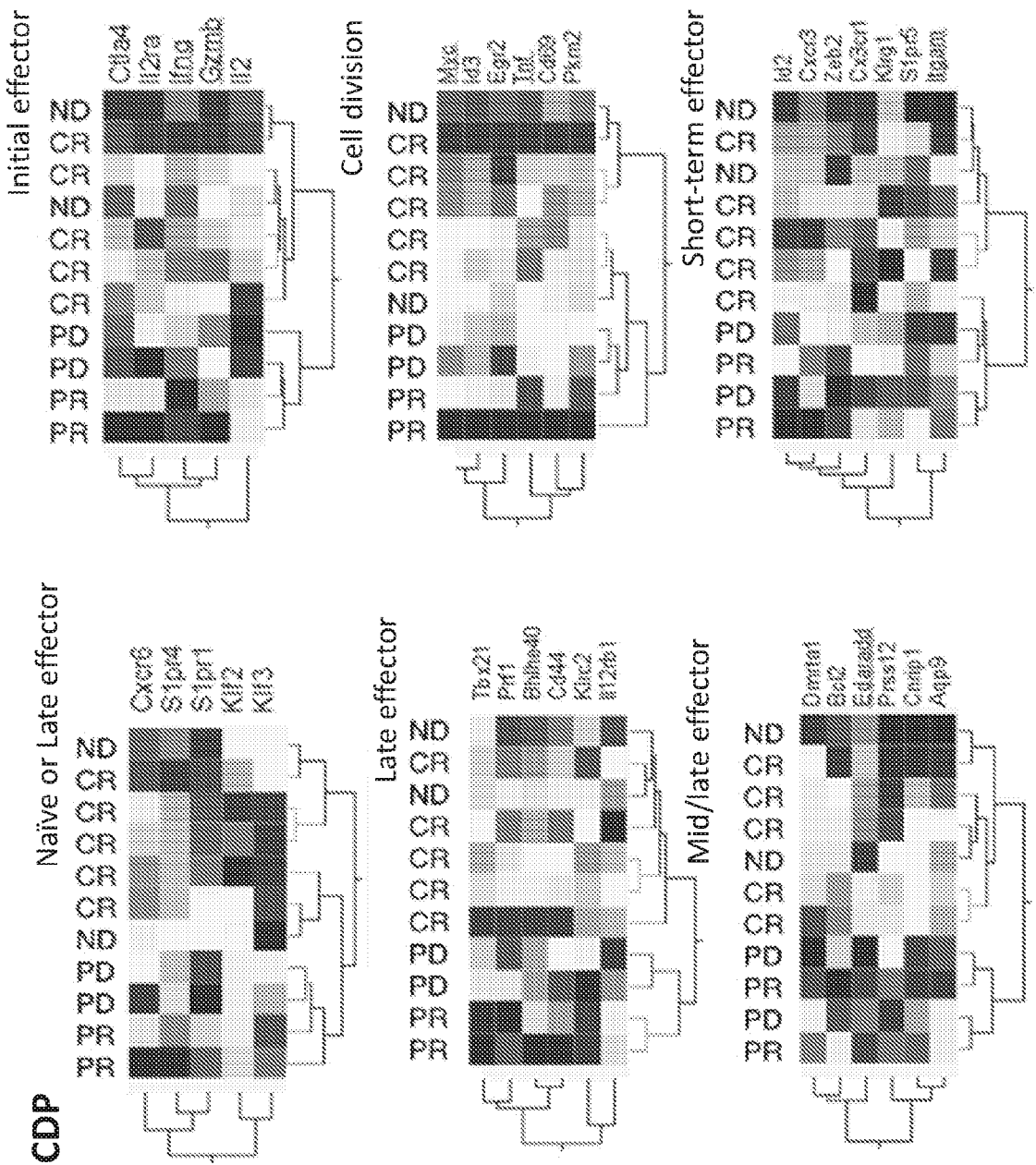
FIG. 5B shows chromatin accessibility by ATAC-seq (represented as relative values of the sum of FPKM over the gene body of each gene) of genes that are indicative of effector cell phenotype in CD8+ CDP.

The same gene panels were used to assess chromatin accessibility in thawed CD8+ cells from a CDP containing genetically engineered human T cells expressing anti-CD19 CARs produced as described above in Example 1. Normal donor (ND) CD8+ cells also were assessed by ATAC-seq. The results of the ATAC-seq were independently further correlated with the response outcome of the subjects to treatment with the autologous engineered cells based on whether the treatment resulted in complete remission (CR), progressive disease (PD) or a partial response (PR). As shown in FIG. 5B, CD8+ CDP from subjects who showed evidence of PR and PD appear to have more of an effector-like phenotype, as determined by chromatin accessibility of genes associated with an effector-like phenotype, compared to subjects who showed evidence of CR or ND.

Example 5: Assessment of CD8+ Chromatin Accessibility by ATAC-Seq at Selected Loci Thawed CD8+ cells from a CDP containing genetically engineered human T cells expressing anti-CD19 CARs produced as described above in Example 1, were further analyzed for chromatin accessibility, as calculated by the sum of FPKM over the gene body of each gene, at loci associated with strength of signal and effector function of T cells. The results of the ATAC-seq were independently further correlated with the response outcome of the subjects to treatment with the autologous engineered cells based on whether the treatment resulted in complete response (CR), progressive disease (PD) or a partial response (PR). Normal donor (ND) CD8+ cells also were assessed by ATAC-seq.

Figure 6B:
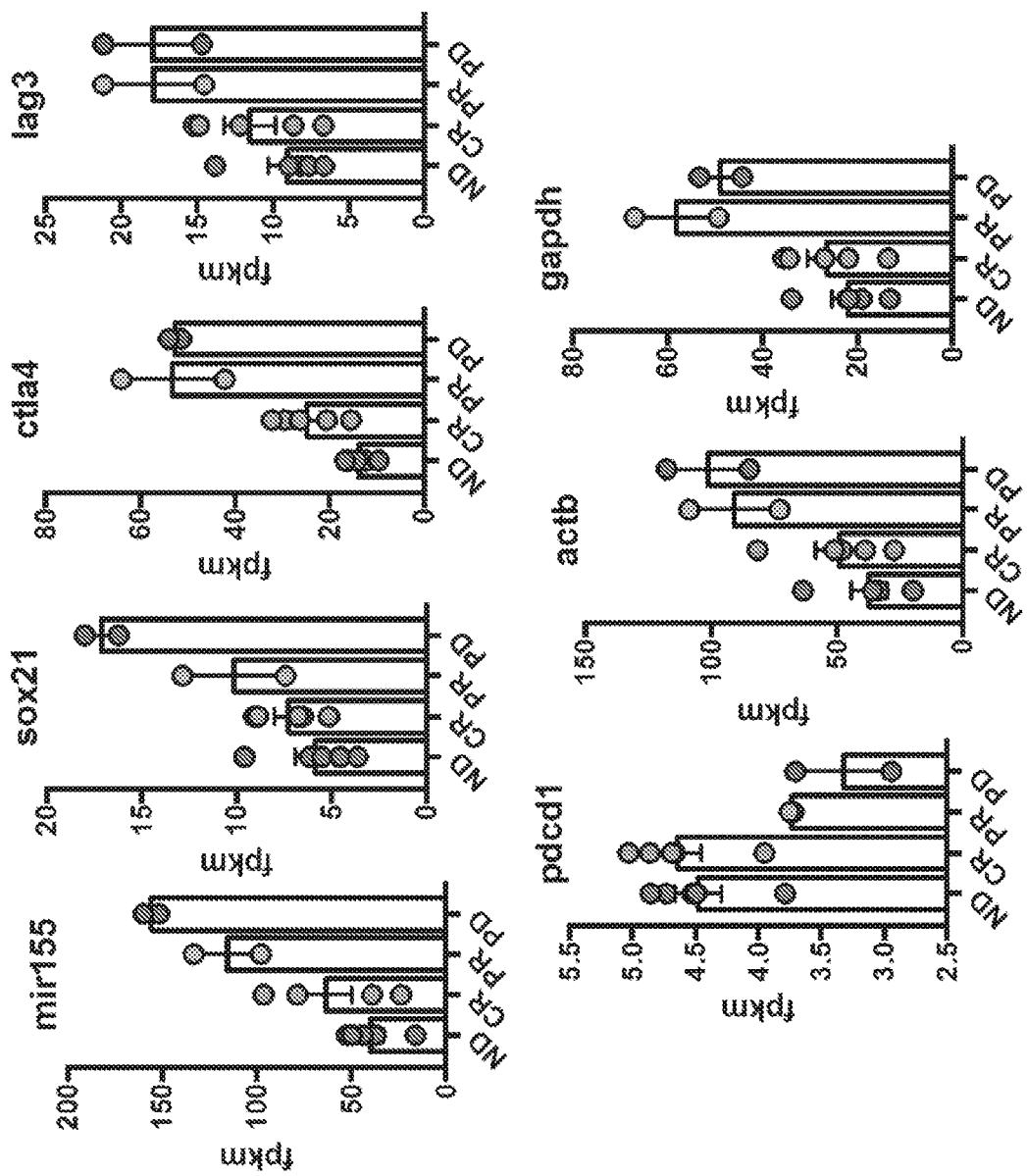

As shown in FIGS. 6A and 6B, higher fpkm levels of chromatin accessibility of all tested genes, except pdcd1, correlated to developing a partial response or progressive disease. Lower fpkm levels of chromatin accessibility of pdcd1 gene loci correlated to developing a partial response or progressive disease. Housekeeping genes Actb and Gapdh, which track with activation state of T cells, were increased in PR and PD, indicating that cells from CDP samples administered to subjects that went on to develop PR or PD may be in a more activated state. These results demonstrated that these genes or panels of genes may be epigenetic markers for predicting response outcome to treatment with a cell therapy.

Example 6: Gene Expression and Chromatin Accessibility Analysis in CAR T Cells in the Presence or Absence of Lenalidomide Gene expression and chromatin accessibility was assessed in CAR T cells upon stimulation, in the presence or absence of lenalidomide.

Anti-BCMA CAR-expressing T cells, generated from four (4) different independent donors, were stimulated with 50 μg/mL BCMA-conjugated beads for 24 hours (24 hr+stim) or 7 days (d7+stim), or cultured without stimulation for 24 hours (24 hr), in the presence or absence of lenalidomide. The CAR-expressing cells were assessed by RNA sequencing (RNA-seq) for gene expression and assayed for transposase-accessible chromatin using sequencing (ATAC-seq) for chromatin accessibility analysis. RNA-seq was performed on the complementary DNA (cDNA) samples prepared from the RNA isolated from the cultured anti-BCMA CAR-expressing cells. ATAC-seq was performed generally as described in Buenrostro et al., Nat Methods. (2013) 10(12): 1213-1218. ATAC-seq accessibility peaks were called using MACS2 (q<0.01) and a consensus set was generated from overlapping peaks present in 2 or more samples, using DiffBind.

Principal component analysis (PCA) was performed for the RNA-seq and ATAC-seq data sets, generated from DESeq2-normalized counts. Differential expression (DE, for RNA-seq) or consensus peak accessibility (DA, for ATAC-seq) were calculated, modeling donor effects (Donors 1-4) and treatment effects (lenalidomide vs. vehicle) at 24 hours and day 7. Differential locus selection cut off was $q \leq 0.05$ and log 2 fold change$\geq 0.5$ for RNA-seq or $q \leq 0.1$ for ATAC-seq. Gene ontology (GO) enrichment analysis was performed and activation z-score was determined on the subset of genes differentially expressed at $q \leq 0.1$ using Ingenuity Pathway Analysis software (Qiagen, Inc.), accounting for donor effects within each treatment condition. A motif enrichment analysis was performed for peaks that were shown to be more accessible in the presence of lenalidomide, with HOMER software, using the consensus peakset as background, for the day 7 stimulation (d7+stim) ATAC-seq data.

Figure 7B:
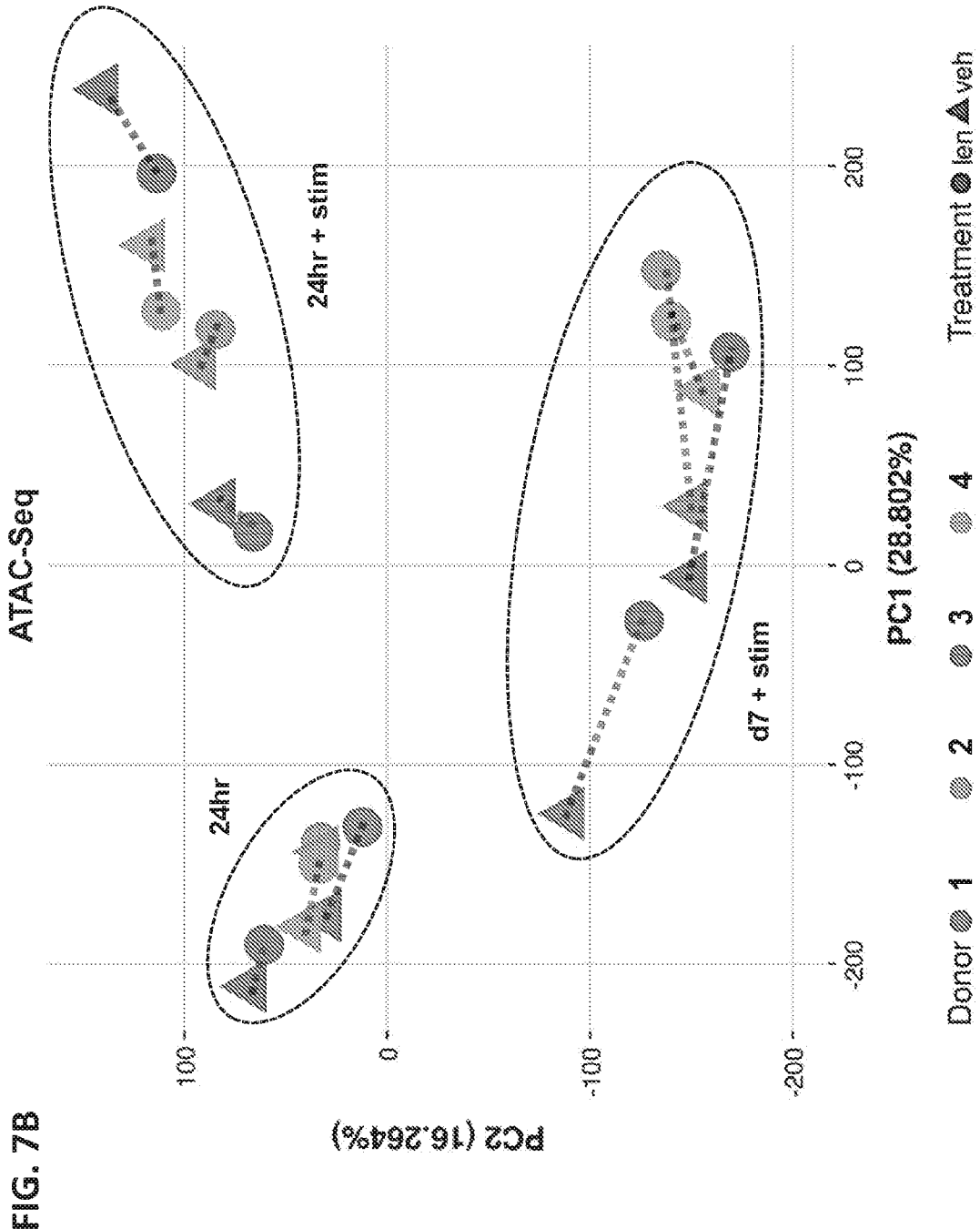

Results of PCA, representing the overall diversity across gene expression or chromatin accessibility on the genome, are shown in FIG. 7A (gene expression; based on RNA-seq results) and FIG. 7B (chromatin accessibility; based on ATAC-seq results). Ellipses were drawn to indicate the groups as it was observed that the major factors that contributed to the variation in gene expression or chromatin accessibility were culture time and presence of stimulation. Cells cultured in the presence of lenalidomide (circles) exhibited different overall gene expression and chromatin accessibility compared to cells cultured in the absence of lenalidomide (triangles, vehicle), showing a lenalidomide treatment effect in each donor and culture condition. For lenalidomide treatment, the general direction of change (shown by dotted line between triangle and circle) was similar in each donor, and the degree of change was generally greater in cells cultured for 7 days with stimulation, compared to the change in cells cultured for 24 hours, with or without stimulation.

Figure 8A:
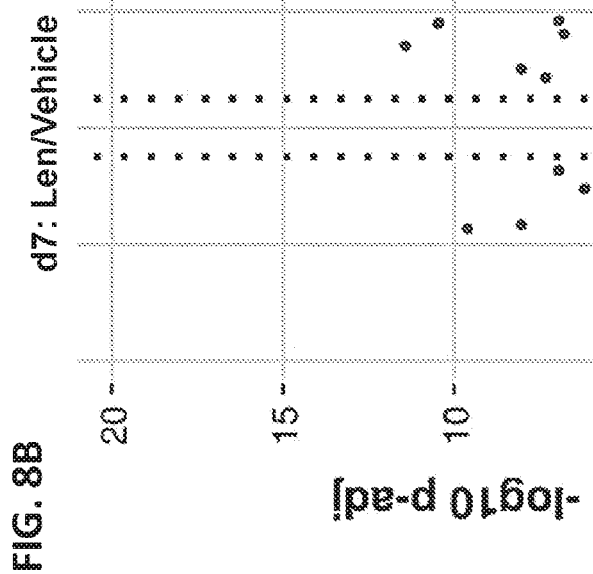
FIGS. 8A and 8B show volcano plots depicting statistical significance of expression ($\log_{10}$ of adjusted p-value) with the $\log_2$ fold-change in gene expression, in CAR+ T cells stimulated with BCMA-conjugated beads, for 24 hours (24 hr+stim, FIG. 8A) or 7 days (d7+stim, FIG. 8B), in the presence or absence of lenalidomide. The tables indicate the number of genes or peaks that showed increase (up) or decrease (down) in expression.
Figure 8B:
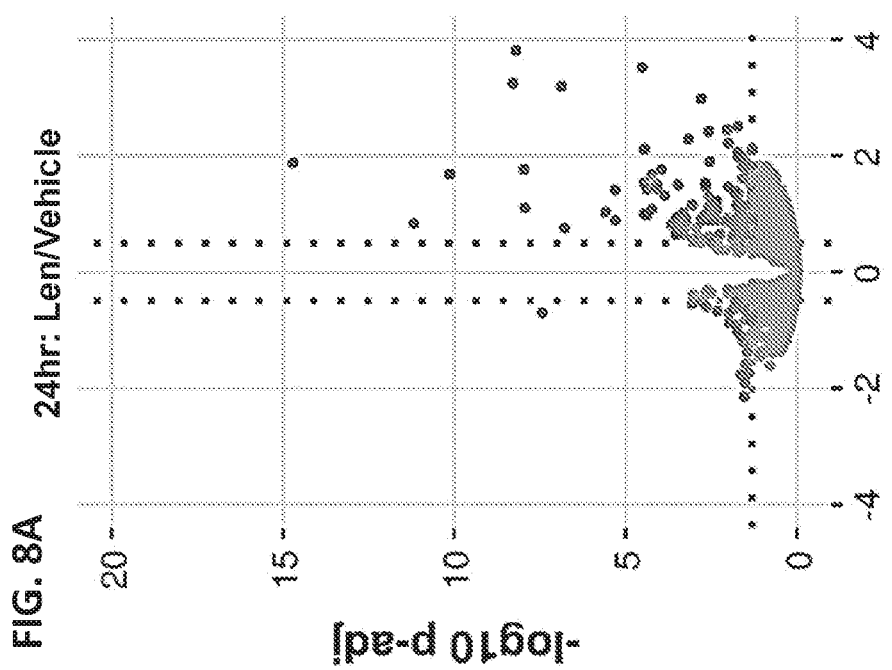
Figure 8C:
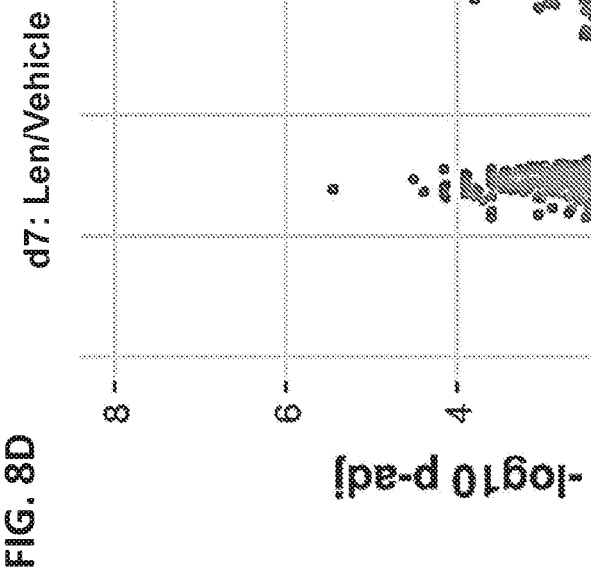
FIGS. 8C and 8D show volcano plots depicting statistical significance of change in chromatin accessibility ($\log_{10}$ of adjusted p-value) with the $\log_2$ fold-change in chromatin accessibility, in CAR+ T cells stimulated with BCMA-conjugated beads, for 24 hours (24 hr+stim, FIG. 8C) or 7 days (d7+stim, FIG. 8D). The tables indicate the number of genes or peaks that showed increase (up) or decrease (down) in accessibility.
Figure 8D:
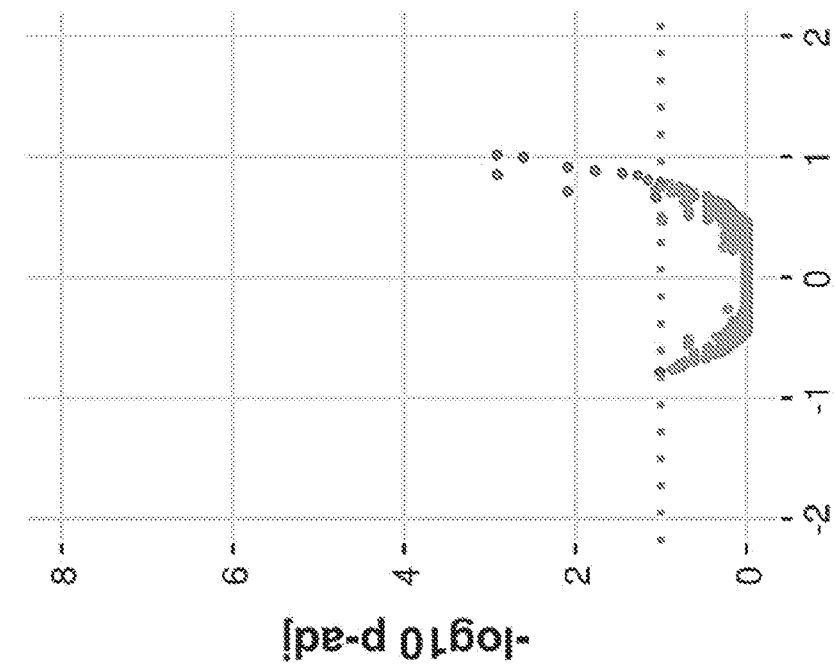

FIGS. 8A-8D show changes in gene expression (FIGS. 8A and 8B, following 24 hour and 7 day cultures with stimulation, respectively) or chromatin accessibility (FIGS. 8C and 8D, following 24 hour and 7 day cultures with stimulation, respectively) in the presence of lenalidomide. As shown, the effect of lenalidomide on gene expression and chromatin accessibility was greater in the 7 day cultures, compared to the 24 hour cultures. Following 7 days of culture in the presence of lenalidomide, a total of 583 genes were altered as shown by gene expression changes (FIG. 8B), whereas chromatin accessibility at 2804 peaks changed (FIG. 8D). These results indicated that lenalidomide treatment altered both the transcriptional and epigenetic profile of CAR-T cells.

Figure 9A:
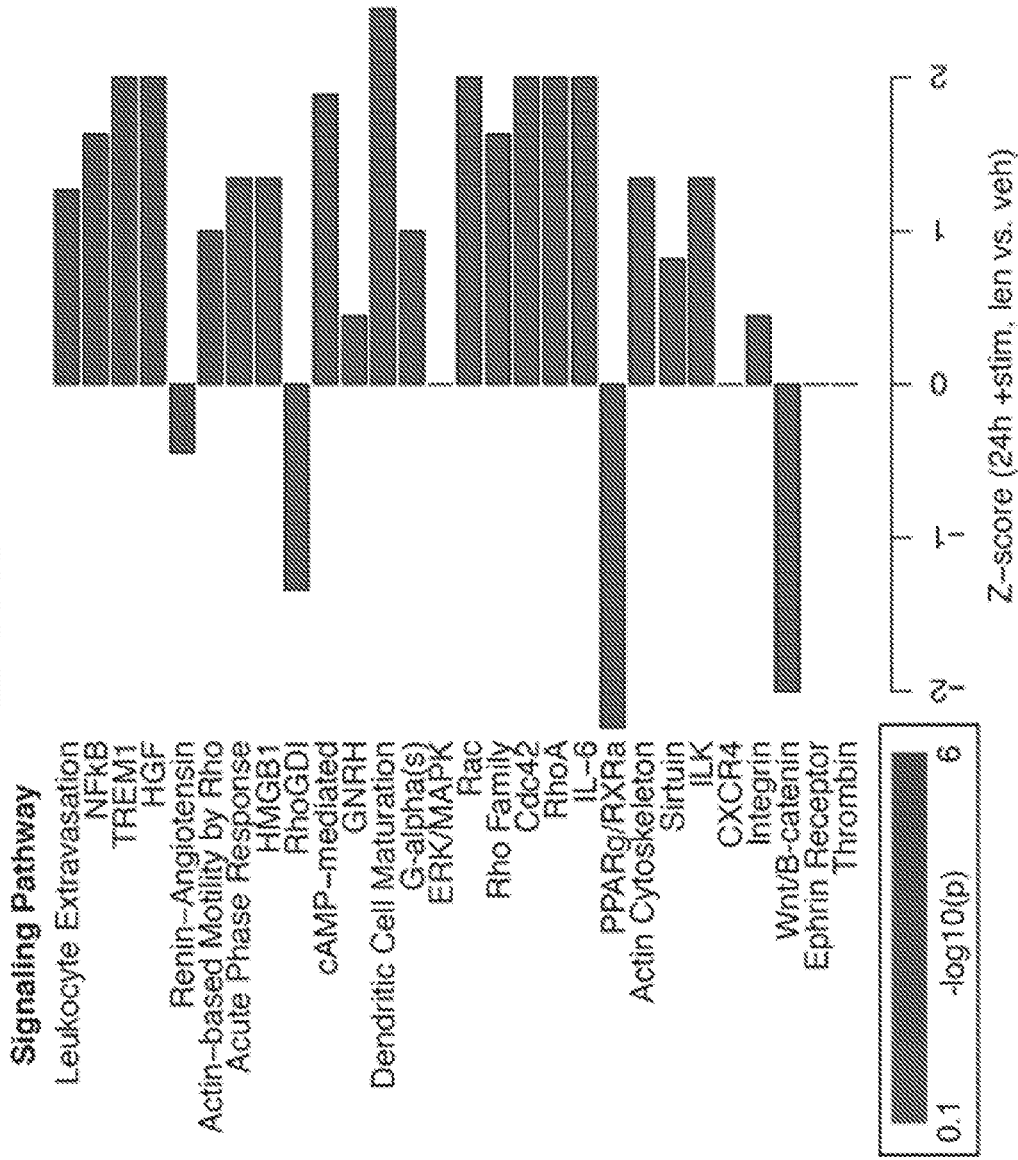
FIGS. 9A and 9B depict directionality and significance of the effects on biological pathways, in CAR+ T cells stimulated with BCMA-conjugated beads, for 24 hours (24 hr+stim, FIG. 9A) or 7 days (d7+stim, FIG. 9B).
Figure 9B:
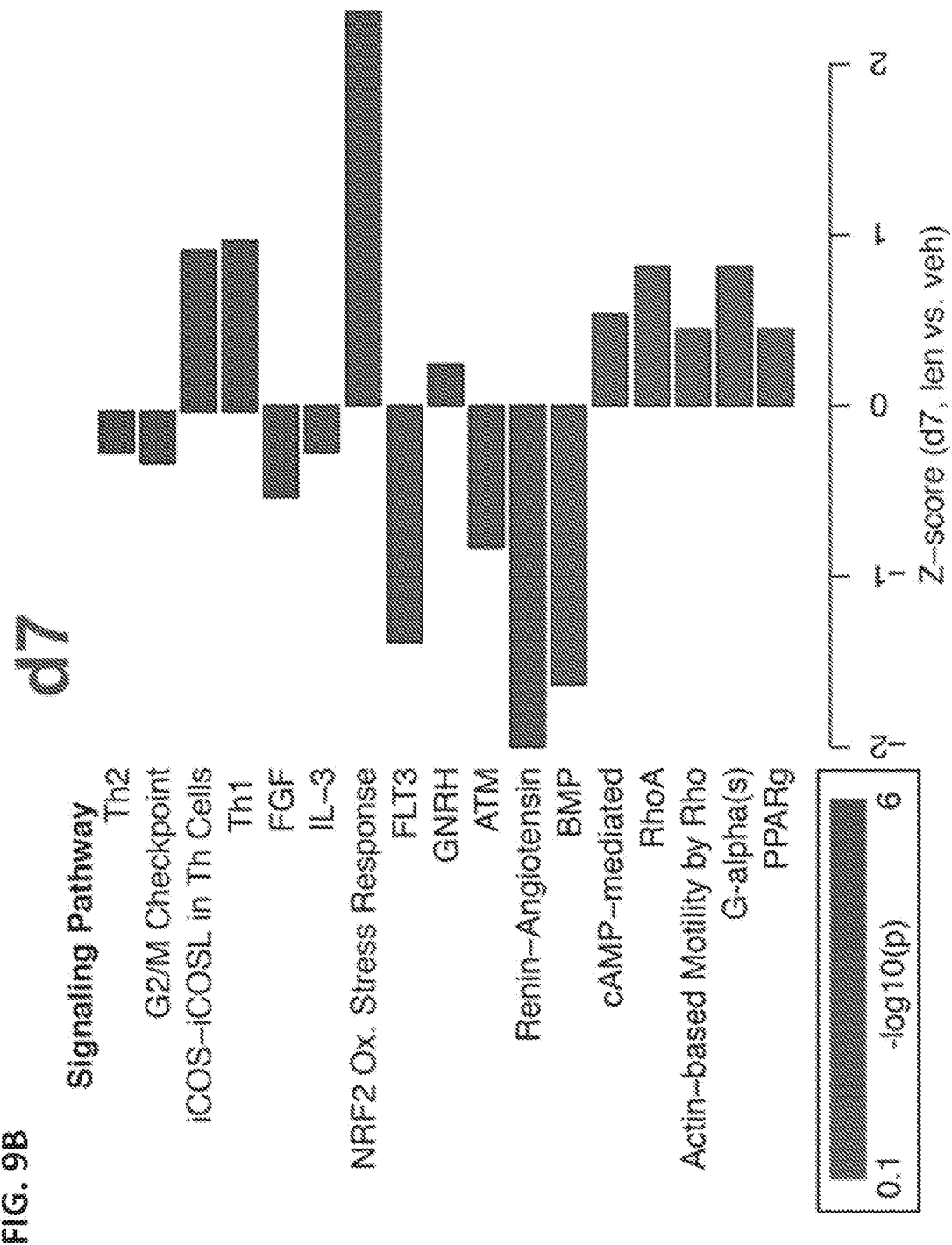
Figure 10:
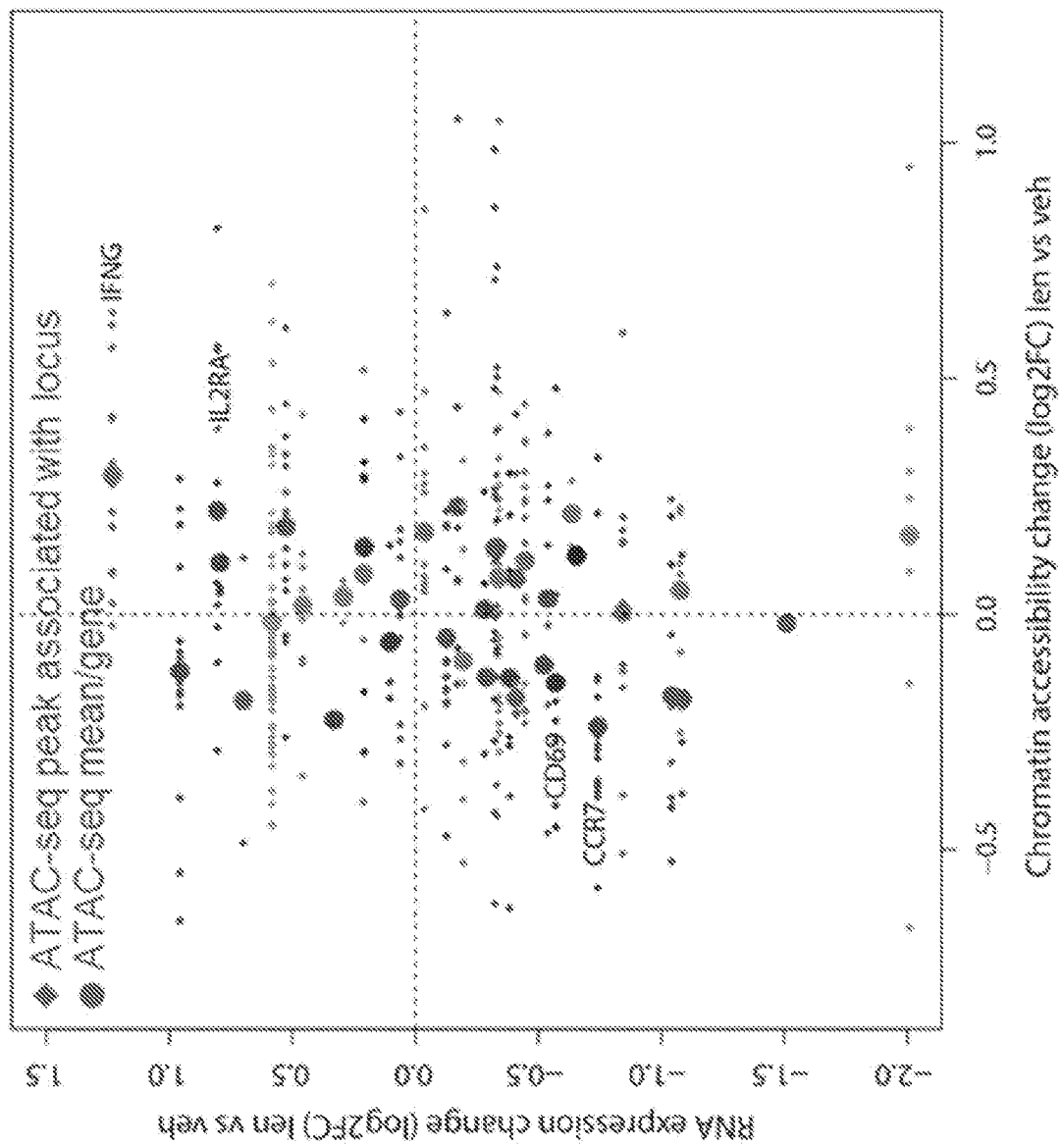
FIG. 10 shows a plot comparing individual chromatin accessibility peaks (diamond) and the mean chromatin accessibility changes for each gene (circle), with the gene expression changes, for selected genes involved in T cell activation and signaling.

Biological signaling pathways that were enriched differentially expressed genes (FIGS. 9A and 9B) were identified. Directionality and significance of the effects on biological pathways are shown at 24 hours (FIG. 9A) or 7 days (FIG. 9B). The results showed that the presence of lenalidomide resulted in increased expression of genes involved in T cell activation and signaling. Results showed that pathways differentially regulated in the presence and absence of lenalidomide showed an enrichment of immune synapse-associated genes, genes involved in cytokine signaling and genes involved in T cell activation pathways For a selected subset of genes, including genes involved in T cell activation and signaling, the gene expression and chromatin accessibility changes in the presence of lenalidomide were compared, for the cells cultured for 7 days with stimulation. FIG. 10 shows individual chromatin accessibility peaks (diamond) and the mean chromatin accessibility change for each gene (circle) plotted against the corresponding gene expression changes measured by RNA-seq showing concordance of signal between the two methods.

Results of the motif enrichment analysis for peaks with increased accessibility in the presence of lenalidomide in day 7 cultures are shown in FIG. 11. Motifs predicted to bind various transcription factors, understood to be involved in T cell activation and signaling, were enriched in peaks with increased accessibility in the presence of lenalidomide.

The results were consistent with an increase in functional activity in the CAR-expressing T cells in the presence of lenalidomide.

Example 7: Chromatin Accessibility Profile Analysisin Cells at Different Stages of Cell Engineering Chromatin accessibility at or near exemplary immune genes (e.g. cytokines, chemokines, cell surface markers) was assessed and compared among samples from cell compositions prior to, and after, genetic engineering with the exemplary anti-CD19 CAR described in Example 1. Samples were thawed from cryopreserved CD4+ or CD8+ engineered cell compositions (CDP) or matched samples that had not been subjected to engineering (CMAT). In some cases, CMAT samples were separated by phenotype as naïve T cells ($T_N$), central memory T cells ($T_{CM}$), effector and effector memory T cells ($T_{E+EM}$) or effector memory RA ($T_{EMRA}$) for analysis. Libraries were generated substantially as described in Example 1.

ATAC-seq reads were aligned and mapped back to a reference genome to determine their position, such as by using bowtie (Langmead et al., (2009) Genome Biology 10:R25.1-R25.10) or bowtie2 and analyzed. Additional processing steps was performed including removing duplicates, filtering out mitochondrial DNA, shifting position of mapped fragments to account for 4 or 5-basepair insertion by the Tn5 transposase during the ATAC-seq library preparation, and filtering out fragments larger than 100 base pairs (bp) which, in some cases, can represent nucleosome-bound chromatin rather than nucleosome-free chromatin. Nucleosome positioning (e.g. using NucleoATAC), transposon insertion sites, and transcription factor occupancy were also assessed. Identification of accessibility peaks, including genomic regions that were enriched for or depleted of accessibility and/or occupancy signal as measured by quantifying ATAC-seq fragments, was performed using MACS2.

Figures 12A, 12B:
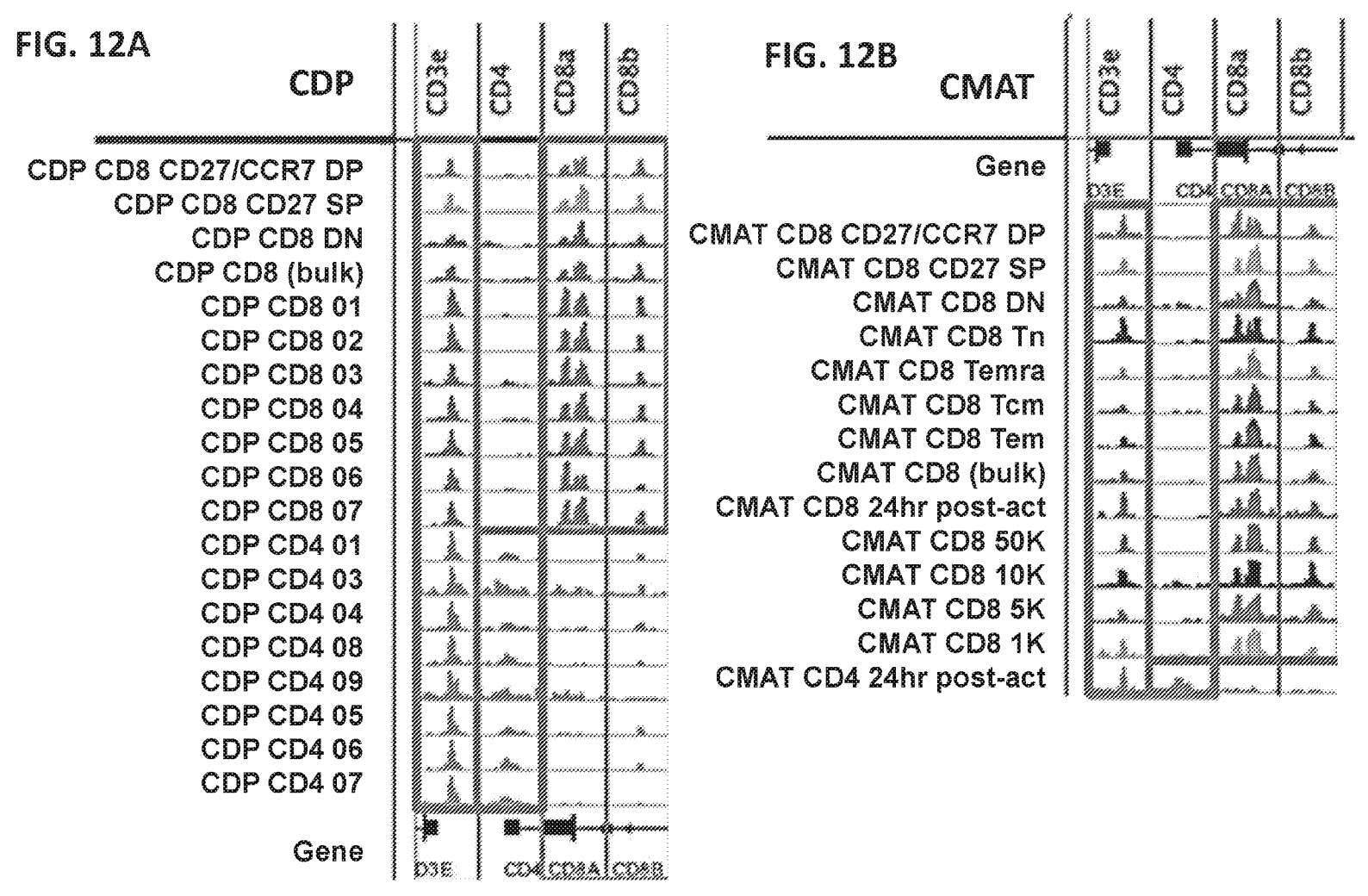

Exemplary profiles for cell surface marker genes are shown in FIGS. 12A and 12B. As shown, chromatin accessibility peaks correlated with expression of specific surface markers (e.g., accessibility peaks were present at or around the genes encoding CD3ε, CD8a and CD8b in CD8+ cells and accessibility peaks were present at or around the gene encoding CD3c and CD4 in CD4+ cells). Some differences in chromatin accessibility peaks at or near other immune genes in matched CDP and CMAT cell samples were observed, consistent with changes in state and/or phenotype of the cells during manufacturing.

Example 8: Genomic Interval Analysis of Peak Profiles in Sub-Populations of Cells CD8+ CDP cells and CD8+ CMAT cells from an identical donor, as described in Example 1, were separated into subpopulations based on surface marker expression and phenotype as follows: CD27+CCR7+, CD27+CCR7−, CD27−CCR7−, naïve T cells ($T_N$), central memory T cells ($T_{CM}$), effector cells and effector memory T cells ($T_{E+EM}$) and effector memory RA ($T_{EMRA}$). ATAC-seq was performed on the sub-populations, generally as described in Example 7. Accessibility peaks were determined and were subjected to genomic interval analysis by assessing common or overlapping peaks and unique peaks between and among the subpopulation of cells.

Analysis of common and unique peaks among different subpopulations of the CDP and CMAT samples showed that the CDP samples contained many more unique accessibility peaks, indicating an increase in chromatin accessibility in the CDP samples, which have been subjected to stimulation and genetic engineering. The majority of the CMAT accessibility peaks were in common with the CDP sample peaks. The accessibility profile of the CD27+ CCR7+ CMAT sample showed substantial overlap with the accessibility profile of $T_N$, $T_{CM}$, $T_{E+EM}$ and $T_{EMRA}$ samples, whereas the CD27+ CCR7+ CDP contained more unique accessibility peaks.

Figure 13A:
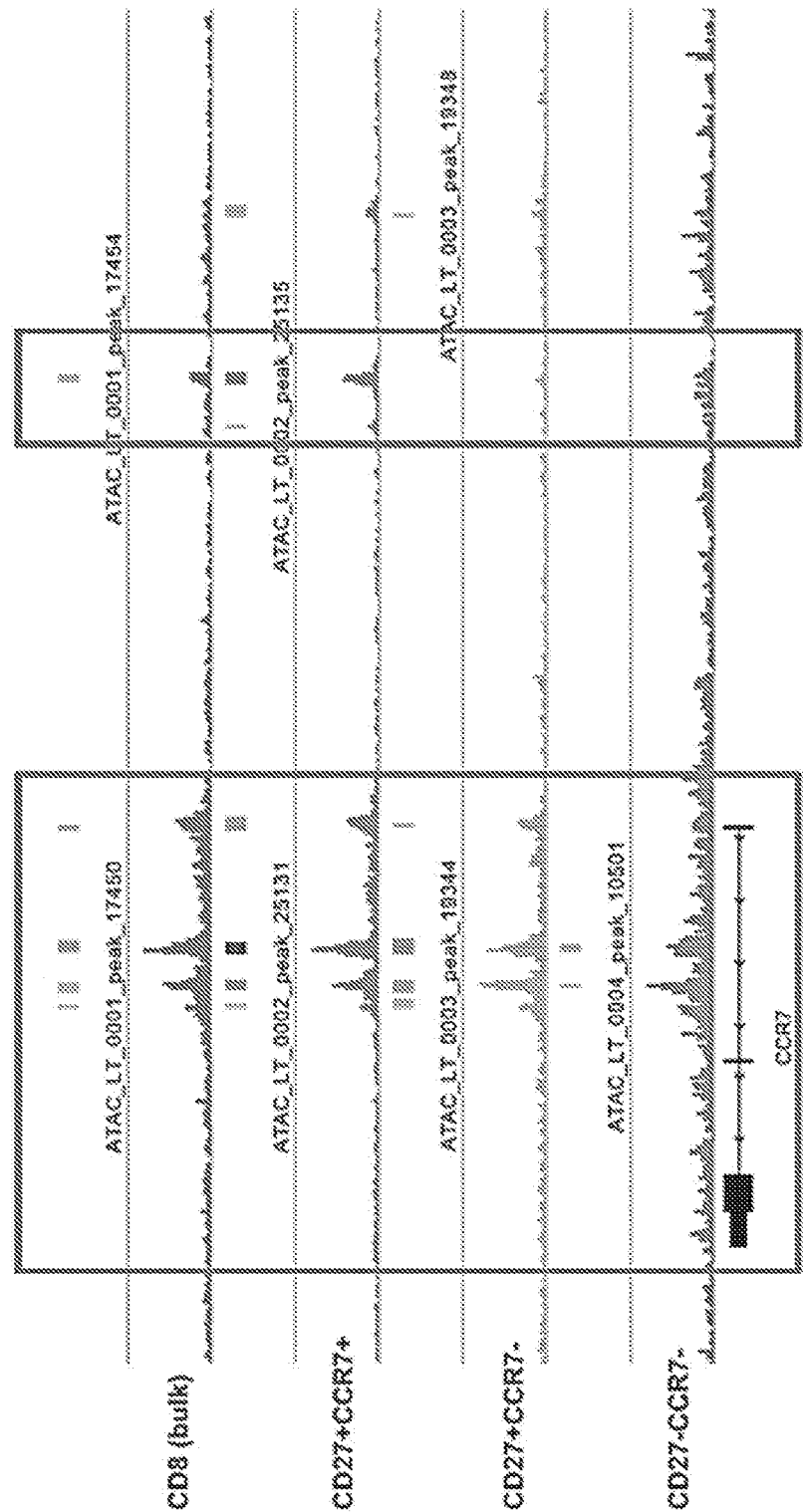
FIG. 13A shows exemplary chromatin accessibility peak profiles in the coding region and the intergenic region near the CCR7 gene was compared in CD27+CCR7+, CD27+ CCR7− and CD27−CCR7− cells, and bulk CD8+ cells.

The peak profile in the coding region and the intergenic region near the CCR7 gene was compared in CD27+CCR7+, CD27+CCR7− and CD27−CCR7− cells, and bulk CD8+ cells. As shown in FIG. 13A, CCR7+ cells showed a similar peak profile over the coding region of the CCR7 gene as CCR7− cells, but a peak was observed in an intergenic region upstream of the coding region in CCR7+ cells, indicative of an upstream enhancer site that associates with the expression of CCR7 in the cell.

Figure 13B:
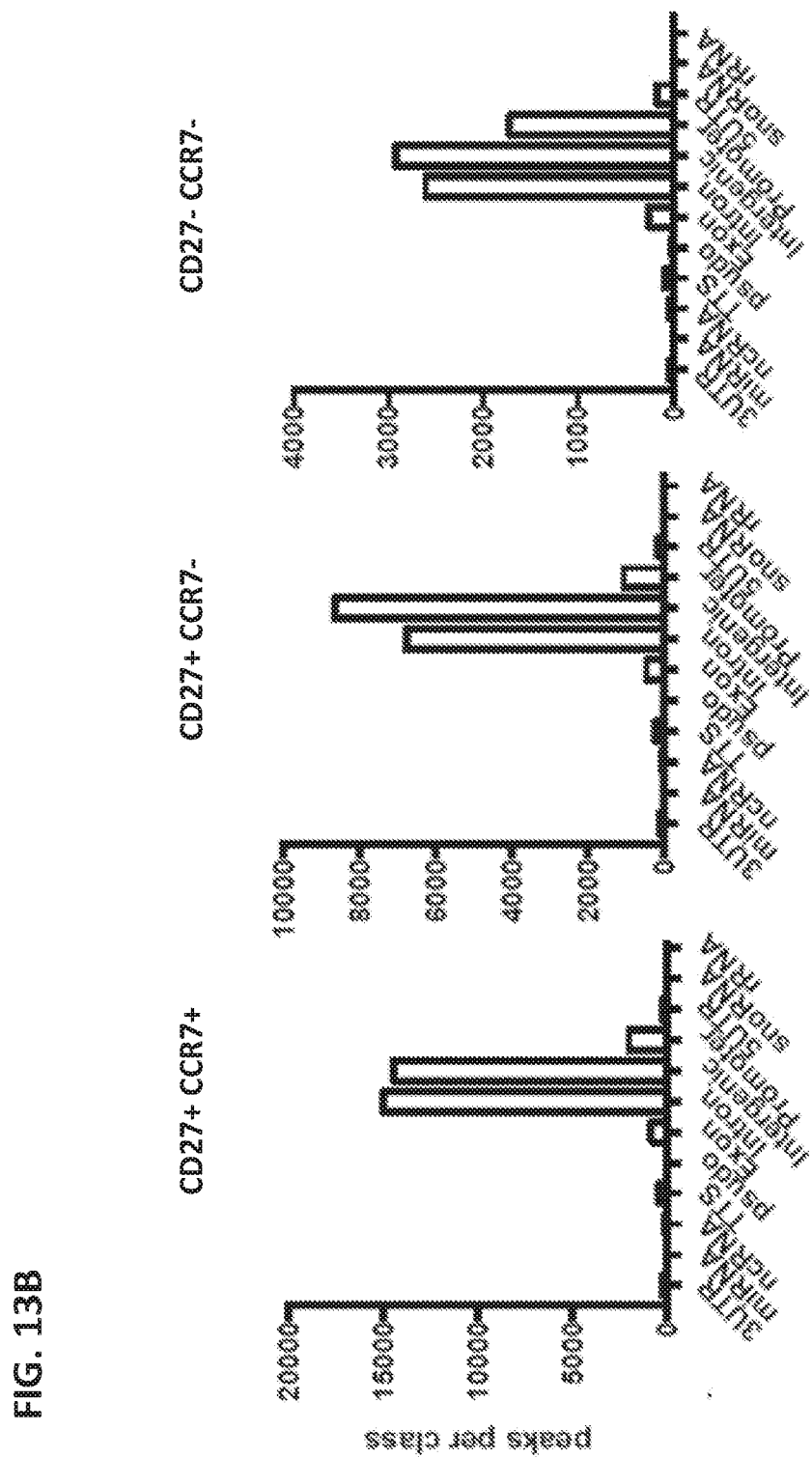
FIG. 13B shows the distribution of accessibility peaks within various genomic locations for the CD27+CCR7+, CD27+ CCR7− and CD27−CCR7− cells, and bulk CD8+ cells, including within intergenic, intron and promoter regions of genes.

The overall peak profiles of CD27+CCR7+ CDP cells, CD27+CCR7− CDP cells and CD27−CCR7− CDP cells were subject to gene accessibility analysis. The largest number of unique peaks was observed for the CD27+ CCR7+ CDP populations. FIG. 13B shows the distribution of accessibility peaks within various genomic locations for the cell populations, including within intergenic, intron and promoter regions of genes.

These results are consistent with a conclusion that accessibility around the coding region of a gene, and not just within a gene coding sequence, can provide information about a cell state.

Example 9: Genomic Accessibility and Peak Profile and Response Outcome in Subjects Administered Engineered T Cells The relationship between genomic accessibility and peak profiles in CDP cell compositions and response outcomes in subjects that have been administered engineered T cell was assessed. CD4+ and CD8+ CDP cell accessibility peak profile was determined by ATAC-seq for subjects that had been administered the autologous engineered cell compositions, generally as described in Examples 1 and 3 above.

Figure 14A:
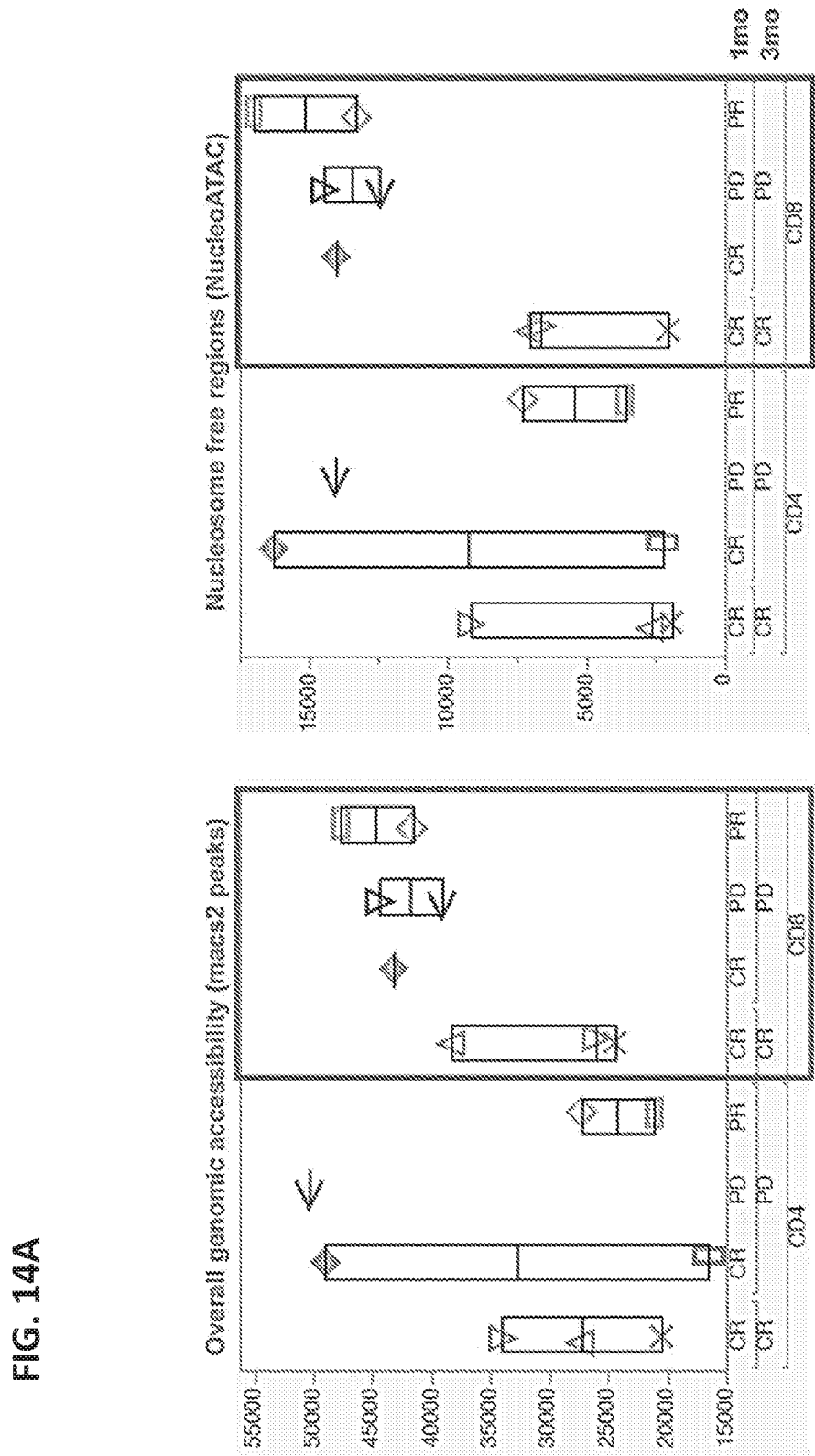
FIG. 14A shows the number of overall chromatin accessibility peaks, called using MACS2, and the number of nucleosome free regions, determined using NucleoATAC, in CD4+ and CD8+ CDP cells, from subjects who had been administered engineered CAR-T cells, grouped by response outcomes (1 month CR, 3 month CR, 1 month PD, 3 month PD, or PR).
Figure 14B:
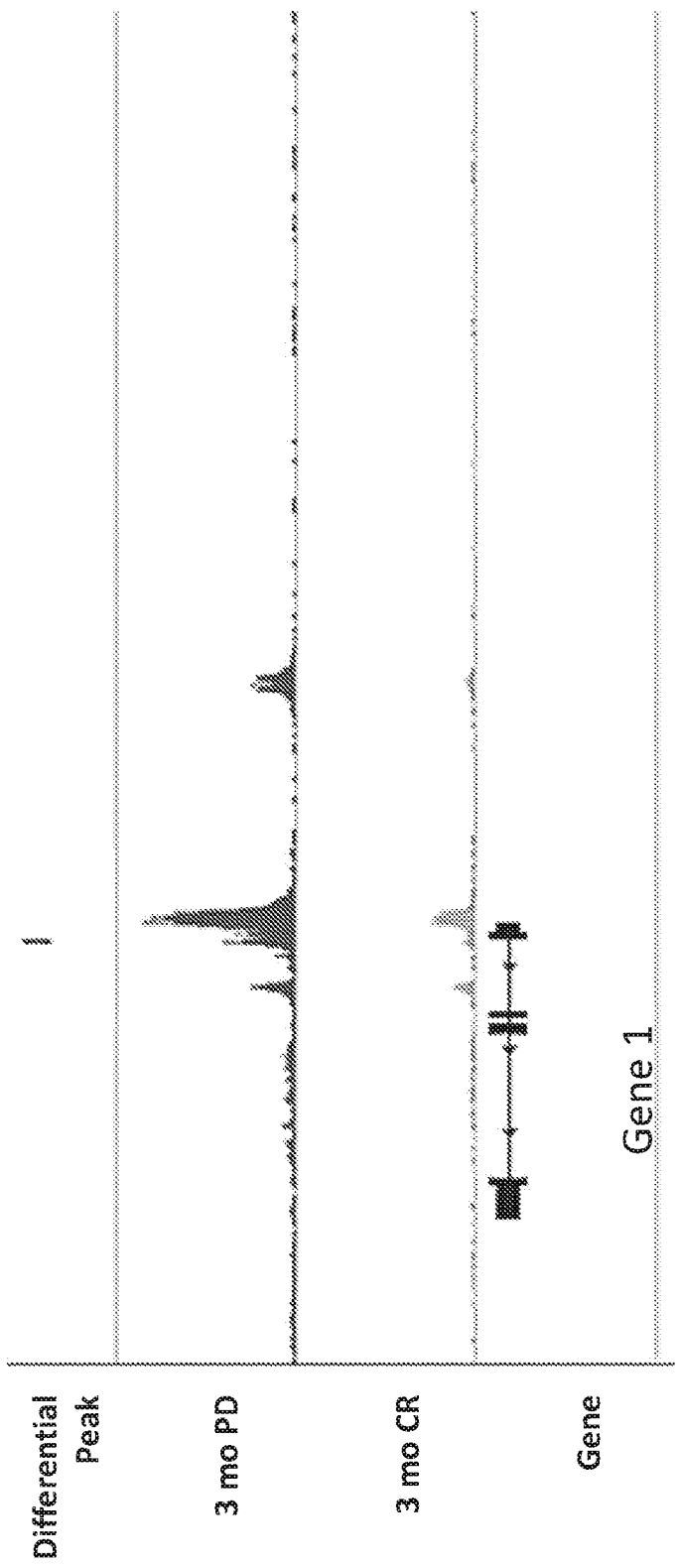
Figure 14D:
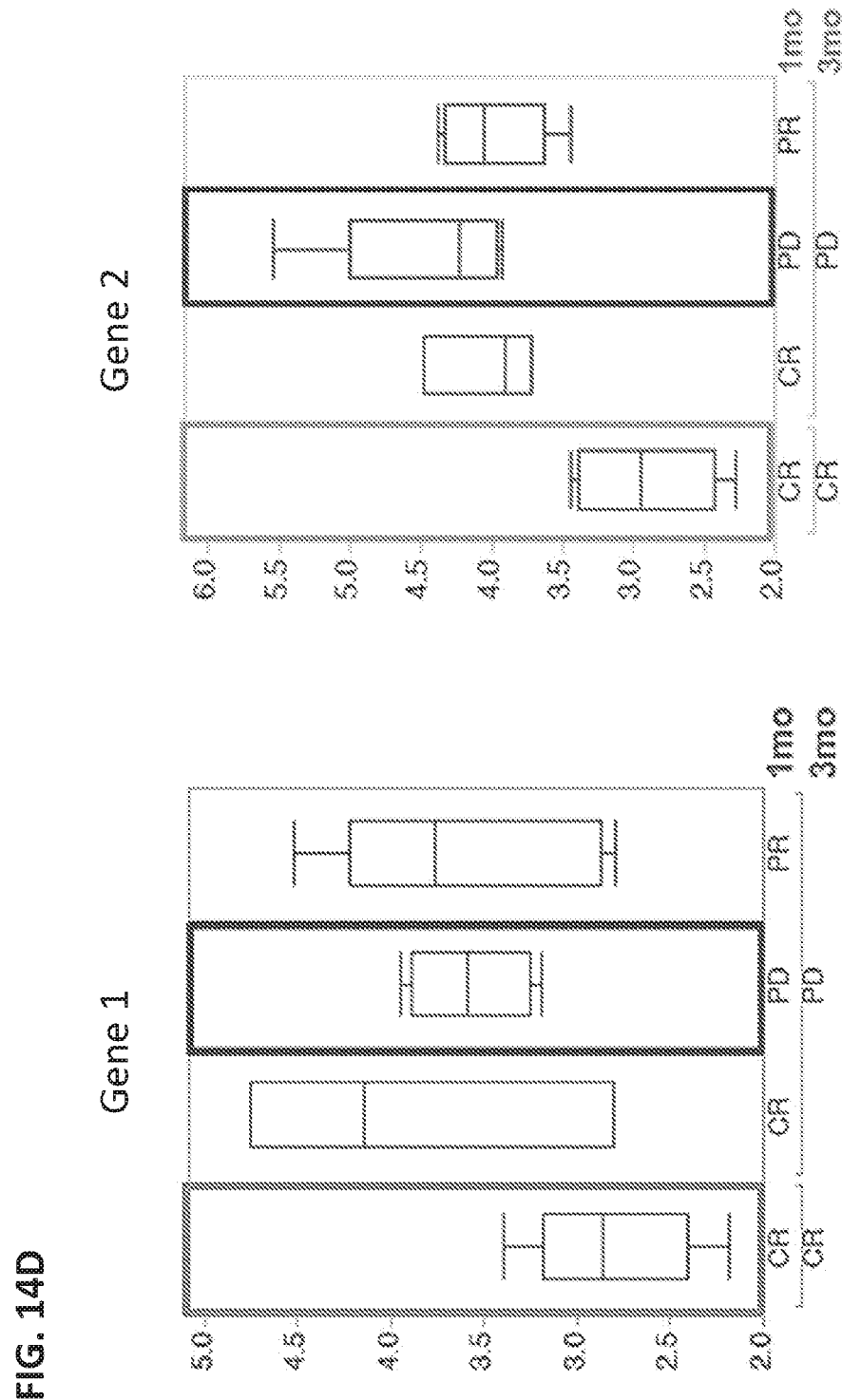

The overall number of genomic accessibility peaks and nucleosome free regions in CD4+ and CD8+ CDP cells and response outcomes (1 month CR, 3 month CR, 1 month PD, 3 month PD, or PR) was assessed. The ATAC-seq accessibility peaks were called using MACS2 and the nucleosome free regions were determined using NucleoATAC, described in Example 7. As shown in FIG. 14A, in CD8+ CDP cells, the number of overall genomic accessibility peaks and nucleosome-free regions was observed to be higher, indicating greater genome-wide accessibility, in subjects that exhibited PD or PR, compared to in subjects who exhibited 3 month CR. Measuring peak nucleosome free regions yielded similar results to analysis measuring chromatin accessibility peaks. Exemplary differential accessibility peak profiles, showing accessibility peaks that are different among samples, at the genomic regions near two exemplary immune-related genes (gene 1 and gene 2) in subjects with different response outcome are shown in FIGS. 14B-14D. As shown, accessibility near the exemplary gene loci were higher in subjects that exhibited a PD at 3 months, compared to subjects that exhibited a CR at 3 months.

Example 10: Assessment of Integration of Chimeric Antigen Receptor-Encoding Vector ATAC-seq was used to assess various parameters related to integration of a viral vector encoding a chimeric antigen receptor (CAR) in engineered cells.

ATAC-seq was performed generally as described in Examples 1 and 7 on a CDP cell composition that was engineered to express an anti-CD19 CAR by transduction with a viral vector encoding the anti-CD19 CAR (CAR integrants). CMAT cell compositions and cells transduced with an empty viral vector (empty integrants) were used as controls. The sequences from the ATAC-seq reads were aligned with the nucleic acid sequences encoding the CAR by treating the construct as an artificial chromosome during the alignment steps. Scaled number of integrants (ATAC-seq CAR integrants) was calculated as (aligned reads×read length)/(construct size)). A receiver operating characteristic (ROC) curve was generated by plotting the true positive rate against the false positive rate, and the area under the curve (AUC) was determined.

Figure 15B:
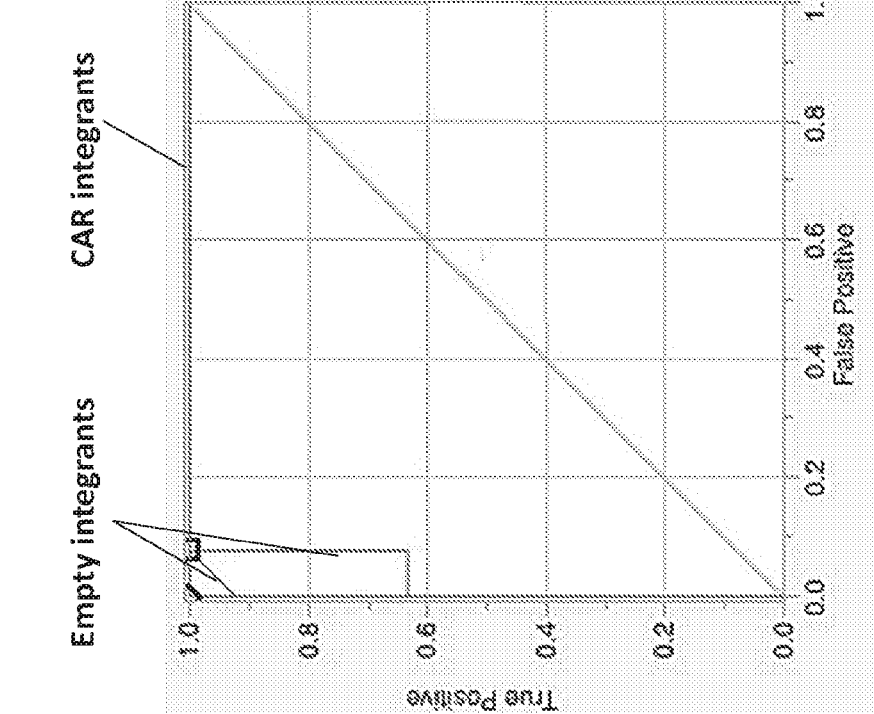
FIG. 15B shows a receiver operating characteristic (ROC) curve was generated by plotting the true positive rate against the false positive rate, for cells transduced with a vector encoding the anti-CD19 CAR (CAR integrants) and cells transduced with an empty viral vector (empty integrants).
Figure 15A:
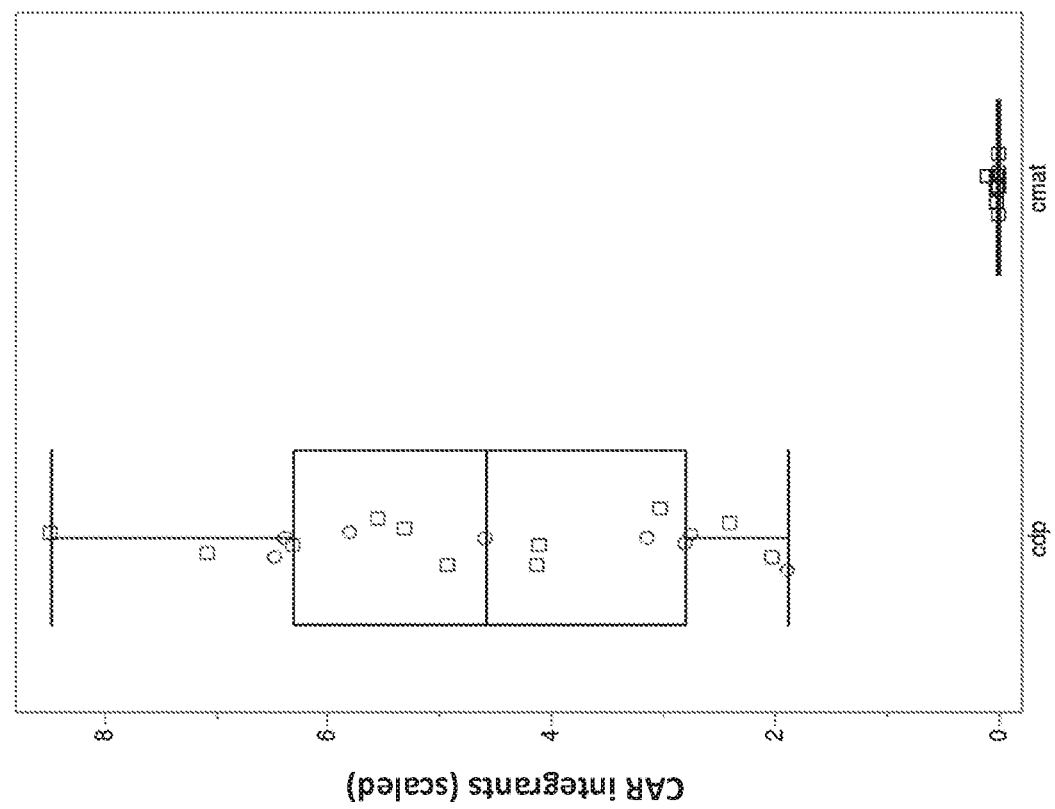
FIG. 15A shows the scaled number of integrants (calculated as (aligned reads×read length)/(construct size)) of viral vector sequences encoding an anti-CD19 CAR, in cryopreserved engineered cell compositions (CDP) engineered to express a CAR or matched samples that had not been subjected to engineering (CMAT).

As shown in FIGS. 15A and 15B, the analysis indicated the CAR-encoding nucleic acid sequence was integrated only in the engineered CDP cells and not in the CMAT cells, and were integrated into accessible regions in the genome, as indicated by ATACseq signal. The AUC (95% confidence interval) of the CAR integrants was 1, with CI low binomial of 0.61847 and CI high binomial of 0.6397; the AUC of the empty integrants was 0.9766, with CI low binomial of 0.056865 and CI high binomial of 0.63939). The results are consistent with the utility of the ATAC-seq methods to assess integration of recombinant vectors, e.g., viral vectors, such as CAR-encoding vectors, into the genome of engineered cells.

Figure 16B:
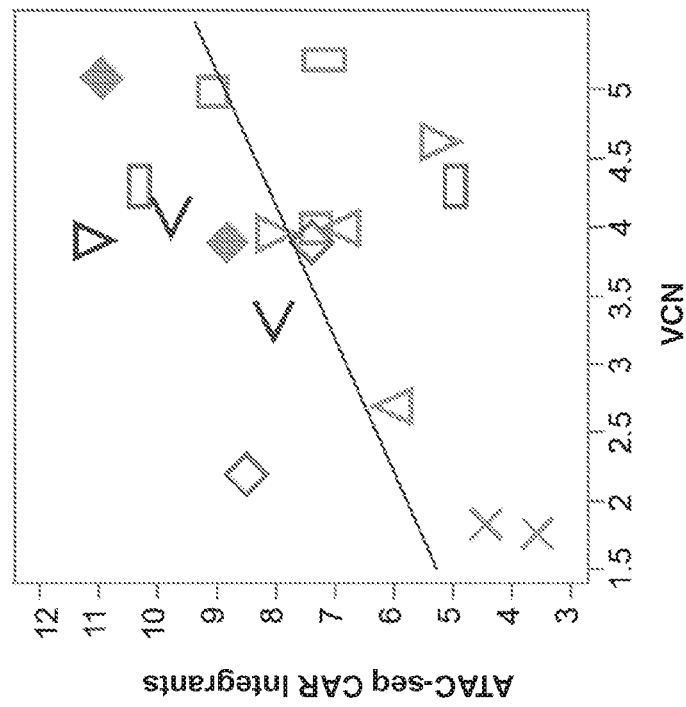
FIG. 16B shows a plot of the number of integrants as determined using ATAC-seq compared to the vector copy number (VCN) as determined by quantitative polymerase chain reaction (qPCR), in engineered cells.
Figure 16A:
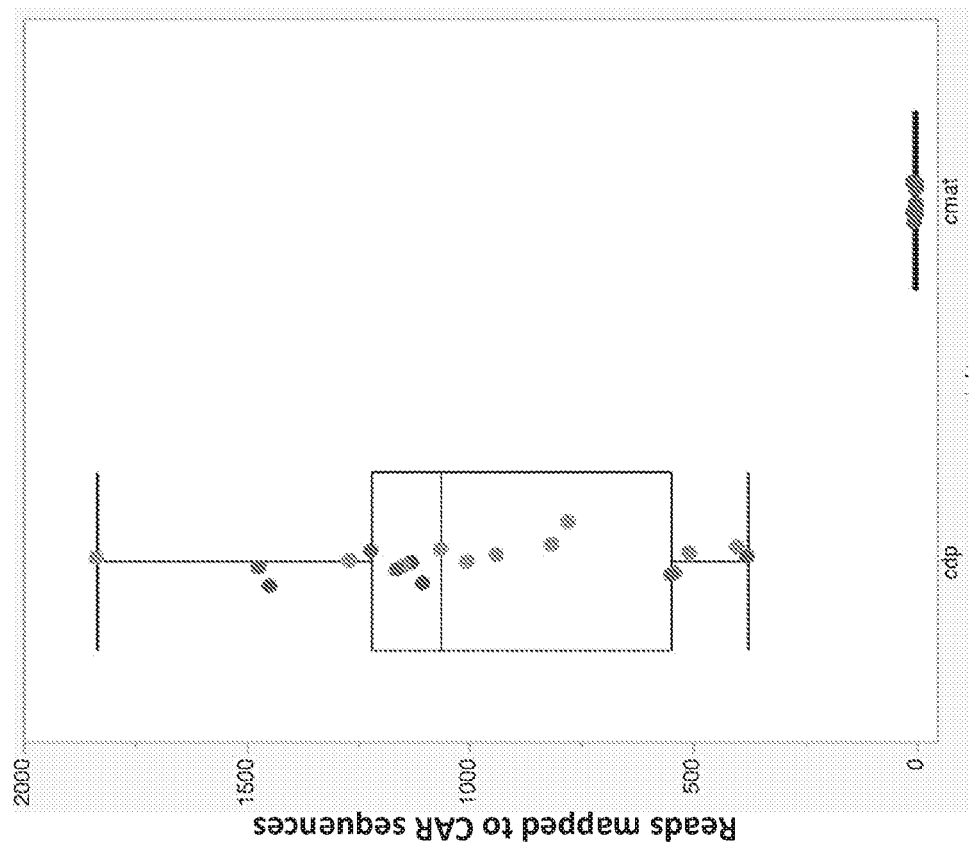
FIG. 16A shows the number of ATACseq reads mapped to CAR sequence, in CDP and CMAT samples.

In another study, the number of integrants as determined using ATAC-seq and vector copy number (VCN) as determined by quantitative polymerase chain reaction (qPCR) were compared, in CMAT and in anti-CD19 CAR T cell CDP compositions. As shown in FIG. 16A, ATAC-seq reads mapped to the CAR-encoding sequences in the CDP cells but not in the CMAT cells. The correlation between the scaled number of integrants as determined by ATAC-seq and VCN as determined by qPCR are shown in FIG. 16B (Nonparametric Spearman's ρ: 0.3121, probability>|ρ|: 0.2073).

Figure 17B:
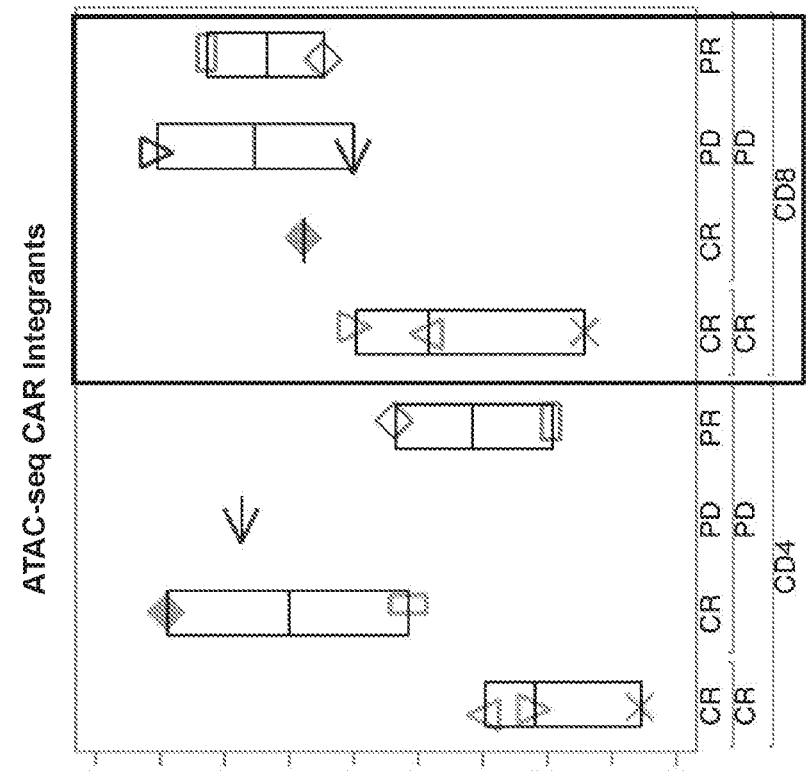
FIGS. 17A and 17B show the VCN (FIG. 17A) and the number of integrants as determined using ATAC-seq (FIG. 17B) in anti-CD19 CAR+ CD4+ and CD8+ T cells subjects who had been administered engineered CAR-T cells, grouped by response outcomes (1 month CR, 3 month CR, 1 month PD, 3 month PD, or PR) (excludes normal donor samples).
Figure 17A:
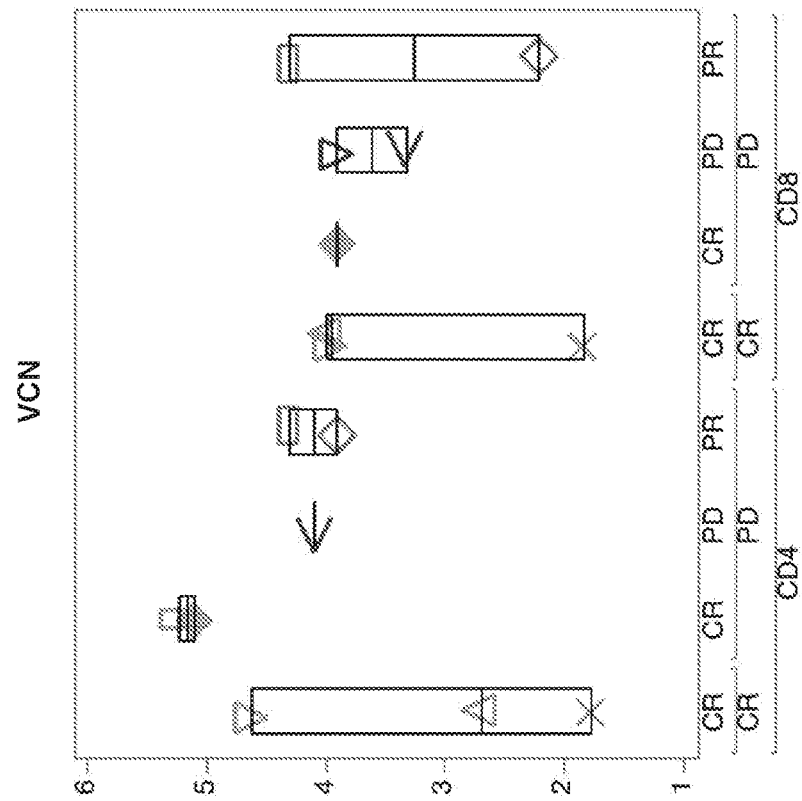

Integrants by ATAC-seq and VCN also was assessed in anti-CD19 CAR+ CD4+ and CD8+ T cells from subjects that had been administered the autologous anti-CD19 CAR+ CDP engineered cell compositions. As shown in FIGS. 17A and 17B (excludes normal donor samples), higher integrant number was observed in CD8+ CDP cells from subjects who achieved PD or PR, consistent with the observation that expression of the CAR construct in certain individuals may differ depending on chromatin accessibility, even when total VCN may be similar.

Figure 18:
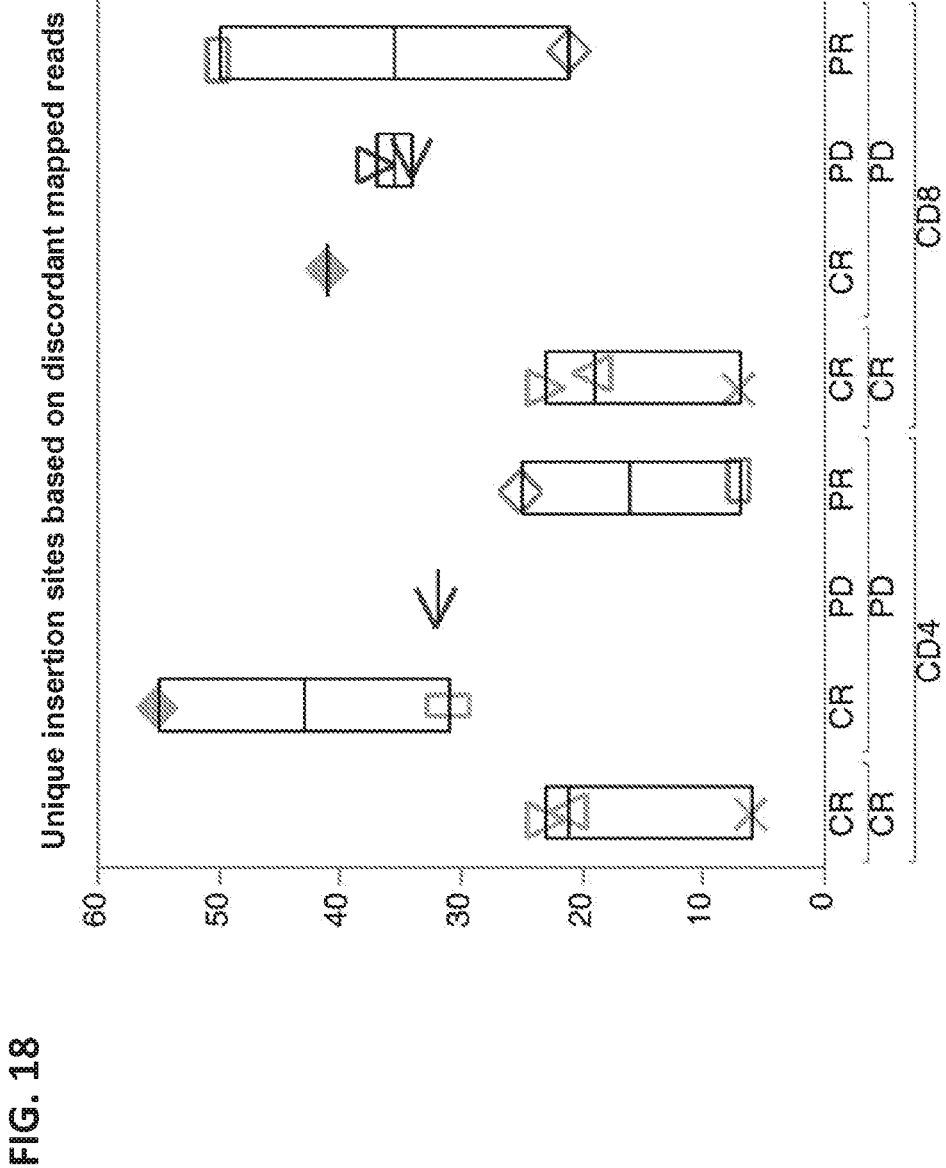
FIG. 18 shows the number of unique integration sites assessed by mapping discordant read pairs across 50,000 cells of unknown clonality, in CD4+ and CD8+ CDP cells from subjects grouped by response outcomes (1 month CR, 3 month CR, 1 month PD, 3 month PD, or PR) (excludes normal donor samples).

Unique integration sites were assessed by mapping discordant read pairs across 50,000 cells of unknown clonality, in CD4+ and CD8+ CDP cells from subjects that achieved different response outcomes (1 month CR, 3 month CR, 1 month PD, 3 month PD, or PR). The results are shown in FIG. 18. The results are consistent with an observation that in different subjects with relatively similar VCN, expression of the CAR construct may vary due to the epigenetic state and health of the cell, resulting in different response or durable response outcomes.

Example 11: Accessibility at T Cell Receptor (TCR) Loci

The chromatin accessibility peak profile was assessed across the loci encoding T cell receptor (TCR) chains in different anti-CD19 CAR+ T cell CDP T cell compositions and CMAT T cell compositions, or in CD8+ anti-CD19 CAR+ T cells from subjects having received administration of anti-CD19 CAR+ T cells.

Figure 19A:
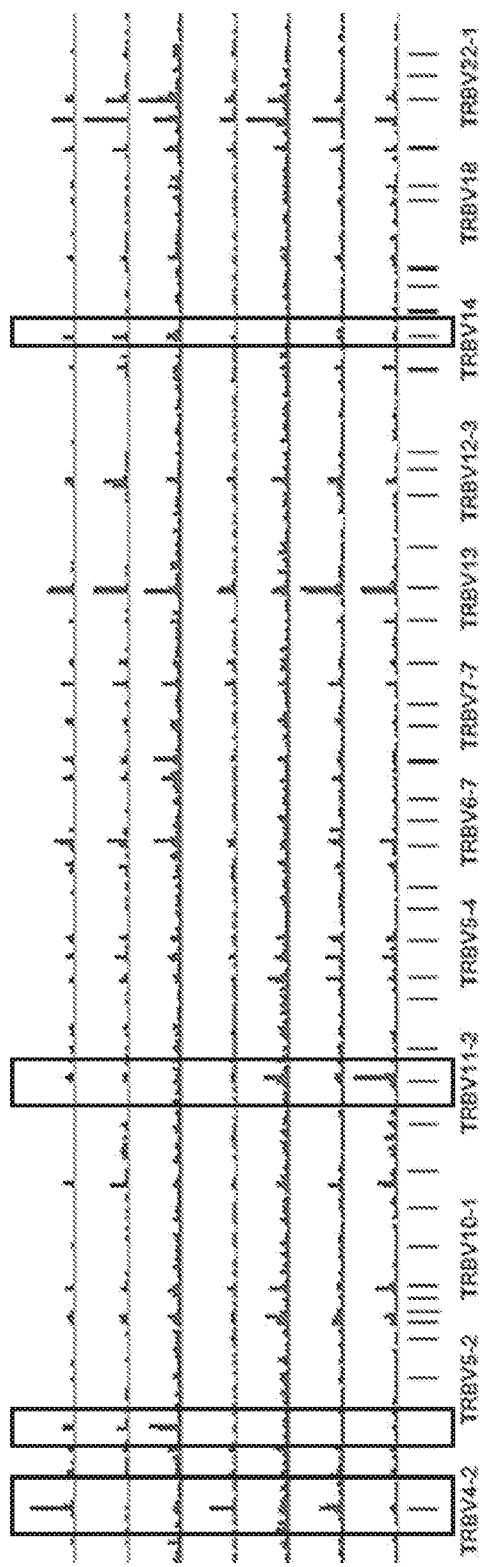
FIG. 19A shows exemplary chromatin accessibility peak profile was assessed across the loci encoding T cell receptor beta variable (TRBV) regions in different CD8+ CMAT cell samples from 7 exemplary subjects.
Figure 19B:
FIG. 19B shows the overall TCR accessibility and % coefficient of variation (CV) in the CD8+ CDP samples in ND or subjects who achieved CR or PD.
Figure 19C:
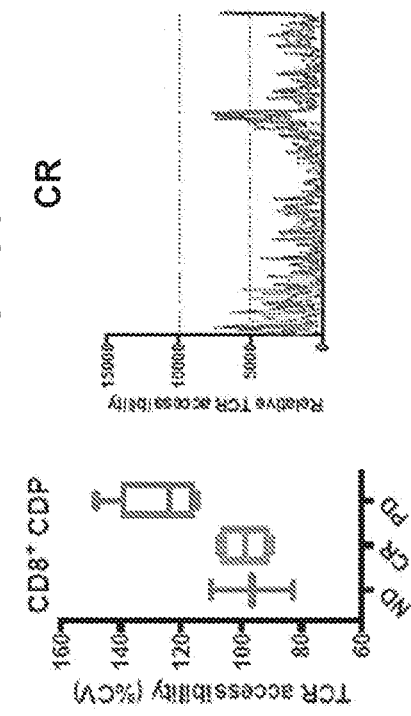
FIG. 19C shows the overall relative TCR accessibility in CD8+ anti-CD19 CAR+ T cells from subjects having received administration of anti-CD19 CAR+ T cells that achieved CR, PR or PD.

As shown in FIG. 19A, the accessibility peaks over the TCR beta chain-encoding loci were observed to be different in CD8+ CMAT samples from 7 exemplary subjects. The overall TCR accessibility and % coefficient of variation (CV) in the CD8+ CDP samples in ND or subjects who achieved CR or PD are shown in FIG. 19B. As shown in FIG. 19C, subjects that achieved different response outcome showed varying relative TCR accessibility across the TCR loci, with samples from subjects with PR or PD being more oligoclonal The results are consistent with the utility of ATAC-seq analysis to assess the differences in accessibility at regions of the TCR loci, and to generally assess clonality of T cells within a composition of cells.

Example 12: Chromatin Accessibility Profile and Additional Analysis in Cells from Different Donors at Different Stages of Cell Engineering Compositions of CD4+/CD8+ T cells from three different healthy donors, prior to and after genetic engineering with different chimeric antigen receptors, were assessed for chromatin accessibility using ATAC-seq, together with additional downstream analyses including principal component analysis (PCA), differential accessibility analysis, biological pathway analysis and analysis at selected subset of genes.

CD4+ and/or CD8+ T cells were isolated from three (3) healthy donors (Donors 1, 2 and 3) by immunoaffinity-based enrichment from leukapheresis of PBMCs and cryopreserved (CMAT, prior to engineering). The isolated CD4+/CD8+ T cells were activated for 24 hours and transduced with a viral vector, encoding one of two different anti-CD19 CARs or an anti-BCMA CAR, or mock transduction as controls, and cryopreserved (CDP, cryopreserved engineered cell compositions). The cells were subject to ATAC-seq analysis, generally as described in Example 1 above.

The obtained sequences were mapped and ATAC-seq accessibility peaks were called using MACS2. Raw sequencing counts were processed with the DESeq2 package to estimate sizing factors, dispersion estimates and perform a negative binomial generalized linear model fit. Fraction of reads in peaks (FRiP; showing enrichment of signal, calculated as (number of reads in peaks)/(number of total reads))-normalized counts were extracted with a betaPrior set to True. After raw data were demultiplexed, aligned and filtered to quality specifications as above they were imported into and the following analysis steps were done in R. Peaks were annotated with the ChIPpeakAnno package or Homer software. Transcription star site (TSS) region was defined as proximal 2000 bp upstream and 500 bp downstream of promoter. Peak overlaps and consensus peaks for group analysis was performed with DiffBind package. After overlaps were calculated, peaks found in more than two libraries were filtered and sequencing counts extracted. The obtained sequences and peaks were analyzed using various sequencing quality control metrics, including unmapped, unpaired and duplicate reads, fraction of mitochondrial DNA, sequence depth, reads mapping to the CAR-encoding constructs, number of MACS2 peaks with a false discovery rate (FDR) of 0.1 or less, FRiP and number of unique peaks, to ensure consistency and fidelity of the data.

Clustering analysis was performed based on overall epigenetic profiles of various samples. The results showed that samples tended to cluster first based on type of sample, e.g. CMAT or CDP, then based on donor, and, for CDP, last based on type of construct.

Principal component analysis (PCA) was performed for dimensionality reduction to examine overall variance in the data and parse out key drivers on consensus peaks, e.g., peaks present in 2 or more samples, on CMAT and various CDP samples from the different donors (PC1, contributing to 33.996% of variation; associated with the difference between CDP and CMAT; PC2, contributing to 10.13% of variation; associated with T cell states). 31 principal components were calculated during this step. The results showed a pattern of three different CMATs, from different donors, resulting in three different CDPs after engineering, consistent with the clustering data described above. The various different CAR constructs used for engineering resulted in similar profiles on the PCA analysis.

Figure 20A:
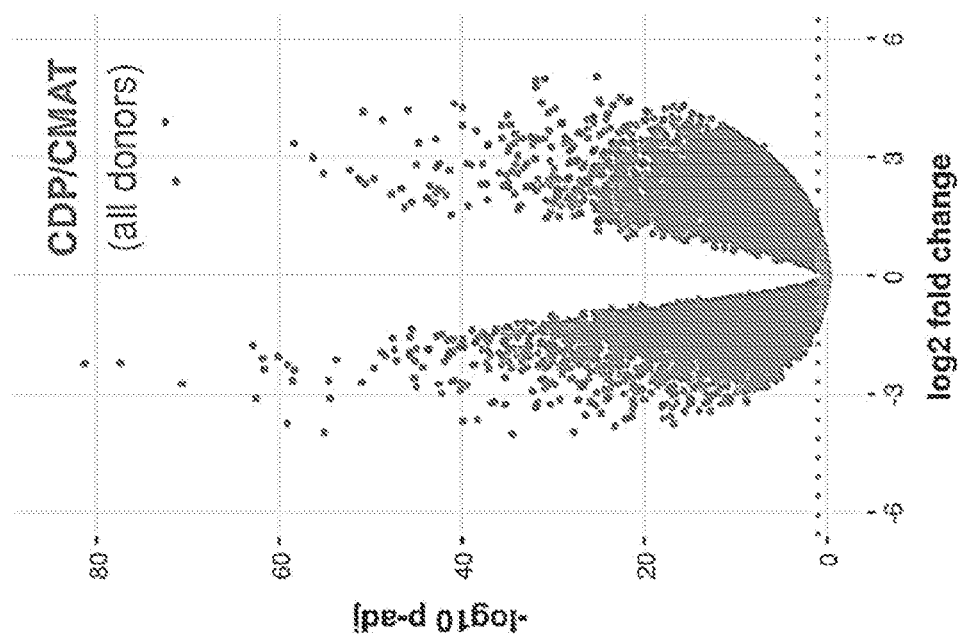
FIG. 20A shows a volcano plots depicting statistical significance of chromatin accessibility ($\log_{10}$ of adjusted p-value) with the $\log_2$ fold-change in chromatin accessibility, from a differential accessibility analysis for CDP and CMAT from T cells isolated from three (3) healthy donors. The tables indicate the number of genes or peaks that showed increase (up) or decrease (down) in accessibility.

Differential accessibility analysis was performed, using models built with DESeq2 package. Differential results were extracted and significance peaks were assigned as those passing a false discovery rate (FDR, or q) of 0.1. Results from an exemplary differential accessibility analysis, for CDP and CMAT from all donors, is shown in FIG. 20A. Biological pathway analysis using differential peaks was performed, based on Gene Set Enrichment Analysis (GSEA) using the Ingenuity Canonical Pathway, Biofunctions and Predicted Upstream Regulators analyses. The results showed enrichment of differential peaks in various pathways involved in T cell response, signaling pathways related to immune cell activity and/or function, biofunctions related to immune cells and predicted upstream regulators of genes related to immune function.

Gene module analysis was performed, using the following selected module of genes: genes in the "T cell module" (Chaussabel et al., (2008), Immunity 29(1): 150-164); genes in the "cytokines" module (Immgen Consortium (Best et al., Nature Immunology (2013) 14:404-412)); genes in the Th1.cells module, CD8pos. $T_{EM}$ module and CD4pos. $T_{EM}$ module (xCell (Aran et al. Genome Biology (2017) 18:220; http://xcell.ucsf.edu/)); "memory" module (Weng et al., (2012) Nat Rev Immunol. 12(4):306-15)), "trafficking" module including chemokine receptor genes and "exhaustion" module (Martinez et al., (2015) Immunity 42(2):265-278). FRiP-normalized or FPKM counts were used for the gene module analysis. In the case of FRiP-normalized counts, peaks at promoters were used as a proxy for a gene-level metric. Counts were log 2 transformed and graphically aligned to color scales. Hierarchical clustering was performed with JMP software or the Pheatmap R package.

Clustering analysis based on a normalized accessibility count metric for the promoter region of each gene (promoter accessibility), showed clustering of CMAT samples separate from the CDP samples, and an analysis of CMAT and CDP profiles showed that the engineering process appears to reduce detectable variation in memory T cell ($T_{MEM}$) and effector cell signature. The results also showed that varied engineered cell composition (CDP) can be produced, with different epigenetic states, from different donors.

Figure 20B:
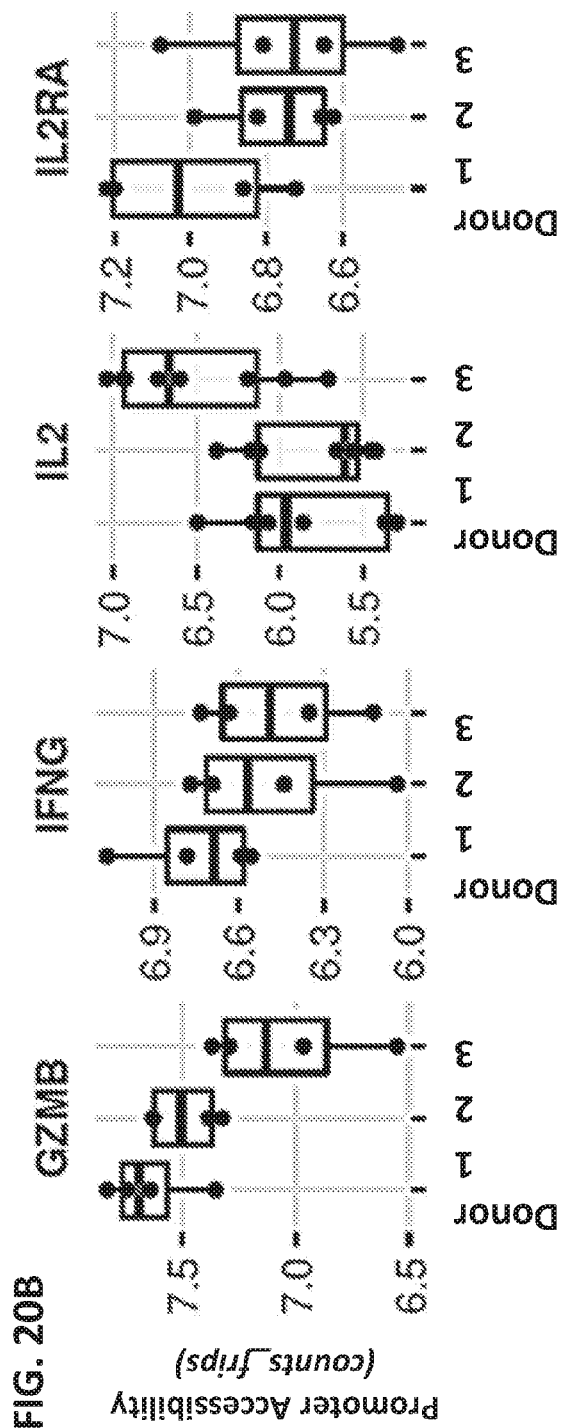
FIGS. 20B and 20C shows promoter accessibility (counts_frips) at exemplary individual promoters of genes in the "cytokines" module (FIG. 20B) and the "exhaustion" module (FIG. 20C), from a gene module analysis of immune related genes.
Figure 20C:
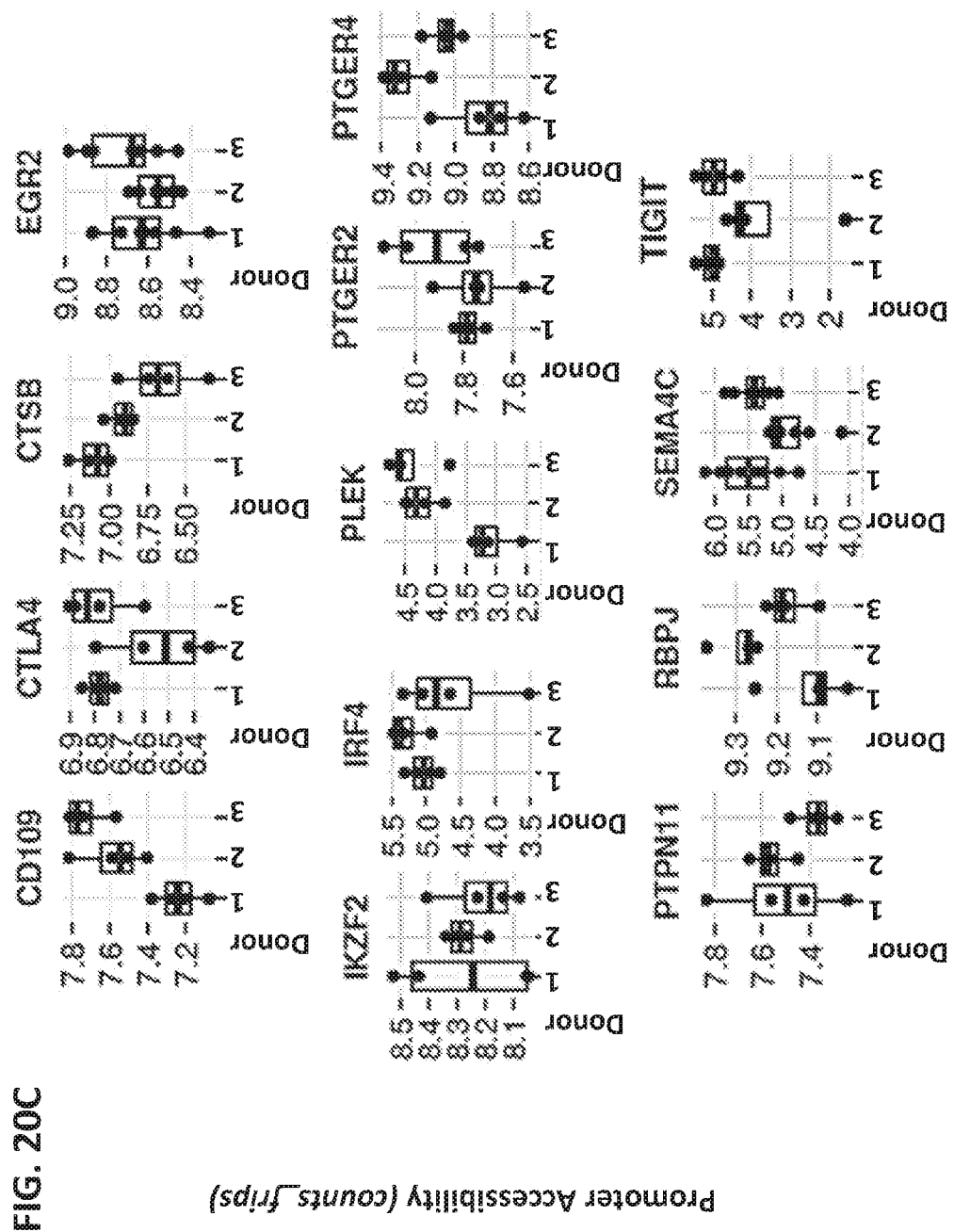

Clustering analysis of CDP samples for the "T cell module," "memory T cell module" and "trafficking module" genes showed that CDPs from different donors generally clustered together, distinguishing donors. Results of promoter accessibility at exemplary individual promoters of genes in the "cytokines" module and the "exhaustion" module are shown in FIGS. 20B ("cytokines") and 20C ("exhaustion").

The results are consistent with the utility of promoter accessibility as a metric to distinguish different states of T cells, e.g., during the manufacturing process.

Example 13: Chromatin Accessibility Analysis and Treatment Outcomes in Subjects Administered Engineered T Cells Chromatin accessibility profiles were assessed in CMAT and CDP samples from subjects in a clinical study who had been administered autologous engineered cells expressing a chimeric antigen receptor (CAR). Accessibility profiles were determined and compared in subjects who achieved certain response outcomes or subjects who developed a toxicity.

A. Subjects and Cell Compositions

Adult human subjects with relapsed or refractory (R/R) aggressive non-Hodgkin's lymphoma (NHL) administered autologous engineered CD4+ and/or CD8+ T cells expressing an anti-CD19 CAR. For generation of engineered cells, CD4+/CD8+ T cells were isolated by immunoaffinity-based enrichment from leukapheresis of PBMCs and cryopreserved (CMAT, prior to engineering). Isolated CD4+/CD8+ T cells were activated and transduced with a viral vector encoding an anti-CD19 CAR, containing an anti-CD19 scFv, an immunoglobulin-derived spacer, a transmembrane domain derived from CD28, a costimulatory region derived from 4-1BB, and a CD3-zeta intracellular signaling domain. The viral vector further contained sequences encoding a truncated receptor, which served as a surrogate marker for CAR expression; separated from the CAR sequence by a T2A ribosome skip sequence. The resulting engineered cells were cryopreserved (CDP, cryopreserved engineered cell compositions).

B. ATAC-Seq and Quality Metrics

A total of 82 CD4+ or CD8+ CMAT or CDP samples from 24 subjects, were assayed by ATAC-seq, generally as described in Example 1. The obtained sequences were mapped and ATAC-seq accessibility peaks were called using MACS2. The obtained sequences and peaks were analyzed using various sequencing quality control metrics, including unmapped, unpaired and duplicate reads, fraction of mitochondrial DNA, effective sequence depth, number of MACS2 peaks with a false discovery rate (FDR) of 0.1 or less, fraction of reads in peaks (FRiP) and number of unique peaks, to ensure consistency and fidelity of the data. Seven (7) samples were excluded for due to low enrichment and/or data fidelity.

In some cases, technical replicate samples were obtained and assayed. Interval analysis, PCA, peak overlaps and Log 2 normalized counts in peaks were assessed for the technical replicates, and Spearman correlations were calculated. The results showed that the replicates showed highly similar profiles, with a large overlap and high correlation coefficients.

C. Analysis of CD4+ and CD8+ CDP and CMAT

Figure 21:
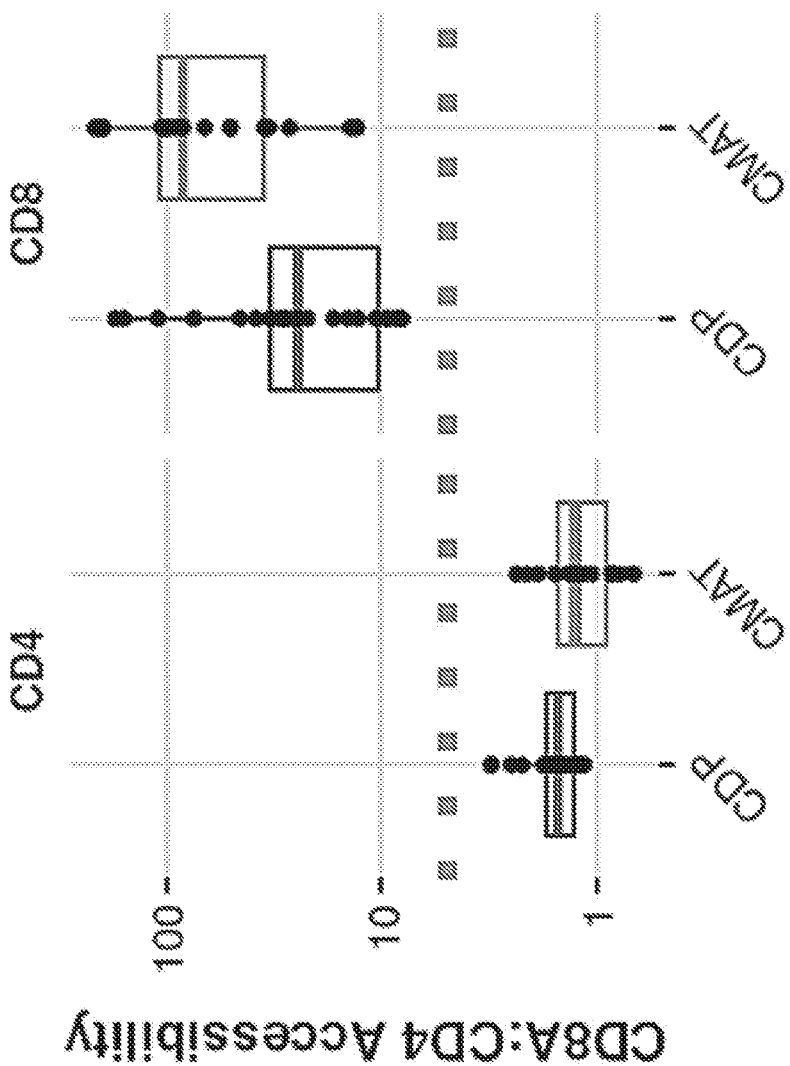
FIG. 21 shows the relative accessibility at ratio of accessibility at CD8A promoter to accessibility at CD4 promoter in CD4+ and CD8+ cell populations.

A normalized accessibility count metric for the promoter region of each gene (promoter accessibility) was assessed at the CD4 and CD8A promoters in the CDP and CMAT cell populations as a confirmation of the cell types, based on the chromatin accessibility at each locus in the CD4+ and CD8+ cell populations. The ratio of accessibility at CD8A promoter to accessibility at CD4 promoter was determined. As shown in FIG. 21, the CD8A:CD4 accessibility ratio reflected the CD4+ or CD8+ status of each composition, for both CDP and CMAT samples.

Principal component analysis (PCA) was performed on the consensus peaks (144,591 peaks) for all samples. The results showed that in general, CMAT CD4+ samples clustered together and CMAT CD8+ cells clustered together, in disparate clusters on the PCA plot. CD4+ CDP samples and CD8+ CDP samples tended to cluster within the same group, with CD4+ CDP samples and CD8+ CDP samples forming sub-clusters based on CD4 or CD8 expression. The results indicated that the engineering process resulted in a reduced variation in overall profile for CD4+ and CD8+ cells. In comparison, prior to engineering, CD4+ and CD8+ samples showed a more varied profile.

Clustering analysis using the total consensus peak set (122,495 peaks for CDP and 106,867 peaks for CMAT) was performed in CD4+ and CD8+ CDP samples. The results showed that for both CMAT and CDP samples, the CD4+ or CD8+ cell types typically clustered together.

D. Analysis Related to Clinical Outcomes

Differential accessibility analysis was performed, for peaks with different accessibility, in samples from subjects that went on to achieve different response outcomes or toxicity outcomes, after administration of the engineered cell composition.

Figure 22A:
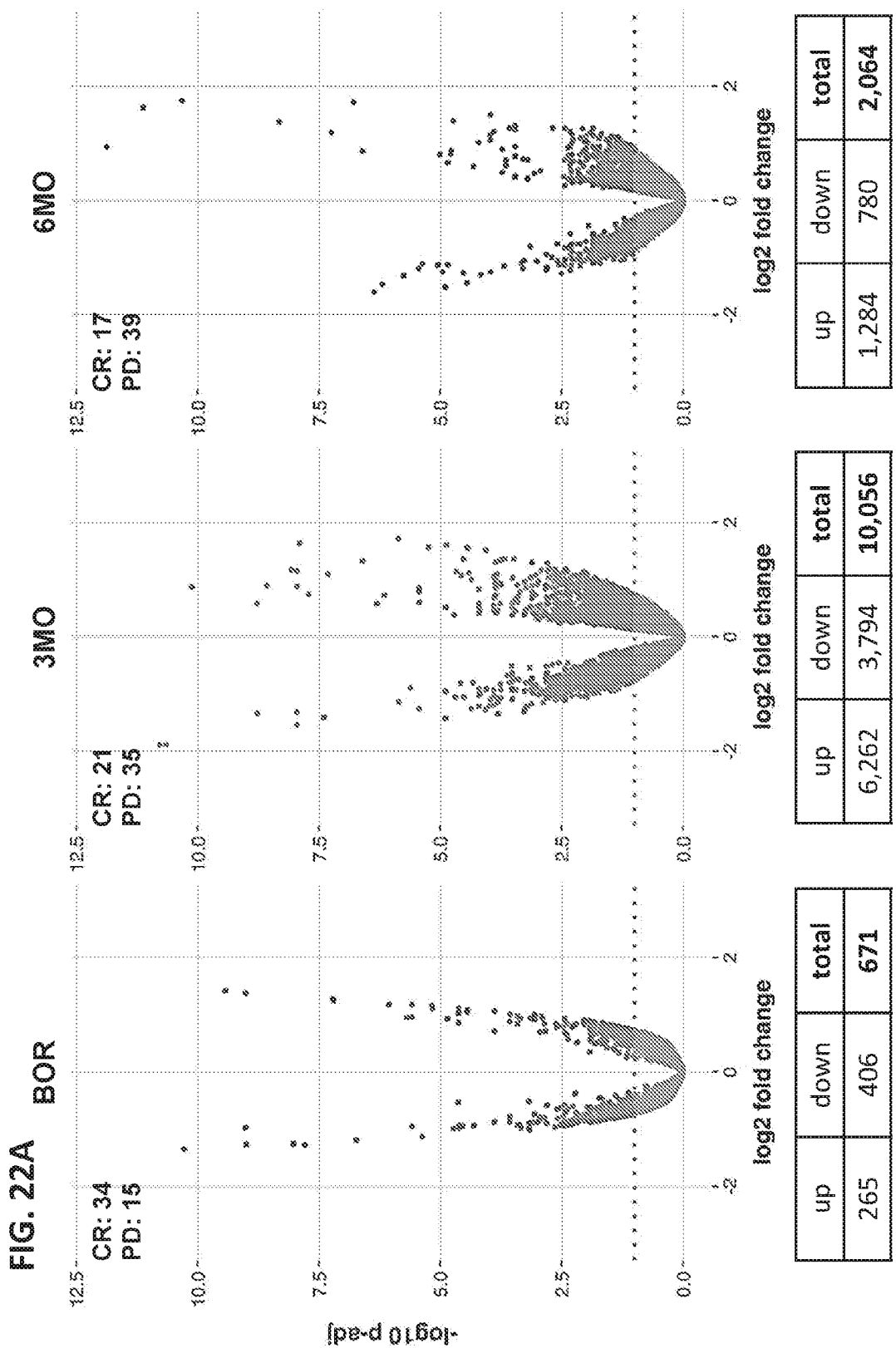
FIG. 22A shows a volcano plot showing the log 2 fold change and adjusted p-value for peaks with higher or lower accessibility, in subjects with progressive disease (PD) compared to subjects who achieved complete response (CR), as the best overall response (BOR), durable response at 3 months (3 MO) or durable response at 6 months (6 MO). The tables indicate the number of genes or peaks that showed increase (up) or decrease (down) in accessibility. The number of subjects in the CR or PD group are shown on the upper left hand side of each graph.

FIG. 22A shows the log 2 fold change and adjusted p-value for peaks with higher or lower accessibility, in subjects with progressive disease (PD) compared to subjects who achieved complete response (CR), as the best overall response (BOR), durable response at 3 months (3 MO) or durable response at 6 months (6 MO), with the corresponding number of peaks that were differentially present in the samples. A large number of differentially accessible peaks were present in the 3 month and 6 month response analysis, indicating that the epigenetic state in the cell compositions were different for subjects who achieved a CR, compared to for subjects who had PD at 3- or 6-months. Peak overlap analysis showed that many of the peaks that were shown to be differentially accessible in the 6 month response analysis overlapped with the peaks in the 3 month response analysis, and some of the peaks in the BOR analysis also overlapped with peaks in the 3 month response analysis.

Figure 22B:
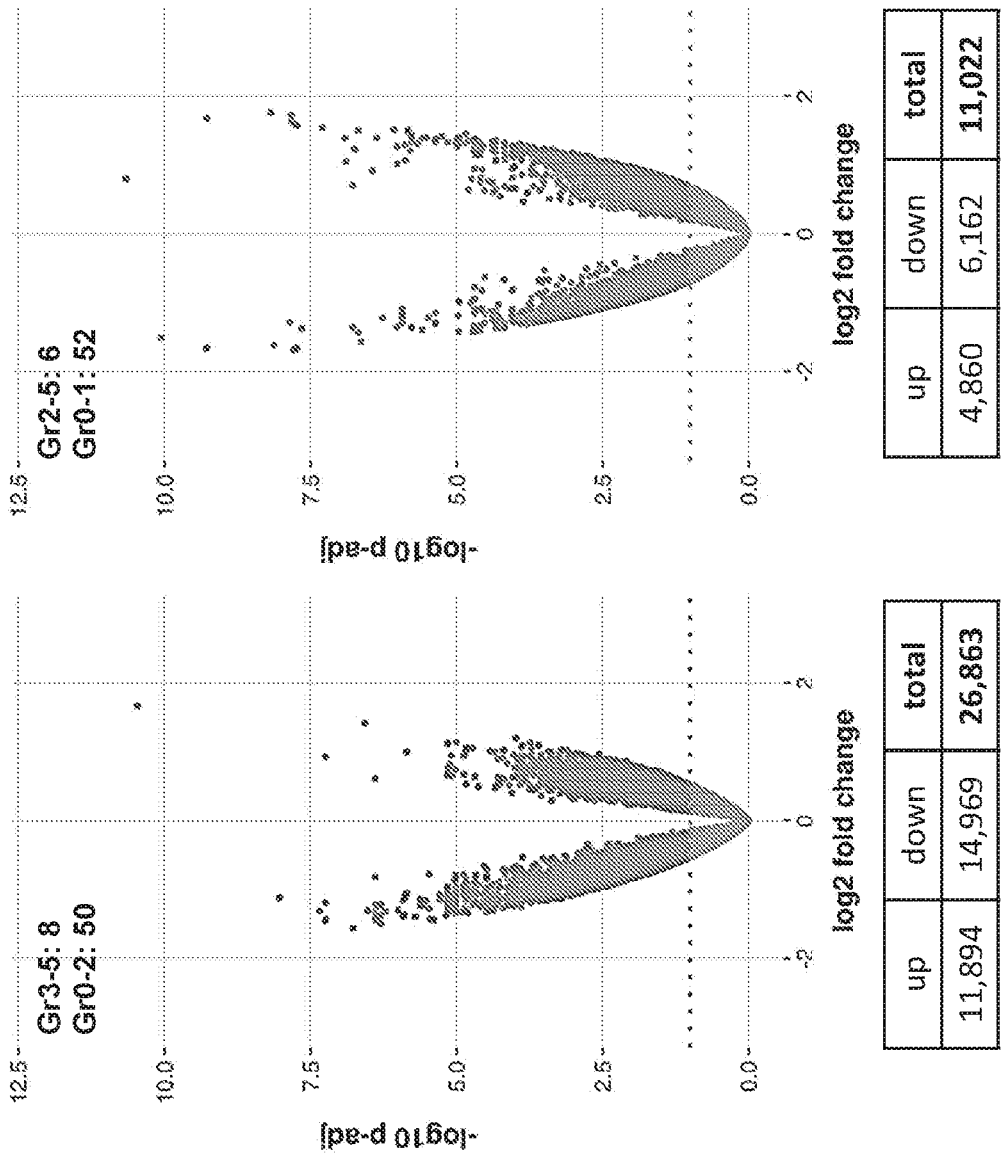
FIG. 22B shows the fold change and adjusted p-value for peaks with higher or lower accessibility, in subjects who developed grade 3-5 neurotoxicity (Ntx), compared to subjects with grades 0-2 Ntx, or grades 2-5 cytokine release syndrome (CRS) compared to subjects with grades 0-1 CRS, with the corresponding number of peaks that were differentially present in the samples. The tables indicate the number of genes or peaks that showed increase (up) or decrease (down) in accessibility. The number of subjects with each grade of the toxicity are shown on the upper left hand side of each graph.

FIG. 22B shows the log 2 fold change and adjusted p-value for peaks with higher or lower accessibility, in subjects who developed grade 3-5 neurotoxicity (Ntx), compared to subjects with grades 0-2 Ntx, or grades 2-5 cytokine release syndrome (CRS) compared to subjects with grades 0-1 CRS, with the corresponding number of peaks that were differentially present in the samples. Overlap analysis showed that only some of the peaks were overlapping between Ntx and CRS analyses. The results show a large number of differential accessibility peaks between the groups for both Ntx and CRS.

E. Analysis of CMAT and CDP Related to Clinical Outcomes

PCA on normalized counts on consensus peak sets, and differential accessibility analysis in CDP or CMAT samples from subjects that achieved different response outcomes or toxicity outcomes, generally as described above. PCA for CDP samples (consensus set: 112,495 peaks) showed that generally CD4+ and CD8+ samples clustered based on the cell type (CD4+ or CD8+ cells). PCA of CMAT samples (consensus set: 106,867 peaks) also showed that generally, samples clustered based on cell type (CD4+ or CD8+), however these samples did not cluster as tightly as the CDP samples indicating that the variability was greater within different CMAT samples, compared to the variability within the CDP samples.

Figure 23B:
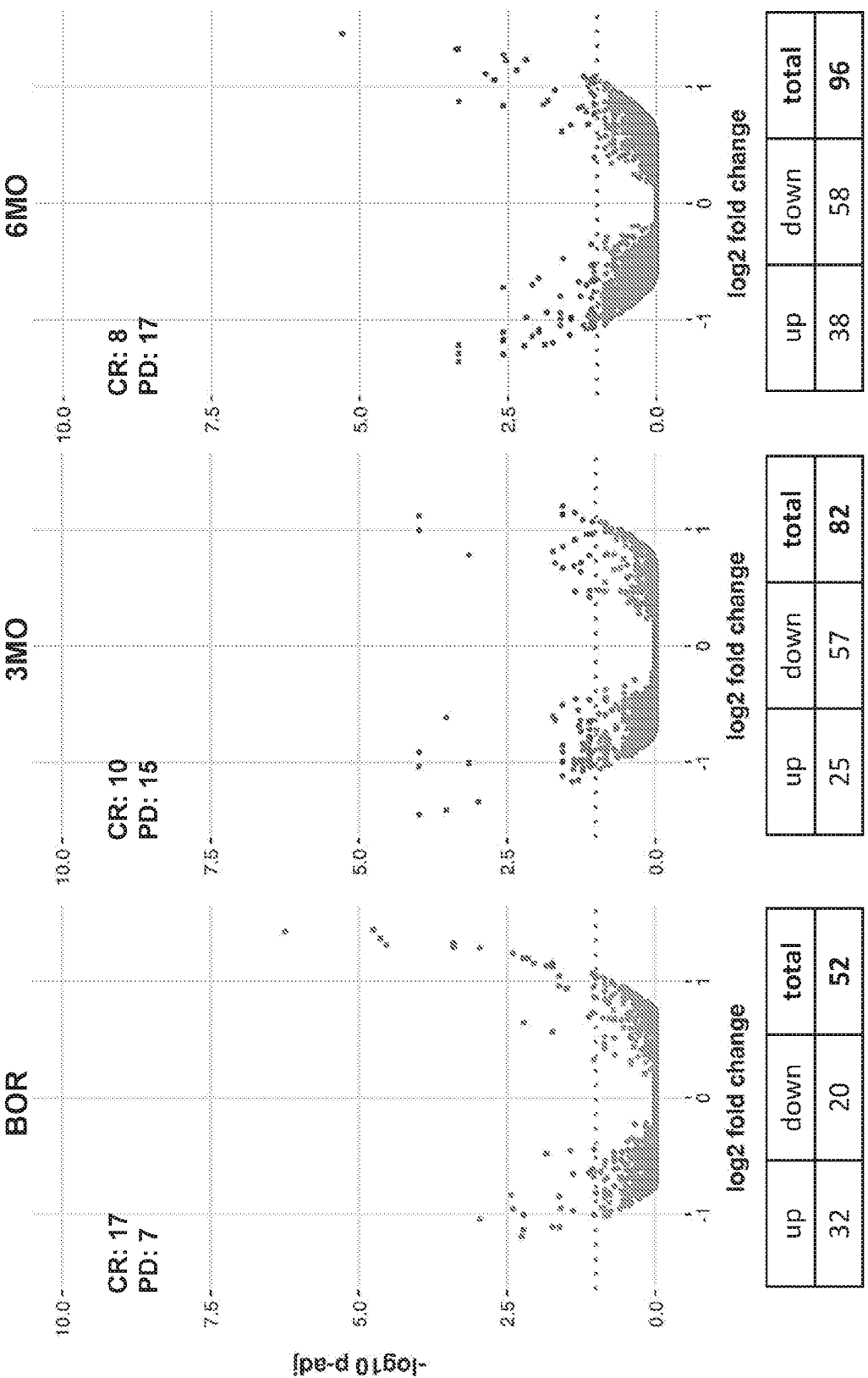
FIGS. 23A and 23B show volcano plots showing peaks with higher or lower accessibility, in subjects based on response groups, for CDP (FIG. 23A) or CMAT (FIG. 23B).

Differential accessibility analysis for response outcome, for BOR, 3-month and 6-month response, was performed in the CDP samples and in the CMAT samples separately. As shown in FIGS. 23A (CDP) and 23B (CMAT), a large number of peaks were differentially accessible for the 3- and 6-month response analysis in the CDP samples, but very few peaks were differentially accessible in the CMAT samples. Overlap analysis showed that for CDP, many of the differentially accessible peaks overlapped in 3- and 6-month response analysis, but the overlap of each with BOR peaks were low, and very few peaks were present and overlapping for CMAT.

Figure 23C:
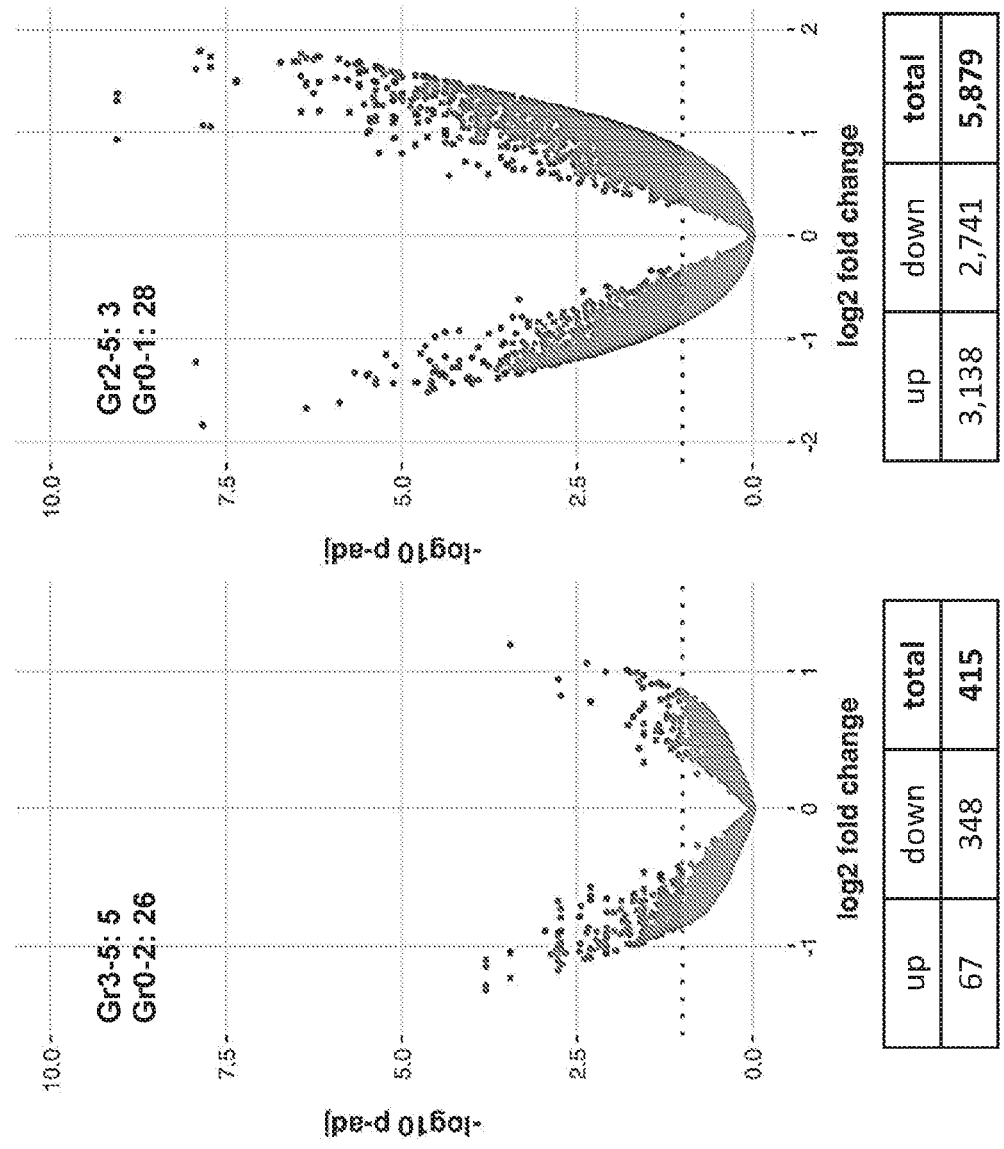
Figure 23D:
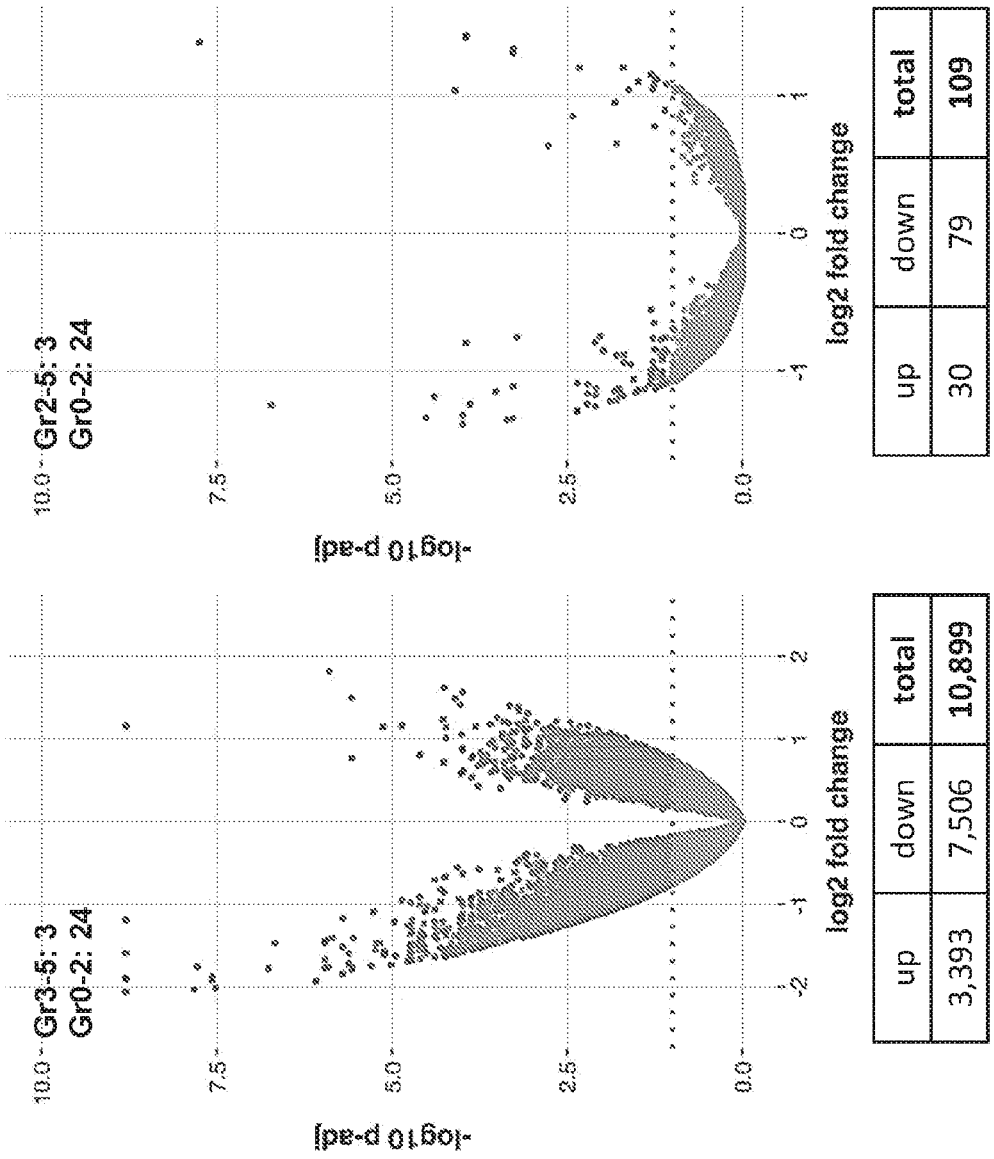

Differentially accessibility analysis for Ntx and CRS were performed in CDP and CMAT samples separately. As shown in FIG. 23C (CDP), few peaks were shown to be differentially accessible for Ntx, whereas a larger number of peaks were differentially accessible for subjects with grades 2-5 CRS. As shown in FIG. 23D (CMAT), a very high number of peaks were observed to be differentially accessible for Ntx, but few were differentially accessible for CRS. Overlap analysis for both CDP and CMAT samples show very few overlapping peaks between the Ntx and CRS analysis.

The results showed that examining CDP alone reduces the overall power of the model to assign differential accessibility peaks relating to clinical outcomes, and examining CMAT alone reduced the power of the model to assign differential accessibility peaks relating to response and CRS, consistent with the observation that interrogating CDP state may be informative with regard to the potential development of CRS. For Ntx, examining CMAT retained a very large number of differential accessibility peaks, consistent with the observation that starting T cell and disease state may be informative with regard to the potential development of neurotoxicity.

The results demonstrate the utility of the ATACseq analysis to identify potential differences in cell types that may correlate with clinical outcomes, e.g., response or safety outcomes, and to identify epigenetic properties or features that are associated with clinical outcomes.

Example 14: Modified ATAC-Seq Method for Chromatin Accessibility Analysis in Analysis of CAR T Cells A modified ATAC-seq method was used to assess chromatin accessibility profiles in CD8+ T cells genetically engineered with a chimeric antigen receptor and compared with the ATAC-seq methods generally described in Example 1.

CD8+ CDP samples from a subject with NHL and CD8+ CMAT samples from a healthy donor were subject to modified ATACseq analysis, generally as described in Corces et al. (2017) Nature Methods 14:959-962, or ATAC-seq methods generally as described in Example 1 (standard ATACseq). Modifications included addition of PBS to wash buffer, addition of Tween-20 and digitonin to lysis buffer and addition of PBS, Tween-20 and digitonin to transposition reaction, and using a different DNA purification column.

The obtained sequences were mapped and ATAC-seq accessibility peaks were called using MACS2. The sequences and peaks obtained from modified or standard ATAC-seq were analyzed using various sequencing quality control metrics, including unmapped, unpaired and duplicate reads, fraction of mitochondrial DNA, effective sequence depth, number of MACS2 peaks with a false discovery rate (FDR) of 0.1 or less, fraction of reads in peaks (FRiP) and number of unique peaks, to ensure consistency and fidelity of the data. Mitochondrial DNA fraction was lower in some samples obtained using modified ATACseq.

Figure 24A:
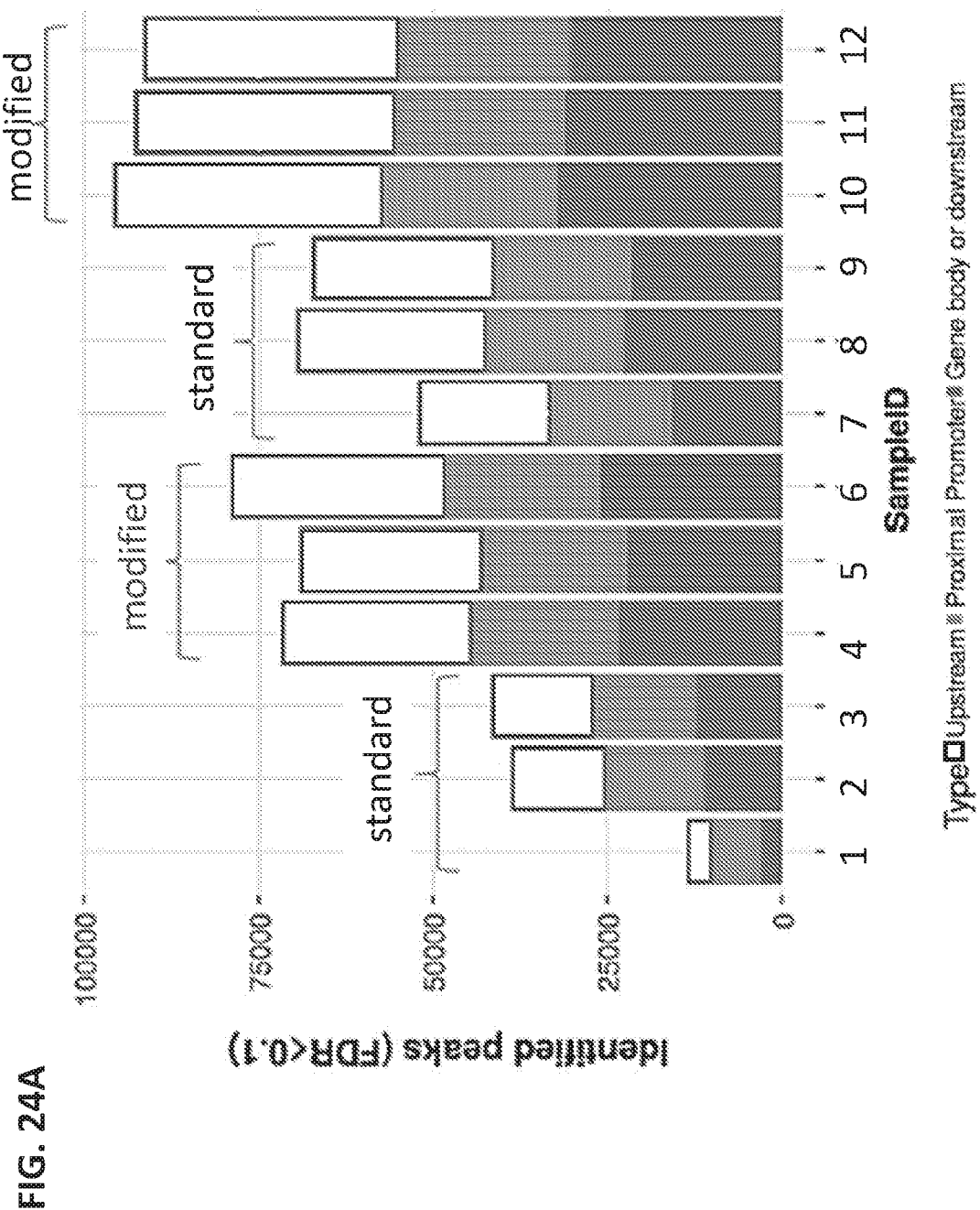
FIG. 24A shows the number of identified peaks with FDR<0.1
Figure 24B:
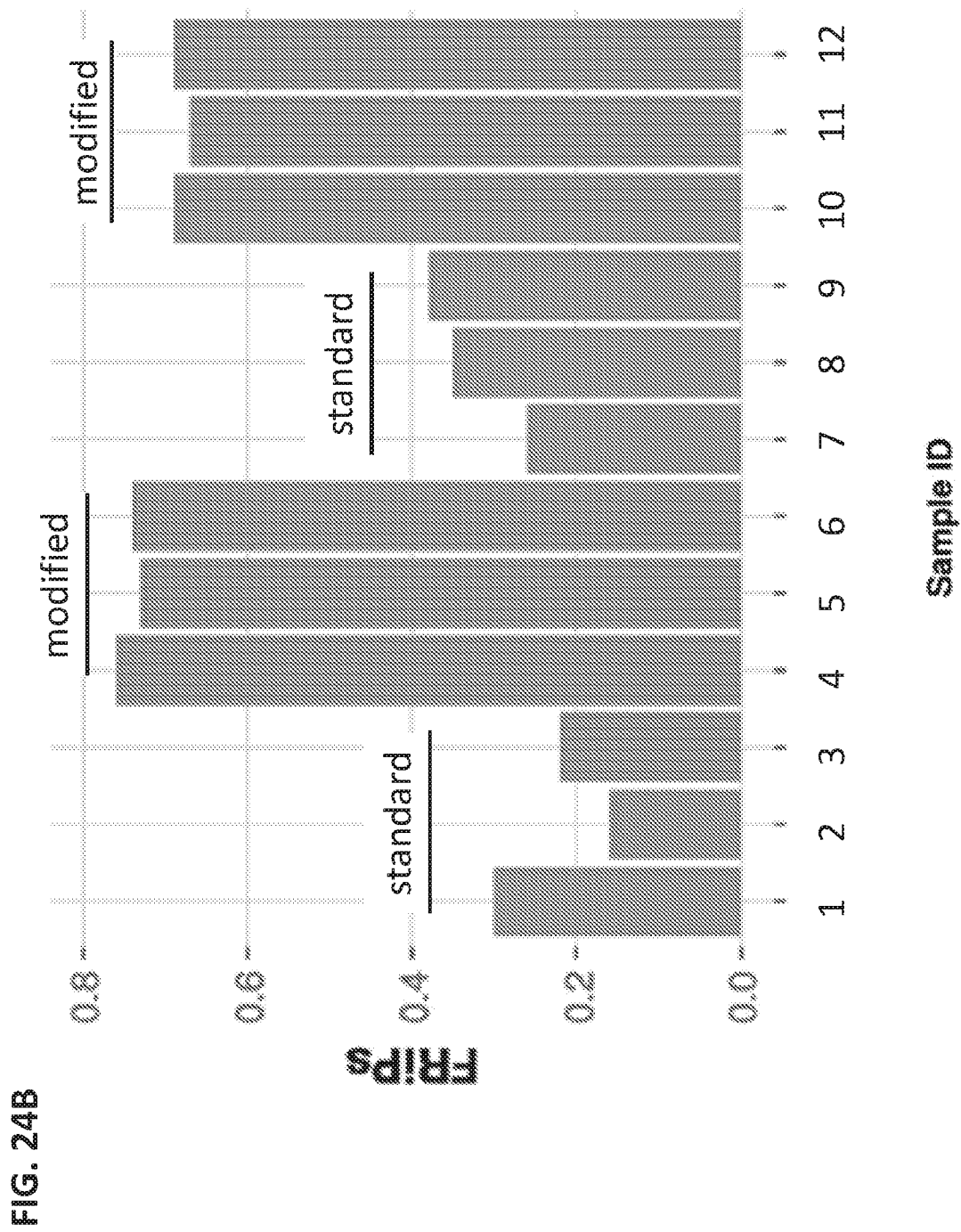
FIG. 24B shows enrichment as indicated by FRiPs, in the CD8+ CDP and CMAT samples using modified or standard ATAC-seq, with 3 technical replicates.

FIG. 24A shows the number of identified peaks with FDR<0.1 and FIG. 24B shows enrichment as indicated by FRiPs, in the CD8+ CDP and CMAT samples using modified or standard ATAC-seq, with 3 technical replicates. The results show that the number of identified peaks is higher using the modified ATAC-seq, and the enrichment signal was substantially higher in samples prepared using modified ATACseq.

Peak overlap analysis showed that the peak overlap was high between technical replicates of the samples, using both standard and modified ATACseq methods. The overlap between standard and modified ATACseq peaks showed that almost all of the standard ATACseq peaks were present in the peaks from modified ATACseq, with more peaks present in samples processed using the modified ATACseq. Inter-sample correlation was high between technical replicates and across different methods. Differential accessibility analysis, genome viewer visualization, clustering analysis using gene modules related to T cells, exhaustion, cytokine and short term effector and memory modules, and Gene Set Enrichment Analysis (GSEA) show consistent results between data obtained using standard and modified ATACseq methods.

The results showed that the modified ATACseq methods generated data with decreased mitochondrial read fraction, increased complexity and efficiency, enriched signal and increased technical reproducibility across samples. Consistent patterns were observed in differential analysis and biological pathway analysis of results from standard and modified ATACseq.

The present invention is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure.

Sequences

| # | SEQUENCE | ANNOTATION |
|---|----------|------------|
| 1 | ESKYGPPCPPCP | spacer (IgG4hinge) (aa) |
| 2 | GAATCTAAGTACGGACCGCCCTGCCCCCCTTGCCCT | spacer (IgG4hinge) (nt) |
| 3 | ESKYGPPCPPCPGQPREPQVYTLPPSQEEMTKNQVSLTCLVKGFYPSDIA VEWESNGQPENNYKTTPPVLDSDGSFFLYSRLTVDKSRWQEGNVFSCSVM HEALHNHYTQKSLSLSLGK | Hinge-CH3 spacer |
| 4 | ESKYGPPCPPCPAPEFLGGPSVFLFPPKPKDTLMISRTPEVTCVVVDVSQ EDPEVQFNWYVDGVEVHNAKTKPREEQFNSTYRVVSVLTVLHQDWLNGKE YKCKVSNKGLPSSIEKTISKAKGQPREPQVYTLPPSQEEMTKNQVSLTCL VKGFYPSDIAVEWESNGQPENNYKTTPPVLDSDGSFFLYSRLTVDKSRWQ EGNVFSCSVMHEALHNHYTQKSLSLSLGK | Hinge-CH2–CH3 spacer |
| 5 | RWPESPKAQASSVPTAQPQAEGSLAKATTAPATTRNTGRGGEEKKKEKEK EEQEERETKTPECPSHTQPLGVYLLTPAVQDLWLRDKATFTCFVVGSDLK DAHLTWEVAGKVPTGGVEEGLLERHSNGSQSQHSRLTLPRSLWNAGTSVT CTLNHPSLPPQRLMALREPAAQAPVKLSLNLLASSDPPEAASWLLCEVSG FSPPNILLMWLEDQREVNTSGFAPARPPPQPGSTTFWAWSVLRVPAPPSP QPATYTCVVSHEDSRTLLNASRSLEVSYVTDH | IgD-hinge-Fc |
| 6 | LEGGGEGRGSLLTCGDVEENPGPR | T2A |
| 7 | MLLLVTSLLLCELPHPAFLLIPRKVCNGIGIGEFKDSLSINATNIKHFKN CTSISGDLHILPVAFRGDSFTHTPPLDPQELDILKTVKEITGFLLIQAWP ENRTDLHAFENLEIIRGRTKQHGQFSLAVVSLNITSLGLRSLKEISDGDV IISGNKNLCYANTINWKKLFGTSGQKTKIISNRGENSCKATGQVCHALCS PEGCWGPEPRDCVSCRNVSRGRECVDKCNLLEGEPREFVENSECIQCHPE CLPQAMNITCTGRGPDNCIQCAHYIDGPHCVKTCPAGVMGENNTLVWKYA DAGHVCHLCHPNCTYGCTGPGLEGCPTNGPKIPSIATGMVGALLLLLVVA LGIGLFM | tEGFR |

-continued

| # | SEQUENCE | ANNOTATION |
|---|----------|------------|
| 8 | FWVLVVVGGVLACYSLLVTVAFIIFWV | CD28 (amino acids 153-179 of Accession No. P10747) |
| 9 | IEVMYPPPYLDNEKSNGTIIHVKGKHLCPSPLFPGPSKP FWVLVVVGGVLACYSLLVTVAFIIFWV | CD28 (amino acids 114-179 of Accession No. P10747) |
| 10 | RSKRSRLLHSDYMNMTPRRPGPTRKHYQPYAPPRDFAAYRS | CD28 (amino acids 180-220 of P10747) |
| 11 | RSKRSRGGHSDYMNMTPRRPGPTRKHYQPYAPPRDFAAYRS | CD28 (LL to GG) |
| 12 | KRGRKKLLYIFKQPFMRPVQTTQEEDGCSCRFPEEEEGGCEL | 4-1BB (amino acids 214-255 of Q07011.1) |
| 13 | RVKFSRSADAPAYQQGQNQLYNELNLGRREEYDVLDKRRGRDPEMGGKPR RKNPQEGLYNELQKDKMAEAYSEIGMKGERRRGKGHDGLYQGLSTATKDT YDALHMQALPPR | CD3 zeta |
| 14 | RVKFSRSAEPPAYQQGQNQLYNELNLGRREEYDVLDKRRGRDPEMGGKPR RKNPQEGLYNELQKDKMAEAYSEIGMKGERRRGKGHDGLYQGLSTATKDT YDALHMQALPPR | CD3 zeta |
| 15 | RVKFSRSADAPAYKQGQNQLYNELNLGRREEYDVLDKRRGRDPEMGGKPR RKNPQEGLYNELQKDKMAEAYSEIGMKGERRRGKGHDGLYQGLSTATKDT YDALHMQALPPR | CD3 zeta |
| 16 | RKVCNGIGIGEFKDSLSINATNIKHFKNCTSISGDLHILPVAFRGDSFTH TPPLDPQELDILKTVKEITGFLLIQAWPENRTDLHAFENLEIIRGRTKQH GQFSLAVVSLNITSLGLRSLKEISDGDVIISGNKNLCYANTINWKKLFGT SGQKTKIISNRGENSCKATGQVCHALCSPEGCWGPEPRDCVSCRNVSRGR ECVDKCNLLEGEPREFVENSECIQCHPECLPQAMNITCTGRGPDNCIQCA HYIDGPHCVKTCPAGVMGENNTLVWKYADAGHVCHLCHPNCTYGCTGPGL EGCPTNGPKIPSIATGMVGALLLLLVVALGIGLFM | tIEGFR |
| 17 | EGRGSLLTCGDVEENPGP | T2A |
| 18 | GSGATNFSLLKQAGDVEENPGP | P2A |
| 19 | ATNFSLLKQAGDVEENPGP | P2A |
| 20 | QCTNYALLKLAGDVESNPGP | E2A |
| 21 | VKQTLNFDLLKLAGDVESNPGP | F2A |
| 22 | -PGGG-(SGGGG)5-P- wherein P is proline, G is glycine and S is serine | Linker |
| 23 | GSADDAKKDAAKKDGKS | Linker |
| 24 | atgcttctcctggtgacaagccttctgctctgtgagttaccacacccagc attcctcctgatccca | GMCSFR alpha chain signal sequence |
| 25 | MLLLVTSLLLCELPHPAFLLIP | GMCSFR alpha chain signal sequence |
| 26 | MALPVTALLLPLALLLHA | CD8 alpha signal peptide |
| 27 | Glu Pro Lys Ser Cys Asp Lys Thr His Thr Cys Pro Pro Cys Pro | Hinge |
| 28 | Glu Arg Lys Cys Cys Val Glu Cys Pro Pro Cys Pro | Hinge |
| 29 | ELKTPLGDTHTCPRCPEPKSCDTPPPCPRCPEPKSCDTPPPCPRCPEPKS CDTPPPCPRCP | Hinge |

-continued

| # | SEQUENCE | ANNOTATION |
|---|---|---|
| 30 | Glu Ser Lys Tyr Gly Pro Pro Cys Pro Ser Cys Pro | Hinge |
| 31 | Glu Ser Lys Tyr Gly Pro Pro Cys Pro Pro Cys Pro | Hinge |
| 32 | Tyr Gly Pro Pro Cys Pro Pro Cys Pro | Hinge |
| 33 | Lys Tyr Gly Pro Pro Cys Pro Pro Cys Pro | Hinge |
| 34 | Glu Val Val Lys Tyr Gly Pro Pro Cys Pro Pro Cys Pro | Hinge |
| 35 | RASQDISKYLN | FMC63 CDR L1 |
| 36 | SRLHSGV | FMC63 CDR L2 |
| 37 | GNTLPYTFG | FMC63 CDR L3 |
| 38 | DYGVS | FMC63 CDR H1 |
| 39 | VIWGSETTYYNSALKS | FMC63 CDR H2 |
| 40 | YAMDYWG | FMC63 CDR H3 |
| 41 | EVKLQESGPGLVAPSQSLSVTCTVSGVSLPDYGVSWIRQPPRKGLEWLGVIWGSETTYYNSALKSRLTIIKDNSKSQVFLKMNSLQTDDTAIYYCAKHYYYGGSYAMDYWGQGTSVTVSS | FMC63 VH |
| 42 | DIQMTQTTSSLSASLGDRVTISCRASQDISKYLNWYQQKPDGTVKLLIYHTSRLHSGVPSRFSGSGSGTDYSLTISNLEQEDIATYFCQQGNTLPYTFGGGTKLEIT | FMC63 VL |
| 43 | DIQMTQTTSSLSASLGDRVTISCRASQDISKYLNWYQQKPDGTVKLLIYHTSRLHSGVPSRFSGSGSGTDYSLTISNLEQEDIATYFCQQGNTLPYTFGGGTKLEITGSTSGSGKPGSGEGSTKGEVKLQESGPGLVAPSQSLSVTCTVSGVSLPDYGVSWIRQPPRKGLEWLGVIWGSETTYYNSALKSRLTIIKDNSKSQVFLKMNSLQTDDTAIYYCAKHYYYGGSYAMDYWGQGTSVTVSS | FMC63 scFv |
| 44 | KASQNVGTNVA | SJ25C1 CDR L1 |
| 45 | SATYRNS | SJ25C1 CDR L2 |
| 46 | QQYNRYPYT | SJ25C1 CDR L3 |
| 47 | SYWMN | SJ25C1 CDR H1 |
| 48 | QIYPGDGDTNYNGKFKG | SJ25C1 CDR H2 |
| 49 | KTISSVVDFYFDY | SJ25C1 CDR H3 |
| 50 | EVKLQQSGAELVRPGSSVKISCKASGYAFSSYWMNWVKQRPGQGLEWIGQIYPGDGDTNYNGKFKGQATLTADKSSSTAYMQLSGLTSEDSAVYFCARKTISSVVDFYFDYWGQGTTVTVSS | SJ25C1 VH |
| 51 | DIELTQSPKFMSTSVGDRVSVTCKASQNVGTNVAWYQQKPGQSPKPLIYSATYRNSGVPDRFTGSGSGTDFTLTITNVQSKDLADYFCQQYNRYPYTSGGGTKLEIKR | SJ25C1 VL |
| 52 | GGGGSGGGGSGGGGS | Linker |
| 53 | EVKLQQSGAELVRPGSSVKISCKASGYAFSSYWMNWVKQRPGQGLEWIGQIYPGDGDTNYNGKFKGQATLTADKSSSTAYMQLSGLTSEDSAVYFCARKTISSVVDFYFDYWGQGTTVTVSSGGGGSGGGGSGGGGSDIELTQSPKFMSTSVGDRVSVTCKASQNVGTNVAWYQQKPGQSPKPLIYSATYRNSGVPDRFTGSGSGTDFTLTITNVQSKDLADYFCQQYNRYPYTSGGGTKLEIKR | SJ25C1 scFv |
| 54 | HYYYGGSYAMDY | FMC63 HC-CDR3 |
| 55 | HTSRLHS | FMC63 LC-CDR2 |
| 56 | QQGNTLPYT | FMC63 LC-CDR3 |
| 57 | gacatccagatgacccagaccacctccagcctgagcgccagcctgggcgaccgggtgaccatcagctgccgggccagccaggacatcagcaagtacctgaactggtatcagcagaagcccgacggcaccgtcaagctgctgatctaccaccagccggctgcacagcggcgtgcccagccggttttagcggcagcggctc | Sequence encoding scFv |

| # | SEQUENCE | ANNOTATION |
|---|---|---|
| | cggcaccgactacagcctgaccatctccaacctggaacaggaagatatcg<br>ccacctacttttgccagcagggcaacacactgccctacacctttggcggc<br>ggaacaaagctggaaatcaccggcagcacctccggcagcggcaagcctgg<br>cagcggcgagggcagcaccaagggcgaggtgaagctgcaggaaagcggcc<br>ctggcctggtggcccccagccagagcctgagcgtgacctgcaccgtgagc<br>ggcgtgagcctgcccgactacggcgtgagctggatccggcagccccccag<br>gaagggcctggaatggctgggcgtgatctggggcagcgagaccacctact<br>acaacagcgccctgaagagccggctgaccatcatcaaggacaacagcaag<br>agccaggtgttcctgaagatgaacagcctgcagaccgacgacaccgccat<br>ctactactgcgccaagcactactactacggcggcagctacgccatggact<br>actggggccagggcaccagcgtgaccgtgagcagc | |
| 58 | X$_1$PPX$_2$P<br>X$_1$ is glycine, cysteine or arginine<br>X$_2$ is cysteine or threonine | Hinge |
| 59 | GSTSGSGKPGSGEGSTKG | Linker |

The invention claimed is:

1. A method of administering a cell therapy to a subject, the method comprising:

(a) determining an epigenetic property of one or more genomic regions of a composition of genetically engineered cells comprising a recombinant receptor;

(b) identifying the epigenetic property of one or more of the genomic regions of cells of the composition as being correlated with a desired response or safety outcome to a cell therapy, said cell therapy comprising the composition, wherein the identifying comprises comparing the epigenetic property for each of the one or more genomic regions, individually, to a corresponding epigenetic property from a reference profile, wherein the reference profile correlates with a cell therapy being likely to produce a desired response or safety outcome when administered;

(c) selecting the composition as a cell therapy likely to produce the desired response or safety outcome based on the identifying of (b); and (d) administering the composition to the subject as a cell therapy.

2. The method of claim 1, wherein the desired response is a complete response, a partial response, or durability of response.

3. The method of claim 1, wherein the composition is enriched for CD4+ primary human T cells or CD8+ primary human T cells.

4. The method of claim 1, wherein the epigenetic property is chromatin accessibility or nucleosome occupancy.

5. The method of claim 4, wherein chromatin accessibility is determined by Assay for Transposase Accessible Chromatin with high-throughput sequencing (ATAC-seq).

6. The method of claim 1, wherein the determining the epigenetic property comprises:

(1) isolating chromatin from the cells of the composition;

(2) treating the chromatin with an insertional enzyme complex to generate tagged fragments of genomic DNA;

(3) sequencing all or a portion of the tagged fragments to produce a plurality of sequence reads;

(4) aligning, filtering and mapping the sequence reads to genomic regions of a genome; and (5) determining peaks of sequence reads in a plurality of genomic regions for the cells of the composition.

7. The method of claim 6, wherein the determining the epigenetic property further comprises:

comparing peaks of sequence reads and identifying peaks of sequence reads that are different between samples from two or more compositions of cells;

determining positions of nucleosomes within genomic regions containing peaks of sequence reads;

generating an epigenetic map showing a profile of sequence reads indicative of the epigenetic property, along each of the one or more genomic regions or a subset thereof; or generating, for each of a plurality of sites or portions along the length of the genomic region, one or more sequence reads indicative of an epigenetic readout, at said site or portion, wherein the quantity of said one or more sequence reads indicates a level of said epigenetic property, at said site or portion.

8. The method of claim 7, wherein the determining comprises:

steps for removal of mitochondrial reads or additional contaminating sequences based on sequence identity, quality, mapping location, or other sequencing properties of said reads;

steps for removal of duplicate reads to improve quantitative accuracy; or steps for separation of sequence reads into subsets representing a specific epigenetic property, wherein the size of the sequenced fragment is used to determine the level to which it represents said epigenetic property.

9. The method of claim 6, wherein said determining further comprises performing principle component analysis (PCA), biological pathway analysis, gene ontology (GO) analysis or motif analysis.

10. The method of claim 1, wherein the determining the epigenetic property is by ATAC-seq of the whole genome of the cells of the composition.

11. The method of claim 1, wherein:
the recombinant receptor binds to, recognizes or targets an antigen associated with the disease or condition; or the recombinant receptor is a T cell receptor or a functional non-T cell receptor.

12. The method of claim 1, wherein the administering of the cell therapy is carried out by autologous transfer.

13. The method of claim 1, wherein the cells of the composition comprise immune cells.

14. The method of claim 1, wherein the cells of the composition comprise T cells or NK cells.

15. The method of claim 14, wherein the T cells comprise CD4+ T cells or CD8+ T cells.

16. The method of claim 1, wherein the desired safety outcome is absence of development of severe cytokine release syndrome (CRS) or severe neurotoxcity (NT).

17. The method of claim 1, wherein the recombinant receptor is a chimeric antigen receptor (CAR).

18. A method of administering a cell composition to a subject comprising:
(a) comparing an epigenetic property of one or more genomic regions of obtained cells or populations of cells to a corresponding epigenetic property from a reference profile,
wherein the cells or populations of cells are comprised in a composition of cells genetically engineered to comprise a recombinant receptor, and
wherein the reference profile correlates with a cell therapy likely to produce a desired response or safety outcome;
(b) indicating whether the cells or population of cells of the composition is likely to produce the desired response or safety outcome;
(c) selecting the composition as likely to produce the desired response or safety outcome; and
(d) administering the composition selected in (c) to the subject.

19. The method of claim 18, wherein the desired outcome is a complete response, a partial response, or a durable response.

20. The method of claim 18, wherein the desired safety outcome is absence of development of severe cytokine release syndrome (CRS) or severe neurotoxicity.

21. The method of claim 18, wherein the recombinant receptor is a chimeric antigen receptor (CAR).

22. The method of claim 18, wherein the epigenetic property is chromatin accessibility or nucleosome occupancy.

23. The method of claim 22, wherein chromatin accessibility is determined by Assay for Transposase Accessible Chromatin with high-throughput sequencing (ATAC-seq).

24. A method of administering a cell therapy to a subject, the method comprising:
(a) determining an epigenetic property of one or more genomic regions of cells obtained from a subject;
wherein the cells are to be genetically engineered to comprise a recombinant receptor;
(b) identifying the epigenetic property of one or more of the genomic regions of the cells as being correlated with a desired response or safety outcome to a cell therapy, said cell therapy comprising the cells from the subject genetically engineered with the recombinant receptor,
wherein the identifying comprises comparing the epigenetic property for each of the one or more genomic regions, individually, to a corresponding epigenetic property from a reference profile, wherein the reference profile correlates with a cell therapy being likely to produce a desired response or safety outcome when administered;
(c) genetically engineering the cells obtained from the subject with the recombinant receptor based on the identifying of (b) to produce said cell therapy; and
(d) administering the cell therapy to the subject.

25. The method of claim 24, wherein the cells obtained from the subject comprises enriched CD4+ primary human T cells or CD8+ primary human T cells.

26. The method of claim 24, wherein the administering of the cell therapy is carried out by autologous transfer.

27. The method of claim 24, wherein the cells obtained from the subject comprise immune cells.

28. The method of claim 24, wherein the cells obtained from the subject comprise T cells or NK cells.

29. A method of administering a cell therapy to a subject comprising:
(a) comparing an epigenetic property of one or more genomic regions of cells obtained from a subject to a corresponding epigenetic property from a reference profile;
wherein the cells are to be genetically engineered to comprise a recombinant receptor,
wherein the reference profile correlates with a cell therapy likely to produce a desired response or safety outcome;
(b) indicating whether the cells are likely to produce the desired response or safety outcome;
(c) selecting the cells indicated as likely to produce the desired response or safety outcome;
(d) genetically engineering the selected cells with the recombinant receptor to produce the cell therapy; and
(e) administering the produced cell therapy to the subject.

* * * * *

UNITED STATES PATENT AND TRADEMARK OFFICE
CERTIFICATE OF CORRECTION

PATENT NO. : 11,821,027 B2
APPLICATION NO. : 16/476856
DATED : November 21, 2023
INVENTOR(S) : Mark L. Bonyhadi Page 1 of 1

It is certified that error appears in the above-identified patent and that said Letters Patent is hereby corrected as shown below:

In the Claims

At Column 189, Claim number 9, Line number 6, please replace "principle" with --principal--

At Column 189, Claim number 16, Line number 3, please replace "neurotoxcity" with --neurotoxicity--

Signed and Sealed this
Eighth Day of July, 2025

Coke Morgan Stewart
*Acting Director of the United States Patent and Trademark Office*